(12) United States Patent
Lindner et al.

(10) Patent No.: US 11,129,919 B2
(45) Date of Patent: Sep. 28, 2021

(54) ABSORBENT ARTICLE WITH ACTIVATABLE MATERIAL

(71) Applicant: The Procter & Gamble Company, Cincinnati, OH (US)

(72) Inventors: Torsten Lindner, Kronberg (DE); Olaf Erik Alexander Isele, Wester Chester, OH (US); Gueltekin Erdem, Hessen (DE); Misael Omar Aviles, Hamilton, OH (US); Holger Beruda, Schwalbach am Taunus (DE); Jan Claussen, Wiesbaden (DE); Kelyn Anne Arora, Cincinnati, OH (US); Nathan Ray Whitely, Liberty Township, OH (US); Franz Josef Lanyi, Erlangen (DE); Dirk Wolfram Schubert, Eggolsheim (DE); Barbara Harling Hede, Aalborg (DK); Thomas Broch, Gistrup (DK); Morten Rise Hansen, Aalborg (DK); Brian Udengaard, Lystrup (DK)

(73) Assignee: The Procter & Gamble Company, Cincinnati, OH (US)

( * ) Notice: Subject to any disclaimer, the term of this patent is extended or adjusted under 35 U.S.C. 154(b) by 1061 days.

(21) Appl. No.: 15/454,128

(22) Filed: Mar. 9, 2017

(65) Prior Publication Data
US 2017/0258955 A1    Sep. 14, 2017

Related U.S. Application Data

(60) Provisional application No. 62/305,726, filed on Mar. 9, 2016.

(51) Int. Cl.
*A61L 15/42* (2006.01)
*A61F 13/513* (2006.01)
(Continued)

(52) U.S. Cl.
CPC ........ *A61L 15/42* (2013.01); *A61F 13/15617* (2013.01); *A61F 13/47* (2013.01);
(Continued)

(58) Field of Classification Search
CPC .... A61F 13/47; A61F 13/49; A61F 13/51113; A61F 13/512; A61F 13/513;
(Continued)

(56) References Cited

U.S. PATENT DOCUMENTS 3,093,612 A    6/1963  Cox
3,139,412 A    6/1964  Sterling
(Continued)

FOREIGN PATENT DOCUMENTS

EP    0735089 A2    10/1996
EP    862402    9/1998
(Continued)

OTHER PUBLICATIONS

12270 International Search Report and Written Opinion, PCT/US2014/023252) dated Jun. 17, 2014.
(Continued)

*Primary Examiner* — Michele M Kidwell
(74) *Attorney, Agent, or Firm* — Gary J. Foose; George H. Leal

(57) ABSTRACT

Material webs suitable for use in conjunction with disposable absorbent articles are disclosed herein. The material webs comprise a melt additive that when subjected to thermal energy may be encouraged to bloom across the entirety of the web or in localized areas of the web where localized thermal energy is applied.

16 Claims, 57 Drawing Sheets

(51) Int. Cl.

| | | |
|---|---|---|
| *A61F 13/511* | (2006.01) | |
| *A61F 13/15* | (2006.01) | |
| *A61F 13/47* | (2006.01) | |
| *A61F 13/51* | (2006.01) | |
| *A61F 13/514* | (2006.01) | |
| *C07F 9/6561* | (2006.01) | |
| *A61F 13/49* | (2006.01) | |
| *A61F 13/512* | (2006.01) | |

(52) U.S. Cl.
  CPC ........... *A61F 13/49* (2013.01); *A61F 13/512* (2013.01); *A61F 13/513* (2013.01); *A61F 13/51113* (2013.01); *A61F 13/51405* (2013.01); *C07F 9/6561* (2013.01); *A61F 2013/51026* (2013.01); *A61F 2013/51078* (2013.01)

(58) Field of Classification Search
  CPC ...... A61F 13/51405; A61F 2013/51026; A61F 2013/51078; A61F 13/15617; A61L 15/42; C07F 9/6561
  See application file for complete search history.

(56) References Cited

U.S. PATENT DOCUMENTS

| | | | |
|---|---|---|---|
| 3,423,491 A | 1/1969 | McLain | |
| 3,785,918 A | 1/1974 | Kawai et al. | |
| 3,870,567 A | 3/1975 | Palmer et al. | |
| 4,020,230 A | 4/1977 | Mahoney et al. | |
| 4,304,234 A | 12/1981 | Hartmann | |
| 4,578,414 A | 3/1986 | Sawyer et al. | |
| 4,666,763 A | 5/1987 | King et al. | |
| 4,818,594 A | 4/1989 | Albien et al. | |
| 4,874,567 A | 10/1989 | Lopatin et al. | |
| 5,045,387 A | 9/1991 | Schmalz | |
| 5,198,292 A | 3/1993 | Lerner et al. | |
| 5,283,023 A | 2/1994 | Nohr et al. | |
| 5,300,167 A | 4/1994 | Nohr et al. | |
| 5,593,768 A | 1/1997 | Gessner | |
| 5,653,930 A | 8/1997 | Noda et al. | |
| 5,667,750 A | 9/1997 | Nohr et al. | |
| 5,780,368 A | 7/1998 | Noda et al. | |
| 6,117,801 A | 9/2000 | McGinty et al. | |
| 6,203,889 B1 | 3/2001 | Quincy, III et al. | |
| 6,300,258 B1 | 10/2001 | Stano et al. | |
| 6,353,149 B1 | 3/2002 | Stone | |
| 6,602,386 B1 | 8/2003 | Takeuchi et al. | |
| 6,686,303 B1 | 2/2004 | Haynes et al. | |
| 6,699,806 B1 | 3/2004 | Takeuchi et al. | |
| 6,713,011 B2 | 3/2004 | Chu et al. | |
| 6,746,755 B2 | 6/2004 | Morrison et al. | |
| 6,746,766 B2 | 6/2004 | Bond et al. | |
| 6,767,498 B1 | 7/2004 | Talley, Jr. et al. | |
| 6,818,295 B2 | 11/2004 | Bond et al. | |
| 6,855,422 B2 | 2/2005 | Magill et al. | |
| 6,890,649 B2 | 5/2005 | Hobbs et al. | |
| 6,890,872 B2 | 5/2005 | Bond et al. | |
| 6,946,506 B2 | 9/2005 | Bond et al. | |
| 7,150,912 B2 | 12/2006 | Mizutani et al. | |
| 7,241,497 B2 | 7/2007 | Magill et al. | |
| 7,267,789 B2 | 9/2007 | Chhabra et al. | |
| 7,271,209 B2 | 9/2007 | Li et al. | |
| 7,291,300 B2 | 11/2007 | Chhabra et al. | |
| 7,781,353 B2 | 8/2010 | Snowden et al. | |
| 7,981,226 B2 | 7/2011 | Pourdeyhimi et al. | |
| 8,026,188 B2 | 9/2011 | Mor | |
| 8,168,550 B2 | 5/2012 | Collias et al. | |
| 8,173,553 B2 | 5/2012 | Aoki et al. | |
| 10,271,999 B2 * | 4/2019 | Arora ................ D04H 1/50 | |
| 2001/0008965 A1 * | 7/2001 | Kinn .................. D04H 3/147 | |
| | | | 604/366 |
| 2002/0168912 A1 | 11/2002 | Bond et al. | |
| 2002/0169429 A1 | 11/2002 | Li et al. | |
| 2003/0091803 A1 | 5/2003 | Bond et al. | |
| 2003/0178166 A1 | 9/2003 | Takeuchi et al. | |
| 2003/0203695 A1 | 10/2003 | Polanco et al. | |
| 2004/0005457 A1 | 1/2004 | DeLucia et al. | |
| 2004/0116018 A1 | 6/2004 | Fenwick et al. | |
| 2004/0119207 A1 | 6/2004 | Stone et al. | |
| 2004/0127128 A1 | 7/2004 | Thomas | |
| 2004/0161994 A1 | 8/2004 | Arora et al. | |
| 2004/0170816 A1 | 9/2004 | Watanabe et al. | |
| 2004/0192818 A1 | 9/2004 | Oriani et al. | |
| 2005/0095695 A1 | 5/2005 | Shindler et al. | |
| 2005/0130539 A1 | 6/2005 | Allen et al. | |
| 2006/0008643 A1 | 1/2006 | Lin et al. | |
| 2006/0147804 A1 | 7/2006 | Yamamoto et al. | |
| 2006/0154548 A1 | 7/2006 | Sheehan et al. | |
| 2006/0172641 A1 | 8/2006 | Hennige et al. | |
| 2006/0286343 A1 * | 12/2006 | Curro .................... A61F 13/00 | |
| | | | 428/131 |
| 2007/0077427 A1 | 4/2007 | Dugan | |
| 2007/0082573 A1 | 4/2007 | Noda et al. | |
| 2007/0232179 A1 | 10/2007 | Polat et al. | |
| 2007/0232180 A1 | 10/2007 | Polat et al. | |
| 2008/0045638 A1 | 2/2008 | Chapman et al. | |
| 2008/0070994 A1 | 3/2008 | Li et al. | |
| 2008/0108962 A1 | 5/2008 | Furuta et al. | |
| 2008/0179777 A1 | 7/2008 | Wild et al. | |
| 2010/0024281 A1 | 2/2010 | Lemke et al. | |
| 2010/0028638 A1 | 2/2010 | Reichardt et al. | |
| 2010/0041292 A1 | 2/2010 | Kim et al. | |
| 2010/0198177 A1 | 8/2010 | Yahiaoui et al. | |
| 2010/0272938 A1 | 10/2010 | Mitchell et al. | |
| 2010/0322989 A1 | 12/2010 | Martin | |
| 2010/0330861 A1 | 12/2010 | Mor | |
| 2011/0104419 A1 | 5/2011 | Barnholtz et al. | |
| 2011/0117176 A1 | 5/2011 | Klun et al. | |
| 2011/0130430 A1 | 6/2011 | Sonneck et al. | |
| 2011/0196332 A1 | 8/2011 | Cheng et al. | |
| 2012/0100772 A1 * | 4/2012 | Hummelgaard ........ C08K 5/103 | |
| | | | 442/327 |
| 2012/0109090 A1 * | 5/2012 | Reichardt ............. A61F 13/494 | |
| | | | 604/370 |
| 2012/0122363 A1 | 5/2012 | Owens | |
| 2012/0204760 A1 | 8/2012 | Puhala et al. | |
| 2012/0296036 A1 | 11/2012 | Allen et al. | |
| 2012/0321869 A1 | 12/2012 | Allen et al. | |
| 2012/0321870 A1 | 12/2012 | Allen et al. | |
| 2012/0321871 A1 | 12/2012 | Bond et al. | |
| 2012/0328804 A1 | 12/2012 | Allen et al. | |
| 2013/0004691 A1 | 1/2013 | Allen et al. | |
| 2013/0012093 A1 | 1/2013 | Bond et al. | |
| 2013/0053478 A1 | 2/2013 | Bond et al. | |
| 2013/0053480 A1 | 2/2013 | Allen et al. | |
| 2013/0053901 A1 | 2/2013 | Cormier et al. | |
| 2013/0089747 A1 | 4/2013 | Allen, Jr. et al. | |
| 2013/0158169 A1 | 6/2013 | Bond et al. | |
| 2014/0272359 A1 | 9/2014 | Cheng et al. | |
| 2014/0276512 A1 | 9/2014 | Cheng et al. | |
| 2016/0067118 A1 * | 3/2016 | Hammons ............ A61F 13/5123 | |
| | | | 428/137 |
| 2016/0166443 A1 * | 6/2016 | Arora .................. A61F 13/5126 | |
| | | | 604/378 |

FOREIGN PATENT DOCUMENTS

| | | | | |
|---|---|---|---|---|
| EP | 1 206 944 A1 * | 5/2002 | ............ | A61F 15/50 |
| EP | 2266514 A1 | 12/2010 | | |
| EP | 2926788 A1 | 10/2015 | | |
| FR | 2789690 A1 | 8/2000 | | |
| GB | 1225824 A | 3/1971 | | |
| GB | 200205029 | 4/2002 | | |
| JP | 62129054 | 6/1987 | | |
| JP | 62133164 | 6/1987 | | |
| JP | 62268861 | 11/1987 | | |
| JP | 1272861 | 10/1989 | | |
| JP | 2191759 | 7/1990 | | |
| JP | 3279452 | 12/1991 | | |
| JP | 4091224 | 3/1992 | | |
| JP | 4136251 | 5/1992 | | |

(56) References Cited

FOREIGN PATENT DOCUMENTS

| | | |
|---|---|---|
| JP | 5051818 | 3/1993 |
| JP | 6070954 | 3/1994 |
| JP | 6245952 | 9/1994 |
| JP | 7258964 | 10/1995 |
| JP | 8158229 | 6/1996 |
| JP | 9049160 | 2/1997 |
| JP | 9111630 | 4/1997 |
| JP | 9273061 | 10/1997 |
| JP | 1025420 A1 | 1/1998 |
| JP | 2000178865 | 6/2000 |
| JP | 2002061060 | 2/2002 |
| JP | 2002146631 A | 5/2002 |
| JP | 2002263137 | 9/2002 |
| JP | 2003138428 | 5/2003 |
| JP | 2004501676 A | 1/2004 |
| JP | 2004169261 | 6/2004 |
| JP | 2004285538 | 10/2004 |
| JP | 2005330637 | 12/2005 |
| JP | 2007113145 | 5/2007 |
| JP | 2008002037 | 1/2008 |
| JP | 2008095254 | 4/2008 |
| JP | 2008161584 | 7/2008 |
| JP | 200915005 | 7/2009 |
| JP | 2009228157 | 10/2009 |
| JP | 200301358 | 10/2013 |
| RU | 64908 U1 | 7/2007 |
| RU | 2412679 C2 | 2/2011 |
| WO | WO1995023249 | 8/1995 |
| WO | WO1995023250 | 8/1995 |
| WO | WO1998008475 | 3/1998 |
| WO | WO1999006207 | 2/1999 |
| WO | WO1998031735 | 10/1999 |
| WO | WO2001090230 | 11/2001 |
| WO | 03105916 A1 | 12/2003 |
| WO | WO2004014997 A2 | 2/2004 |
| WO | WO2005042824 | 5/2005 |
| WO | WO2010149239 A1 | 12/2010 |
| WO | WO2011090425 A1 | 7/2011 |
| WO | WO2012162083 A1 | 11/2012 |
| WO | WO2012162085 A1 | 11/2012 |
| WO | WO2012162092 A1 | 11/2012 |
| WO | WO2012162135 | 11/2012 |
| WO | WO2012162146 A1 | 11/2012 |
| WO | WO2012162149 A1 | 11/2012 |
| WO | WO2012162084 A3 | 3/2013 |
| WO | 2016002092 A1 | 1/2016 |

OTHER PUBLICATIONS

14235MQ International Search Report for PCT/US2017/021522, dated May 19, 2017.
Devesh, Tripathi, "Practical Guide to Polypropylene", Smithers RAPRA Technology, 2002.
Drexel University, Fiber Spinning—Drexel University Chemical Engineering Department, Feb. 16, 1999.
Flow Polymers Effect of SureFlo (TM) on Polypropylene Contamination in Nylon, 2011 Flow Polymers, LLC.
Kim, "Effects of Nucleating Agents on Preparation of Polypropylene Hollow Fiber Membranes by Melt Spinning Process", Maromolecular Research, vol. 10, No. 2, 127-134 pgs. (2002).
Kim, Microporous Membrane Formation Via Thermally Induced Phase Separation, Journal of Membrane Science, 64, (1991) 13-29.
Kim, Operation Parameters of Melt Spinning of Polypropylene Hollow Fiber Membranes, Journal of Membrane Science 108 (1995) 25-36, 12 pages.
Krupa, Polypropylene as a Potential Matrix for the Creation of Shape Stabilized Phase Change Materials, European Polymer Journal 43 (2007) 895-907, 13 pages.
Krupa, Thermal Properties of Polypropylene/Wax Blends, Thermochimica Acta 372 (2001) 137-141, 5 pages.
Mpanza, Comparison of Different Waxes as Processing Agents for Low-Density Polyethylene, Polymer Testing 25 (2006)436-442, 7 pages.
Tolinski, Additives for Polyolefins, 2009, pp. 158-168.
Xiaofan, Flow Polymers, Effects of SureFlo® on the Crystallization and Melting Behavior of Semi-Crystalline Polyethylene (PE) and Polypropylene (PP) Systems, Flow Polymers, LLC, 3 pages.
Yoo, Effects of the Diluent Mixing Ratio and Conditions of the Thermally Induced Phase-Separation Process on the Pore Size of Microporous Polyethylene Membranes, Journal of Applied Polymer Science, vol. 108, 3154-3162 (2008).
All Office Actions, U.S. Appl. No. 13/833,311.
All Office Actions, U.S. Appl. No. 13/833,456.
All Office Actions, U.S. Appl. No. 13/833,503.
All Office Actions, U.S. Appl. No. 14/247,588.
All Office Actions, U.S. Appl. No. 14/861,004.

* cited by examiner

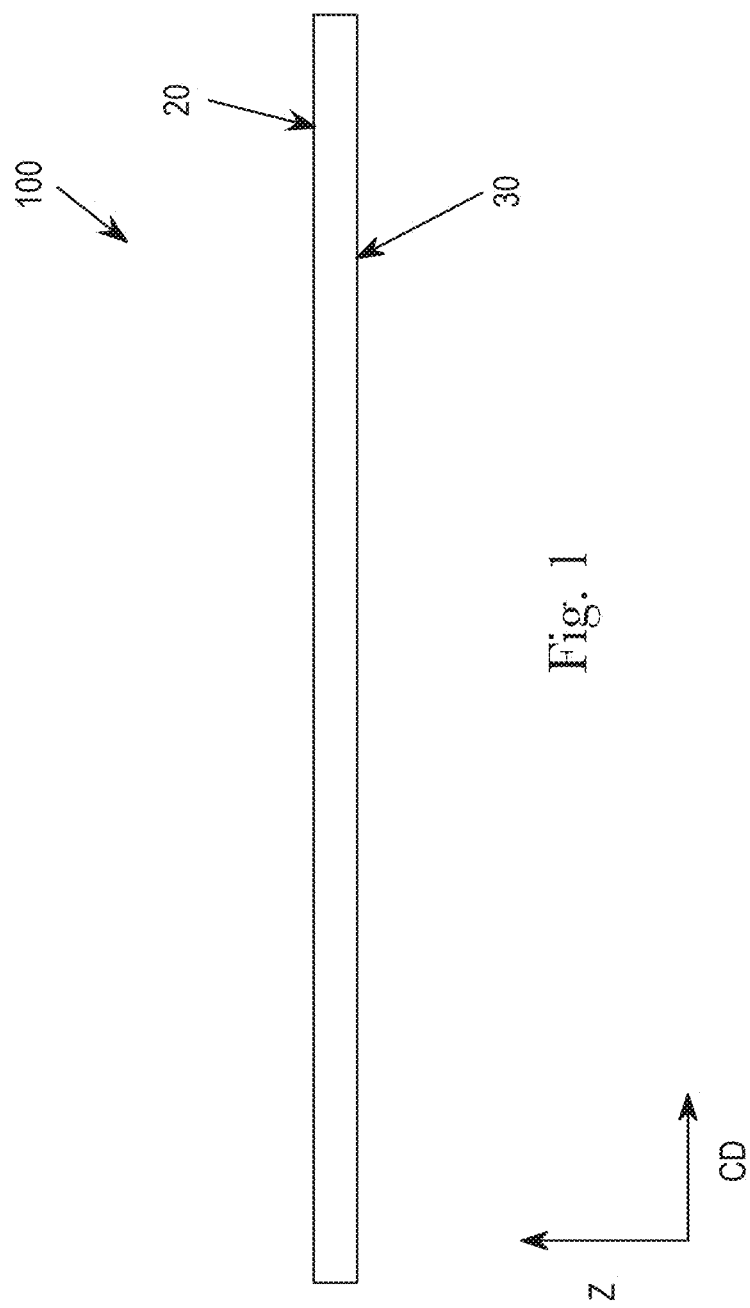

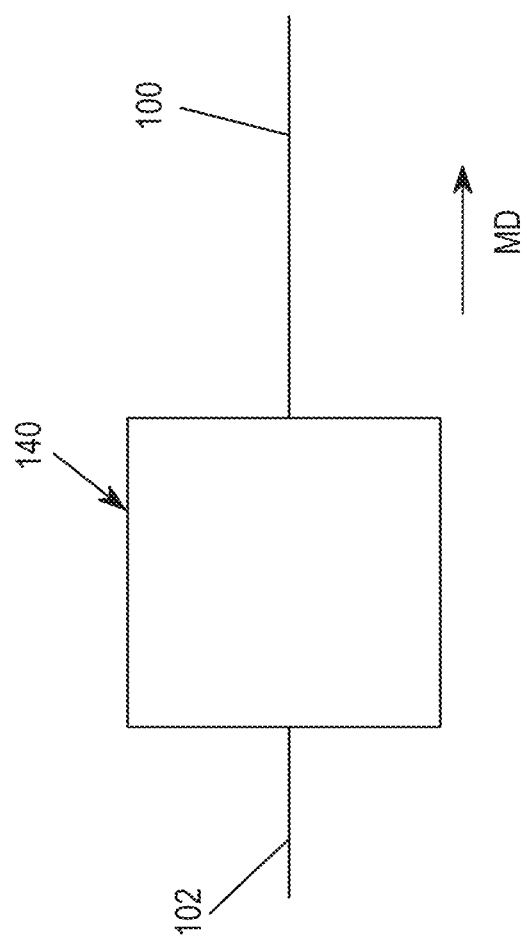

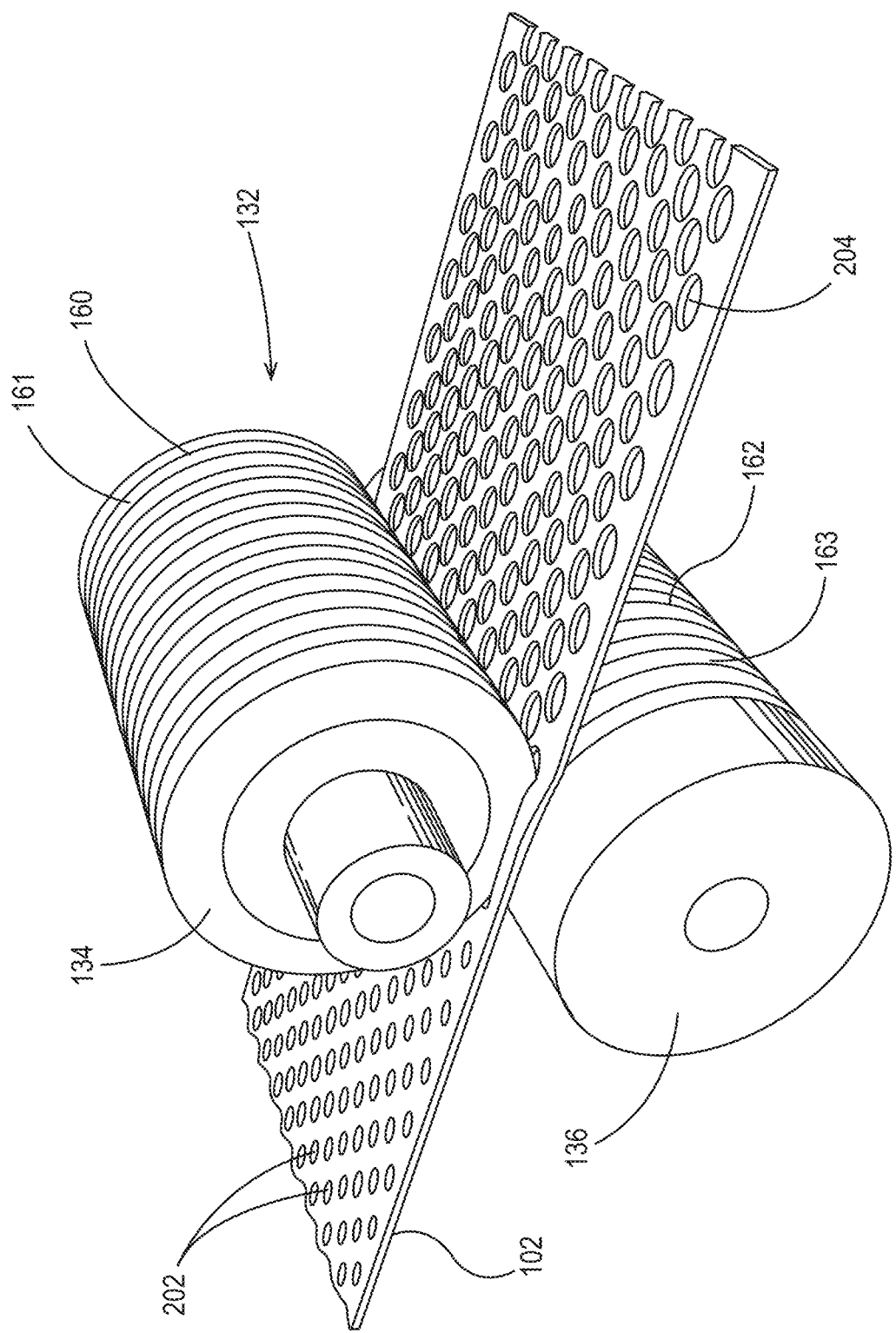

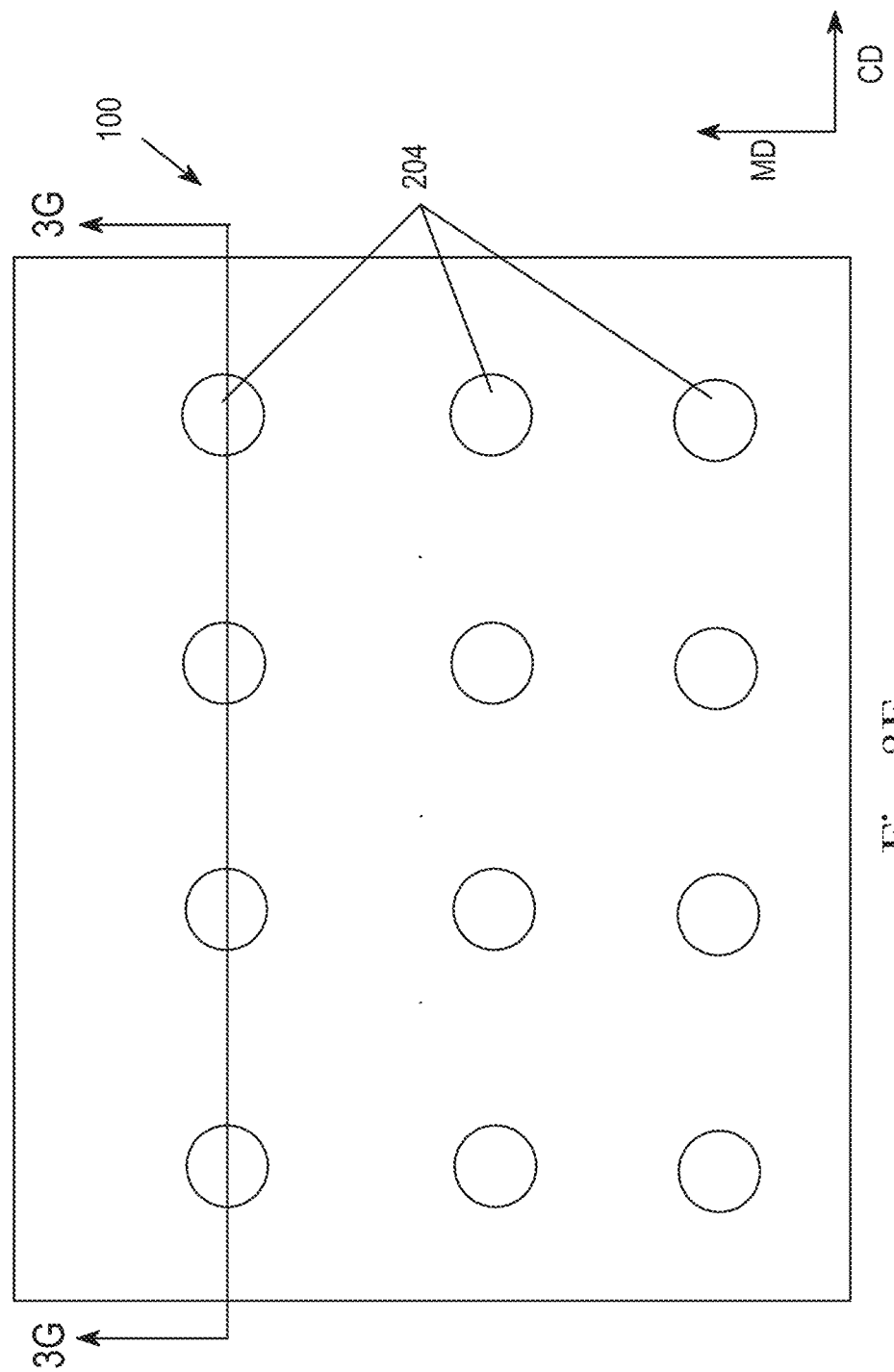

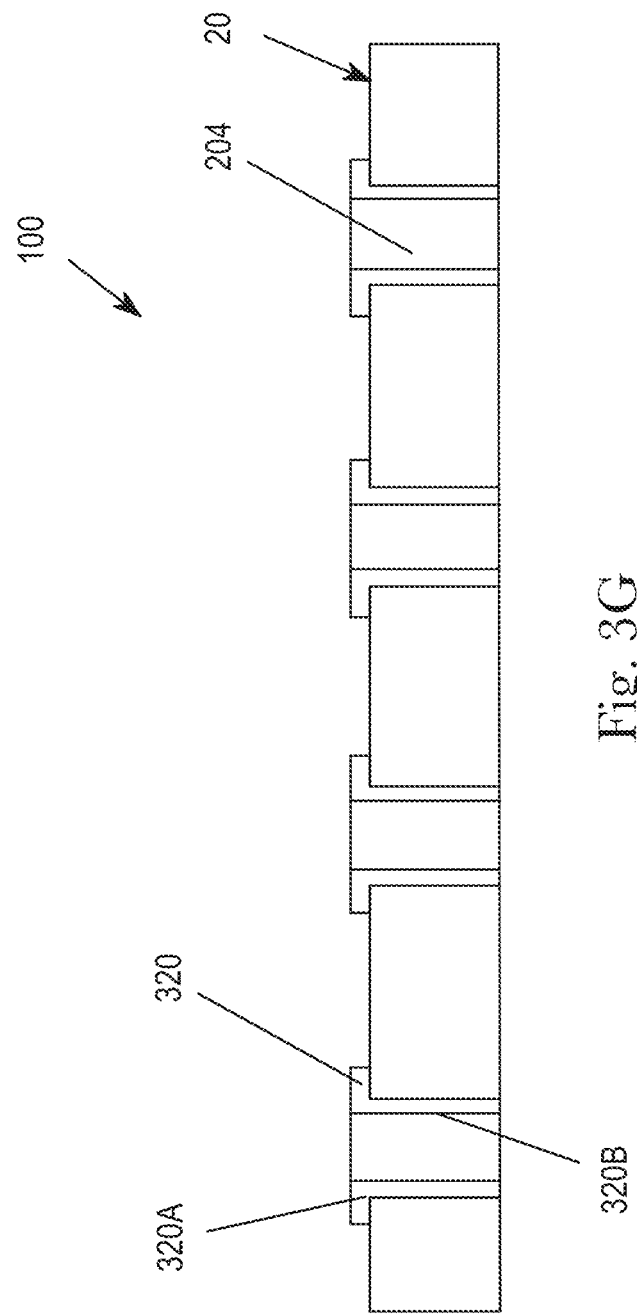

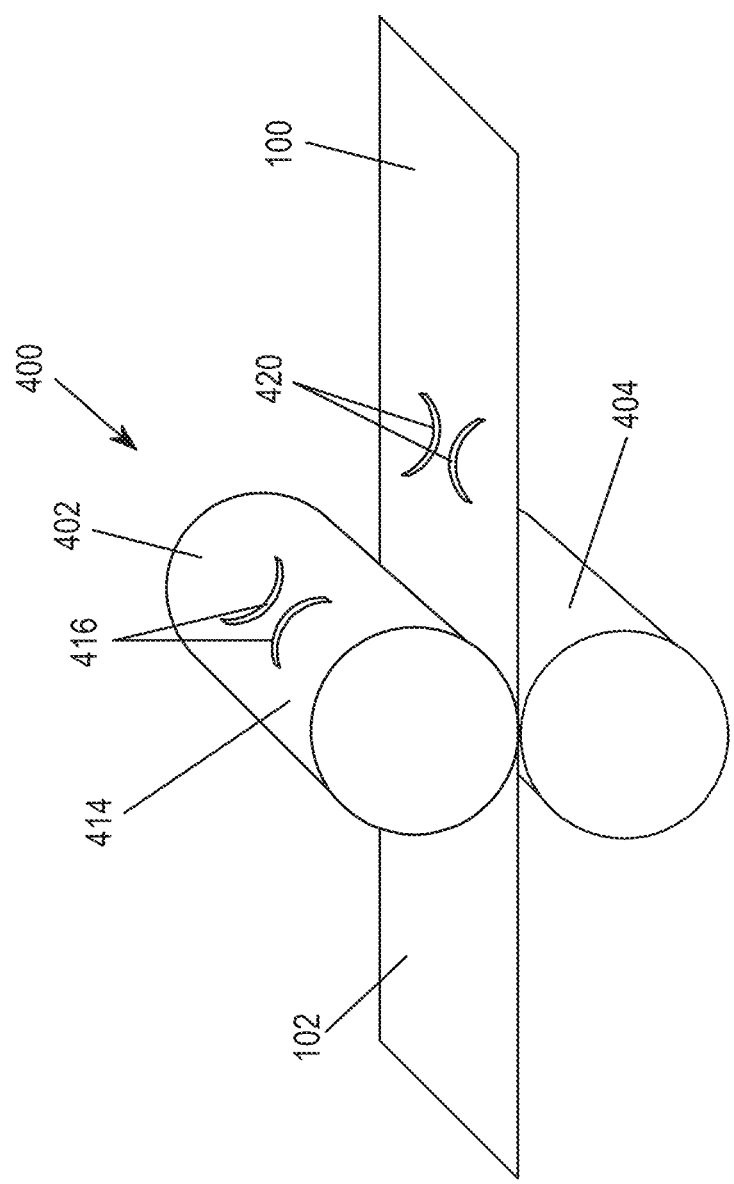

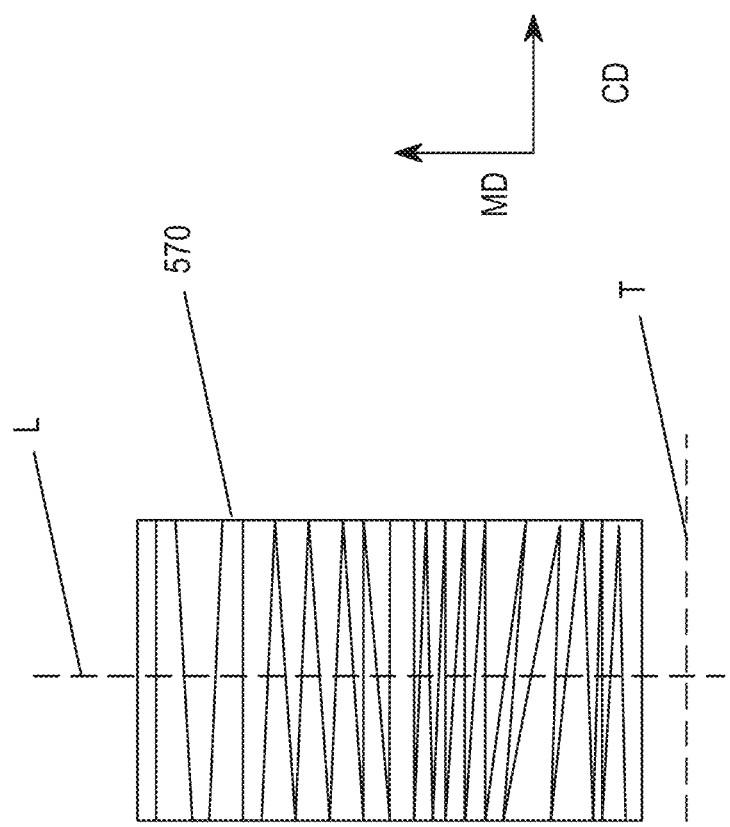

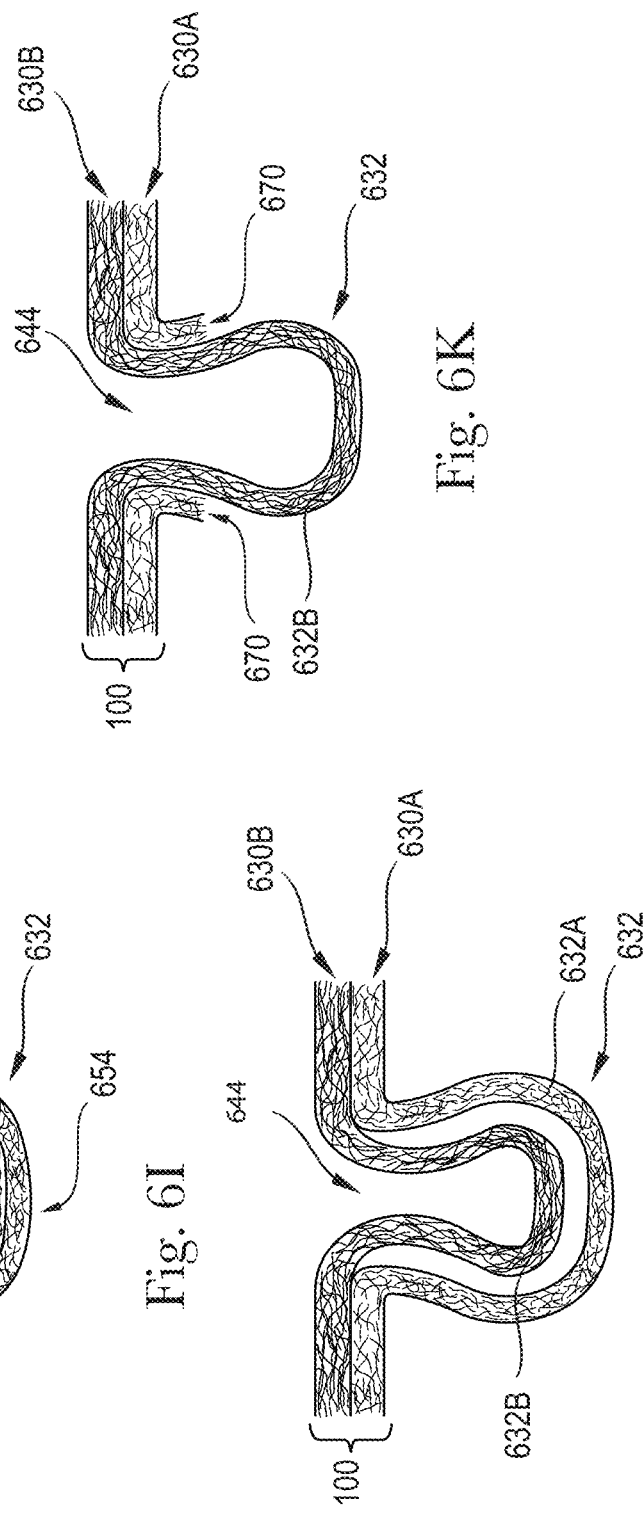
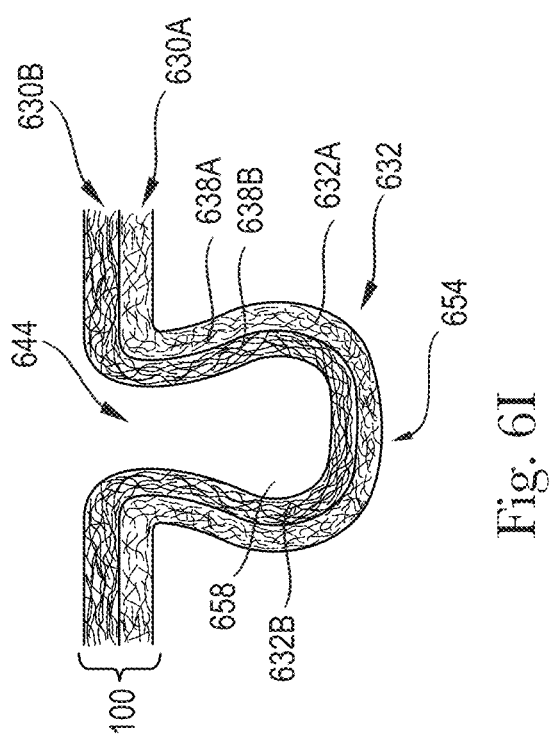

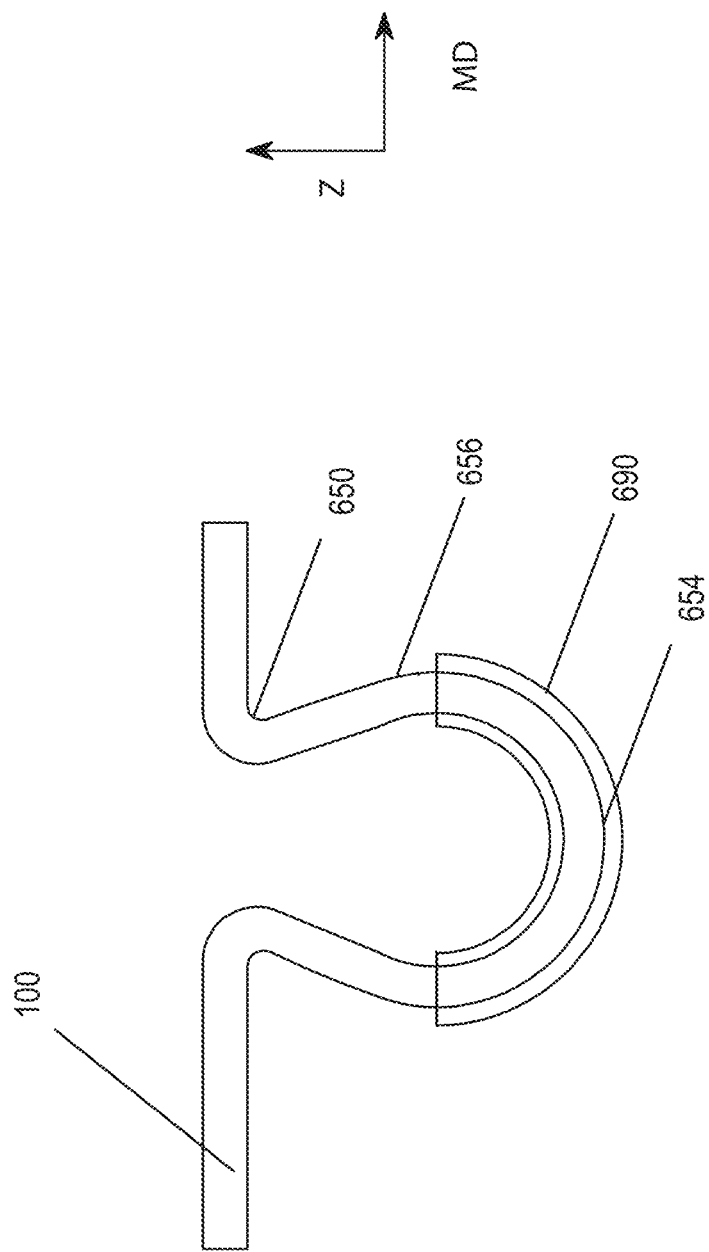

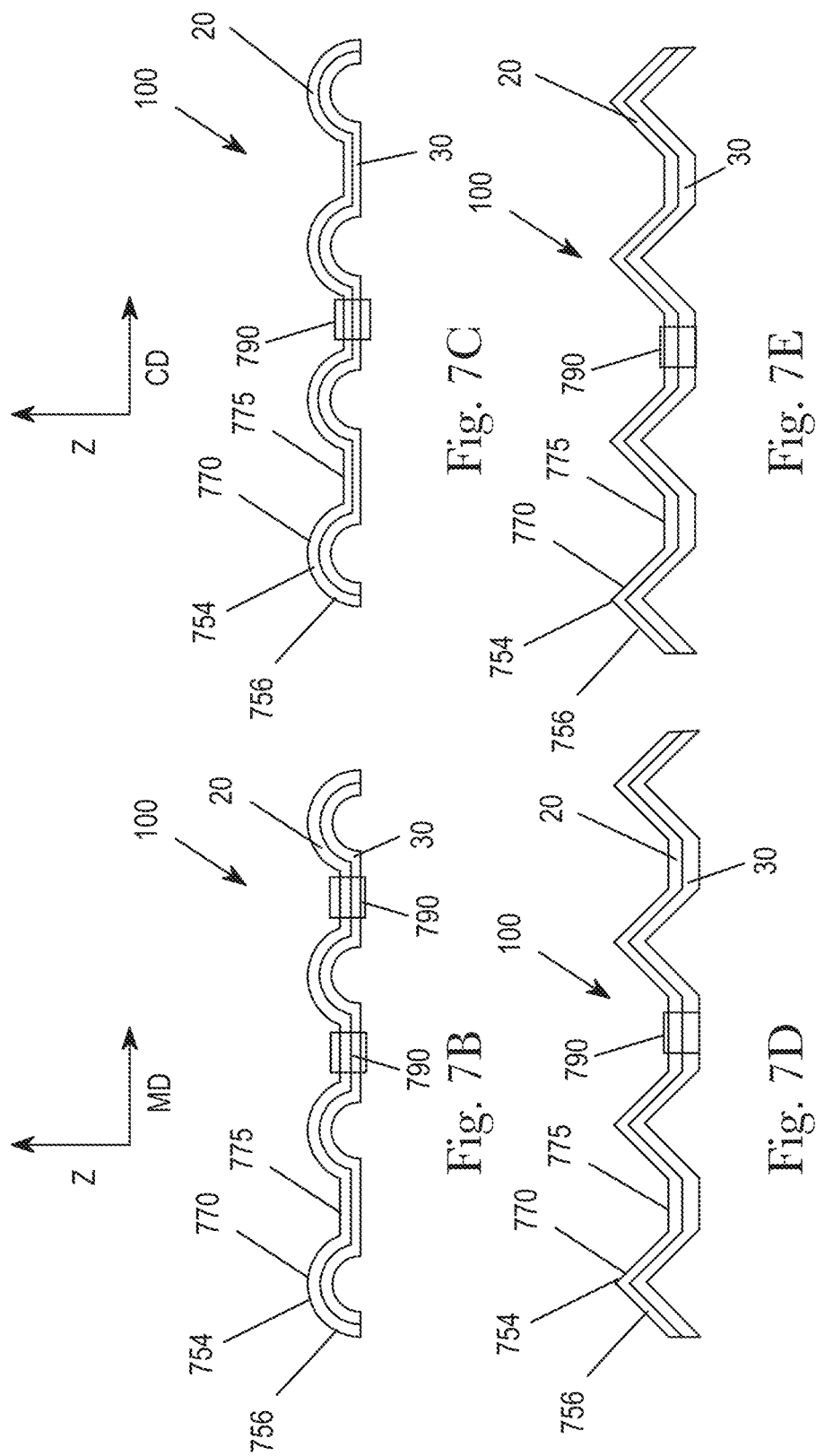

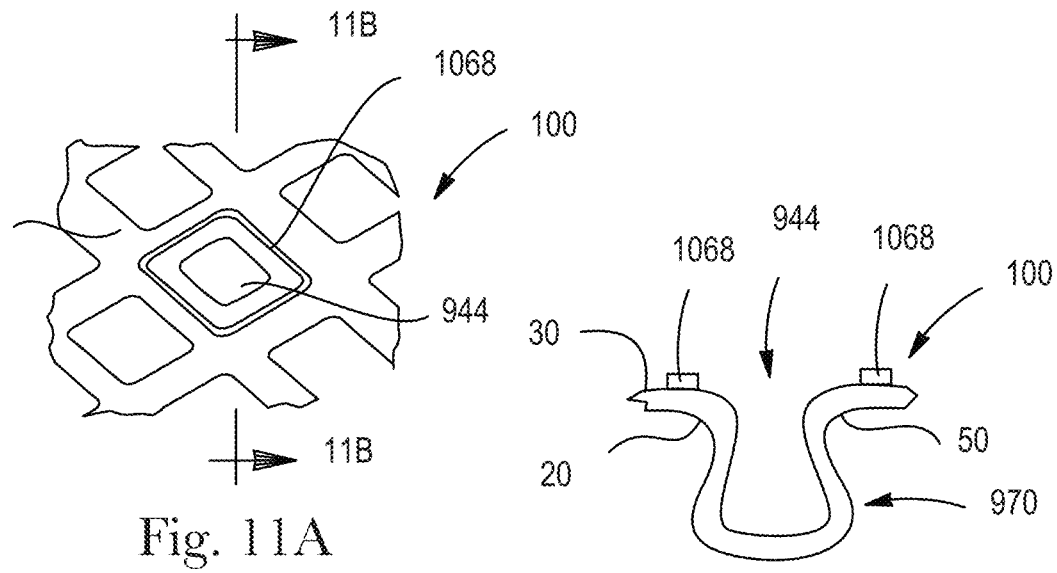
Fig. 11A
Fig. 11B
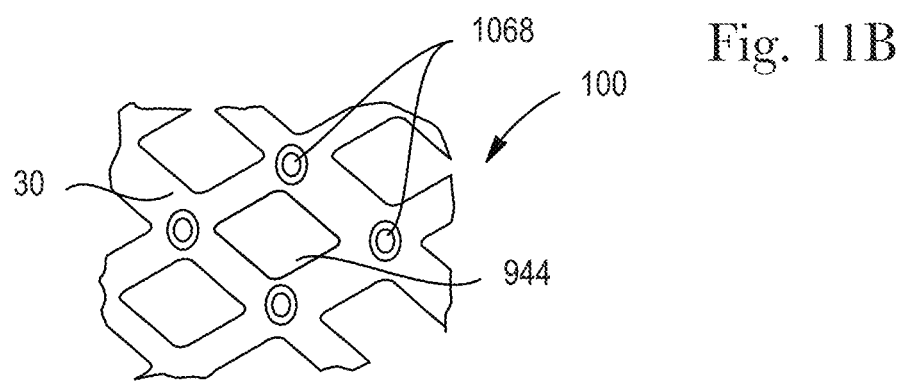
Fig. 12

ABSORBENT ARTICLE WITH ACTIVATABLE MATERIAL

FIELD OF THE INVENTION

The disclosure herein relates generally to thermoplastic polymeric materials with varying property zones created via the application of thermal energy and articles incorporating such materials.

BACKGROUND OF THE INVENTION

Nonwovens and films have been used in a myriad of absorbent articles over the past several years. In some particular absorbent articles, e.g. diapers, feminine hygiene pads, nonwovens and/or films may be utilized as a topsheet, backsheet, or some other feature of these particular absorbent articles.

The requirements for these absorbent articles may be disparate depending use. For example, a nonwoven and/or film used as a topsheet for diapers may not be suitable for adult incontinence products. Similarly, a nonwoven and/or film suitable as a topsheet for adult incontinence products may not be suitable for feminine hygiene pads.

Additionally, requirements for nonwoven and/or films in absorbent articles may vary by geography. For example, in one geography an absorbent article with a soft topsheet may be a factor which is foremost in consumer's minds. In another geography, absorbent articles which minimize the amount of rewet may be foremost in consumer's minds. In yet another geography, the speed of acquisition of liquid insults may be foremost in consumer's minds. In yet another geography, the amount of masking provided by a topsheet may be foremost in consumer's minds.

It would be beneficial for a nonwoven and/or film web to address one or more of the above concerns and allow for the flexibility of addressing multiple of the above concerns. It would also be beneficial to have a process which facilitated the production of nonwoven and/or film webs capable of addressing one or more of the above concerns and to provide a process providing the flexibility to address multiple of the above concerns.

SUMMARY OF THE INVENTION

Disclosed herein are material webs which can be used in absorbent articles including disposable absorbent articles. Some exemplary uses include a topsheet or a backsheet of a diaper or feminine pad or as an overwrap for a tampon. Some additional uses are discussed herein. The material webs of the present invention, when utilized as a topsheet of a feminine hygiene article, can provide a soft feel to the user and can provide quick acquisition of menses/urine insults. Other benefits and configurations are discussed hereinafter. The material webs of the present invention may be heated treated to create discrete melt additive bloom areas. In other forms, the material webs of the present invention may be heated treated across the entirety of the web to encourage melt additive blooming across the entirety of the web. Still in other forms, the addition of nucleating agents can facilitate blooming of melt additive either across the entirety of a web or increase blooming in melt additive bloom areas. Additional benefits are described herein.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1 is a schematic representation of a cross section of a material web of the present invention.

FIG. 2 is a schematic representation of a generalized process for making the material webs of the present invention.

FIG. 3C is a perspective view of an incremental stretching system of the process of FIG. 3A in accordance with the present disclosure.

FIG. 3F is a schematic illustration of an exemplary material web in accordance with the present disclosure.

FIG. 3G is a cross-sectional view of the material web of FIG. 3F along line 3G-3G.

FIG. 4A is a schematic representation of an exemplary process for producing material webs of the present disclosure.

FIGS. 5B-5J are schematic representations of tufts on material webs of the present invention.

FIG. 6I is a cross-sectional view taken along a transverse axis of a nested tuft in accordance with the present disclosure.

FIG. 6J is a cross-sectional view taken along a transverse axis of a nested tuft in accordance with the present disclosure.

FIG. 6K is a cross-sectional view taken along a transverse axis of a nested tuft in accordance with the present disclosure.

FIG. 6O is a cross-sectional view taken along a transverse axis of a nested tuft in accordance with the present disclosure.

FIGS. 7B-7E are cross-sectional views showing a variety of material webs comprising corrugations in accordance with the present disclosure.

FIG. 11A is a plan view of an exemplary base bonded material web by the apparatus shown in FIG. 10 (shown with the base opening oriented upward).

FIG. 11B is a schematic cross-sectional view of the base bonded material web in FIG. 11A taken along line 11B-11B.

FIG. 12 is a plan view of another exemplary based bonded material web by the apparatus shown in FIG. 10.

DETAILED DESCRIPTION OF THE INVENTION

Figure 3A:
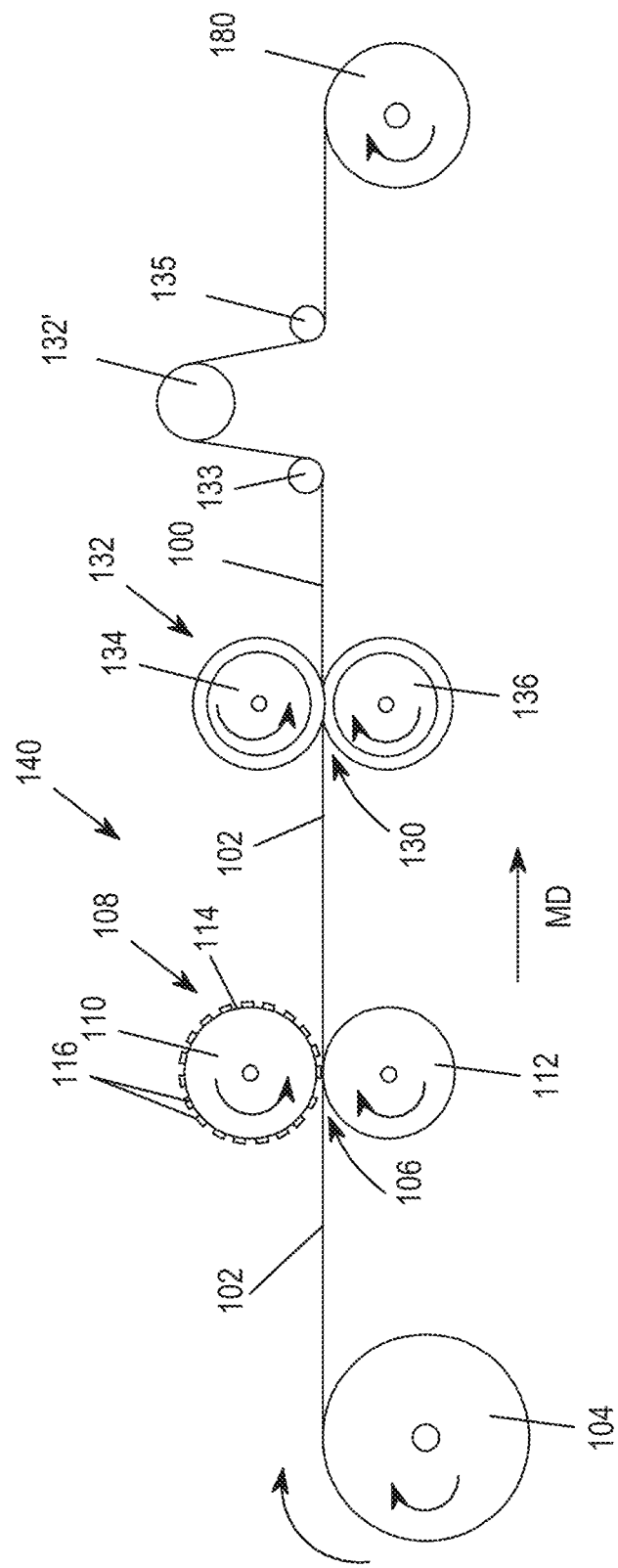
FIG. 3A is a schematic representation of an exemplary process for producing the material webs of the present disclosure.

As used herein "disposable absorbent article" or "absorbent article" shall be used in reference to articles such as diapers, training pants, diaper pants, refastenable pants, adult incontinence pads, adult incontinence pants, feminine hygiene pads, tampons, and pessary devices.

As used herein "hydrophilic" and "hydrophobic" have meanings well established in the art with respect to the contact angle of a referenced liquid on the surface of a material. Thus, a material having a liquid contact angle of greater than about 90 degrees is considered hydrophobic, and a material having a liquid contact angle of less than about 90 degrees is considered hydrophilic. Compositions which are hydrophobic, will increase the contact angle of a referenced liquid on the surface of a material while compositions which are hydrophilic will decrease the contact angle of a referenced liquid on the surface of a material. Notwithstanding the foregoing, reference to relative hydrophobicity or hydrophilicity between material(s) and/or composition(s) does not imply that the material or composition are hydrophobic or hydrophilic. For example, a composition may be more hydrophobic than a material. In such a case neither the composition nor the material may be hydrophobic; however, the contact angle of water droplets on the composition is greater than that of water droplets on the material. As another example, a composition may be more hydrophilic than a material. In such a case, neither the composition nor the material may be hydrophilic; however, the contact angle with respect to water droplets exhibited by the composition may be less than that exhibited by the material. In general, materials which demonstrate a high surface energy may be considered to be more hydrophilic than materials which have a low surface energy.

As used herein, "spunbond filaments" refers to small diameter filaments which are formed by extruding molten thermoplastic material as filaments from a plurality of fine capillaries of a spinneret with the diameter of the extruded filaments then being rapidly reduced. Spunbond filaments are generally not tacky when they are deposited on a collecting surface. Spunbond filaments are generally continuous and have average diameters (from a sample of at least 10) larger than 7 microns, and more particularly, between about 8 and 40 microns.

The term "filament" refers to any type of artificial continuous strand produced through a spinning process, a meltblowing process, a melt fibrillation or film fibrillation process, or an electrospinning production process, or any other suitable process to make filaments. The term "continuous" within the context of filaments are distinguishable from staple length fibers in that staple length fibers are cut to a specific target length. In contrast, "continuous filaments" are not cut to a predetermined length, instead, they can break at random lengths but are usually much longer than staple length fibers.

By "substantially randomly oriented" it is meant that, due to processing conditions of a nonwoven web, there may be a higher amount of filaments oriented in the machine direction (MD) than the cross direction (CD), or vice-versa.

The material webs of the present invention may comprise a film, a nonwoven, or a laminate created therefrom, e.g. a film/nonwoven laminate, a film/film laminate, a nonwoven/nonwoven laminate. Additionally, the material webs of the present invention may comprise any suitable nonwoven and/or any suitable film. Some exemplary nonwovens and films are discussed in additional detail in the section entitled, "Precursor Material." The material webs of the present invention are suitable for use in disposable absorbent articles.

Referring to FIG. 1, material webs 100 of the present invention comprises a first surface 20 and an opposing second surface 30. The material webs 100 of the present invention have a machine direction (MD) (perpendicular to the plane of the sheet showing FIG. 1), a cross machine direction (CD), and the Z-direction, as is commonly known in the art of web manufacture.

The material web 100 of the present invention comprises a constituent composition. The constituent composition comprises a thermoplastic polymeric material and a melt additive. For example, in the case of nonwoven materials, the fibers or filaments of the material web 100 may comprise a hydrophobic melt additive, a hydrophilic melt additive, or a softness melt additive. Suitable melt additives are discussed hereafter.

The melt additive may be homogeneously mixed with the thermoplastic polymeric material. In the case of bi-component or multi-component fibers or filaments, the melt additive may homogeneously mixed with a component of the bi-component or multi-component fiber or filament but not necessarily across the entirety of the fiber or filament. For example, a fiber or filament having a core-sheath configuration may comprise a melt additive homogeneously mixed with the thermoplastic polymeric material of the sheath, while the core does not comprise the melt additive of the sheath. Or, the core may comprise the melt additive of the sheath, but in a different amount than that of the sheath.

In some forms of the present invention, processing of the web as described herein can create discrete melt bloom areas, e.g. discrete areas with lower surface energy, discrete areas with higher surface energy, discrete soft areas, areas with higher or lower coefficient of friction, etc. The inventors have surprisingly found that the application of thermal energy to the material web 100, can facilitate the blooming of the melt additive to the surface of the material web. For example, the application of localized thermal energy to the material web 100 can promote the creation of discrete melt additive bloom areas on the material web 100, e.g. on the first surface 20 and/or second surface 30. As such, a material web 100, despite having a homogenous mixture of polymer material and melt additive, can have discrete areas of higher or lower surface energy, higher or lower coefficient of friction, or softness.

"Discrete" as used herein does not mean that the "discrete" melt additive bloom areas must be completely isolated from one another. Rather, where thermal energy is applied in localized areas, melt additive blooming will be promoted. As such, the melt additive bloom areas corresponding to the localized thermal energy areas should have more melt additive that blooms to the surface of the material in those localized areas than those without localized application of thermal energy. In some cases—where the melt additive forms fibrils or some other topographical structure at the surface of the filament—the enhanced blooming may be seen via SEM in that there may be a stark difference between fibril growth on the material web in one portion versus another. The stark difference in fibril growth can be a sign of localized heat treatment. Or, one of the other methods described herein may determine whether melt additive bloom areas are localized as opposed to being provided across the entirety of the material web.

In general, discrete melt bloom areas versus adjacent non-thermally treated areas exhibit a migration coefficient which is two times that of a non-thermally treated area of a material web. Depending on the thermal conductance of the thermoplastic polymeric material, the localized application of thermal energy may create heat affected zones which also encourages blooming. So when measuring, care should be taken to ensure that a centralized location of expected thermal energy application should be analyzed.

Still referring to FIG. 1, the resulting material webs 100 of the present invention may then comprise varying property zones in a variety of predetermined patterns along the MD and/or CD. For example, selected portions of a hydrophobic web can be rendered hydrophilic. As another example, selected portions of a hydrophilic web can be rendered hydrophobic. Still as another example, selected portions of a material web can be made softer via softness melt additive selective blooming. Additional examples are provided herein.

As another example, thermal energy can be applied to the entirety of the material web 100 to facilitate the melt additive blooming across the first surface and/or second surface of the material web 100. This can provide the ability to raise or lower the surface energy of the material web 100 where normal processing, e.g. coating, would not be feasible. For example, where the material web 100 comprises multiple strata (discussed hereafter), post treatment of the material web 100 may impact the entirety of the material web 100 rather than a desired stratum which may not be desirable.

So, the amount of melt additive which blooms in the material web can increase with the application of heat. Accordingly, the material webs may be rendered more hydrophobic, more hydrophilic, or softer than what would otherwise be the case sans the heat treatment of the material web. This allows for much versatility of the use of the material web. For example, a material web with a hydrophobic melt additive may be processed into a liquid-impermeable barrier material. However, such material may also be subsequently processed into, a liquid-permeable material (with the provision of apertures or appropriate basis weight selection), a soft feeling material, etc., depending, in part, on the thermal treatment applied.

Notwithstanding the potential drawbacks of topically applied chemistries, the material webs of the present invention may be combined/laminated with other webs which comprise topically applied chemistries. As noted, the topically applied chemistry of the other webs should occur prior to the combination with the material web to minimize the possibility of the topically applied chemistry from impacting the material web.

Material Web—Processing, in General

There are many methods by which the material web 100 of the present invention may be provided with discrete melt additive bloom areas. Similarly, there are a myriad of methods by which the material web 100 of the present invention may be provided with melt additive blooming across its entirety. Some specific examples—regarding discrete melt additive bloom area creation—are provided with regard to FIGS. 3A-16, 21, 22A-22D, and 30A-30C. But, a general process description for the formation of both discrete melt additive bloom areas and melt additive blooming across the entirety of the material web 100 of the present invention is provided with regard to FIG. 2.

As shown in FIG. 2, a precursor material 102 may be provided to a first unit operation 140. In some forms, the first unit operation 140 can manipulate the precursor material 102 to form the material web 100. In some forms, the first unit operation 140 can provide discontinuities in the precursor material 102 thereby forming the material web 100. Discontinuities are disruptions to the planar surface—either the first surface 20 and/or the second surface 30 (shown in FIG. 1). Some exemplary discontinuities include apertures, embossments, tunnel tufts, filled tufts, nested tufts, ridges, grooves and corrugations. The discontinuities are discussed in additional detail hereafter. And, as noted previously, the material webs 100 of the present invention comprise a melt additive. Accordingly, the precursor materials 102 of the present invention comprise the melt additive of the material web 100.

In some forms, the discontinuities may extend away from the first surface 20 or the second surface 30 in a positive Z-direction or negative Z-direction. In such forms, the discontinuities may comprise a distal end which is superjacent to the first surface or subjacent to the second surface, sidewalls extending from the distal end toward the first surface or second surface, and, in some specific forms, a base disposed between the sidewalls and the first surface or second surface. Discontinuities are discussed in additional detail hereafter.

The first unit operation 140, in some forms of the present invention, may provide sufficient thermal energy in a plurality of discrete locations on the precursor material 102 to provide the material web 100 with a plurality of discrete melt additive bloom areas sans the formation of discontinuities. The discrete melt additive bloom areas correspond with the discrete locations of applied thermal energy. In some forms, at least a portion of the plurality of melt additive bloom areas may be joined together to form a pattern. Examples of melt additive bloom areas and their formation are discussed hereafter. In some forms, as noted above, the first unit operation 140 may provide sufficient thermal energy to the entirety of the material web 100 to increase the melt additive bloom areas for the entire material web 100.

The precursor material 102, which as shown in FIG. 2 subsequently becomes the material web 100, may be one or more nonwoven materials (same or different), one or more films (same or different), a combination of one or more nonwoven materials and one or more films, or any other suitable materials or combinations thereof. The precursor material 102 may be purchased from a supplier and shipped to where the material webs 100 are being formed, or the precursor material 102 may be subjected to the first unit operation 140 by the manufacturer of the precursor web.

The precursor material 102 may be extensible, elastic, or non-elastic. Further, the precursor material 102 may be a single layer material or a multilayer material. For example, the precursor material 102 may be joined to a polymeric film to form a laminate. As another example, the precursor film 102 may comprise two or more layers of film, two or more layers of nonwoven material, or combinations thereof.

Additionally, forms of the present invention are contemplated where the precursor material 102 comprises a nonwoven web composite comprising multiple strata. A nonwoven stratum may comprise spunbond, staple, or fine fibers, e.g. meltblown or nanofibers. For example, in some forms, a first spinbeam may deposit a first plurality of spunbond filaments onto a belt thereby forming a first nonwoven stratum. A second spinbeam may deposit a second plurality of spunbond filaments onto the belt over the top of the first plurality of spunbond filaments. The second plurality of spunbond filaments form a second nonwoven stratum. Additional forms of the present invention are contemplated where additional spinbeams are provided to provide additional spunbond filaments/nonwoven strata. As another example, a first nonwoven stratum may comprise a plurality of staple fibers upon which a plurality of spunbond filaments are deposited. Additionally, the precursor webs 102/material webs 100 of the present invention may comprise a third stratum a fourth stratum and so on. And, the strata of the precursor web 102/material web 100 may be configured such that at least two of the strata are different. As such, precursor web 102/material web 100 may be one layer comprising multiple strata as described herein and/or may comprise multiple layers in addition to multiple strata.

The precursor material 102 may be provided as discrete webs, e.g. sheets, patches, etc. of material for batch processing. For commercial processing, however, the precursor material 102 may be supplied as roll stock, and, as such it can be considered as having a finite width and an infinite length. In this context, the length is measured in the machine direction (MD). Likewise, the width is measured in the cross machine direction (CD).

Zoned Application of Thermal Energy

As noted previously, in some forms, thermal energy may be applied to the web during the formation of discontinuities within the precursor material 102. In such forms, localized areas of the precursor material 102 may be heated which promotes discrete melt bloom areas which correspond to the localized heat application. Exemplary processes are discussed below.

Apertures

Referring to FIG. 3A, in one specific example, the first unit operation 140 may comprise a process for forming apertures in the precursor web 102. In some forms of the present invention, the first unit operation 140 may comprise a weakening roller arrangement 108 and an incremental stretching system 132. As shown, the precursor material 102 may be unwound from a supply roll 104 and travel in a direction indicated by the arrow associated therewith as the supply roll 104 rotates in the direction indicated by the arrow associated therewith. The precursor material 102 can pass through a nip 106 of the weakening roller (or overbonding) arrangement 108 formed by rollers 110 and 112, thereby weakening the precursor material 102 at a plurality of discrete locations. The weakened precursor material 102 has a pattern of overbonds, or densified and weakened areas, after passing through the nip 106. At least some of, or all of, these overbonds are used to form apertures in the material web 100. Therefore, the overbonds can correlate generally to the patterns of apertures created in the material web 100.

Figure 3B:
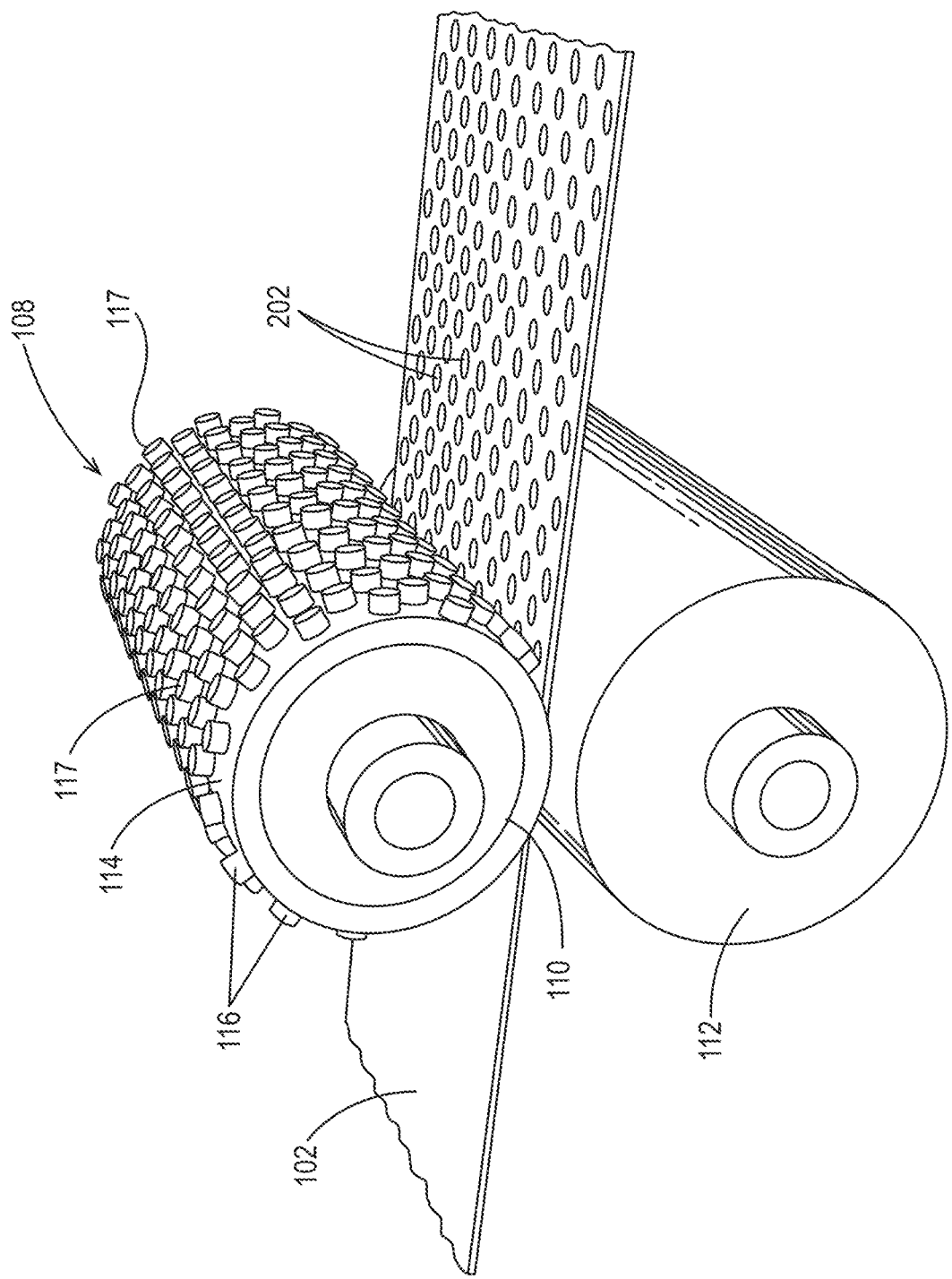
FIG. 3B is a perspective view of a web weakening arrangement of FIG. 3A in accordance with the present disclosure.

Referring to FIGS. 3A and 3B, the weakening roller arrangement 108 may comprises a patterned calendar roller 110 and a smooth anvil roller 112. One or both of the patterned calendar roller 110 and the smooth anvil roller 112 may be heated and the pressure between the two rollers may be adjusted to provide the desired temperature, if any, and pressure to concurrently weaken and melt-stabilize (i.e., overbond) the precursor material 102 at a plurality of locations 202. As will be discussed in further detail below, after the precursor material 102 passes through the weakening roller arrangement 108, the weakened precursor material 102 may be stretched in the CD, or generally in the CD, by a cross directional tensioning force to at least partially, or fully, rupture the plurality of weakened, melt stabilized locations 202.

The patterned calendar roller 110 is configured to have a cylindrical surface 114, and a plurality of protuberances or pattern elements 116 which extend outwardly from the cylindrical surface 114. The pattern elements 116 are illustrated as a simplified example of a patterned calendar roller 110, but more detailed patterned calendar rollers are contemplated and will be discussed hereafter. The protuberances 116 may be disposed in a predetermined pattern with each of the protuberances 116 being configured and disposed to precipitate a weakened, melt-stabilized location in the weakened precursor material 102 to affect a predetermined pattern of weakened, melt-stabilized locations 202. The protuberances 116 may have a one-to-one correspondence to the pattern of melt stabilized locations in the weakened precursor material 102. As shown in FIG. 3B, the patterned calendar roller 110 may have a repeating pattern of the protuberances 116 which extend about the entire circumference of surface 114. Alternatively, the protuberances 116 may extend around a portion, or portions of the circumference of the surface 114. Also, a single patterned calendar roller may have a plurality of patterns in various zones (i.e., first zone, first pattern, second zone, second pattern, etc.). The protuberances 116 may extend radially outwardly from surface 114 and have distal end surfaces 117. The anvil roller 112 may be a smooth surfaced, circular cylinder of steel, rubber or other material. The anvil roller 112 and the patterned calendar roller 110 may be switched in position (i.e., anvil on top) and achieve the same result.

Referring back to FIG. 3A, from the weakening roller arrangement 108, the weakened precursor material 102 passes through a nip 130 formed by the incremental stretching system 132 employing opposed pressure applicators having three-dimensional surfaces which at least to a degree may be complementary to one another.

Referring now to FIG. 3C, there is shown a fragmentary enlarged view of the incremental stretching system 132 comprising two incremental stretching rollers 134 and 136. The incremental stretching roller 134 may comprise a plurality of teeth 160 and corresponding grooves 161 which may about the entire circumference of roller 134. The incremental stretching roller 136 may comprise a plurality of teeth 162 and a plurality of corresponding grooves 163. The teeth 160 on the roller 134 may intermesh with or engage the grooves 163 on the roller 136 while the teeth 162 on the roller 136 may intermesh with or engage the grooves 161 on the roller 134. As the precursor material 102 having weakened, melt-stabilized locations 202 passes through the incremental stretching system 132 the precursor material 102 is subjected to tensioning in the CD causing the material 102 to be extended (or activated) in the CD, or generally in the CD. Additionally the precursor material 102 may be tensioned in the MD, or generally in the MD. The CD tensioning force placed on the material 102 is adjusted such that it causes the weakened, melt-stabilized locations 202 to at least partially, or fully, rupture thereby creating a plurality of partially formed, or formed apertures 204 coincident with the weakened melt-stabilized locations 202 in the precursor material 102. The melt-stabilized locations 202 form melt lips defining the periphery of the apertures 204. However, the bonds of the precursor material 102 (in the non-overbonded areas) are strong enough such that many do not rupture during tensioning, thereby maintaining the precursor material 102 in a coherent condition even as the weakened, melt-stabilized locations rupture. However, it may be desirable to have some of the bonds rupture during tensioning.

Figure 3D:
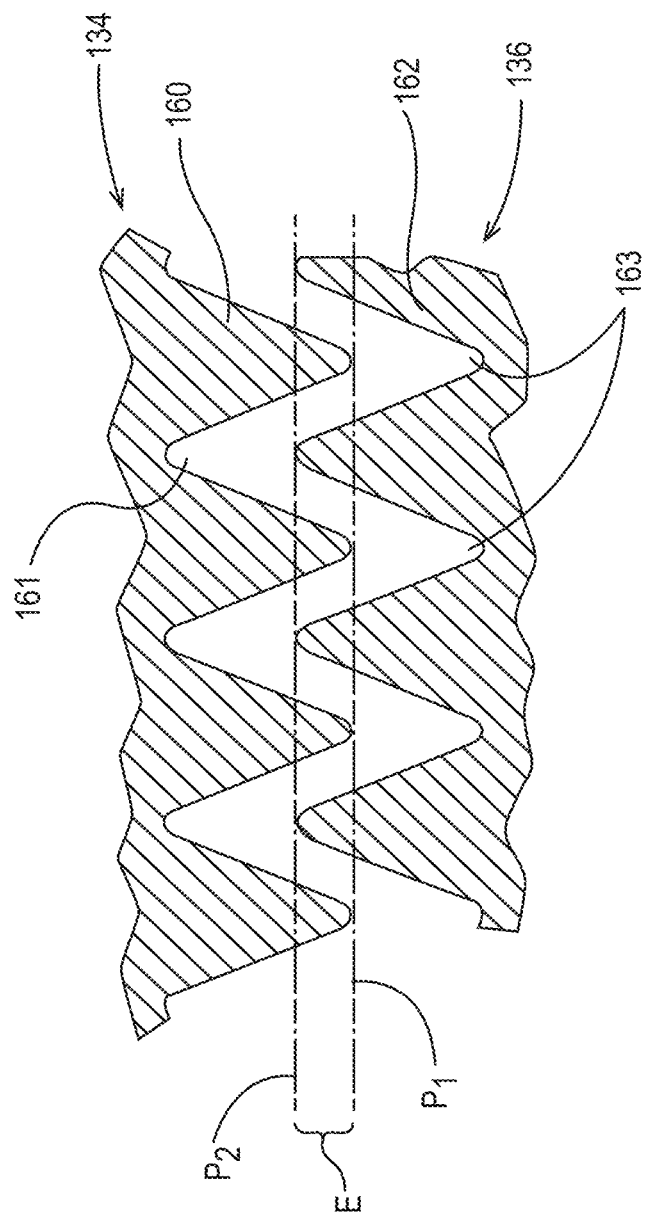
FIG. 3D is an enlarged view showing the details of teeth of the incremental stretching system of FIG. 3C in accordance with the present disclosure.

Referring to FIG. 3D, a more detailed view of the teeth 160 and 162 and the grooves 161 and 163 on the rollers 134 and 136 is illustrated. The term "pitch" refers to the distance between the apexes of adjacent teeth. The pitch may be between about 0.02 inches to about 0.30 inches (about 0.51 mm to about 7.62 mm) or preferably may be between about 0.05 inches and about 0.15 inches (about 1.27 mm to about 3.81 mm), specifically reciting all 0.001 inch increments within the above-specified ranges and all ranges formed therein or thereby. The height (or depth) of the teeth is measured from the base of the tooth to the apex of the tooth, and may or may not be equal for all teeth. The height of the teeth may be between about 0.010 inches (about 0.254 mm) and about 0.90 inches (about 22.9 mm) or preferably may be between about 0.025 inches (about 0.635 mm) and about 0.50 inches (about 12.7 mm), specifically reciting all 0.01 inch increments within the above-specified ranges and all ranges formed therein or thereby. The teeth 160 in one roll may be offset by about one-half of the pitch from the teeth 162 in the other roll, such that the teeth of one roll (e.g., teeth 160) mesh in the valley (e.g., groove 163) between teeth in the mating roll. The offset permits intermeshing of the two rolls when the rolls are "engaged" or in an intermeshing, operative position relative to one another. The teeth of the respective rolls may only be partially intermeshing in some instances. The degree to which the teeth on the opposing rolls intermesh is referred to herein as the "depth of engagement" or "DOE" of the teeth. The DOE may be constant or not constant. As shown in FIG. 3D, the DOE, indicated as "E", is the distance between a position designated by plane P1 where the apexes of the teeth on the respective rolls are in the same plane (0% engagement) to a position designated by plane P2 where the apexes of the teeth of one roll extend inward beyond the plane P1 toward the groove on the opposing roll. The optimum or effective DOE for particular material webs may be dependent upon the height and the pitch of the teeth and/or the structure of the material. Some example DOEs may in the range of about 0.01 inches to about 0.5 inches, about 0.03 inches to about 0.2 inches, about 0.04 inches to about 0.08 inches, about 0.05 inches, or about 0.06 inches, specifically reciting all 0.001 inch increments within the above-specified ranges and all ranges formed therein or thereby.

Referring back to FIG. 3A, after the weakened precursor material 102 passes through the incremental web stretching apparatus 132, the web 102 may be advanced to and at least partially around a cross machine directional tensioning apparatus 132' (described further in U.S. patent application Ser. No. 14/933,001). The cross machine directional tensioning apparatus 132' may be offset from the main processing line by running the web partially around two idlers 133 and 135 or stationary bars, for example. In other instances, the cross machine tensioning apparatus 132' may be positioned in line with the main processing line.

If desired, the incremental stretching step or the cross machine directional stretching step described herein may be performed at elevated temperatures. For example, the weakened precursor material 102 and/or the rolls may be heated. Utilizing heat in the stretching step may serve to soften the material, and may aid in extending the fibers without breaking.

Still referring to FIG. 3A, the material web 100 may be taken up on wind-up roll 180 and stored. Alternatively, the material web 100 may be fed directly to a production line where it is used to form a portion of an absorbent article, or other consumer product. This particular aperturing process is further described in U.S. Pat. Nos. 5,658,639; 5,628,097; 5,916,661; 7,917,985; and U.S. Patent Application Publication No. 2003/0021951 and U.S. patent application Ser. Nos. 14/933,028; 14/933,017; and 14/933,001.

It is important to note that the overbonding step illustrated in FIGS. 3A and 3B could be performed by the material supplier and then the material may be shipped to a consumer product manufacturer for the incremental stretching 132. In such forms, the rolls 134 and 136 of the incremental web stretching apparatus may be heated to create discrete areas on the web. Additionally, the overbonding step may be used in the material web production process to form overbonds, which may be in addition to, or in lieu of, primary bonds formed in the material web production process. Alternatively, the material supplier may fully perform the steps illustrated in FIG. 3A and then the material web 100 may be shipped to the manufacturer. The manufacturer may also perform all of the steps in FIG. 3A after obtaining a precursor material 102 from a manufacturer.

Figure 3E:
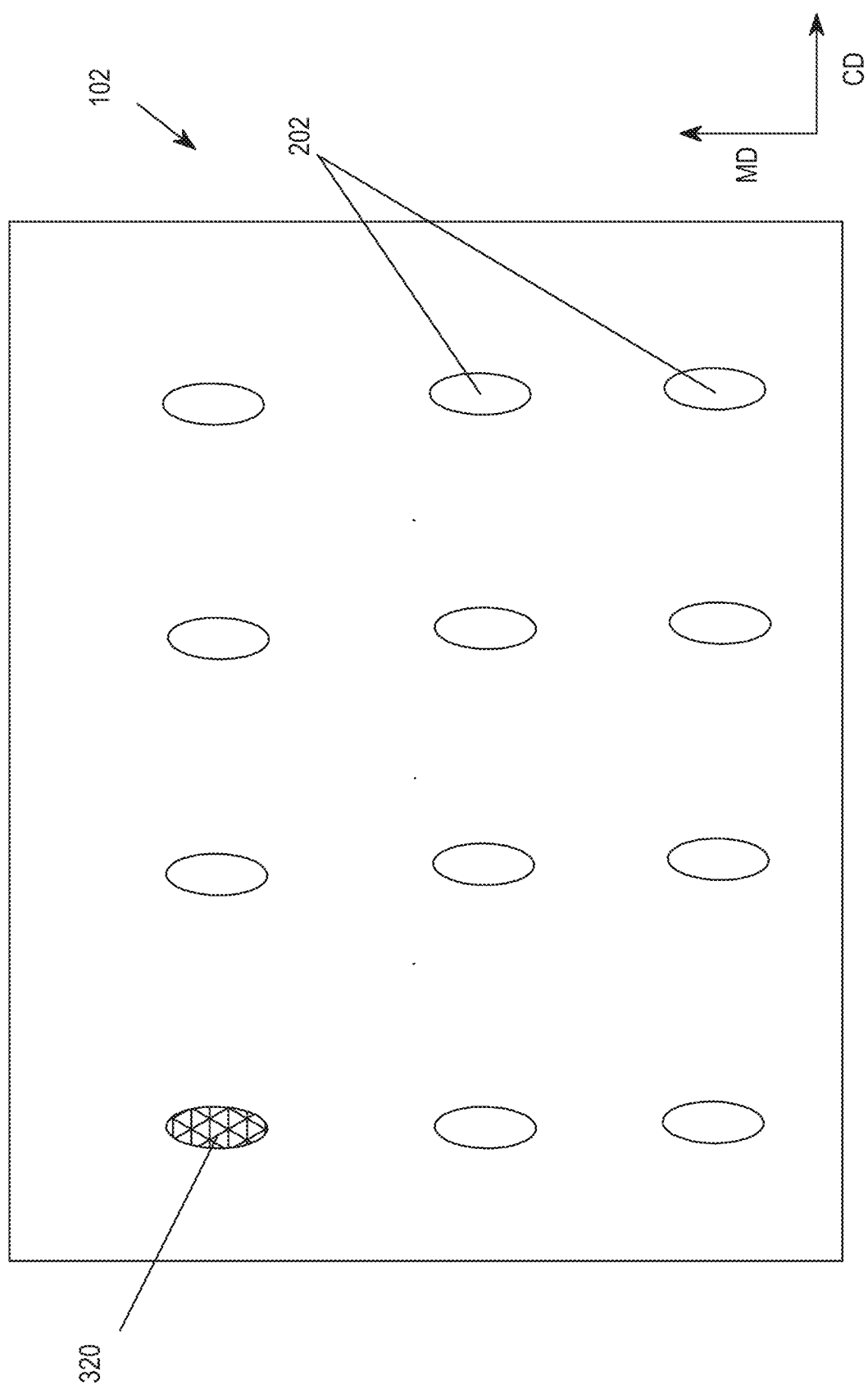
FIG. 3E is a schematic illustration of a weakened precursor material in accordance with the present disclosure.

Referring to FIGS. 3A, 3B and 3E, as noted previously, the precursor web 102 of the present invention comprises the melt additive in the material web 100. And, with the application of heat with the weakening roller arrangement 108, particularly with heat being applied by the pattern elements 116 of the patterned calendar roller 110, heat is applied to the precursor material 102 in a plurality of discrete locations on the precursor web 102, i.e. the melt-stabilized areas 202. It is believed that with the application of heat by the pattern elements 116 to the melt-stabilized areas 202, that the melt additive may bloom to the surface of the precursor material 102 in the melt-stabilized areas 202 and about a periphery (or portions thereof) of the melt-stabilized areas 202. An example is shown in FIG. 3E where the melt additive bloom area 320 is depicted in only one melt-stabilized area 202. The melt additive bloom areas 320 may occur in all, substantially all, or a portion of the melt-stabilized areas 202 assuming that the heat applied by the patterned calendar roller 110 limited to a specific pattern of the pattern elements 116. For those areas of the precursor material 102 that were not exposed to heat via the weakening roller arrangement, the melt additive may stay locked in the polymer matrix of the material web for a long period of time. This will be discussed in additional detail hereafter.

In some forms, the calendar roller 110 may be heated such that the pattern elements 116 apply thermal energy to the precursor material 102. In such forms, the surface 114 of the calendar roller 110 may comprise an insulating material such that any thermal energy provided by the surface 114 to the precursor web is reduced/minimized. Forms of the present invention are contemplated where a portion of the pattern elements 116 are insulated. In such forms, a plurality of melt additive bloom areas 320 may be provided to the weakened precursor web 102 in a pattern. Any suitable insulating material may be utilized. Some examples include ceramics and/or rubber based compositions. Thermal insulators are generally known in the art.

For those forms of the present invention where the melt additive is hydrophilic, the heat applied by the pattern elements 116 during the formation of the melt-stabilized areas 202 can cause the hydrophilic melt additive to bloom on the melt-stabilized areas 202 and portions of the weakened precursor web 102 in close proximity to the melt-stabilized areas 202. However, for the remainder of the weakened precursor material 102, the hydrophilic melt additive may be locked in the polymer matrix of the precursor material 102.

Referring back to FIG. 3B, additional forms of the present invention are contemplated where a portion of the distal end 117 of the pattern elements 116 are insulated such that only a portion of each of the melt-stabilized area 202 is heated. So for example, where a distal end 117 comprises an area of 5 mm$^2$, only 50 percent of the distal end 117 may provide sufficient thermal energy to the precursor web 102 to provide a melt additive bloom area 320. In such forms, at least a portion of the distal ends 117 may be insulated such that thermal energy supplied to the precursor web 102 via the insulated portions is reduced. Additionally, in such forms, the resultant melt-stabilized area 202 may comprise a melt additive bloom area 320 which comprised about 50 percent of the melt-stabilized area 202. In some forms, less than about 80 percent, less than about 70 percent, less than about 60 percent, less than about 50 percent, less than about 40 percent, less than about 30 percent, less than about 20 percent, less than about 10 percent of the melt-stabilized areas 202 area may comprise a melt additive bloom area, specifically including all values within these ranges and any ranges created thereby. Referring to FIG. 3F, subsequent to the incremental stretching step, the material web 100 comprising a plurality of apertures 204 is shown. With the above example in mind (hydrophilic melt additive) the apertures 204 can be hydrophilic even where the material web 100 comprises hydrophobic material, e.g. polypropylene, polyethylene. Such constructions can be beneficial, particularly in the absorbent article context when the material web 100 is utilized as a topsheet. For example, the hydrophilic apertures 204 can provide adequate acquisition time for liquid insults while reducing the likelihood of liquid resurfacing and contacting a user, e.g. rewet, and minimizing retention of liquid within the fiber matrix.

Regarding FIG. 3G, the melt additive bloom areas 320 may comprise a first portion 320A disposed on the first surface 20. Additionally, each of the melt additive bloom areas 320 may comprise a second portion 320B which is disposed on melt lips of the apertures 204. The size of the first portion 320A may be varied depending upon the heat transfer characteristics of the composition of the material web 100 and the amount of thermal energy transferred to the precursor material 102 (shown in FIG. 3A) by the patterned calendar roll 110 (shown in FIG. 3A). In some forms, the first portion 320A may extend outboard in the MD and/or CD of the sidewalls. In some forms, the first portion 320A may have an area which is less than an Effective Aperture AREA of the apertures 204. In some forms, the first portion 320A may have an area which is about equal to the Effective Aperture AREA of the apertures 204. In some forms, the first portion 320A may have an area which is greater than the Effective Aperture AREA of the apertures 204. Forms are contemplated where the second portion 320B comprises a higher percentage of melt additive blooming than does the first portion 320A. Depending on the insulation provided to the weakening roller arrangement 108, forms of the present invention are contemplated where the first portion 320A comprises a higher percentage of melt additive blooming than does the second portion 320B.

Additionally, referring back to FIG. 3C, while forms of the present invention are contemplated where rolls of the incremental web stretching apparatus 132 are heated, such forms may provide the material web 100 with the different properties. In such forms, the melt additive bloom areas 320 may be provided as described above with regard to FIG. 3G; however, melt additive bloom areas 320 may additionally be provided as a plurality of stripes extending in the MD direction extending between adjacent apertures 204. Such a configuration for the material web 100—particularly when utilized as a topsheet in a disposable absorbent article—while possibly improving liquid acquisition time, may facilitate rewet conditions.

The apertures 204 may be any suitable size. For example, apertures 204 may have an Effective Aperture AREA in the range of about 0.1 mm$^2$ to about 15 mm$^2$, about 0.3 mm$^2$ to about 14 mm$^2$, about 0.4 mm$^2$ to about 12 mm$^2$, and about 1.0 mm$^2$ to about 5 mm$^2$, specifically including all 0.05 mm$^2$ increments within the specified ranges and all ranges formed therein or thereby. All Effective Aperture Areas are determined using the Aperture Test described herein. Effective Aperture Area is discussed in further detail in U.S. patent application Ser. Nos. 14/933,028; 14/933,017; and 14/933,001. For those forms of the present invention where the melt additive bloom areas 320 comprise a hydrophilic composition, acquisition speeds may be improved particularly where Effective Aperture Areas are small. Smaller apertures may be more aesthetically pleasing to users of absorbent articles; however, the smaller apertures can have a negative impact on fluid acquisition speed.

Additional processes for aperturing nonwoven webs are described in U.S. Pat. Nos. 8,679,391 and 8,158,043, and U.S. Patent Application Publication Nos. 2001/0024940 and 2012/0282436. Other methods for aperturing nonwoven webs are provided in U.S. Pat. Nos. 3,566,726; 4,634,440; and 4,780,352. Regardless of the process utilized to create the apertures 204, the addition of thermal energy can create the melt additive bloom areas as discussed herein in localized areas where thermal energy is applied to the precursor material 102 or the material web 100. In such forms, referring back to FIG. 3A, a perforating roll may engage an anvil roll. The perforating roll may have heated pins or rods which can create apertures without the need for a subsequent stretching step. The resultant melt bloom area 320 may be as described with regard to FIG. 3G.

Additional forms of the present invention are contemplated where the melt additive comprises a hydrophobic composition. In such forms, referring to FIG. 3B, the cylindrical surface 114 may be heated while the pattern elements 116 extending therefrom are not. In such forms, melt additive blooms would be created in areas of the material web 100 between the melt-stabilized areas 202 but not in the melt-stabilized areas. Such configuration may be beneficial where the material web 100 comprises a hydrophilic material. Additionally, such configurations can help prevent rewet conditions in an absorbent article where the material web 100 is utilized as a topsheet of the absorbent article.

Additional forms of the present invention are contemplated where the apertures are provided to the material web 100 in an array and/or pattern or a plurality thereof. Such configurations and processes are described in additional detail in U.S. patent application Ser. Nos. 14/933,028; 14/933,017; and 14/933,001.

Embossments

Referring to FIG. 4A, in another specific example, the first unit operation 140 (shown in FIG. 2) may comprise a process for forming embossments in the material web 100. Referring to FIG. 4A, the precursor material 102 may be subjected to an apparatus 400 for providing embossments 420 to the material web 100.

The apparatus 400 may comprise a forming roll 402 comprising a plurality of forming elements 416 and an anvil roll 404. The forming elements 416 of the forming roll 402 may protrude outward from a surface 414 of the forming roll 402. The anvil roll 404 may comprise a smooth outer surface.

In contrast to fusion bond sites, discussed hereafter, embossments 420 generally do not cause the fusion of the constituent material of the material web 100 to adjacent materials. Instead, embossments 420 tend to compress the material web 100. Embossments 420 can provide an acquisition zone in an absorbent article. For example, where the material web 100 forms a portion of a topsheet of an absorbent article, the embossment 420 may not readily receive a liquid insult. Instead, the embossment 420 may act as a fluid highway which can distribute the insult to multiple areas of an absorbent core in the absorbent article.

Figure 4B:
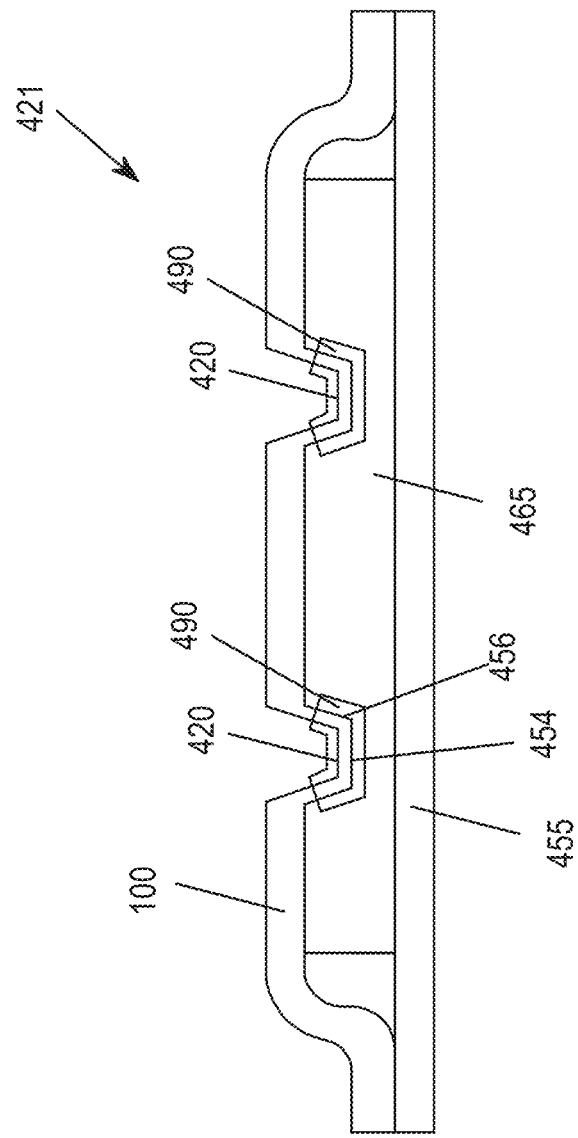
FIG. 4B is a cross-sectional view of a disposable absorbent article in accordance with the present disclosure.

An exemplary cross section of the material web 100 in an absorbent article 421 after embossing is shown in FIG. 4B. As shown, the absorbent article 421 comprises the material web 100 as a topsheet, a backsheet 455 and an absorbent core 465 disposed between the backsheet 455 and the topsheet (material web 100). In some forms, the material web 100 may comprise embossments 420. In some forms, the material web 100 along with the absorbent core 465 may comprise embossments 420. In some forms, the material web 100 along with additional layers between topsheet and the absorbent core 465, e.g. acquisition layers, distribution layers, secondary topsheets, may comprise embossments 420.

Forms are contemplated where 100 percent of each of the forming elements provides heat to the material web 100 and optionally additional materials. In some forms, only portions of the forming elements may provide thermal energy to the material web 100 and optionally other components.

With the application of thermal energy to the forming elements 416 (shown in FIG. 4A), each of the embossments 420 may comprise a melt additive bloom area 490. The melt additive bloom areas 490 are exaggerated for ease of visualization. As shown, with the application of thermal energy by the forming elements 416 (shown in FIG. 4A), the melt additive bloom areas 490 may be provided in a distal end 454 of the embossment 420. Additionally, the melt additive bloom areas 490 may be provided on sidewalls 456 of the embossments 420.

In some forms, the melt additive bloom area 490 may comprise a hydrophobic composition. The compression which creates the embossments 420 can inhibit fluid acquisition in the embossment 420. A hydrophobic composition in the distal end 454 of the embossment 420 can assist in transporting liquid insults to additional areas of the absorbent article. Additionally, the hydrophobic composition can provide a cleaner look to the absorbent article in the area of the embossment 420 since the hydrophobic composition would discourage liquid insults from residing in the embossment 420.

In contrast, forms of the present invention are contemplated where the melt additive bloom areas 490 comprise a hydrophilic composition. In such forms, the hydrophilic composition may facilitate fluid acquisition by the embossments 420. It is worth noting however, that in such forms, the level of compression in the embossments 420 can offset the hydrophilic composition. For example, where the embossments 420 are formed with high compression, the embossments 420 have an increased density which generally inhibits fluid acquisition. In contrast, embossments 420 derived from lighter compression can drive better interaction between layers of the absorbent article 421 which can improve liquid acquisition.

Embossments 420 may be used in conjunction with apertures 204 or may be utilized independently thereof. Any suitable embossment pattern may be utilized in conjunction with the material web 100 of the present invention. Some suitable examples of embossment patterns are provided with regard to U.S. Pat. Nos. 6,170,393; 6,652,500; 7,056,404; 8,030,535; 8,492,609; 8,496,775; and U.S. Patent Application Publication Nos. 2013/0281953; and 2014/0031779.

Tunnel Tufts/Filled Tufts

Figure 5A:
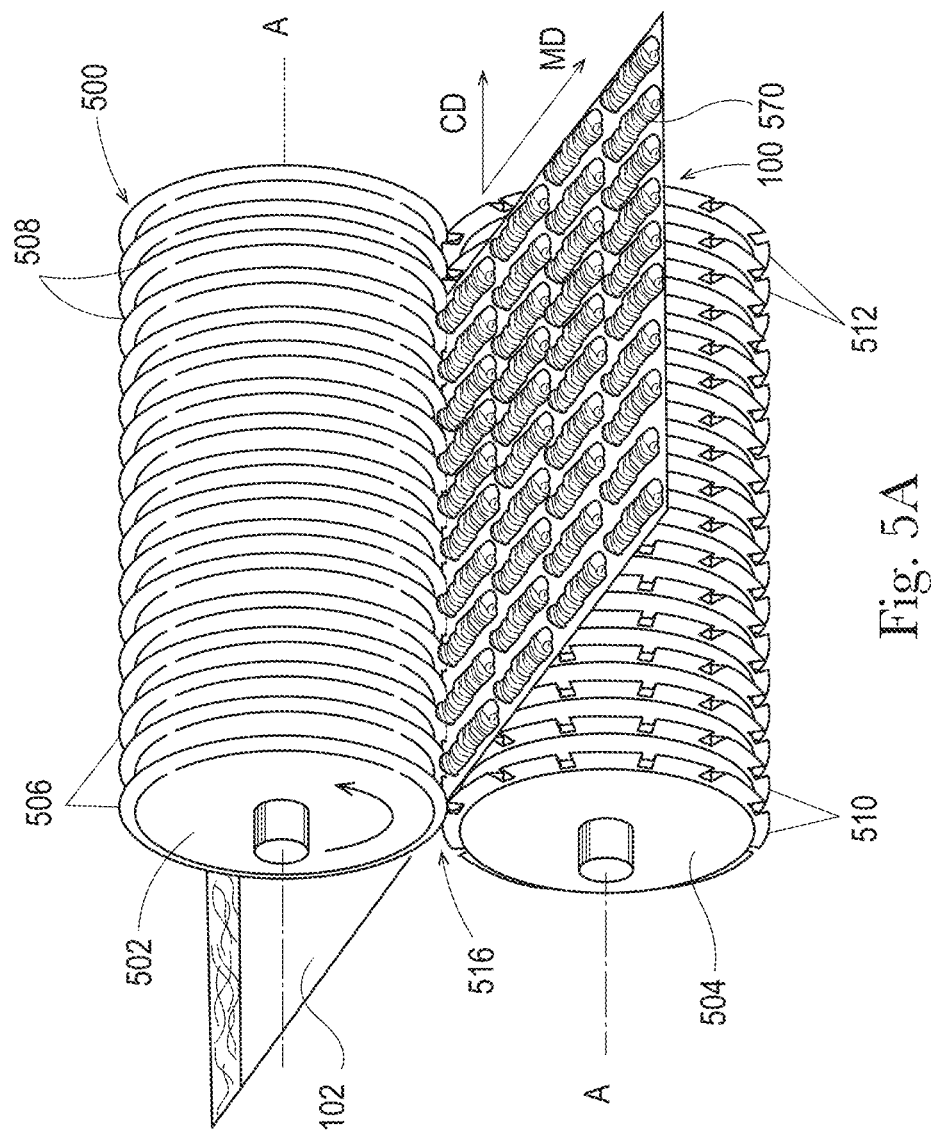
FIG. 5A is a schematic representation of an exemplary process for producing material webs of the present disclosure.

Referring to FIG. 5A, in another specific example, the first unit operation 140 (shown in FIG. 2) may comprise an apparatus 500 for forming tufts in the material web 100. The apparatus 500 comprises a pair of intermeshing rolls 502 and 504, each rotating about an axis A—the axes A being parallel and in the same plane. Roll 502 comprises a plurality of ridges 506 and corresponding grooves 508 which extend unbroken about the entire circumference of roll 502.

Roll 504 is similar to roll 502, but rather than having ridges that extend unbroken about the entire circumference, roll 504 comprises a plurality of rows of circumferentially-extending ridges that have been modified to be rows of circumferentially-spaced teeth 510 that extend in spaced relationship about at least a portion of roll 504. The individual rows of teeth 510 of roll 504 are separated by corresponding grooves 512. In operation, rolls 502 and 504 intermesh such that the ridges 506 of roll 502 extend into the grooves 512 of roll 504 and the teeth 510 of roll 504 extend into the grooves 508 of roll 502. A nip 516 is formed between the counter-rotating intermeshing rolls 502 and 504. Both or either of rolls 502 and 504 can be heated by means known in the art such as by using hot oil filled rollers or electrically-heated rollers.

The apparatus 500 is shown in a configuration having one patterned roll, e.g., roll 504, and one non-patterned grooved roll 502. However, in certain forms it may be preferable to use two patterned rolls similar to roll 504 having either the same or differing patterns, in the same or different corresponding regions of the respective rolls. Such an apparatus can produce material webs with tufts protruding from both sides of the material web 100.

Material webs 100 of the present invention can be made by mechanically deforming the precursor material 102 that can be described as generally planar and two dimensional prior to processing by the apparatus shown in FIG. 5A. By "planar" and "two dimensional" is meant simply that the webs start the process in a generally flat condition relative to the finished material web 100 that has distinct, out-of-plane, Z-direction three-dimensionality due to the formation of tufts 570. "Planar" and "two-dimensional" are not meant to imply any particular flatness, smoothness or dimensionality. The intermeshing rolls 502 and 504 can urge the material of the material web 100 in the positive Z-direction or negative Z-direction depending on whether roll 504 engages the second surface 30 (shown in FIG. 1) or the first surface 20 (shown in FIG. 1), respectively.

The process described with regard to FIG. 5A can provide for a variety of tufts, e.g. tunnel tufts, filled tufts, outer tufts. Each of these tufts is described in additional detail hereafter. Tunnel tufts 570 are described with regard to FIGS. 5B-5E. For the sake of clarity, the material web 100 depicted in FIGS. 5B-5E comprises multiple layers, e.g. first layer 25 and second layer 35, or multiple strata; however, forms of the present invention are contemplated where the material web 100 comprises only a single layer or a single strata.

Figure 5C:
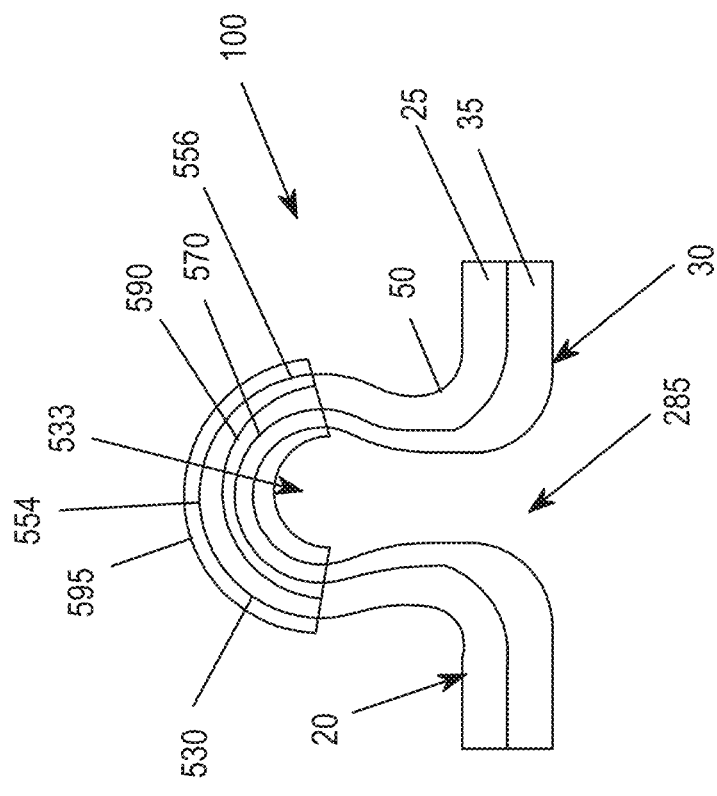
Figure 5B:
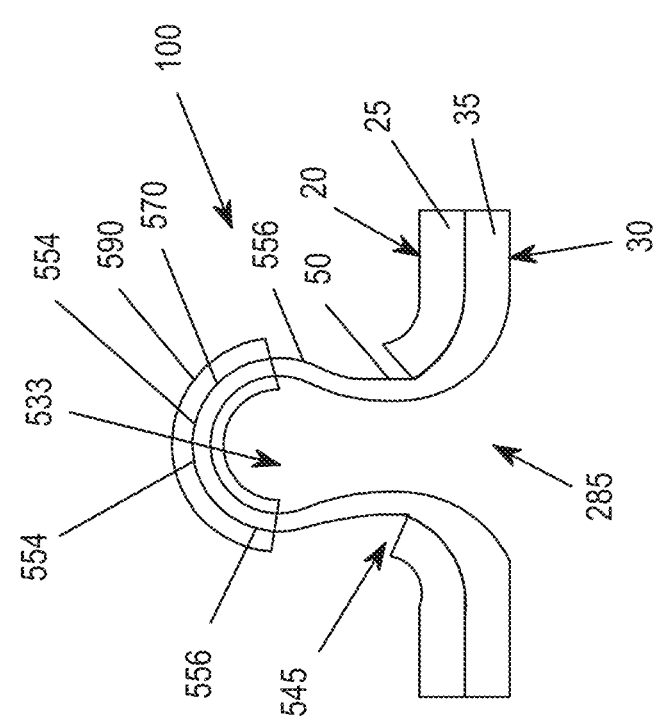

The tunnel tuft 570 may be created when localized areas of constituent material of the material web 100 are urged in the positive Z-direction such that material of the material web 100 in the localized area may be disposed superjacent to the first surface 20 of the material web 100. The disposition of the material web 100 in the localized areas may form the tunnel tuft 570. For such forms, an opening 285 may be produced on the second surface 30 of the material web 100 which corresponds to the tuft 570. And, as shown in FIG. 5B, in some forms, the urging of the material web 100 in the localized areas may cause at least a portion of the first layer 25 to break. In such forms, the tunnel tufts 570 may extend through ends 545 of the first layer 25. However, as shown in FIG. 5C, the urging of the material of the material web 100 in the localized areas can create an outer tuft 530. In some forms, the outer tuft 530 may form a cap over the tunnel tuft 570.

In some forms, material webs 100 of the present invention may comprise a plurality of tunnel tufts 570 for which there are no corresponding outer tufts 530 and/or similarly may comprise a plurality of tunnel tufts 570 each of which are disposed within a corresponding outer tuft 530.

Figure 5D:
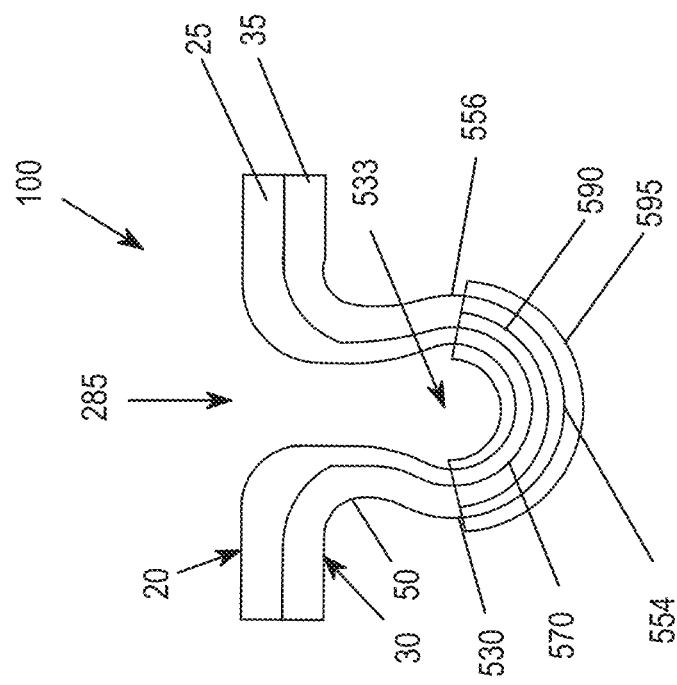
Figure 5E:
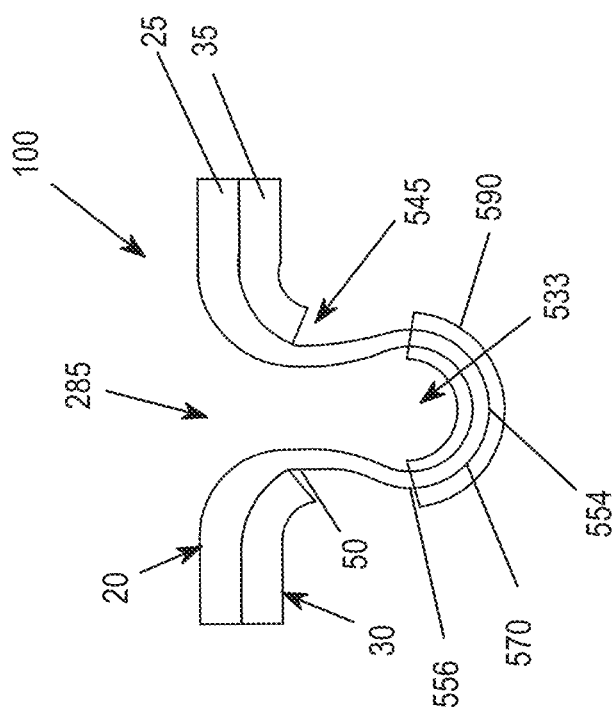

Additional arrangements of tunnel tufts 570 and outer tufts 530 are provided with respect to FIGS. 5D and 5E. As shown, the tunnel tuft 270 and/or outer tuft 530 may extend beyond the second surface 30 of the material web 100. However, instead being urged in the positive Z-direction, urging of the material of the material web 100 in the localized areas may be in the negative Z-direction. And, similar to FIG. 5B, some of the material of the second layer 35 may break as shown in FIG. 5D or may form the outer tuft 530 as shown in FIG. 5E.

FIGS. 5B-5F illustrate tunnel tufts 570 which may be formed with nonwoven webs comprising extensible fibers. The tunnel tufts 570 and outer tufts 530 disclosed herein comprise a plurality of looped filaments that are substantially aligned such that each of the tunnel tufts 570 and outer tufts 530 have a distinct linear orientation and a longitudinal axis L of the tuft, e.g. 570, 530. By "aligned", it is meant that looped fibers are all generally oriented such that, if viewed in plan view, each of the looped fibers has a significant vector component parallel to a transverse axis and can have a major vector component parallel to the transverse axis. The transverse axis T is generally orthogonal to longitudinal axis in the MD-CD plane and the longitudinal axis is generally parallel to the MD.

Another characteristic of the tunnel tufts 570 and outer tufts 530 shown in FIGS. 5B-5F—formed with extensible non-crimped fibers—can be their generally open structure characterized by open void area 533 defined interiorly of the tunnel tuft 570. The term "void area" is not meant to refer to an area completely free of any fibers. The void area 533 of tunnel tufts 570 may comprise a first void space opening and a second void space opening. Rather, the term is meant as a general description of the general appearance of tunnel tuft 570. Therefore, it may be that in some tunnel tufts 570 a non-looped filaments or a plurality of loose non-looped filaments may be present in the void area 533. By "open" void area is meant that the two longitudinal ends of tunnel tuft 570 are generally open and free of filaments, such that the tunnel tuft 570 can form something like a "tunnel" structure in an uncompressed state, as shown in FIGS. 5B-5F.

The extension and/or urging of the material of the material web 100, as shown in FIGS. 5A-5F, can be accompanied by a general reduction in filament cross sectional dimension (e.g., diameter for round filaments) due to plastic deformation of the filaments and Poisson's ratio effects.

Referring to FIGS. 5A-5E, as noted the intermeshing rolls 502 and 504 may be heated. For example, the circumferentially spaced teeth 510 of roll 504 may be heated while the ridges 506 of roll 502 are not. In such forms, the tunnel tufts 570 may further comprise melt additive bloom areas 590 and/or 595 associated with the second layer 35 and first layer 25, respectively. The melt additive blooms 590 and 595 are exaggerated for ease of explanation. The melt additive blooms are discussed further hereafter. As shown, each of the tunnel tufts 570 and outer tufts 530 comprise a base 50, a distal end 554 spaced from the base 50 and sidewalls 556 between the base 50 and the distal end 554.

Referring specifically to FIG. 5B, forms where the material web 100 comprises a first layer 25 and a second layer 35, the melt additive bloom 590 may comprise a hydrophobic composition. As shown, for those forms of the present invention where the material web 100 comprises multiple layers or strata, the melt additive bloom area 590 may be associated with the second layer 35 or second strata. Forms of the present invention are contemplated where the material web 100 comprise a first strata and a second strata, and wherein the melt additive bloom area 590 is present on the tunnel tuft 570 formed by the second strata. In such forms, the melt additive bloom area 590 may comprise a hydrophobic composition. As shown, with the application of thermal energy during the formation of the tunnel tuft 570, the melt additive bloom area 590 may be disposed on the distal end 554 of the tunnel tuft 570. In some forms, the melt additive bloom area 590 may be disposed on at least a portion of sidewalls 556 of the tunnel tuft 570. Where the material web 100 is utilized as a topsheet, such forms can allow for reduction in rewet while providing adequate liquid acquisition. Additionally, in such forms, the melt additive bloom area 590 may help with masking of liquid insults to a disposable absorbent article.

Referring to FIG. 5C, for those forms of the present invention comprising both outer tufts 530 and tunnel tufts 570, the heated circumferentially spaced teeth 510 of roll 504 may facilitate a melt additive bloom area 595 associated with the first layer 25 or first strata and the melt additive bloom area 590 associated with the second layer 35. In such forms, the melt additive bloom area 595 may comprise a hydrophobic composition and the melt additive bloom area 590 may comprise a hydrophilic composition. In some forms, the melt additive bloom area 590 and the melt additive bloom area 595 may each comprise hydrophobic compositions. As shown, the melt additive bloom area 595 may be disposed on the distal end 554 of the outer tuft 530 and a portion of sidewalls 556 of the outer tuft 530. Similarly, in such forms, where the material web 100 is utilized as a topsheet of an absorbent article, the above configuration can allow for sufficient liquid acquisition time while reducing rewet. Such configurations may additionally provide a benefit in masking liquid insults.

Referring specifically to FIG. 5D, for those forms of the present invention comprising tunnel tufts 570 in the negative Z-direction, the heated circumferentially spaced teeth 510 of roll 504 may facilitate the melt additive bloom area 590 associated with the first layer 25 or first strata. In such forms, the melt additive bloom area 590 may comprise a hydrophilic composition. As shown, the melt additive area 590 may be configured as described above with regard to FIG. 5B. Namely, the melt additive bloom area 590 may be disposed on the distal area 554 of the tunnel tuft 570 and on a portion of the sidewalls 556 of the tunnel tuft 570. In such forms, where the material web 100 is utilized as a topsheet of a disposable absorbent article, the melt additive bloom area 590 may comprise a hydrophilic composition which can improve the liquid acquisition time of the absorbent article.

Referring to FIG. 5E, for the forms of the present invention comprising both outer tufts 530 and tunnel tufts 570, the heated circumferentially spaced teeth 510 of roll 504 may facilitate a melt additive bloom area 595 associated with the second layer 25 or second strata and the melt additive bloom area 590 associated with the first layer 35 or first strata. In such forms, the melt additive bloom area 595 may comprise a hydrophilic composition, and the melt additive bloom area 590 may comprise a hydrophilic composition. As shown, the melt additive bloom area 595 may be disposed on the distal end 554 of the outer tuft 530 and a portion of sidewalls 556 of the outer tuft 530. In such forms, the melt additive bloom areas 590 and 595 can improve the liquid acquisition time of topsheets of a disposable absorbent article.

Tunnel tufts 570 and/or outer tufts 530 can provide a masking benefit for liquid insults in a disposable absorbent article. Additionally, tunnel tufts 570 and/or outer tufts 530 can provide a softness benefit as well. Tunnel tufts 570 and outer tufts 530 are discussed in additional detail, including methods of making, in U.S. Pat. Nos. 7,172,801; 7,838,099; 7,754,050; 7,682,686; 7,410,683; 7,507,459; 7,553,532; 7,718,243; 7,648,752; 7,732,657; 7,789,994; 8,728,049; and 8,153,226.

The tunnel tufts 570 and/or outer tufts 530 may be used in conjunction with the apertures, and/or embossments. Or, the tunnel tufts 570 and/or outer tufts 530 may be utilized independently thereof.

Figure 5G:
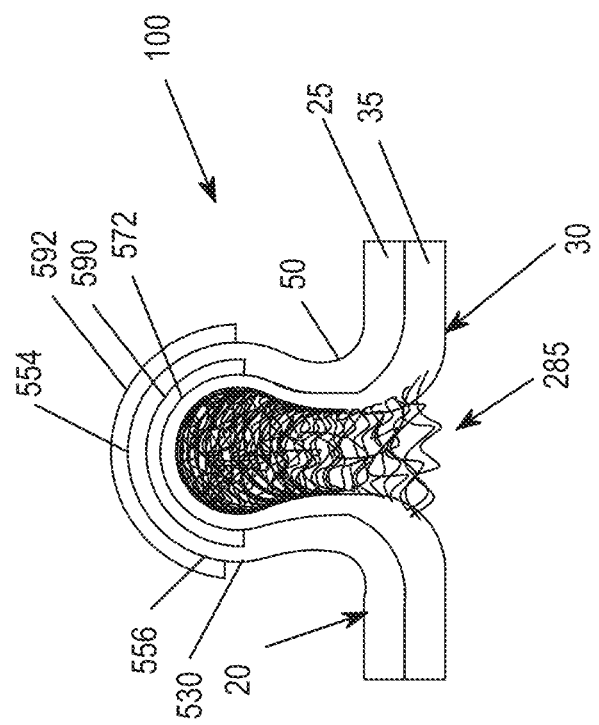

In contrast to the tunnel tufts 570 shown in FIGS. 5A-5F, material webs 100 of the present invention comprising crimped filament spunbond nonwoven layer(s) or strata may form filled tufts 572 (shown in FIGS. 5G-5J). As shown, each of the filled tufts 572 and outer tufts 530 comprise a base 50, the distal end 554 spaced from the base 50 and sidewalls 556 between the base and the distal end 554. Referring specifically to FIG. 5G, forms where the material web 100 comprises a first layer 25 and a second layer 35, the melt additive bloom area 590 may comprise a hydrophobic composition and be associated with the second layer 35 or second strata. Forms of the present invention are contemplated where the material web 100 comprise a first strata and a second strata, and wherein the melt additive bloom area 590 is present on the filled tuft 572 formed by the second strata. For the sake of convenience, the melt additive bloom area 590 is shown on the filled tuft 572; however, the melt additive bloom area 590 may be comprised by a majority of filaments which comprise the filled tuft 572. As shown, the melt additive bloom area 590 may be present at a distal end 554 of the filled tuft 570 and a sidewall 556 of the filled tuft 572.

In such forms, the melt additive bloom area 590 may comprise a hydrophobic composition. Where the material web 100 is utilized as a topsheet of a disposable absorbent article, such forms can allow for reduction in rewet while providing adequate liquid acquisition. Additionally, in such forms, the melt additive bloom area 590 may help with masking of liquid insults to a disposable absorbent article.

Figure 5H:
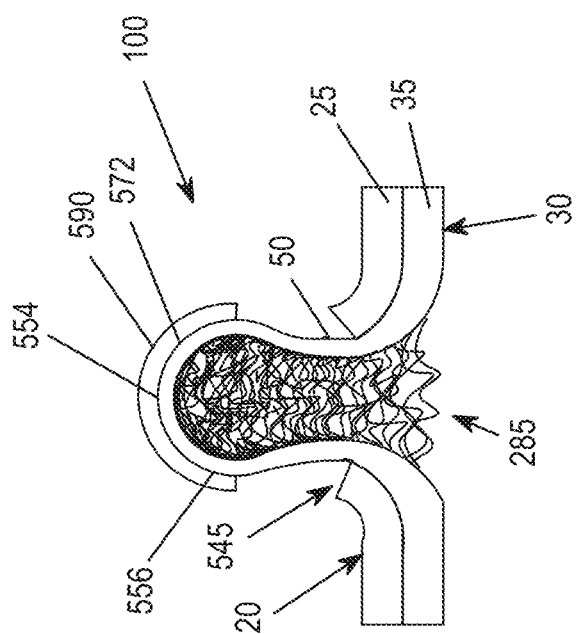

Referring to FIG. 5H, the material web 100 of the present invention may comprise outer tufts 530 and filled tufts 572. As shown, the outer tuft be a portion of the first layer 25 or first strata which is urged in the positive Z-direction. As shown, the second plurality of filaments of the second layer 35 or second strata form the filled tuft 572. The first layer 25 or first strata may similarly form an outer tuft 530 which covers the filled tuft 572. For those forms of the present invention comprising outer tufts 530, the melt additive bloom area 592 may exist in the distal end 554 of the outer tuft 530 and on the sidewalls 556 of the outer tuft 530.

In such forms, the melt additive bloom area 592 may comprise a hydrophobic composition, and the melt additive bloom area 590 may comprise a hydrophilic composition. In some forms, the melt additive bloom area 592 may comprise a hydrophobic composition and the melt additive bloom area 590 may comprise a hydrophobic composition.

Figure 5J:
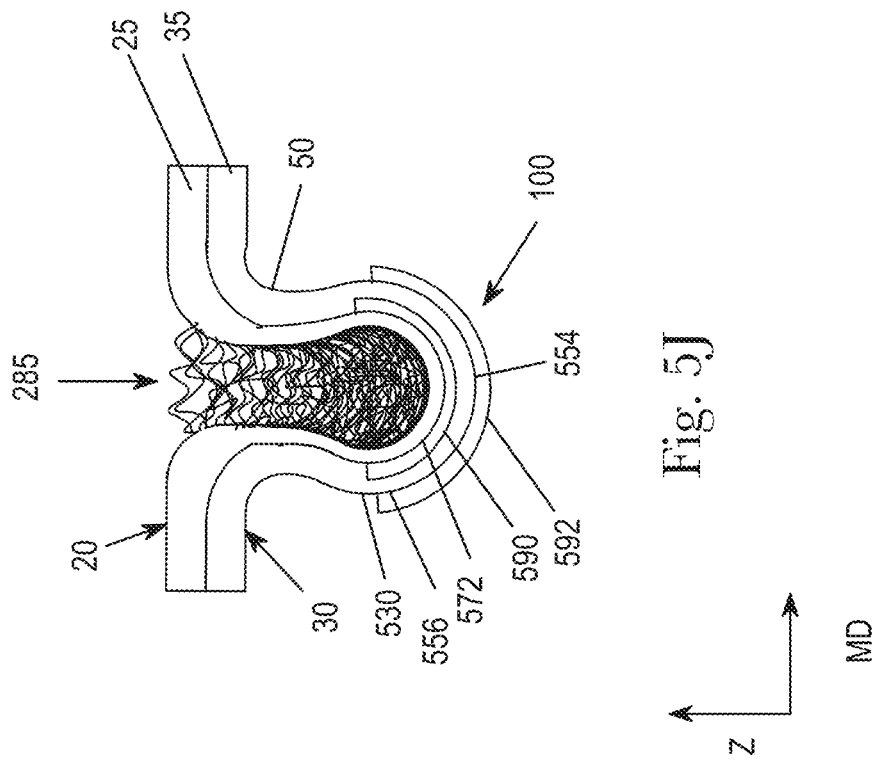
Figure 5I:
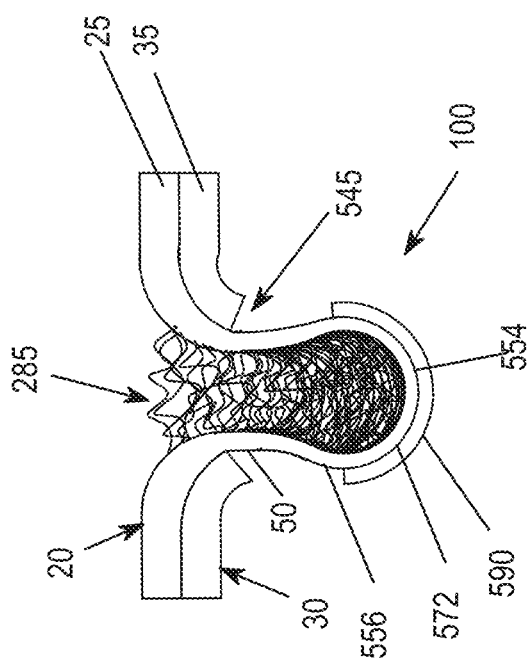

Regarding FIGS. 5I and 5J, the material web 100 may be urged in a plurality of localized areas in the negative Z-direction. In such forms, the material web 100 may comprise a plurality of filled tufts 572 which extend in the negative Z-direction. As shown, the filled tufts 572 may be formed in part from the first layer 25 or first strata. So, in such forms, the first layer 25 or first strata may comprise a spunbond crimped nonwoven layer or strata. As shown, in some forms, the second layer 35 or second strata may break with the negative Z-direction urging or may form outer tufts 530. In such forms, the melt additive bloom area 590 may comprise a hydrophilic composition, and/or the melt additive bloom area 592 may similarly comprise a hydrophilic composition.

Where the material webs 100 of the present invention comprise crimped filaments, the material web 100 has a higher caliper for a given basis weight. This higher caliper can in turn deliver consumer benefits of comfort due to cushiony softness, faster absorbency due to higher permeability, and improved masking. Additional benefits may include less redmarking, higher breathability and resiliency.

Methods of making filled tufts 572 and outer tufts 530 are discussed in U.S. Pat. Nos. 7,172,801; 7,838,099; 7,754,050; 7,682,686; 7,410,683; 7,507,459; 7,553,532; 7,718,243; 7,648,752; 7,732,657; 7,789,994; 8,728,049; and 8,153,226. Filled tufts 572 and corresponding outer tufts 530 are discussed in additional detail in U.S. patent application Ser. No. 14/933,028.

The filled tufts 572 and/or outer tufts 530 may be used in conjunction with the apertures and/or embossments. Or, the filled tufts 572 and/or outer tufts 530 may be utilized independently thereof.

Referring back to FIGS. 5A-5J, for those forms of the present invention where the roll 502 is heated as opposed to the roll 504, the distal ends 554 and the sidewalls 556—to a larger extent than if only the roll 504 were heated—may comprise the melt additive bloom area 590. Additionally, the melt additive bloom area 590 may be a stripe which connects adjacent tufts (either tunnel or filled).

Nested Tufts

Another example of a first unit operation 140 (shown in FIG. 2) that may be utilized in conjunction with the present invention is shown in FIGS. 6A-6D. As shown, the precursor web 102 may be subjected to the apparatus 600. The apparatus 600 may comprise forming members 602 and 604 which may be in the form of non-deformable, meshing, counter-rotating rolls that form a nip 606 therebetween. The precursor web 102 may be fed into the nip 606 between the rolls 6102 and 604. Although the space between the rolls 602 and 604 is described herein as a nip, as discussed in greater detail below, in some cases, it may be desirable to avoid compressing the precursor web 102 to the extent possible.

The first forming member (such as "male roll") 602 has a surface comprising a plurality of first forming elements which comprise discrete, spaced apart male forming elements 612. The male forming elements are spaced apart in the machine direction and in the cross-machine direction. The term "discrete" does not include continuous or non-discrete forming elements such as the ridges and grooves on corrugated rolls (or "ring rolls") which have ridges that may be spaced apart in one, but not both, of the machine direction and in the cross-machine direction.

Figures 6A, 6B:
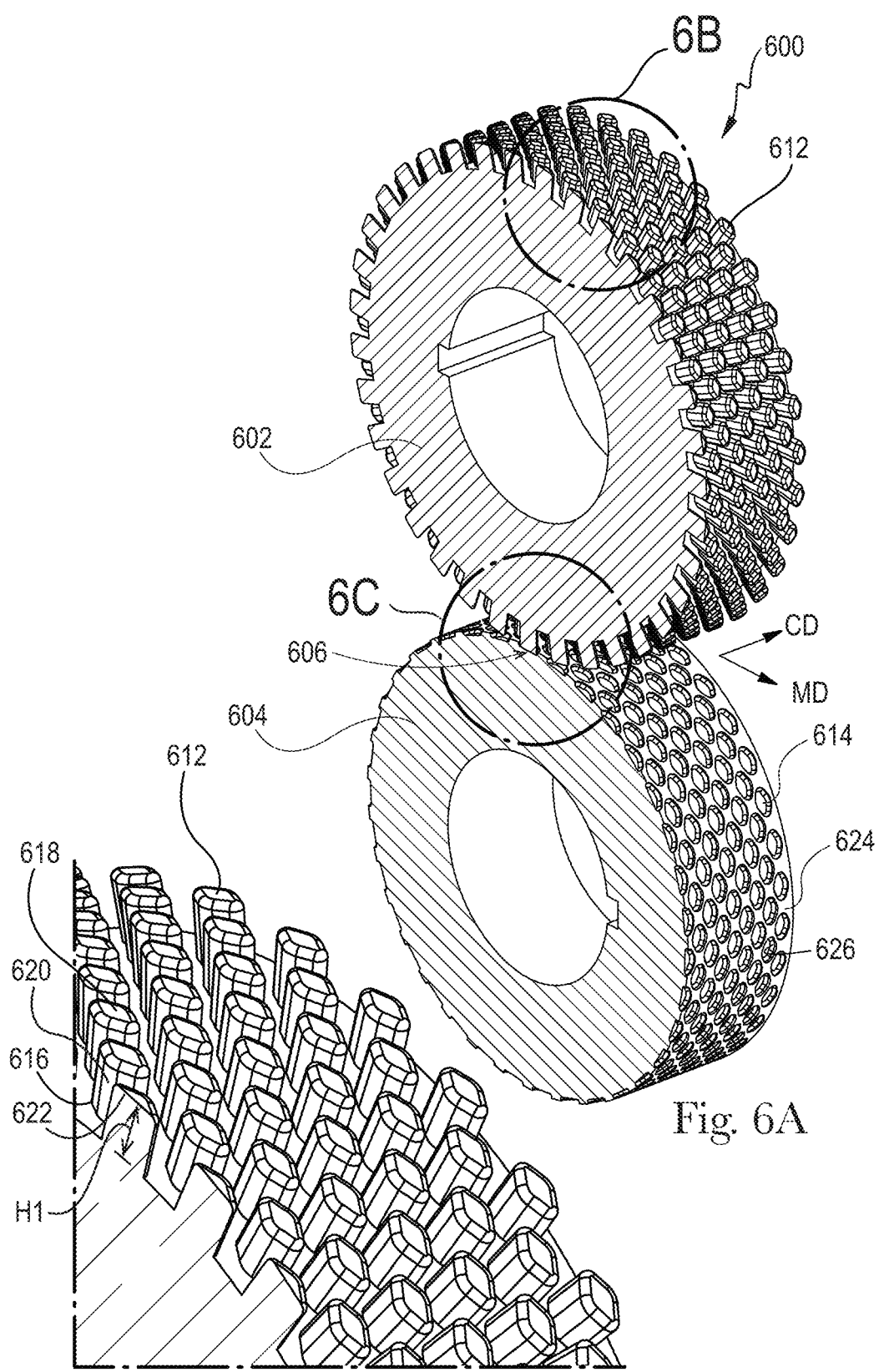
FIGS. 6A-6D are schematic representations of an apparatus capable of producing nested tufts on material webs in accordance with the present disclosure.

As shown in FIG. 6B, the male forming elements 612 have a base 616 that is joined to (in this case is integral with) the first forming member 602, a top 618 that is spaced away from the base, and sidewalls (or "sides") 620 that extend between the base 616 and the top 618 of the male forming elements. The male elements 612 may also have a transition portion or region 622 between the top 618 and the sidewalls 620. The forming elements 612 also have a plan view periphery, and a height $H_1$ (the latter being measured from the base 616 to the top 618). The tops 618 of the forming elements 612 on the first forming member 602 may have a relatively large surface area (e.g., from about 1 mm to about 10 mm in width, and from about 1 mm to about 20 mm in length) for creating a wide discontinuity in the precursor material 102. The forming elements 612 may, thus, have a plan view aspect ratio (ratio of length to width) that ranges from about 1:1 to about 10:1. For the purpose of determining the aspect ratio, the larger dimension of the forming elements 612 will be consider the length, and the dimension perpendicular thereto will be considered to be the width of the forming element. The forming elements 612 may have any suitable configuration.

The base 616 and the top 618 of the forming elements 612 may have any suitable plan view configuration, including but not limited to: a rounded diamond configuration as shown in FIGS. 6A and 6B, an American football-like shape, triangle, circle, clover, a heart-shape, teardrop, oval, or an elliptical shape. The configuration of the base 616 and the configuration of the top 618 of the forming elements 612 may be in any of the following relationships to each other:

the same, similar, or different. The top 618 of the male elements 612 can be flat, rounded, or any configuration therebetween.

Additional forms of the male forming elements 612 are possible. For example, the top 618 of the forming elements 612 can be of different shapes from those shown in the drawings. As another example, the male forming elements 612 can be disposed in other orientations on the first forming member 602 rather than having their length oriented in the machine direction (including CD-orientations, and orientations between the MD and CD). The male forming elements 612 on the first forming member 602 may, but need not, all have the same configuration or properties. In certain embodiments, the first forming member 602 can comprise some male forming elements 612 having one configuration and/or properties, and other male forming elements 612 having one or more different configurations and/or properties.

Figure 6C:
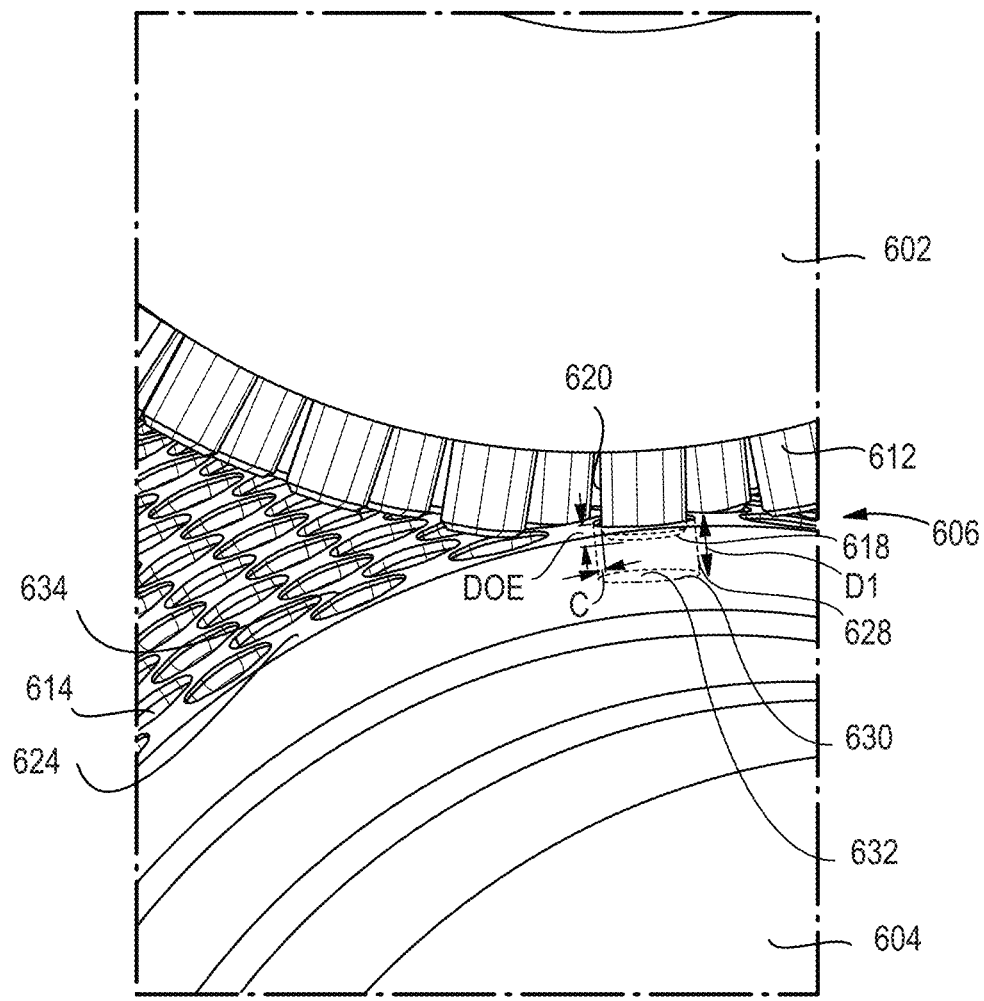

Referring again to FIGS. 6A through 6D, the second forming member (such as "female roll") 604 has a surface 624 having a plurality of cavities or recesses 614 therein. The recesses 614 are aligned and configured to receive the male forming elements 612 therein. Thus, the male forming elements 612 mate with the recesses 614 so that a single male forming element 612 fits within a periphery of a single recess 614, and at least partially within the recess 614 in the Z-direction. The recesses 614 have a plan view periphery 626 that is larger than the plan view periphery of the male elements 612. As a result, the recesses 614 on the female roll 604 may completely encompass the male forming elements 612 when the rolls 602 and 604 are intermeshed. As shown in FIG. 6C, the recesses 614 have a depth D1 which in some forms may be greater than the height $H_1$ of the male forming elements 612. The recesses 614 have a plan view configuration, sidewalls 628, a top edge or rim 634 around the upper portion of the recess where the sidewalls 628 meet the surface 624 of the second forming member 604, and a bottom edge 630 around a bottom 632 of the recesses where the sidewalls 628 meet the bottom 632 of the recesses.

As discussed above, the recesses 614 may be deeper than the height $H_1$ of the forming elements 612 so the precursor web 102 is not nipped (or squeezed) between the male and female rolls 602 and 604 to the extent possible. However, it is understood that passing the precursor web between two rolls with a relatively small space therebetween will likely apply some shear and compressive forces to the material. The present method, however, differs from some embossing processes in which the top of the male elements compress the material to be embossed against the bottom of the female elements, thereby increasing the density of the region in which the material is compressed.

The depth of engagement (DOE) is a measure of the level of intermeshing of the forming members. As shown in FIG. 6C, the DOE is measured from the top 618 of the male elements 612 to the (outermost) surface 624 of the female forming member 614 (e.g., the roll with recesses). The DOE should be sufficiently high, when combined with extensible nonwoven materials, to create nested tufts. For example, for the precursor web 102 of the present invention, the DOE may, for example, range from at least about 1.5 mm, or less, to about 5 mm, or more. In certain forms, the DOE may be between about 2.5 mm to about 5 mm, alternatively between about 3 mm and about 4 mm.

Still referring to FIG. 6C, there is a clearance, C, between the sides 620 of the forming elements 612 and the sides (or sidewalls) 628 of the recesses 614. The clearances and the DOE's are related such that larger clearances can permit higher DOE's to be used. The clearance, C, between the male and female roll may be the same, or it may vary around the perimeter of the forming element 612. For example, the forming members can be designed so that there is less clearance between the sides of the forming elements 612 and the adjacent sidewalls 628 of the recesses 614 than there is between the sidewalls at the end of the male elements 612 and the adjacent sidewalls of the recesses 614. In other cases, the forming members can be designed so that there is more clearance between the sides 620 of the male elements 612 and the adjacent sidewalls 628 of the recesses 614 than there is between the sidewalls at the end of the male elements 612 and the adjacent sidewalls of the recesses. In still other cases, there could be more clearance between the side wall on one side of a male element 612 and the adjacent side wall of the recess 614 than there is between the side wall on the opposing side of the same male element 612 and the adjacent side wall of the recess. For example, there can be a different clearance at each end of a forming element 612; and/or a different clearance on each side of a male element 612. Clearances can range from about 0.005 inches (about 0.1 mm) to about 0.1 inches (about 2.5 mm).

Some of the aforementioned forming element 612 configurations alone, or in conjunction with the second forming member 604 and/or recess 614 configurations may provide additional advantages. This may be due to by greater lock of the precursor material on the male elements 612, which may result in more uniform and controlled strain on the precursor material. The apparatus 600 is further described in U.S. patent application Ser. No. 14/844,459.

Figure 6D:
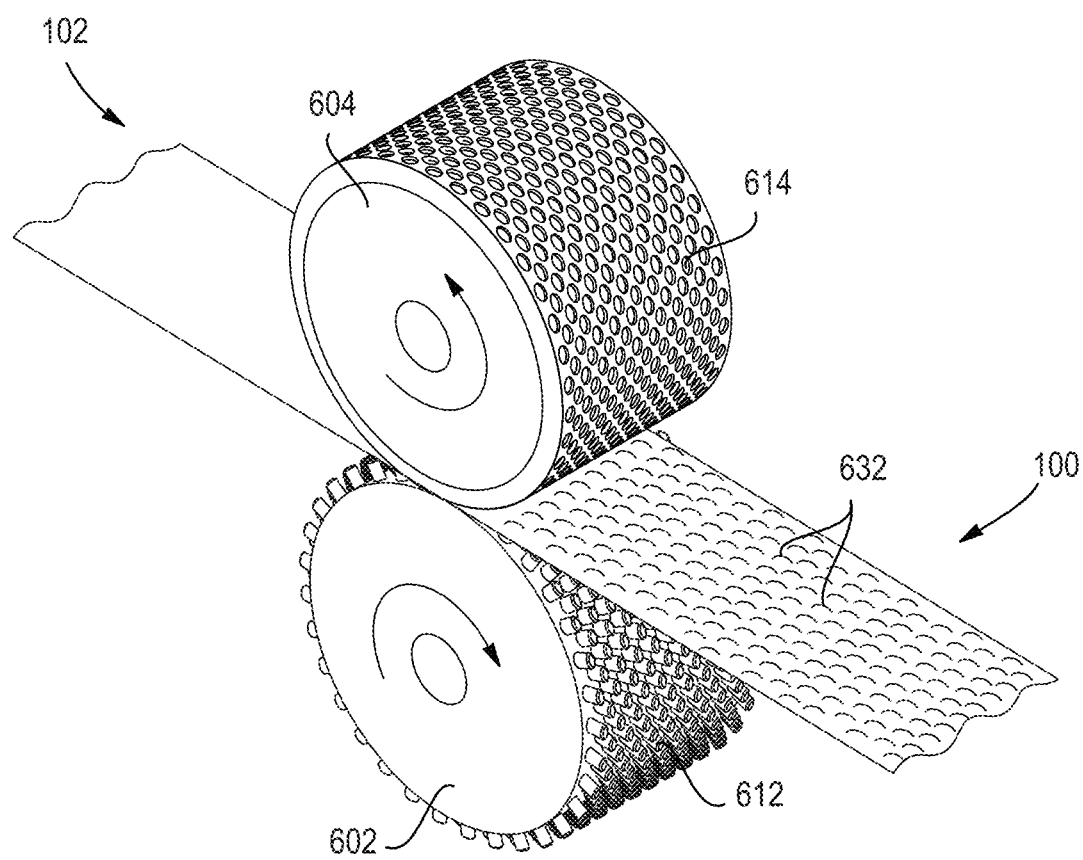
Figure 6E:
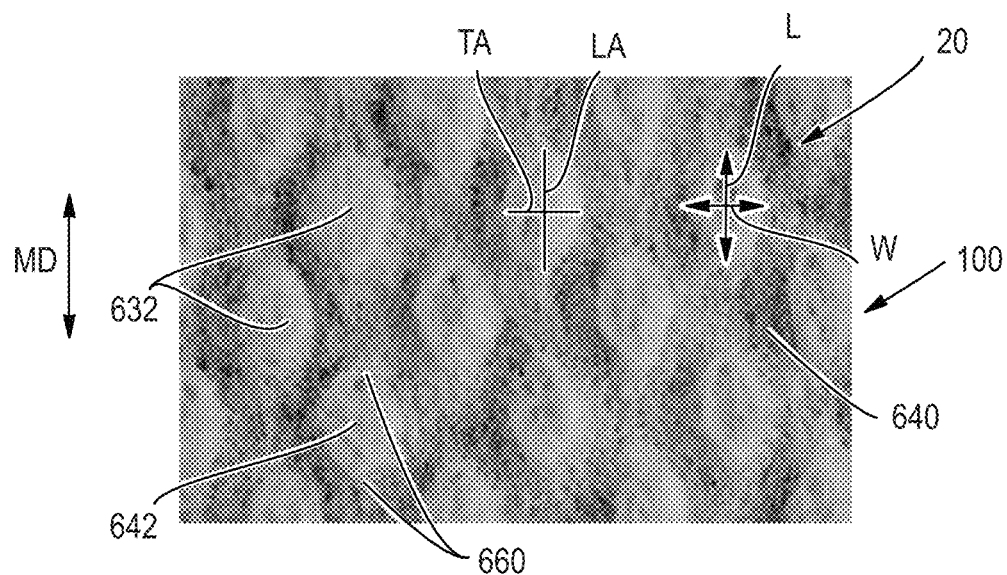
FIG. 6E is a plan view photomicrograph showing one side of a material web having three-dimensional discontinuity formed therein in accordance with the present disclosure.
Figure 6F:
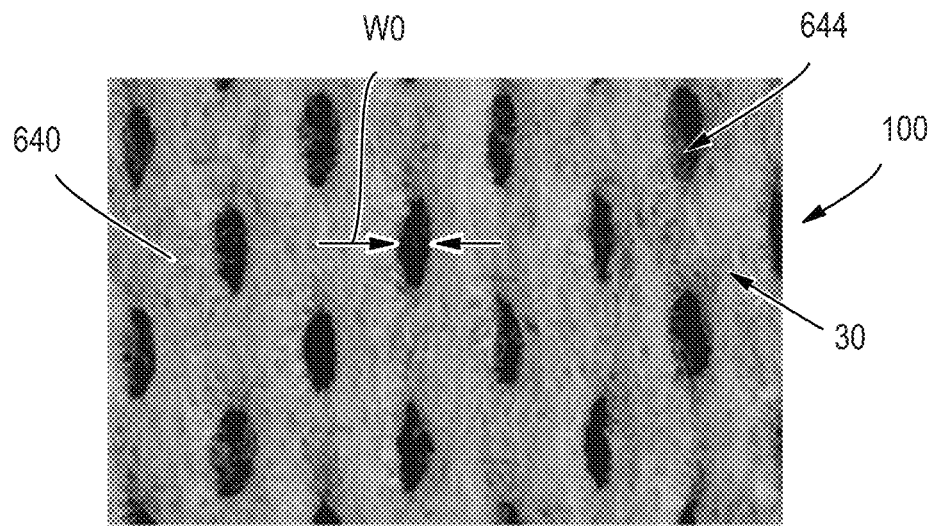
FIG. 6F is a plan view photomicrograph showing the other side of the material web of FIG. 6E, with the openings.

As shown in FIGS. 6D-6F, the precursor web 102 may be provided to the nip 606 between the first roll 602 and the second roll 604. As the precursor web 102 passes through the nip 606, the forming members 612 engage the second surface 30 (shown in FIG. 6F as the second surface 30 of the material web 100) of the precursor web 102 and urge the precursor web 102 into the recesses 614. The process forms the material web 100 comprising the generally planar first surface 20 and a plurality of integrally formed nested tufts 632 extending outward from the first surface 20 of the material web 100 and openings in the second surface 30 of the material web 100. (Of course, if the second surface 30 of the precursor web 102 is placed in contact with the second forming member 604, the nested tufts 632 will extend outward from the second surface of the material web 100 and the openings will be formed in the first surface 20 of the material web 100.) Without wishing to be bound by any particular theory, it is believed that the extensibility of the precursor material 102 (or at least one of the layers of the same) when pushed by the forming elements 612 into the recesses 614 with depth of engagement DOE being less than the depth $D_1$ of the recesses, stretches a portion of the precursor material 102 to form a nested tuft 632.

Referring now to FIGS. 6E-6H, examples of material webs 100 comprising nested tufts 632 are shown. As noted heretofore, the material web 100 has the first surface 20, the opposing second surface 30, and a thickness T therebetween (the thickness being shown in FIG. 6H). FIG. 6E shows the first surface 20 of the material web 100 with nested tufts 632 that extend outward (out of the plane of the sheet comprising FIG. 6E) from the first surface 20 of the material web 100. As shown, the material web 100 may comprise a generally planar first region 640 and a plurality of discrete integral second regions 642 which comprise nested tufts 632.

As shown, the nested tufts 632 may have a width, W, that varies from one end 660 to the opposing end 660 when the nested tufts 632 are viewed in plan view. As shown, the width W may be generally parallel to a transverse axis TA. The width W may vary with the widest portion of the nested tufts 632 in the middle of the nested tufts 632, and the width of the nested tufts 632 decreasing at the ends 660 of the nested tufts 632. In other cases, the nested tufts 632 could be wider at one or both ends 60 than in the middle of the nested tufts 632. In still other cases, nested tufts 632 can be formed that have substantially the same width from one end of the nested tufts 632 to the other end of the nested tufts 632. If the width of the nested tufts 632 varies along the length of the nested tufts 632, the portion of the nested tufts 632 where the width is the greatest is used in determining the aspect ratio of the nested tufts 632.

Similarly, the nested tufts 632 may have a length L which is generally parallel to a longitudinal axis LA. When the nested tufts 632 have a length L that is greater than or less than their width W, the length of the nested tufts 632 may be oriented in any suitable direction relative to the material web 100. For example, the length of the nested tufts 632 (that is, the longitudinal axis, LA, of the nested tufts 632) may be oriented in the MD, the CD, or any desired orientation between the MD and the CD. As shown, the transverse axis TA is generally orthogonal to the longitudinal axis LA in the MD-CD plane. In some forms, as shown, the longitudinal axis LA is parallel to the MD. In some forms, all the spaced apart nested tufts 632 may have generally parallel longitudinal axes LA.

FIG. 6F shows the second surface 30 of a material web 100 such as that shown in FIG. 6E, having nested tufts 632 formed therein, with the nested tufts 632 being oriented into the sheet showing FIG. 6F. The second surface 30 may comprise a plurality of base openings 644. In some forms, the base openings 644 may not be in the form of an aperture or a through-hole. The base openings 644 may instead appear as depressions. In some forms, the base openings 644 may open into the interior of the nested tuft 632.

Figure 6G:
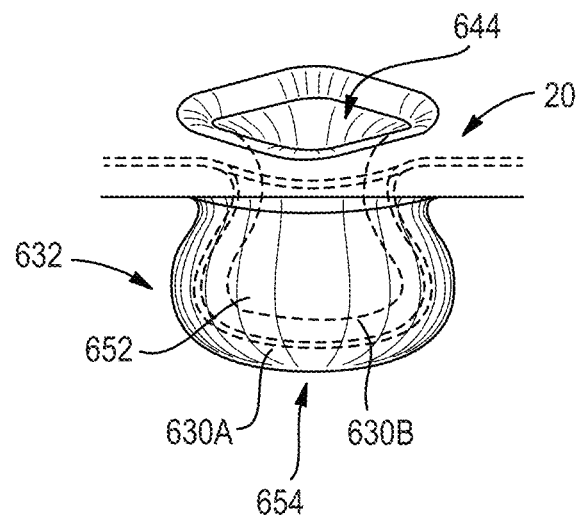
FIG. 6G is a perspective view of a nested tuft in a two layer material web in accordance with the present disclosure.
Figure 6H:
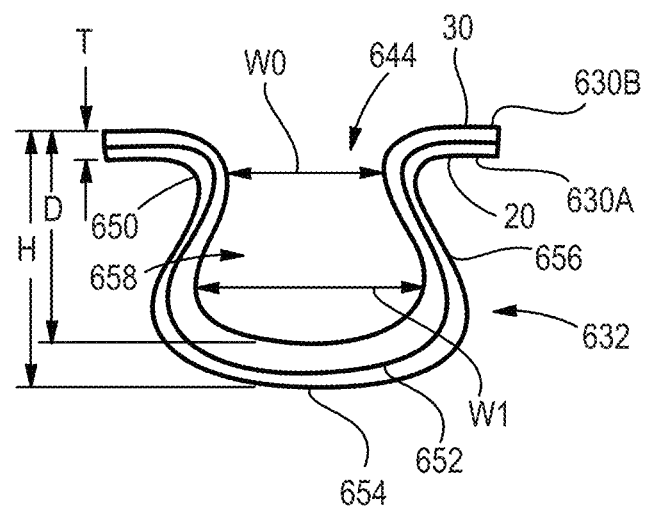
FIG. 6H is a schematic view of a nested tuft in accordance with the present disclosure.

Referring to FIGS. 6E, 6G and 6H, the nested tufts 632 may have any suitable shape when viewed from the side. Suitable shapes include those in which there is a distal portion or "cap" with an enlarged dimension and a narrower portion at the base when viewed from at least one side. The term "cap" is analogous to the cap portion of a mushroom. (The cap does not need to resemble that of any particular type of mushroom. In addition, the nested tufts 632 may, but need not, have a mushroom-like stem portion.) In some cases, the nested tufts 632 may be referred to as having a bulbous shape when viewed from the end 660. The term "bulbous", as used herein, is intended to refer to the configuration of the nested tufts 632 as having a cap 652 with an enlarged dimension and a narrower portion at the base when viewed from at least one side (particularly when viewing from one of the shorter ends 660) of the nested tufts 632. The term "bulbous" is not limited to nested tufts 632 that have a circular or round plan view configuration that is joined to a columnar portion. The bulbous shape, in the form shown (where the longitudinal axis LA of the nested tufts 632 is oriented in the machine direction), may be most apparent if a section is taken along the transverse axis TA of the nested tufts 632 (that is, in the cross-machine direction). The bulbous shape may be less apparent if the nested tufts 632 is viewed along the length (or longitudinal axis LA) of the nested tufts 632.

Referring to FIGS. 6E-6H, an example of a multi-layer material web 100 having a nested tuft 632 on one side of the material web 100 and a wide base opening 644 on the other side of the material web 100 is shown. As shown, the base opening 644 is oriented upward in the figure. When there is more than one layer, the individual layers can be designated 630A, 630B, etc. As shown, the nested tufts 632 may comprise: a base 650 proximate the first surface 20 of the material web 100; an opposed enlarged distal portion or cap portion, or "cap" 652, that extends to a distal end 654; sidewalls (or "sides") 656; an interior 658; and a pair of ends 660. The "base" 650 of the nested tufts 632 comprises the narrowest portion of the nested tufts 632 when viewed from one of the ends of the nested tufts 632. The term "cap" does not imply any particular shape, other than it comprises the wider portion of the nested tufts 632 that includes and is adjacent to the distal end 654 of the nested tufts 632. The sidewalls 656 have an inside surface and an outside surface. The sidewalls 656 transition into, and may comprise part of the cap 652. Therefore, it is not necessary to precisely define where the sidewalls 656 end and the cap 652 begins. The cap 652 will have a maximum interior width, $W_1$, between the inside surfaces of the opposing sidewalls 656. The cap 652 will also have a maximum exterior width W between the outside surfaces of the opposing sidewalls 656. The ends 660 of the nested tufts 632 are the portions of the nested tufts 632 that are spaced furthest apart along the longitudinal axis, L, of the nested tufts 632.

Still referring to FIGS. 6E-6H, the narrowest portion of the nested tufts 632 defines the base opening 644. The base opening 644 has a width $W_O$. The base opening 644 may be located (in the Z-direction) between a plane defined by the second surface 30 of the material web 100 and the distal end 654 of the nested tuft 632. The material web 100 may have an opening in the second surface 30 that transitions into the base opening 644 (and vice versa), and is the same size as, or larger than the base opening 644. The base opening 644 will, however, generally be discussed more frequently herein since its size will often be more visually apparent to the consumer in those embodiments where the material web 100 is placed in an article with the base openings 644 visible to the consumer. It should be understood that in certain forms of the present invention, base openings 644 face outward (for example, toward a consumer and away from the absorbent core in an absorbent article), it may be desirable for the base openings 644 not to be covered and/or closed off by another web.

The nested tufts 632 have a depth D measured from the second surface 30 of the material web 100 to the interior of the nested tufts 632 at the distal end 654 of the nested tufts 632. The nested tufts 632 have a height H measured from the second surface 30 of the material web 100 to the exterior of the nested tuft 632 at the distal end 654. In most cases the height H of the nested tufts 632 will be greater than the thickness T of the first region 640. The relationship between the various portions of the nested tufts 632 may be such that as shown in FIG. 6H, when viewed from the end, the maximum interior width $W_I$ of the cap 652 of the nested tufts 632 is wider than the width, $W_O$, of the base opening 644.

For those forms of the present invention where the material web 100 comprises a nonwoven material, the nested tufts 632 may, in some cases, be formed from looped fibers (which may be continuous) that are pushed outward so that they extend away from the first surface 20 in the Z-direction or away from the second surface 30 in the negative Z-direction. The nested tufts 632 will typically comprise more than one looped fiber. In some cases, the nested tufts 632 may be formed from looped fibers and at least some broken fibers. In addition, in the case of some types of nonwoven materials (such as carded materials, which are comprised of shorter fibers), the nested tufts 632 may be formed from loops comprising multiple discontinuous fibers. Multiple discontinuous fibers in the form of a loop are described in U.S. patent application Ser. No. 14/844,459. The looped fibers may be: aligned (that is, oriented in substantially the same direction); not be aligned; or, the fibers may be aligned in some locations within the protrusions 32, and not aligned in other parts of the protrusions.

In some forms, if male/female forming elements are used to form the nested tufts 632, and the female forming elements substantially surround the male forming elements, the fibers in at least part of the nested tufts 632 may remain substantially randomly oriented (rather than aligned), similar to their orientation in the precursor web(s). For example, in some cases, the fibers may remain substantially randomly oriented in the cap of the nested tufts 632, but be more aligned in the sidewalls such that the fibers extend in the Z-direction (positive or negative depending on the orientation of the nested tuft 632) from the base of the protrusions to the cap. In addition, if the precursor web comprises a multi-layer nonwoven material, the alignment of fibers can vary between layers, and can also vary between different portions of a given nested tufts 632 within the same layer.

Where the precursor web comprises a nonwoven material, the nested tufts 632 may comprise a plurality fibers that at least substantially surround the sides of the nested tufts 632. This means that there are multiple fibers that extend (e.g., in the positive or negative Z-direction) from the base 650 of the nested tufts 632 to the distal end 654 of the nested tufts 632, and contribute to form a portion of the sides 656 and cap 652 of a nested tufts 632. In some cases, the fibers may be substantially aligned with each other in the Z-direction in the sides 656 of the nested tufts 632. The phrase "substantially surround", thus, does not require that each individual fiber be wrapped in the X-Y plane substantially or completely around the sides of the nested tufts 632. If the fibers are located completely around the sides of the nested tufts 632, this would mean that the fibers are located 360° around the nested tufts 632. The nested tufts 632 may be free of large openings at their ends 660. In some cases, the nested tufts 632 may have an opening at only one of their ends, such as at their trailing end.

In some forms, similar-shaped looped fibers may be formed in each layer of multiple layer nonwoven materials, including in the layer 630A that is spaced furthest from the discrete male forming elements during the process of forming the nested tufts 632 therein, and in the layer 630B that is closest to the male forming elements during the process. In the nested tufts 632, portions of one layer such as 630B may fit within the other layer, such as 630A. These layers may be referred to as forming a "nested" structure in the nested tufts 632. Formation of a nested structure may require the use of two (or more) highly extensible nonwoven precursor webs. In the case of two layer materials, nested structures may form two complete loops, or (as shown in some of the following drawing figures) two incomplete loops of fibers.

The nested tufts 632 may have certain additional characteristics. As shown in FIGS. 6G and 6H, the nested tufts 632 may be substantially hollow. As used herein, the term "substantially hollow" refers to structures which the nested tufts 632 are substantially free of fibers in interior of nested tuft. The term "substantially hollow", does not, however, require that the interior of the nested tuft must be completely free of fibers. Thus, there can be some fibers inside the nested tufts 632. "Substantially hollow" nested tufts are distinguishable from filled three-dimensional structures, such as those made by laying down fibers, such as by airlaying or carding fibers onto a forming structure with recesses therein.

The sidewalls 656 of the nested tufts 632 can have any suitable configuration. The configuration of the sidewalls 656, when viewed from the end of the nested tuft such as in 6G, can be linear or curvilinear, or the sidewalls can be formed by a combination of linear and curvilinear portions. The curvilinear portions can be concave, convex, or combinations of both. For example, the sidewalls 656 may comprise portions that are curvilinear concave inwardly near the base of the nested tuft and convex outwardly near the cap of the nested tuft. The sidewalls 656 and the area around the base opening 644 of the nested tuft may have significantly lower concentration of fibers per given area (which may be evidence of a lower basis weight or lower opacity) than the portions of the first region 640. The nested tufts 632 may also have thinned fibers in the sidewalls 656. The fiber thinning, if present, will be apparent in the form of necked regions in the fibers. Thus, the fibers may have a first cross-sectional area when they are in the undeformed precursor material 102, and a second cross-sectional area in the sidewalls 656 of the nested tufts 632 of the deformed material web 100, wherein the first cross-sectional area is greater than the second cross-sectional area. The sidewalls 656 may also comprise some broken fibers as well. In some forms, the sidewalls 656 may comprise greater than or equal to about 30%, alternatively greater than or equal to about 50% broken fibers.

In some forms, the distal end 654 of the nested tufts 632 may be comprised of original basis weight, non-thinned, and non-broken fibers. If the base opening 44 faces upward, the distal end 654 will be at the bottom of the depression that is formed by the nested tuft. The distal end 654 will be free from apertures formed completely through the distal end. Thus, the nonwoven materials may be nonapertured. The term "apertures", as used herein, refers to holes formed in the nonwovens after the formation of the nonwovens, and does not include the pores typically present in nonwovens. The term "apertures" also does not refer to irregular breaks (or interruptions) in the nonwoven material(s) resulting from localized tearing of the material(s) during the process of forming nested tufts therein, which breaks may be due to variability in the precursor material(s). The distal end 654 may have relatively greater fiber concentration in comparison to the remaining portions of the structure that forms the protrusions. The fiber concentration can be measured by viewing the sample under a microscope and counting the number of fibers within an area.

The nested tufts 632 may be of any suitable shape. Since the nested tufts 632 are three-dimensional, describing their shape depends on the angle from which they are viewed. When viewed from above (that is, perpendicular to the plane of the web, or plan view) such as in FIG. 6E, suitable shapes include, but are not limited to: circular, diamond-shaped, rounded diamond-shaped, U.S. football-shaped, oval-shaped, clover-shaped, heart-shaped, triangle-shaped, teardrop shaped, and elliptical-shaped. (The base openings 644 will typically have a shape similar to the plan view shape of the nested tufts 632.) In other cases, the nested tufts 632 (and base openings 644) may be non-circular. The nested tufts 632 may have similar plan view dimensions in all directions, or the nested tufts 632 may be longer in one dimension than another. That is, the nested tufts 632 may have different length and width dimensions. If the nested tufts 632 have a different length than width, the longer dimension will be referred to as the length of the nested tufts 632. The nested tufts 632 may, thus, have a ratio of length to width, or an aspect ratio. The aspect ratios can range from about 1:1 to about 10:1.

In some forms, the length of the cap 652 may be in a range from about 1.5 mm to about 10 mm. In some forms, the width of the cap (measured where the width is the greatest) may be in a range from about 1.5 mm to about 5 mm. The cap portion of the protrusions may have a plan view surface area of at least about 3 mm$^2$. In some embodiments, the protrusions may have a pre-compression height H that is in a range from about 1 mm to about 10 mm, alternatively from about 1 mm to about 6 mm. In some embodiments, the protrusions may have a post-compression height H that is in a range from about 0.5 mm to about 6 mm, alternatively from about 0.5 mm to about 1.5 mm. In some embodiments, the protrusions may have a depth D, in an uncompressed state that is in a range from about 0.5 mm to about 9 mm, alternatively from about 0.5 mm to about 5 mm. In some embodiments, the protrusions may have a depth D, after compression that is in a range from about 0.25 mm to about 5 mm, alternatively from about 0.25 mm to about 1 mm.

For those forms of the present invention where the material web 100 comprises a first layer and a second layer many configurations may be achieved. In such forms, the first layer may be incorporated into an absorbent article as, for example, an acquisition layer and the second layer may be a topsheet of the absorbent article. Each of the first layer and the second layer may form nested tufts which fit into one another. Such examples are described with regard to FIGS. 6I-6N.

For the examples shown in FIGS. 6I-6N, each of the nested tufts formed by the first layer 630A and second layer 630B may comprise a plurality of fibers. In addition, for any of the forms comprising nested tufts, the nonwoven layers can be inverted when incorporated into an absorbent article, or other article, so that the nested tufts 632 face upward (or outward). In such a case, the material suitable for the topsheet will be used in layer 630A, and material suitable for the underlying layer will be used in layer 630B.

As shown in FIG. 6I, a nested tuft 632 may comprise a compound nest. As shown, the nested tuft 632 may comprise a first nested tuft 632A formed in the first layer 630A and a second nested tuft 632B formed in the second layer 630B. In one form, the first layer 630A may be incorporated into an absorbent article as an acquisition layer, and the second layer 630B may be a topsheet, and the nested tufts 632 formed by the two layers may fit together (that is, are nested). In some forms, the fibers 638A in the first layer 630A are shorter in length than the fibers 638B in the second layer 630B. In other forms, the relative length of fibers in the layers may be the same, or in the opposite relationship wherein the fibers in the first layer are longer than those in the second layer.

FIG. 6J shows that the nonwoven layers need not be in a contacting relationship within the entirety of the nested tuft 632. Thus, the first nested tuft 632A and second nested tuft 632B formed by the first and second layers 630A and 630B may have different heights and/or widths. The two materials may have substantially the same shape in the nested tuft 632 as shown in 6J (where one of the materials has the same the curvature as the other). In other forms, however, the layers may have different shapes. It should be understood that FIG. 6J shows only one possible arrangement of layers, and that many other variations are possible, but that as in the case of all the figures, it is not possible to provide a drawing of every possible variation.

As shown in FIG. 6K, one of the layers, such as first layer 630A (e.g., an acquisition layer) may be ruptured in the area of the nested tuft 632. As shown in FIG. 6K, the nested tufts 632 are only formed in the second layer 630B (e.g., the top sheet) and extend through openings in the first layer 630A. That is, the second nested tuft 632B in the second layer 630B interpenetrates the ruptured first layer 630A. Such a structure may place the topsheet in direct contact an underlying distribution layer or absorbent core, which may lead to improved dryness. In such forms, the layers are not considered to be "nested" in the area of the protrusion. (In the other embodiments shown in FIGS. 6L-6N, the layers would still be considered to be "nested".) Such a structure may be formed if the material of the second layer 630B is much more extensible than the material of the first layer 630A. For some materials, portions of the first layer 630A can be deflected or urged out-of-plane (i.e., out of the plane of the first layer 630A) to form flaps 670. The form and structure of any flaps is highly dependent upon the material properties of the first layer 630A. Flaps can have the general structure shown in FIG. 6K. In other forms, the flaps 670 can have a more volcano-like structure, as if the second nested tuft 632B is erupting from the flaps.

Figure 6N:
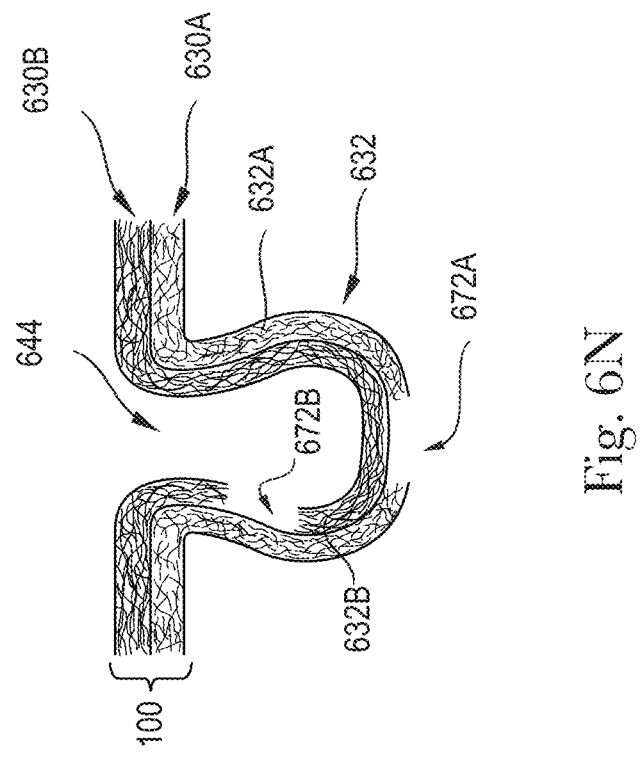
FIG. 6N is a cross-sectional view taken along a transverse axis of a nested tuft in accordance with the present disclosure.
Figure 6L:
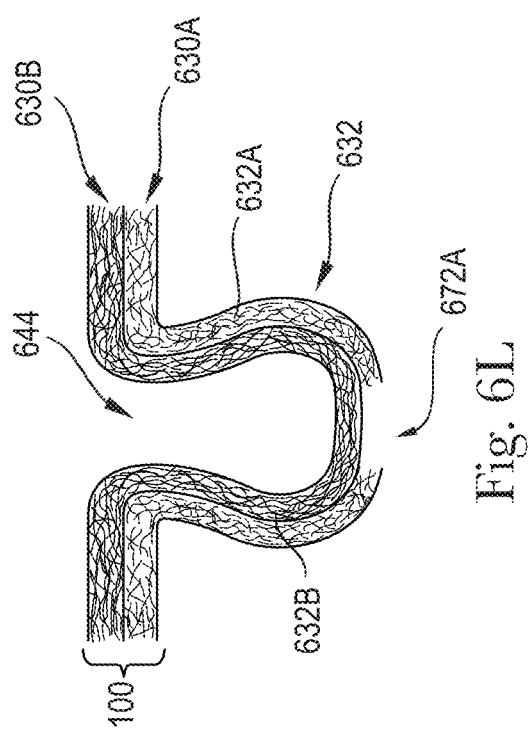
FIG. 6L is a cross-sectional view taken along a transverse axis of a nested tuft in accordance with the present disclosure.
Figure 6M:
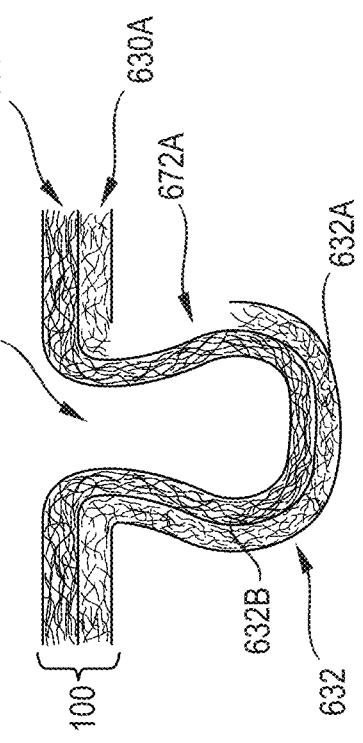
FIG. 6M is a cross-sectional view taken along a transverse axis of a nested tuft in accordance with the present disclosure.

Alternatively, as shown in FIGS. 6L-6N, one or both of the first layer 630A and the second layer 630B may be interrupted (or have a break therein) in the area of the nested tuft 632. FIGS. 6L and 6M show that the first nested tuft 632A of the first layer 630A may have an interruption 672A therein. The second nested tuft 632B of the non-interrupted second layer 630B may coincide with and fit together with the first nested tuft 632A of the interrupted first layer 630A. Alternatively, FIG. 6N shows an embodiment in which both the first and second layers 630A and 630B have interruptions, or breaks, therein (672A and 672B, respectively). In this case, the interruptions in the layers 630A and 630B are in different locations in the nested tuft 632. FIGS. 6L-6N show unintentional random or inconsistent breaks in the materials typically formed by random fiber breakage, which are generally misaligned and can be in the first or second layer, but are not typically aligned and completely through both layers. Thus, there typically will not be an aperture formed completely through all of the layers at the distal end 654 of the nested tuft 632.

For dual layer and other multiple layer structures, the basis weight distribution (or the concentration of fibers) within the material web 100, as well as the distribution of any thermal point bonds can be different between the layers. As used herein, the term "fiber concentration" has a similar meaning as basis weight, but fiber concentration refers to the number of fibers/given area, rather than g/area as in basis weight. In the case of bond sites, the fibers may be melted which may increase the density of the material in the bond sites 46, but the number of fibers will typically be the same as before melting.

Some such dual and multiple layer nonwoven materials may be described in terms of such differences between layers, without requiring one or more of the other features described herein (such as characteristics of the cap portion; controlled collapse under compression; and varying width of the protrusions). Of course such dual and multiple layer nonwoven materials may have any of these other features.

In such dual and multiple layer nonwoven materials each of the layers comprises a plurality of fibers, and in certain embodiments, the nested tufts 632 will be formed from fibers in each of the layers. Referring back to FIGS. 6E-6H, for example, one of the layers, a first layer, may form the first surface 20 of the material web 100, and one of the layers, a second layer, may form the second surface 30 of the material web 100. A portion of the fibers in the first layer form part of: the first region 640, the sidewalls 656 of the nested tuft 632, and the distal ends 654 of the nested tuft 632. A portion of the fibers in the second layer may form part of: the first region 640, the sidewalls 656 of the nested tufts 632, and the distal ends 654 of the nested tuft 632.

Referring back to FIGS. 6A-6E, forms of the present invention are contemplated where the first forming member 602 and/or the second forming member 604 are heated or portions thereof. For example, the forming elements 612 may be heated including the base 616, the top 618, sidewalls 620 that extend between the base 616 and the top 618, and/or the transition region 622 between the top 618 and the sidewalls 620. As another example, the recesses 614 may be heated including the sidewalls 628, the top edge or rim 634, and/or a bottom edge 630 of the recesses 614. In some forms, the surface 624 of the second forming member 604 may not be heated.

Forms of the present invention are contemplated where only a portion of the number of forming elements are heated and/or only a portion of the number of recesses 614 are heated. For example, in some forms, every third forming member 612 may be heated and/or every third recess 614 may be heated. Any suitable configuration may be utilized. In some forms, patterns of heated forming elements 612 and/or recesses 614 may be utilized.

For those forms comprising heated forming elements 612 and/or recesses 614, melt additive blooms may be provided in the resultant material web. For example, as shown in FIG. 6O, in conjunction with FIGS. 6A-6D, where forming members 612 are heated a melt additive bloom area 690 may be provided on a portion of the sidewalls 656 and distal end 654 of the material web 100. Where the corresponding recesses 614 are also heated, the melt additive bloom area 690 may extend closer to the neck 650 of the nested tuft 632. As shown, for those forms of the present invention where the nested tufts 632 extend in the negative Z-direction (away from a user of a disposable absorbent article), the melt additive bloom area 690 may comprise a hydrophilic composition. For those forms of the present invention where the nested tufts 632 extend in the positive Z-direction (toward the user of a disposable absorbent article), the melt additive bloom area 690 may comprise a hydrophobic composition.

Figure 6P:
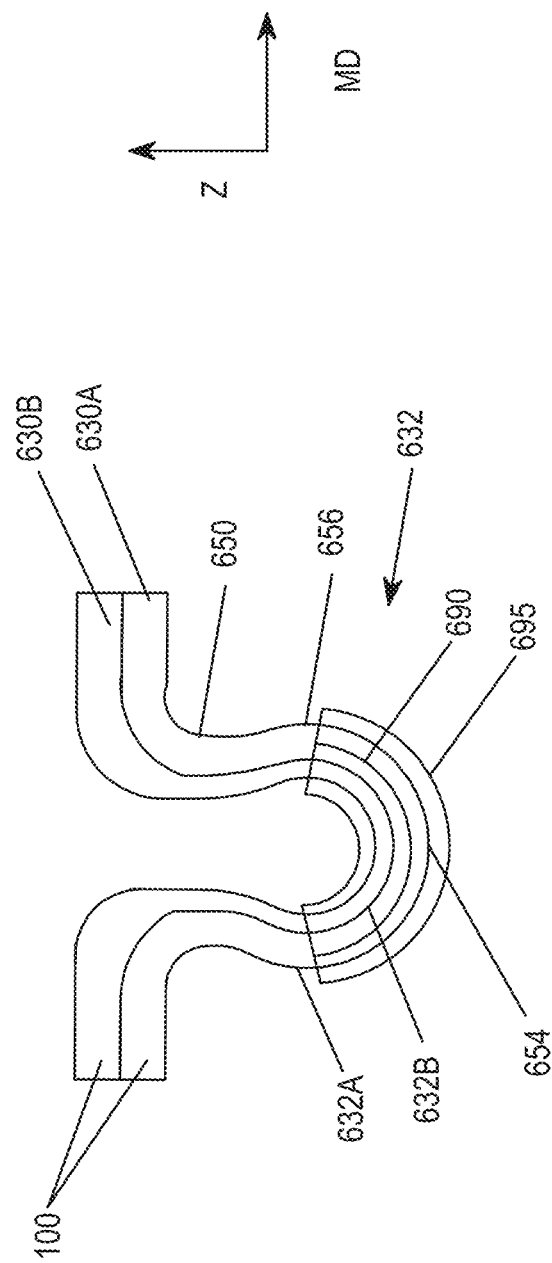
FIG. 6P is a cross-sectional view taken along a transverse axis of another nested tuft in accordance with the present disclosure.

For those forms of the present invention where the material web 100 comprises multiple layers, the nested tufts 632 may comprise a plurality of melt additive bloom areas. For example, as shown in FIG. 6P, in conjunction with FIGS. 6A-6D, the material web 100 comprises the first layer 630A and the second layer 630B. Where the forming elements 612 are heated, melt additive bloom areas 690 and 695 may be provided at the distal end of the nested tuft 632. Specifically, the melt additive area 695 may be provided on the first nested tuft 632A, and the melt additive area 590 may be provided on the second nested tuft 632B. Where the corresponding recesses 614 are also heated, the melt additive areas 690 and 695 may extend toward the neck 650 of the nested tuft 632. As shown, the nested tuft 632 may extend in the negative Z-direction (away from a user of a disposable absorbent article). In such forms, the melt additive areas 590 and 595 may comprise a hydrophilic composition to facilitate liquid acquisition. For those forms where the nested tuft 632 extends in the positive Z-direction (toward a user of a disposable absorbent article) the melt additive areas 590 and 595 may comprise a hydrophobic composition to reduce the likelihood of rewet and/or increase the masking of any liquid induced stains in the disposable absorbent article. Forms of the present invention are contemplated where the melt additive bloom area 595 comprises a hydrophobic composition while the melt additive area 590 comprises a hydrophilic composition. Such forms may be useful where the nested tufts 632 are configured as shown with regard to FIGS. 6L-6N. In such forms, the second layer 630B may have access to liquid insults due to the disruption in the first layer 630A. So, the hydrophilic composition may facilitate liquid acquisition while the hydrophobic composition of the melt additive bloom area 595 may provide adequate masking and reduction of rewet characteristics.

The nested tufts 632 of the present invention may be utilized in conjunction with the tunnel tufts, outer tufts, filled tufts, apertures, and/or embossments described herein.

Corrugations

Figure 7A:
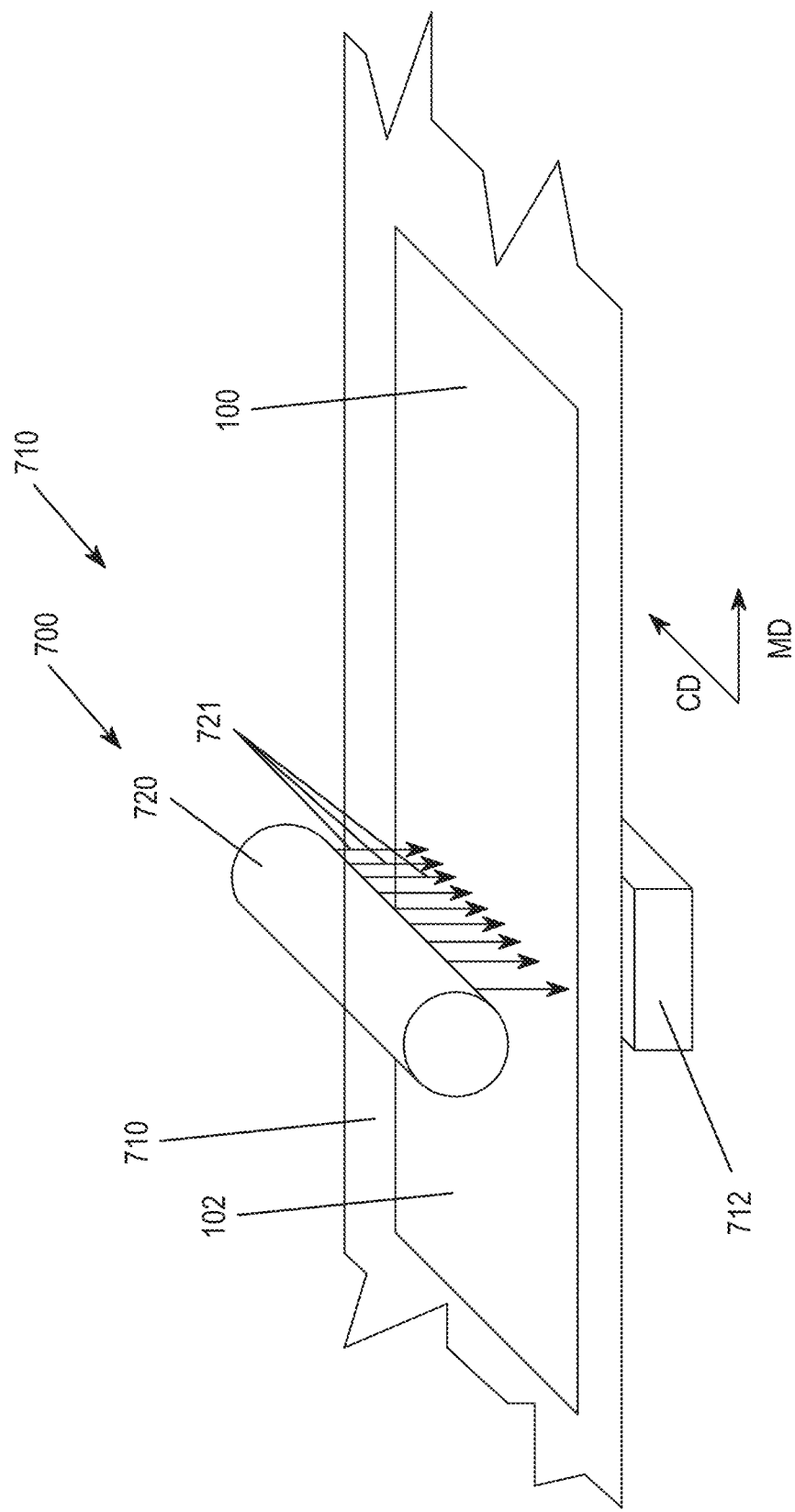
FIG. 7A is a schematic representation of an exemplary process for producing the material webs of the present disclosure.

Another example of a first unit operation 140 (shown in FIG. 2) that may be utilized in conjunction with the present invention is shown in FIGS. 7A-7E. As shown in FIG. 7A, the material web 100 of the present invention may be created, in some forms via apparatus 700. The precursor web 102 is provided to a running belt 710 which has air-permeability in its thickness direction. The running belt 710 runs in the MD as shown. In some forms of the present invention, the precursor web 102 may subjected to a plurality of air jets 721 from a manifold of nozzles 720. The plurality of air jets 721 blast the precursor web 102 with a plurality of air streams which are sucked through the running belt 710 via a suction box 712. The plurality of air streams provided by the plurality of air jets 721 heave the precursor web 102 in the CD direction so that the precursor web 102 can be formed with ridges between adjacent air jets 721. Additional description regarding the creation of corrugations can be found in U.S. Pat. Nos. 6,458,447; 7,270,861; 8,502,013; 7,954,213; 7,625,363; 8,450,557; 7,741,235; US Patent Application Publication Nos. US2003/018741; US2009/0240222; US2012/0045620; US20120141742; US20120196091; US20120321839; US2013/0022784; US2013/0017370; US2013/013732; US2013/0165883; US2013/0158497; US2013/0280481; US2013/0184665; US2013/0178815; US2013/0236700; PCT Patent Application Publication Nos. WO2008/156075; WO2010/055699; WO2011/125893; WO2012/137553; WO2013/018846; WO2013/047890; and WO2013/157365.

Subsequent to the blasting of the precursor web 102 with air streams, the material web 100 may comprise a plurality of corrugations. Some exemplary corrugations are shown in FIGS. 7B-7E. As shown, the material web 100 of the present invention may comprise corrugations 770 which can extend in a direction generally parallel to the MD or generally parallel to the CD. The corrugations 770 may comprise any suitable shape. For example, as shown, the corrugations 770 may have an arcuate shape. As another example, the corrugations 770 may comprise a triangular shape. Regardless of the shape of the corrugations 770, may comprise—similar to their tuft counterparts—a distal end 754 and sidewalls 756 extending from a groove 775. Additionally, examples are contemplated where a nonwoven web constructed in accordance with the present invention comprises at least one ridge having an arcuate shape and one ridge comprising a triangular shape.

As noted above, the air streams which impact the precursor web 102 are heated. And as the corrugations 770 form between adjacent air streams, the air streams form the grooves 775 of the material web 100. The heat associated with the air streams can create melt additive blooms in the material web 100. For example, still referring to FIGS. 7B-7E, melt additive bloom areas 790 may be provided in the grooves 775 of the material web 100. Where the distal ends 754 are oriented in the positive Z-direction (facing toward a user of a disposable absorbent article) the melt additive areas 790 may comprise a hydrophilic composition. Where distal ends 754 are oriented in the negative Z-direction (facing away from a user of a disposable absorbent article) the melt additive areas 790 may comprise a hydrophobic composition.

Additional forms of the present invention are contemplated where the corrugations 770 comprise a melt additive bloom area in addition to the melt additive bloom area 790 in the grooves 775. For such forms, the suction box 712 may comprise discrete heated portions which correspond to the distal ends 754 of the material web 100.

Figure 15:
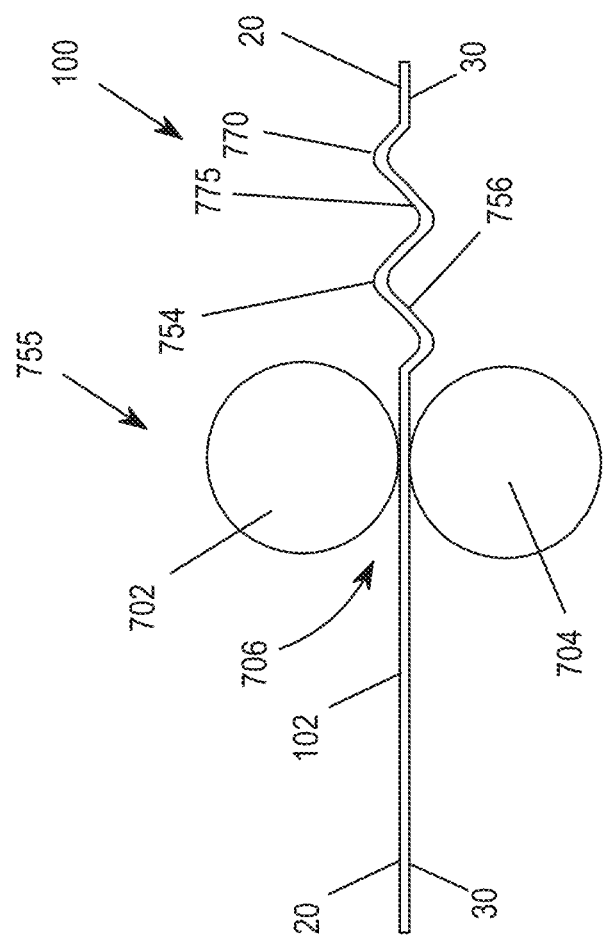
FIG. 15 is a schematic side view of an exemplary process for deforming the material web and providing corrugations therein.

The utilization of corrugations 770 may provide softness benefits to the material web 100. Additionally, the material web 100 may have higher permeability in the corrugations 770. The utilization of corrugations may be done in conjunction with apertures, embossments, outer tufts, tunnel tufts, and/or nested tufts described herein. Referring to FIG. 15, in some forms, an apparatus 755 may be utilized in addition to the apparatus 700. In such forms, corrugations in both the MD and CD may be provided to the material web 100. Or, in some forms, the apparatus 755 may be utilized independently of the apparatus 700 to provide corrugations in the MD and CD on the material web 100.

Figure 16:
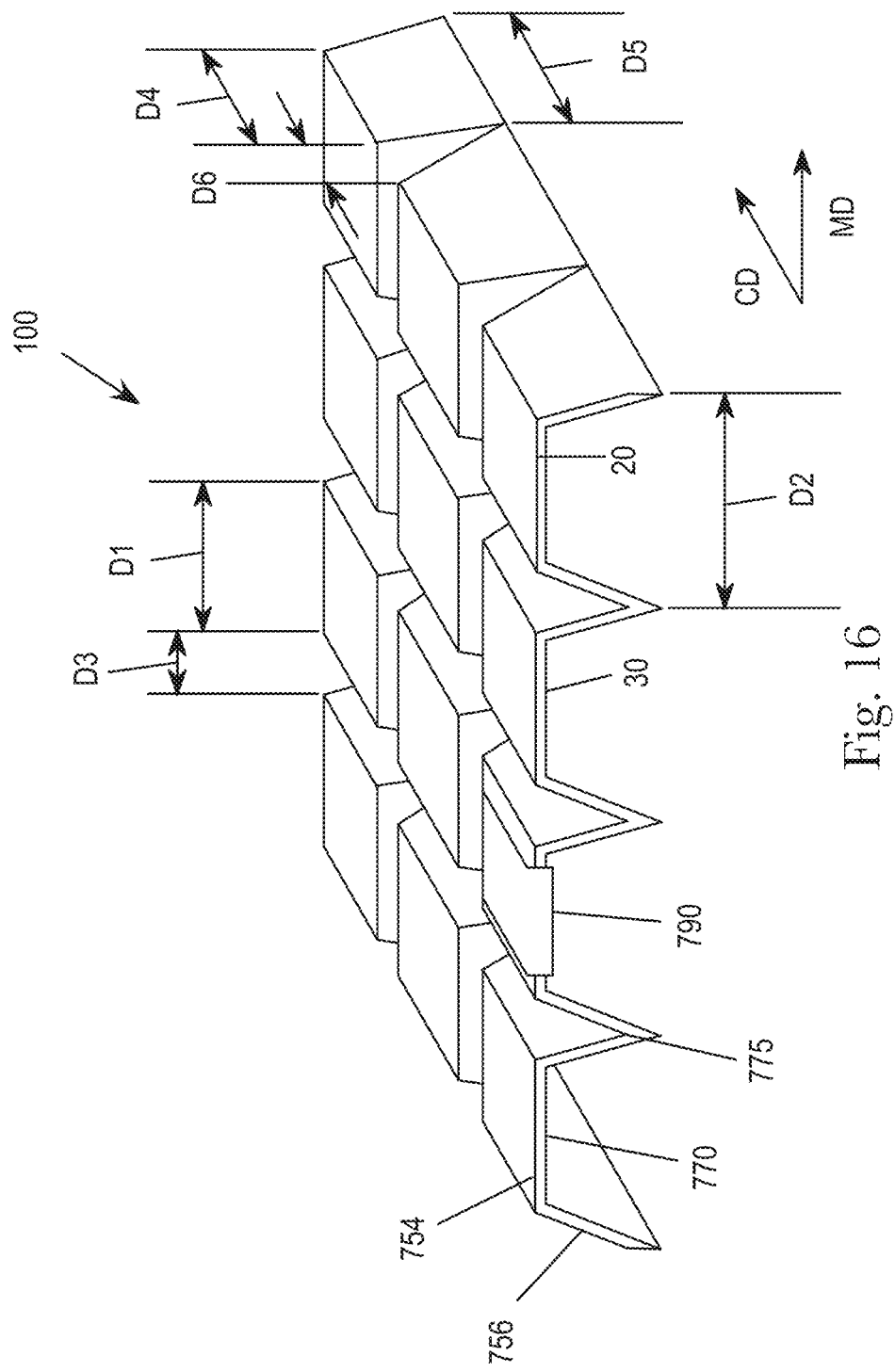
FIG. 16 is an isometric view of an exemplary material web derived from the process of FIG. 15.

As shown, the precursor material 102 may be provided to a nip 706 between intermeshing rolls 702 and 704. The intermeshing rolls 702 and 704 may comprise a surfaces wherein each of the surfaces comprise concave and convex patterns, for example, as shown in FIG. 16 are formed. In such forms, tension is applied to the precursor web 102 during processing. The dimensions D1, D2, and D3 of the corrugations 770 correlate to the spacing of the concave/convex patterns on the rolls 702 and 704 in the MD. The dimensions D4, D5, D6 correlate to the concave/convex patterns on the rolls 702 and 704 in the CD. The concave and convex patterns on the rolls 702 and 704 are configured to mesh with each other such that the convex portions of roll 702 engage with the concave portions of roll 704 and vice versa. The density of the material web 100 at the sidewalls 756 can be changed by adjusting the depths and the like of the rollers 702 and 704 as needed.

In some forms, the roll 702 and/or 704 may be selectively heated. For example, as shown, the convex portion of roll 704 may be heated to provide melt additive bloom areas 790 on the distal ends 754 of the corrugations. In some forms, the corresponding concave portions of roll 702 may also be heated to provide the melt additive bloom areas 790 on the distal ends 754 of the corrugations. The heating of the convex portions of roll 704 and/or the concave portions of roll 702 may also provide the melt additive bloom area 790 on the sidewalls 756 of the corrugations 770.

In other forms, the convex portions of roll 702 may be heated to provide melt additive bloom areas in the grooves 775 between adjacent corrugations. The concave portions of the roll 704 may similarly be heated to facilitate the creation of the melt additive bloom areas in the grooves. The heating of the convex portions of the roll 702 and/or the concave portions of the roll 704 may also provide melt additive bloom areas on the sidewalls 756 of the corrugations 770. Forms of the present invention are contemplated where only a portion of the distal ends 754 comprise a melt additive bloom area 790.

Referring to FIGS. 22A through 22D, in some forms, an apparatus 2200 may be utilized to create corrugations in the precursor web 102. The apparatus 2200 of the present invention which comprises a single pair of counter-rotating, intermeshing rolls 2202, 2204 that form a single nip N therebetween. As shown in, the first roll 2202 comprises a plurality of grooves 2210 and ridges 2220 and a plurality of staggered, spaced-apart teeth 2230 extending outwardly from the top surface 2222 of the ridges 2220. The configuration of the roll 2202 is such that the top surface 2222 of the ridges 2220 is disposed between the tips 2234 of the teeth 2230 and the bottom surface 2212 of the grooves 2210, directionally relative to the axis A of the roll.

As shown, the second roll 2204 comprises a plurality of grooves 2240 and ridges 2250. The grooves 2240 have a bottom surface 2242 and the ridges 2250 have a top surface 2252. Here, the distance between the top surfaces 2252 of the ridges 2250 and the bottom surfaces 2242 of the grooves 2240 is substantially the same around the circumference of the roll. The teeth 2230 and ridges 2220 of the first roll 2202 extend toward the axis A of the second roll 2204, intermeshing to a depth beyond the top 2252 of at least some of the ridges 2250 on the second roll 2204.

Teeth suitable for this process may be conducive to aperturing webs. The teeth on the rolls may have any suitable configuration. A given tooth can have the same plan view length and width dimensions (such as a tooth with a circular or square shaped plan view). Alternatively, the tooth may have a length that is greater than its width (such as a tooth with a rectangular plan view), in which case, the tooth may have any suitable aspect ratio of its length to its width. Suitable configurations for the teeth include, but are not limited to: teeth having a triangular-shaped side view; square or rectangular-shaped side view; columnar shaped; pyramid-shaped; teeth having plan view configurations including circular, oval, hour-glass shaped, star shaped, polygonal, and the like; and combinations thereof. Polygonal shapes include, but are not limited to rectangular, triangular, pentagonal, hexagonal, or trapezoidal. The side-walls of the teeth may taper at a constant angle from the base to the tip, or they may change angles. The teeth may taper towards a single point at the tooth tip, like that shown in FIG. 22A. The teeth can have tips that are rounded, flat or form a sharp point. In some forms, the tip of the tooth may form a sharp vertex with at least one of the vertical walls of the tooth (for example, the vertical walls on the leading and trailing ends of the teeth so the teeth aperture or puncture the web. In some forms, each tooth may form 2 apertures, one at the leading edge and one at the trailing edge of each tooth.

Figure 23:
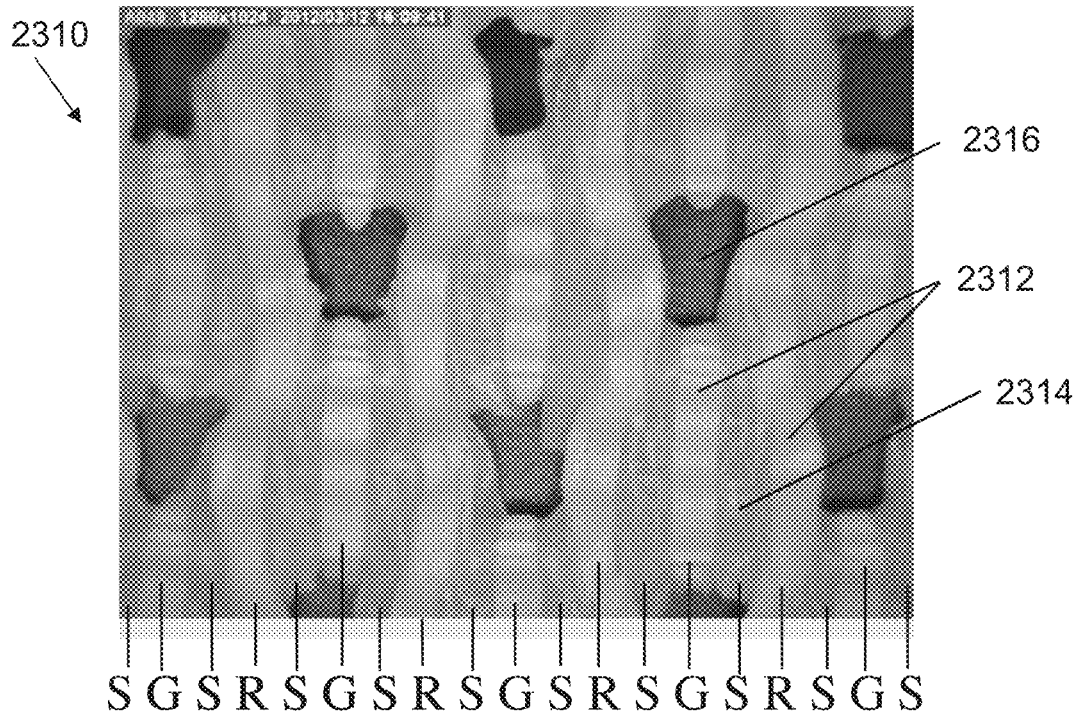
FIG. 23 is a top view of a 25 gsm polyethylene film web (film is stretched/flattened out to show high and low basis weight regions).

The apparatus 2200 can deform the precursor web creating alternating regions of higher and lower caliper, and alternating regions of higher and lower basis weight, with the higher caliper and higher basis weight regions being located in the tops of the ridges and bottoms of the grooves, and the regions with lower caliper and lower basis weight located in the sidewalls in-between. FIG. 23 is a top view of a 25 gsm polyethylene film web 2310 (film is stretched/flattened out to show high basis weight regions 2312 and low basis weight regions 2314). Web 2310 further shows ridges R, grooves G, and sidewalls S. Apertures 2316 are present in the grooves G. As apparent, the high basis weight regions 2312 are located in the ridges R and grooves G, whereas the low basis weight regions 2314 are located in the sidewalls S.

Figure 24:
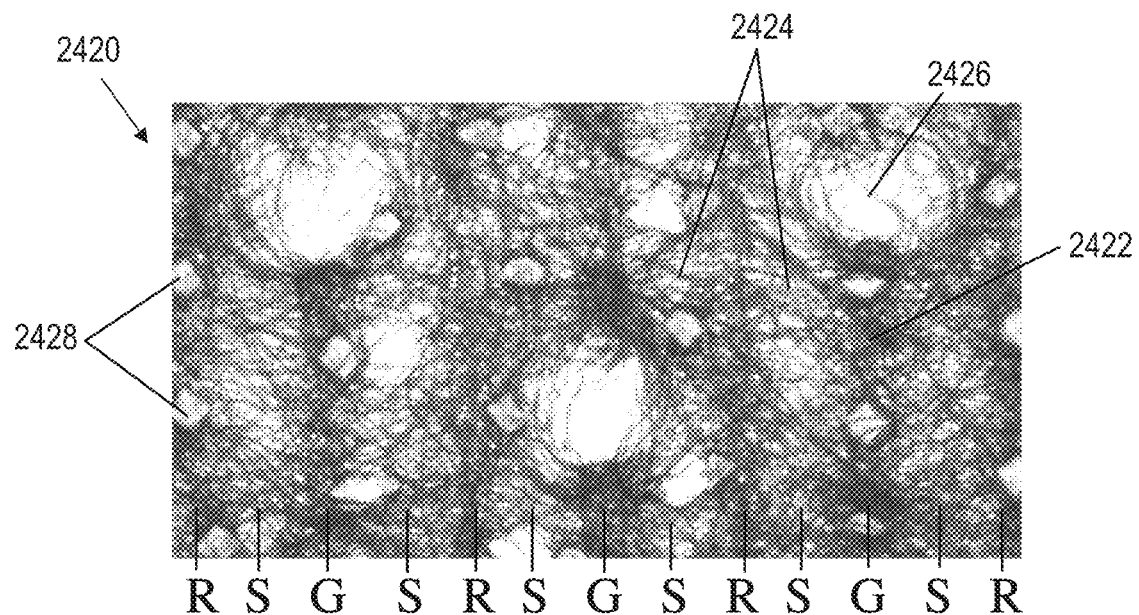
FIG. 24 is a top view of a 60 gsm polypropylene nonwoven web (nonwoven is stretched/flattened out to show high and low basis weight regions).

In the case of a nonwoven, the basis weight is also decreased in the stretched areas, again resulting in a web with alternating regions of higher and lower basis weight, with the higher basis weight regions located in the tops of the ridges and bottoms of the grooves, and the lower basis weight regions located in the sidewalls in-between. FIG. 24 is a top view of a 60 gsm polypropylene nonwoven web 2420 (nonwoven is stretched/flattened out to show high basis weight regions 2422, and low basis weight regions 2424). Web 2420 further shows ridges R, grooves G, and sidewalls S. Apertures 2426 are present in the grooves G. Thermal or fusion bond points 2428 may be present in various locations on the web 2420. As apparent, the high basis weight regions 2422 are located in the ridges R and grooves G, whereas the low basis weight regions 2424 are located in the sidewalls S. In the case of a nonwoven, the web thickness may not decrease in the stretched regions because the fibers may detangle and move away from each other. However, the thickness of some of the individual fibers may decrease as a result of the stretching. Note that the "regions" of the web used to characterize basis weight exclude the apertures themselves.

Figure 25:
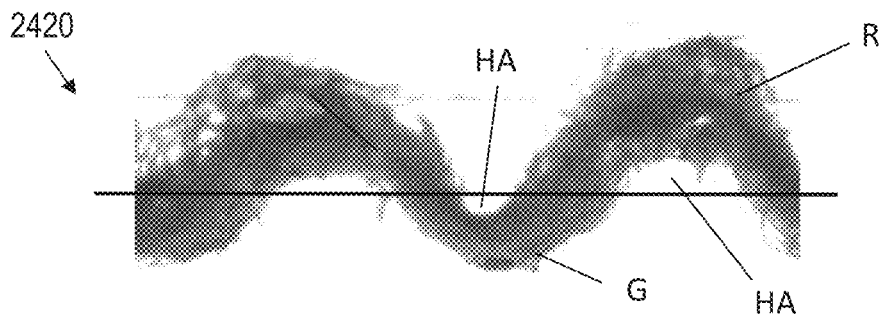
FIG. 25 is a cross-section view of the web shown in FIG. 24.
Figure 26:
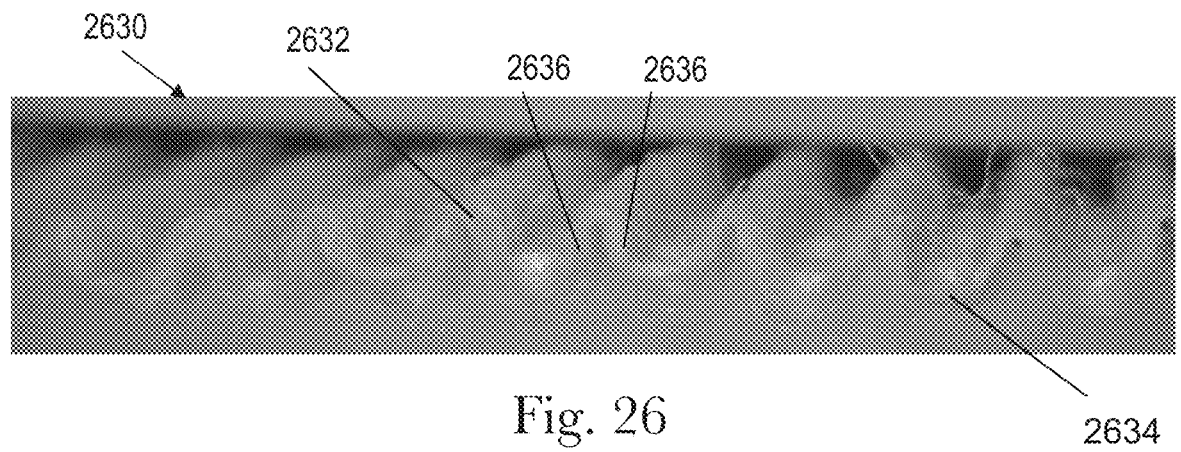
FIG. 26 is side perspective view of another nonwoven web.
Figure 27:
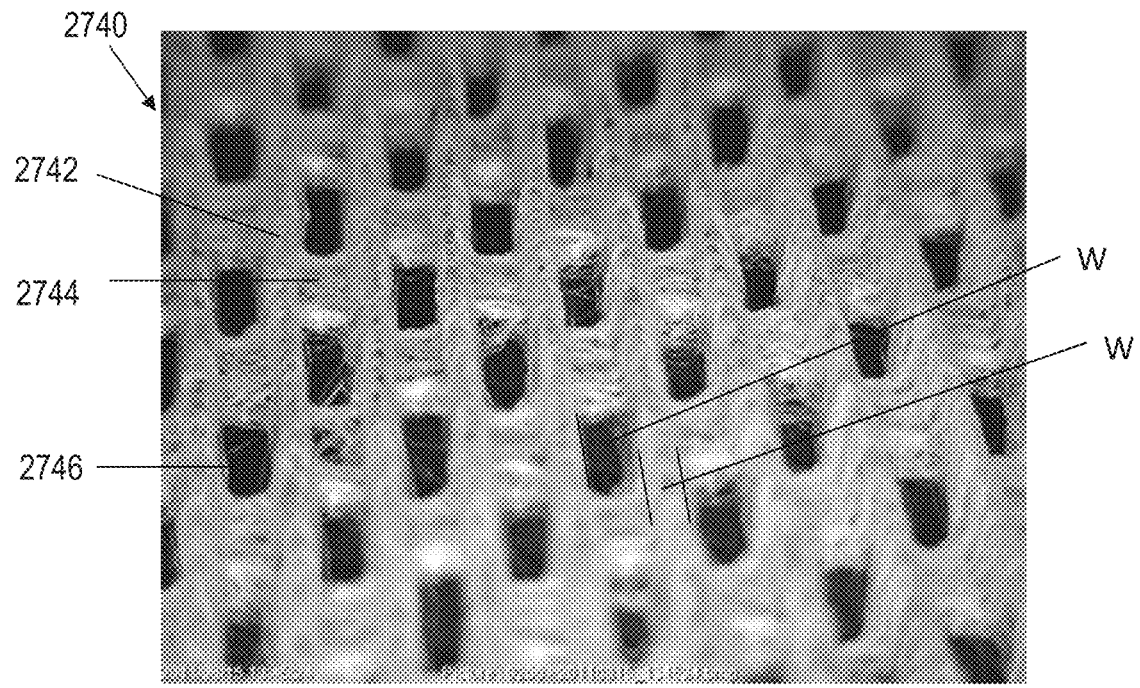
FIG. 27 is a top perspective view of another nonwoven web.

FIG. 25 is a cross-section view of the web 2420 shown in FIG. 24 showing ridges R, grooves G, and axis X drawn horizontally through a cross-section of the web; the area above the X axis but under the top of the ridge is hollow, or comprises a hollow area HA. Likewise, the area below the X axis but above the bottom of the groove is hollow, or comprises a hollow area HA. Suitably, the web thickness at the tops of the ridges and the web thickness at the bottoms of the grooves are similar. The web thickness at the tops of the ridges and the web thickness at the bottoms of the grooves may be similar to the web thickness at the sidewalls. By similar, it is meant that the thicknesses are within about 60% of one another. Or, the web thickness at the tops of the ridges and the web thickness at the bottoms of the grooves is greater than the web thickness at the sidewalls. FIG. 26 is side perspective view of another nonwoven web 2630 having ridges 2632, grooves 2634, and sidewalls 2636. FIG. 27 is a top perspective view of 28 gsm polyethylene/polypropylene bico nonwoven web 2740 comprising ridges 2742 and grooves 2744 and apertures 2746 wherein the aperture width $W_a$ is greater than the ridge width $W_r$.

Webs made by the processes and apparatuses described herein may comprise ridges that run discontinuously across a deformed zone, or, ridges that run continuously across a deformed zone. To create such apertured web materials, the rolls used may comprise zones of ridges and grooves. Or, the rolls can have zones where the ridges are different heights, thereby creating differing depth of engagement (DOE), differing depth below the raised ridge, and thus apertures with differing widths and open areas. Alternatively or in addition, the rolls may comprise different zones, wherein ridge heights are different in different zones.

Referring back to FIGS. 22A-22D, forms of the present invention are contemplated where the rolls 2202 and/or 2204 are heated. For example, the spaced-apart teeth 2230 may be heated. In such forms, the apertures formed (the outer periphery thereof) may comprise a corresponding melt additive bloom area. In such forms, the melt additive bloom area may comprise a hydrophilic composition. As another example, the ridges 2220 may be heated. In such forms, the grooves of the material web 100 may comprise a corresponding melt additive bloom area. In such forms, particularly where the material web 100 forms a portion of a topsheet of an absorbent article, where the grooves are oriented away from a user of the absorbent article, the melt additive bloom areas may comprise a hydrophilic composition.

In some forms, the second roll 2204 may be heated. For example, the ridges 2250 of the second roll 2204, particularly the top surface 2252, may provide the material web 100 with melt additive bloom areas which correspond to the ridges on the material web 100. In such forms, the melt additive bloom areas may comprise a hydrophobic composition. In such forms, particularly where the material web 100 forms a portion of a topsheet of an absorbent article, where the ridges are oriented toward the wearer of the absorbent article. In such forms, the material web 100 can provide masking benefits to liquid insults.

Figure 30A:
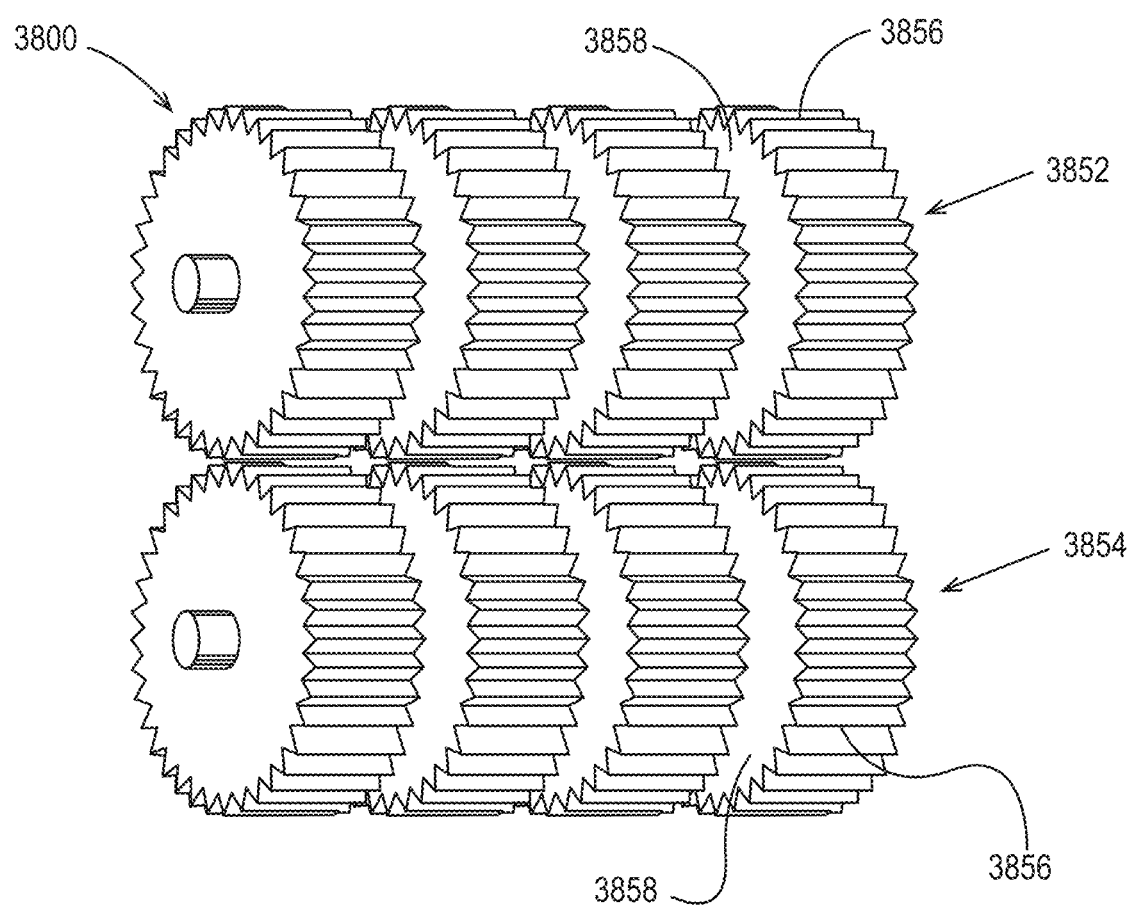
FIG. 30A is an isometric view showing an apparatus for creating corrugations in a material web of the present disclosure.
Figure 30B:
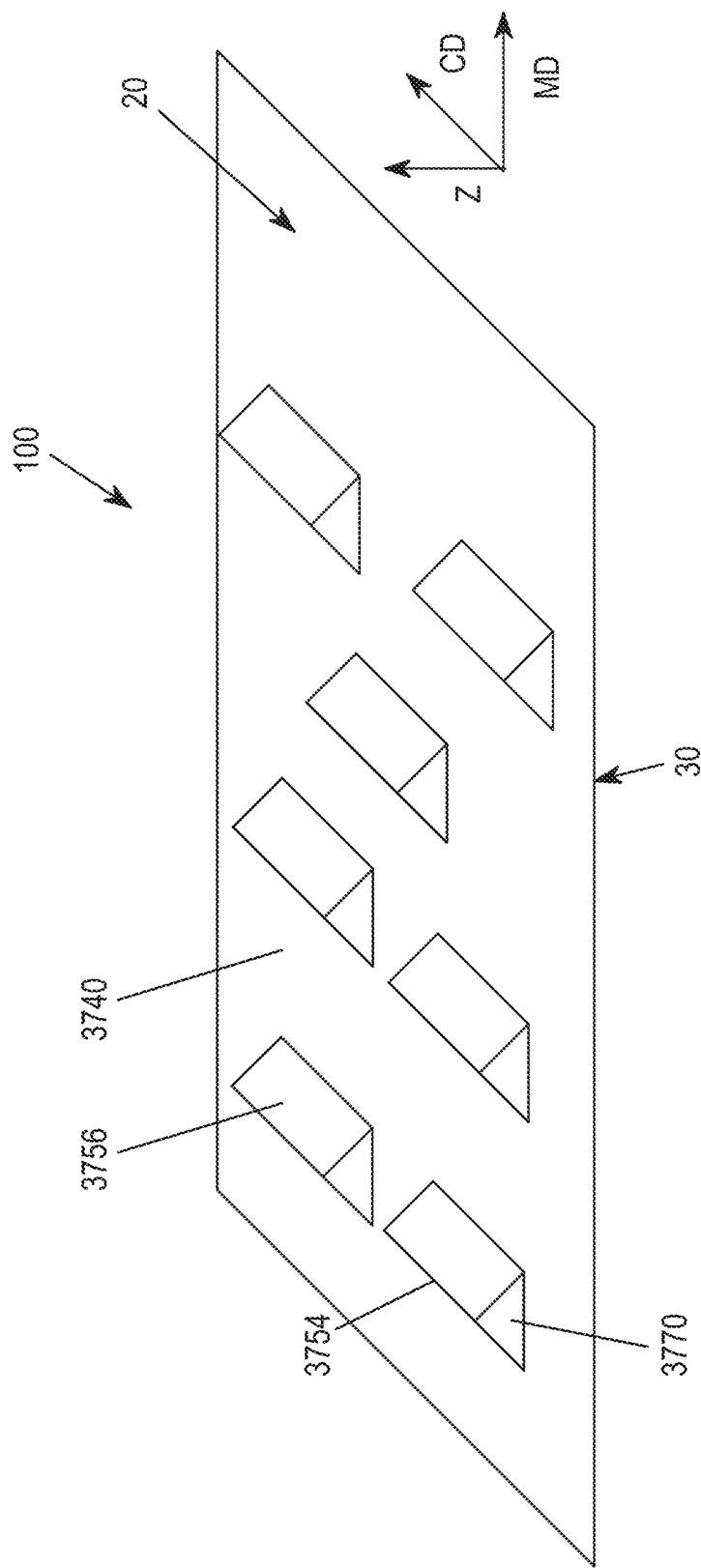
FIG. 30B is an isometric view showing an exemplary material web with corrugations in accordance with the present disclosure.
Figure 30C:
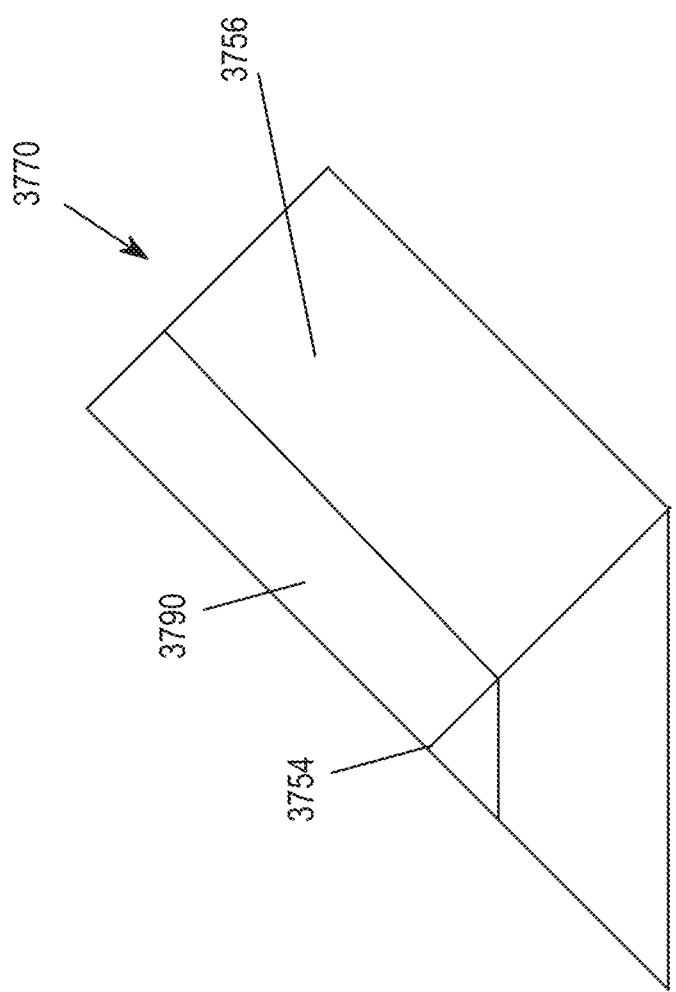
FIG. 30C is a close up view of a corrugation of the material web of FIG. 30B.

Still in other forms of the present invention, the material web 100 may comprise rib like elements 3770 (corrugations) shown in FIG. 30B. The corrugations 3770 comprise a major axis and a minor axis defining an elongated cubical, ellipsoidal or other similar rib-like shape. The major axis and the minor axis of the corrugations 3770 may each be linear, curvilinear or a combination of linear and curvilinear. Each of the corrugations 3770 comprises a distal end 3754 and sidewalls 3756 extending from the generally planar first surface 20. Forms of the present invention are contemplated where the material web 100 comprises an undeformed first region 3740.

Referring now to FIGS. 30A and 30B, the first and second regions of the material web 100 may be formed from a precursor web that is substantially planar. Said starting precursor web cab be fed through that apparatus 3800 which forms the corrugations 3770 of the material web 100 in predefined areas resulting in corrugated second regions of the material web and undeformed regions 3740 of the material web 100. As shown, apparatus 3800 includes a pair of rolls 3852 and 3854. Rolls 3852 and 3854 each have a plurality of toothed regions 3856 and grooved regions 3858 extending about the circumference of rolls 3852 and 3854 respectively. As the starting precursor web passes between 3852 and 3854, the grooved regions 3858 will leave portions of the precursor web unformed, while the portions of the precursor web passing between toothed regions 3856 will be formed producing the corrugations 3770. To lock constituent material of the material web 100 in the second regions of the material web 100, the rolls 3852 and 3854 may be heated. In some forms, one of the rolls 3852 and 3854 may be heated.

Where the rolls 3852 and/or 3854 are heated, the corrugations may comprise melt additive bloom areas 3790. The melt additive bloom areas 3790 may be disposed in the distal ends 3754 of the corrugations. Additionally, the melt additive bloom areas 3790 may extend along the sidewalls 3756 as well. In some forms, the melt additive bloom area 3790 may extend the entirety of the sidewalls 3756. In some forms, the material web 100 may be utilized as a topsheet of an absorbent article. In such forms, where the distal ends 3754 are oriented in the positive Z-direction, the melt additive bloom areas 3790 may comprise a hydrophobic melt additive. In such forms, the hydrophobic melt additive may provide good masking of liquid insults. Additionally, in such forms, the hydrophobic melt additive may reduce the likelihood of rewet by liquid insults. Where the distal ends 3754 are oriented toward an absorbent core of the disposable absorbent article, the melt additive bloom areas 3790 may comprise a hydrophilic composition. In such forms, the hydrophilic composition can improve liquid acquisition.

Instead of rolls, plates may be utilized to create the corrugations 3770. In such forms, teeth of one or more of the plates may be heated such that at least a portion of the corrugation may be provided with a corresponding melt additive bloom area 3790. Processes for forming the corrugations 3770 are discussed in additional detail in U.S. Patent Application Publication No. 2004/0137200.

Fusion Bonds

Still another exemplary process which may be utilized as a first unit operation 140 (shown in FIG. 2) is a process that can provide fusion bonding to an absorbent article. The distinction between embossments (discussed with regard to FIGS. 4A and 4B) and fusion bonding is that generally, embossing does not result in the fusion of layers.

Figure 8A:
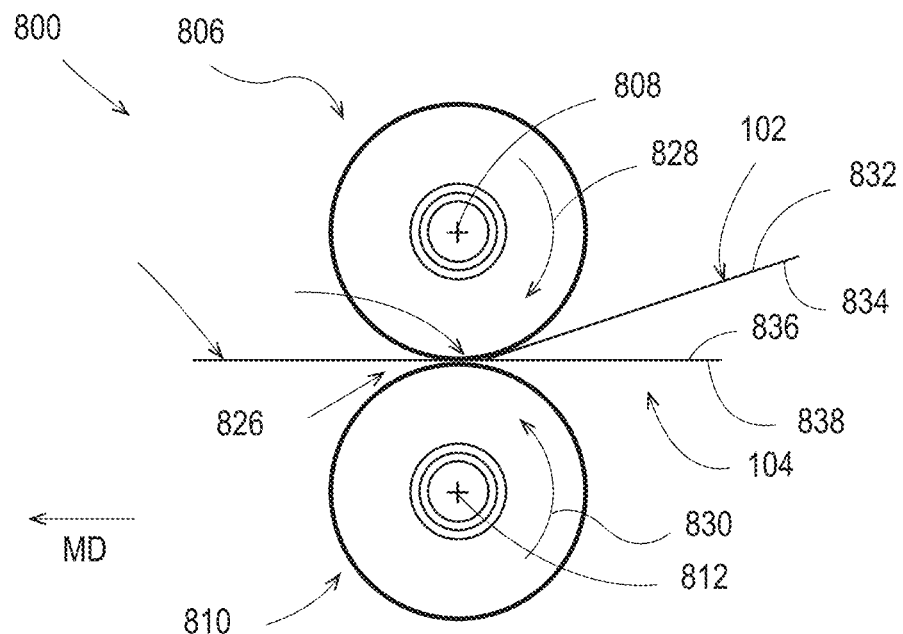
FIGS. 8A-8B are schematic representations of an exemplary process for producing the material webs of the present disclosure.
Figure 8B:
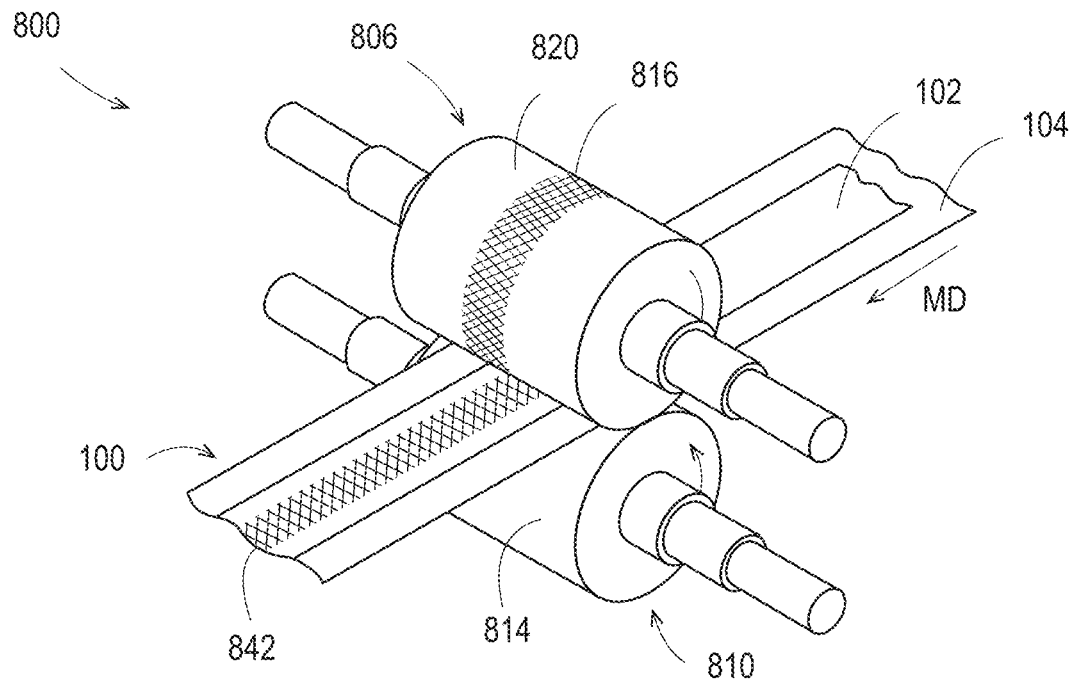

FIGS. 8A and 8B show an exemplary bonding apparatus 800 that may be used to bond the precursor material 102 and a second substrate 104 together to form the material web 100. The bonding apparatus 800 may include a bonding roll 806 adapted to rotate around an axis of rotation 808, and an anvil roll 810 adapted to rotate around an axis of rotation 812. The anvil roll 810 includes an outer circumferential surface 814 which is preferably smooth. Bonding roll 806 includes a base circumferential surface 820, from which one or more bonding elements, or nubs 816 extend. The bonding roll 806 is adjacent the anvil roll 810 so as to define a nip 826 between the bonding roll 806 and the anvil roll 810, and more particularly, to define the nip 826 between the bonding surface of each nub 816 and the anvil roll 810. It is to be appreciated that the bonding roll 806 and the anvil roll 810 may be configured to rotate such that the bonding surfaces on the bonding roll 806 and the outer circumferential surface 814 of the anvil roll 810 move at the same speeds or different speeds.

During the bonding operation, the bonding roll 806 may rotate in a first direction 828 around the axis of rotation 808 of the bonding roll 806, and the anvil roll 810 may rotate in a second direction 830, opposite the first direction 828, around the axis of rotation 812 of the anvil roll 810. The precursor material 102 and second substrate 104 may advance in a machine direction MD between the bonding roll 806 and the anvil roll 810. As shown, the precursor material 102 includes a first surface 832 and a second surface 834 opposite the first surface 832, and the second substrate 104 includes a first surface 836 and a second surface 838 opposite the first surface 836. As such, the first surface 832 of the precursor material 102 is contacted by the bonding roll 806, and the second surface 838 of the second substrate 104 is contacted by the anvil roll 810. And the second surface 834 of the precursor material 102 and the first surface 836 of the second substrate 104 contact each other. As the precursor material 102 and second substrate 104 advance through the nip 826 between the bonding surface of a nub 816 and the anvil roll 810, the nub 816 contacts the precursor material 102 and compresses the precursor material 102 and second substrate 104 between the bonding surface of the nub 816 and the anvil roll 810. In turn, heat generated by the nip pressure causes the precursor material 102 and second substrate material to yield. The bonding surface of the nubs 816 presses yielded material of the precursor material 102 and second substrate 104 together to form a plurality of discrete bond sites 842 between the precursor material 102 and second substrate 104. Thus, the apparatus 800 may form the material web 100 which includes the precursor material 102 and the second substrate 104 bonded together by discrete bond sites 842, without the use of adhesives. It is to be appreciated, however, that the bonding apparatus 800 may also be used in combination with adhesives. Although FIG. 8A shows the apparatus 800 bonding two substrates together, it is to be appreciated that the apparatus may bond more than two substrates together. In addition, it is to be appreciated that the apparatus 800 may also be used to bond fibers of nonwoven together on a single substrate. The anvil roll and bonding roll may or may not be heated. Additionally, forms of the present invention are contemplated where the precursor material 102 is fed to the nip 826 of the apparatus 800 in place of the second substrate 104 and the second substrate 104 is fed to the nip 826 of the apparatus 800 in place of the precursor material 102.

Figure 8C:
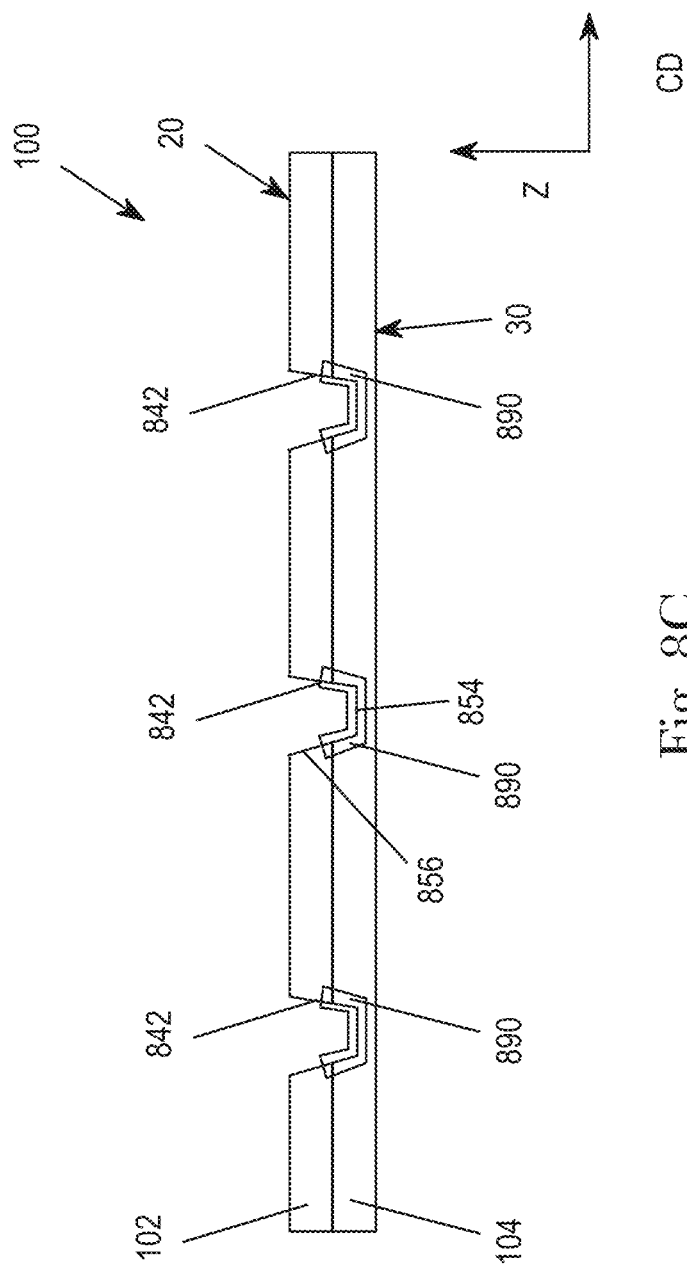
FIG. 8C is a cross-sectional view showing a material web in accordance with the present disclosure.

As shown in FIG. 8C, the material web 100 may comprise a plurality of discrete bond sites 842 which bond the precursor material 102 to the second substrate 104. In some forms of the present invention, the bonding roll 806 (shown in FIG. 8A) and/or the forming elements 816 (shown in FIG. 8A) thereof may be heated. In such forms, the resultant material web 100 may comprise melt additive bloom areas 890. The melt additive bloom areas 890 are exaggerated for ease of explanation.

As shown, the melt additive bloom areas 890 may be provided in a distal end 854 of the discrete bond site 842 and on a portion of sidewalls 856 of the discrete bond sites 842. In such forms, the melt additive bloom areas 890 may comprise a hydrophobic composition. Where the material web 100 is utilized as a topsheet of a disposable absorbent article, the hydrophobic composition of disposed in the discrete bond sites 842 can reduce the likelihood that liquid insults stay in the bond site 842. As such, the hydrophobic composition can help provide a cleaner looking article even post liquid insult.

The utilization of discrete bond sites 842 may be done in conjunction with apertures, embossments, outer tufts, tunnel tufts, nested tufts, and/or corrugations described herein.

Distal End/Land Area Bonds

Still another exemplary process which may be utilized as a first unit operation 140 (shown in FIG. 2) is a process that can provide fusion bonds on the distal ends of tufts (including tunnel, nested, outer), on land areas adjacent the tufts, on ridges and on grooves. The localized fusion bonding of these discontinuities can provide for melt additive bloom areas where the fusion bonds occur.

Figure 9A:
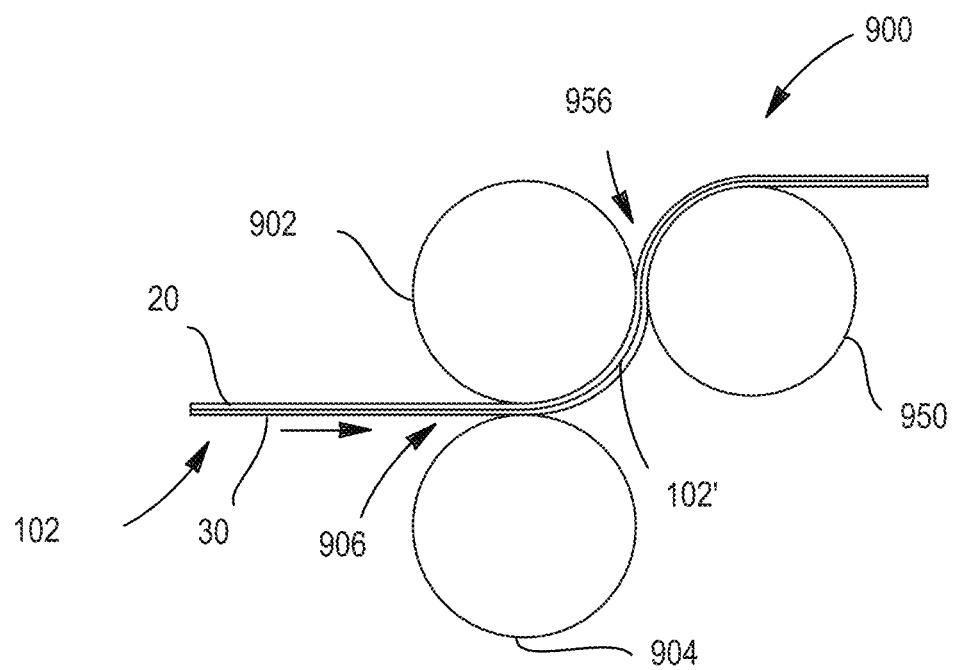
FIG. 9A is a schematic side view of an exemplary process for forming the material web which includes an additional roll for tip bonding discontinuities in the material web.

FIG. 9A shows an apparatus 900 for deforming the material web which includes an additional bonding roll 950 for bonding the distal ends (554 shown in FIGS. 5B, 5C and 5G-5J; 654 shown in FIGS. 6G-6I, 6O and 6P). As shown, the precursor web 102 is fed into a deforming nip 906 between first roll 902 and second roll 904. After leaving the deforming nip 906, the deformed precursor web 102' is wrapped partially around the first roll 902. Vacuum, hold down belts, or some other mechanism may be used to keep the deformed precursor web 102' seated on the first roll 902. While the deformed precursor web 102' is still in contact with the first roll 902, the deformed precursor web 102' passes through a second nip 956 between first roll 902 and the additional bonding roll 950. The additional bonding roll 950 can compress the fibers at the distal ends 554 and 654 of the tufts 530, 570, 572 (shown in FIGS. 5B, 5C and 5G-5J) and tufts 632 (shown in FIGS. 6G-6I, 6O and 6P) sufficient to partially melt and bond the fibers at this location together. The bonding roll 950 may be heated to help facilitate bonding. Alternatively, ultrasonics could be used to facilitate bonding. In the case of at least some of the precursor materials described herein, the materials can be bonded together if the bonding roll 950 surface temperature is between about 120° F. (about 50° C.) and about 270° F. (about 130° C.). Upon exit of the second nip 956, the material web may wrap the bonding roll 950 as shown in FIG. 28, or it may wrap the first roll 902.

Referring to FIGS. 5A-5J and 9A, in some forms, the first roll 902 may be configured as described heretofore with regard to roll 504. As noted above, with the addition of heat to the bonding roll 950, the first roll 902 and/or second roll 904 may not need to be heated to provide a melt additive bloom area at the distal ends 554 of the tufts 530, 570, or 572.

Referring to FIGS. 6A-6P and 9A, in some forms, the first roll 902 may be configured as described heretofore with regard to roll 602. As noted above, with the addition of heat to the bonding roll 950, the first roll 902 and/or second roll 904 may not need to be heated to provide a melt additive bloom area at the distal ends 654 of the tufts 632.

As shown in 9B, the process of FIG. 9A produces a tuft in which the layers are bonded together at the tops (or distal ends 954) of the tufts 970. With the above in mind, tufts 970 may be configured as described heretofore with regard to the tufts 530, 570, 572 (shown in FIGS. 5A-5J) or tufts 632 (shown in FIGS. 6A-6P). The process described in FIG. 9B will form a tip bonded portion 952. The tip bonded portion 952 will often differ in at least one of: size (that is, they may be larger), shape, and location from any thermal point bonds present in spunbonded nonwoven layers. The tip bonded portion 952 will typically be registered with the tuft 970 in the material web 100, while thermal point bonds may be provided in a separate and different pattern. The tip bonding may result in a more translucent (film-like) bonded portion 952. Placing a layer containing color adjacent to the tuft 970 could result in color showing through primarily in the translucent bonded portion 952, highlighting the tuft 970. For those forms where the material web 100 comprises a single layer or integrated strata of nonwoven material, the tip bonded portion 952 may bond the constituent fibers of the material web 100 and may be configured as described above.

As noted above, the bonding roll 950 may apply heat during the bonding process. In such forms, a melt additive bloom area may correspond to the tip bonded portion 952. Without wishing to be bound by any particular theory, it is believed that bonding material web 100 at the distal ends 954 of the tufts 970 may provide benefits which include: 1) increased perception of the depth of base openings 944 when the base openings 944 are oriented toward the consumer, as well as 2) improved dryness (by reducing the hang-up of fluid in the bottoms of the tufts 970 when the base openings 944 are oriented toward the consumer); and 3) reduction or elimination of the need to glue or otherwise bond the layers of a dual or multilayer precursor web 102 together.

In other forms of the present invention, an apparatus may bond the material web 100 adjacent the tufts 970—adjacent the base 50, 650 (shown in FIGS. 5B-5J and 6H, 60, and 6P, respectively, termed "base bonding". If the material web 100 is a single layer material, then this step will bond the fibers of the material web 100 together adjacent the bases 50, 650. If the deformed material web 100 is a dual or multiple layer nonwoven material, then this step will bond the fibers of each layer together adjacent the base 50, 650 and will also bond fibers in each of the layers together adjacent the base 50, 650.

Figure 10:
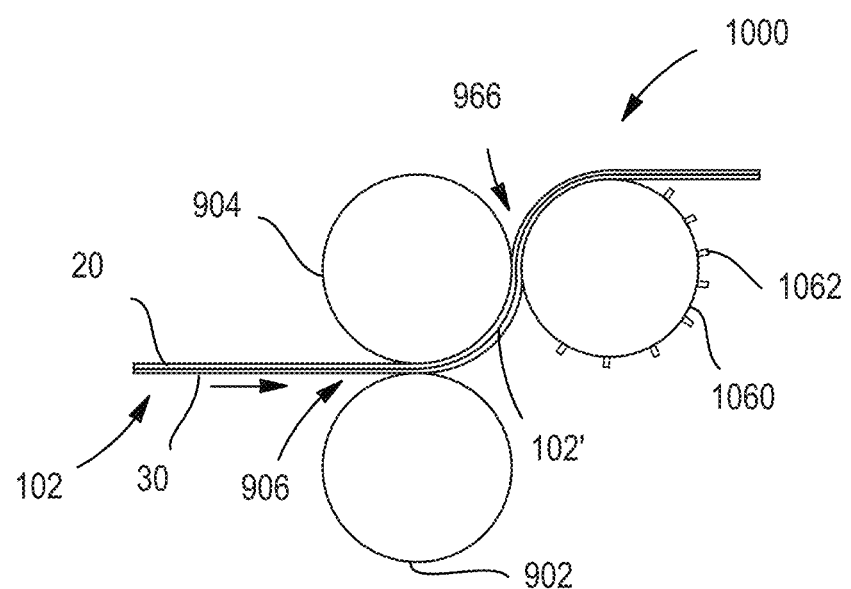
FIG. 10 is a schematic side view of an exemplary process for forming the material web which includes an additional roll for base bonding the material web.

Another exemplary process for the first unit operation 140 (shown in FIG. 2) is shown with regard to FIG. 10. An apparatus 1000 for deforming the material web 100 which includes an additional bonding roll 1060 for base bonding the deformed material web 100 is shown. The position of first and second rolls 902 and 904 from FIG. 9A are reversed. As shown, the precursor web 102 is fed into the deforming nip 906 between first roll 902 and second roll 904. After leaving the deforming nip 906, the deformed precursor web 102' is wrapped partially around the second forming roll 904. Vacuum, hold down belts, or some other mechanism could be used to keep the deformed precursor web 102' seated on the second roll 904. While the deformed precursor web 102' is still in contact with the second roll 904, it passes through a second nip 966 between second roll 904 and the additional bonding roll 1060. The additional bonding roll 1060 can compress the fibers in the undeformed portions of the deformed precursor web 102' adjacent the bases 50, 650 sufficient to partially melt and bond the fibers at this location together. The bonding roll 1060 may be heated to facilitate bonding in the case of at least some of the precursor materials described herein. Ultrasonics may also be used to facilitate bonding. Upon exit of the second nip 966, the material web may wrap the bonding roll 1060 as shown in 10A, or it may wrap the second roll 904.

There are a number of variations of the roll configurations in the bonding step. The surface of the bonding roll 1060 may be substantially smooth or may comprise a plurality of bonding elements 1064. Similarly, the second roll 904 may comprise a smooth surface or may comprise a plurality of bonding elements 1062 (shown in FIGS. 13A and 13B).

Referring to FIGS. 11A and 11B, in those cases in which the surface of the bonding roll 1060 is substantially smooth, base bond portions 1068 may be at least substantially continuous and may substantially or completely surround the base opening 944 in the material web 100. FIG. 11A shows the material web 100 having continuous base bond sites 168. FIG. 11B is a cross-section of the material web 100 shown in FIG. 11A.

As shown in FIG. 12, in those cases in which the bonding roll 1060 or the second roll 904 have a plurality of discrete, spaced-apart bonding elements 1062 and 1064, respectively, protruding from their surfaces, the bonding elements will only bond discrete, spaced-apart regions of the material web 100 in adjacent the base 50 outside of the openings 944 and/or tufts 970. In such cases, the base bond portions 1068 may be located in at least two discrete portions of the material web 100 which are adjacent to but lie outside of at least some of the tufts 970. In other words, in such cases there may be at least two base bond portions 1068 for a given tuft 970.

Figure 13A:
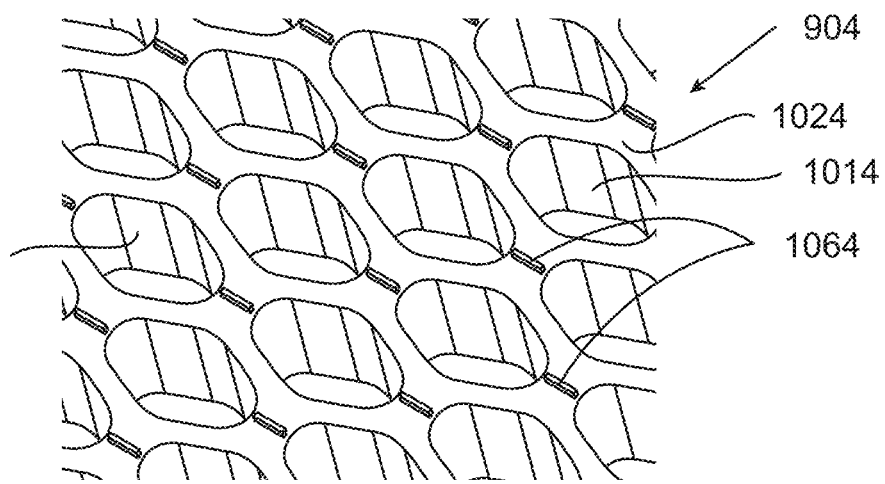
FIG. 13A is an enlarged perspective view of a portion of an exemplary roll having a plurality of discrete bonding elements on its surface.
Figure 13B:
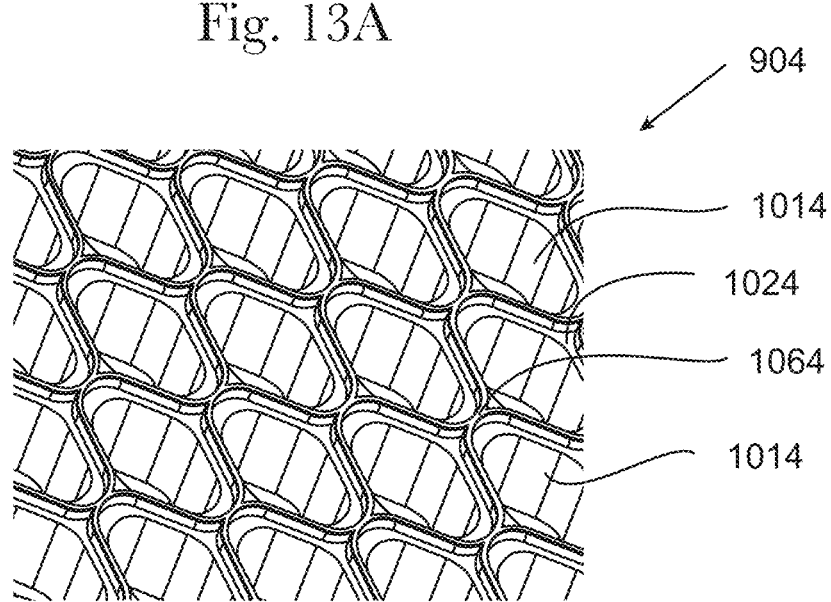
FIG. 13B is an enlarged perspective view of a portion of an exemplary roll having continuous bonding elements on its surface.
Figure 13C:
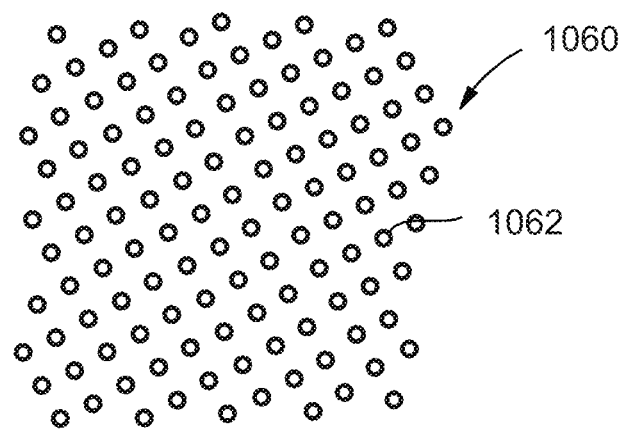
FIG. 13C is a plan view of a portion of the surface of an exemplary bonding roll with a plurality of discrete bonding elements thereon.

Referring to FIGS. 10, and 13A-13C, the bonding roll 1060 can have a plurality of discrete, spaced-apart bonding elements 1062 protruding from its surface as shown in FIG. 13C. In some forms, particularly with regard to nested tufts disclosed herein, the second roll 904 may be configured similarly to the roll 502 (shown in FIG. 5A) or female roll 604 (shown in FIG. 6A). In some forms, portions of the surface 1024 of the second roll 904 that are located outside of the recesses 1014 in the second roll 904 may also be substantially smooth, or they may have a plurality of discrete, spaced-apart bonding elements 1064 protruding from the surface 1024. The bonding elements 1064 on the surface 1024 of the female roll 904 may be discrete, spaced-apart bonding elements 1064 as shown in FIG. 13A, or they may be continuous bonding elements 1064 as shown in FIG. 13B.

As noted above, the bonding roll 1060 may apply heat during the bonding process. In such forms, a melt additive bloom area may correspond to the base bond portions 1068. In such forms, the melt additive bloom areas may be disposed adjacent the base opening 944 about the tuft 970. And, the melt additive bloom areas may comprise a plurality of discrete portions or may be continuous as shown in FIG. 11A.

Figure 14:
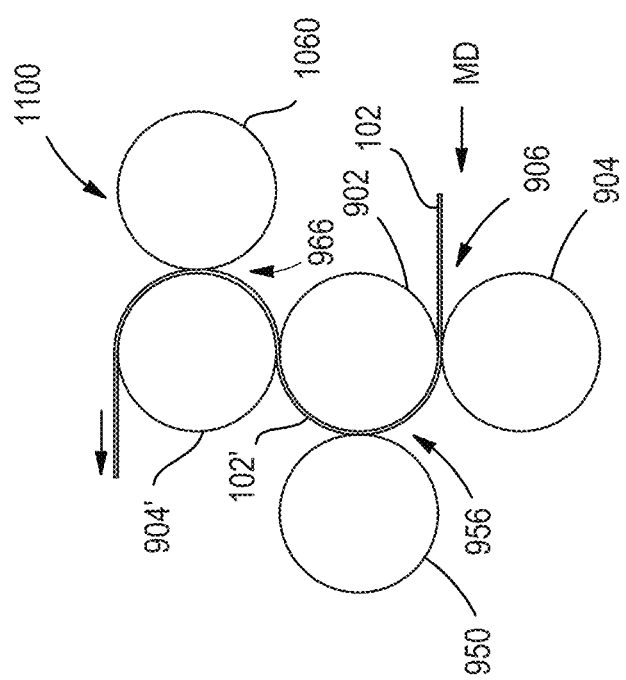
FIG. 14 is a schematic side view of an exemplary process for deforming the material web which includes additional rolls for tip bonding and base bonding the material web.

Still another apparatus for use as the first unit operation 140 (shown in FIG. 2) is provided with regard to FIG. 14. The apparatus 1100 is shown which can provide—referring back to FIGS. 9A and 11A-11B—both tip bonded portions 952 and base bonded portions 1068. As shown the apparatus 1100 may comprise rolls 902, 904, and 950 which comprise the tip bonding portion of the apparatus 1100, which is similar to the apparatus shown in FIG. 9A. FIG. 14 differs in that the precursor web 102 is shown as being fed into the deforming nip 906 from the right side in FIG. 14, instead of the left side, and the deformed precursor web 102' wraps around first roll 902 instead of bonding roll 950 after it leaves the deforming nip 906. Therefore, the description of this portion of the apparatus will incorporate the above description of the apparatus shown in FIG. 9A, and will not be repeated in its entirety herein.

The apparatus shown in FIG. 14 further comprises a second roll 904' and a base bonding roll 1060. The first roll 902, the second roll 904', and the base bonding roll 1060 comprise the base bonding portion of the apparatus, which is similar to the apparatus shown in FIG. 10. FIG. 14 differs in that the deformed precursor web 102' is shown as wrapping around the second roll 904' as it leaves the apparatus in FIG. 14, instead of wrapping around the base bonding roll 1060. Therefore, the description of this portion of the apparatus will incorporate the above description of the apparatus shown in FIG. 10, and will not be repeated in its entirety herein.

Figure 9B:
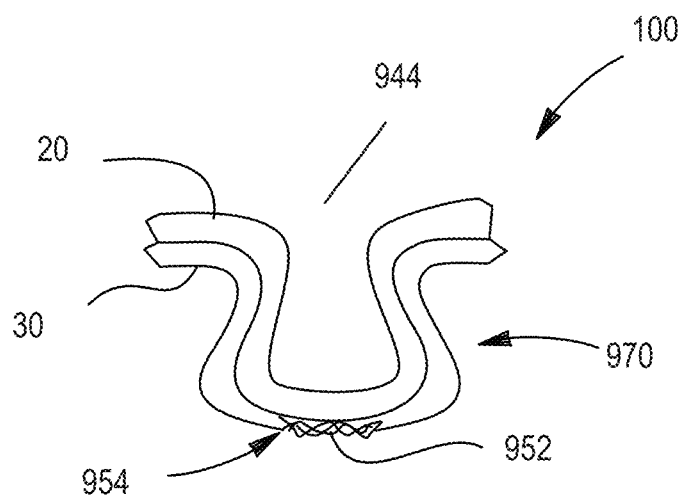
FIG. 9B is a schematic cross-sectional view of a tip bonded discontinuity (shown oriented downward) made by the apparatus shown in FIG. 9A.

As shown in FIG. 14, the precursor web 102 is fed into the deforming nip 906 between first forming roll 902 and second roll 904. After leaving the deforming nip 906, the deformed precursor web 102' is wrapped partially around the first roll 902. While the web 102' is still in contact with the first roll 902, it passes through a second nip 956 between first roll 902 and the additional bonding roll 950. The additional bonding roll 950 can compress the fibers at the distal ends 954 of the tufts 970 sufficient to partially melt and bond the fibers at this location together. Heat and/or ultrasonics may also be used to help facilitate bonding. As shown in FIG. 9B, this produces the tuft 970 in which the constituent material is bonded together at the tops (or distal ends 954) of the tufts 970. The deformed tip bonded web 102' then passes between first roll 902 and second female roll 904'. After that, the deformed tip bonded web 102' is wrapped partially around the second female roll 904'. While the web 102' is still in contact with the second female roll 904', it passes through a second nip 966 between the second female roll 904' and the additional bonding roll 1060. The additional bonding roll 1060 can compress the fibers adjacent the bases 50 of the tufts 970 sufficient to partially melt and bond the fibers at this location together. Heat and/or ultrasonics may also be used to help facilitate bonding. This will provide the tip bonded web with base bonds 1068 which may be continuous as shown in FIG. 11A, or discrete as shown in FIG. 12.

Referring back to FIGS. 9A-14, the addition of heat to the rolls described above can provide melt additive bloom areas which correspond to the tip bond 952 and/or the base bonds 1068. In some forms, the melt additive bloom areas may comprise a hydrophobic composition and may correlate to the tip bonds 952. In such forms, particularly where the material web 100 comprises a topsheet of an absorbent article and where the distal ends 954 of the tufts are facing toward a user, the hydrophobic composition can provide masking of liquid insults to an absorbent article. In other forms, where the material web 100 comprises a topsheet of an absorbent article and where the distal ends 954 are facing away from a user, the melt additive bloom areas may comprise a hydrophilic composition. In such forms, the hydrophilic composition can reduce the liquid insult acquisition time.

Additional Processes

Still other examples of first unit operations 140 (shown in FIG. 2) comprise infrared heating and/or ultrasonic heating. With such forms, portions of the material web 100 for which no melt additive bloom area is desired would require shielding of some kind, e.g. reflective foil or protective mask. However, forms of the present invention are contemplated where the infrared heating is applied via a laser or a plurality thereof. Such forms may obviate the need for shielding since the thermal energy provided by infrared laser can be applied with a high degree of accuracy to the material web 100. As such, any suitable pattern of melt additive bloom areas may be provided.

As an example, a material web that is apertured can be exposed to ultrasonic and/or laser energy. In such forms, melt additive bloom areas may be provided over the majority of the material web with the exception of the apertures. Such forms, may be useful as a topsheet of a disposable absorbent article, particularly when the melt additive bloom areas comprise a hydrophobic composition. In other forms, a material web may comprise one or more of the discontinuities described herein, apertures, embossments, tunnel tufts, outer tufts, filled tufts, nested tufts, ridges, grooves, etc. In such forms, the material web may be exposed to ultrasonic and/or laser energy. In such forms, melt additive bloom areas may be provided over the majority of the material web with the exception of the apertures. Where the material web is utilized as a topsheet of a disposable absorbent article, the melt additive bloom areas may comprise a hydrophobic composition. Such forms, may be useful in reducing the likelihood of rewet while the addition of apertures can allow for adequate liquid acquisition time.

Additionally, forms are contemplated, as discussed previously, where the material web comprises multiple layers or strata. In such forms, an upper layer or strata may comprise a hydrophobic melt additive while a subjacent layer or strata may comprise a hydrophilic melt additive. In such forms, the application of ultrasonic and/or laser energy to the material web, can provide disparate melt additive bloom areas in the upper layer or strata versus the lower layer or strata. In such forms, the discontinuities comprising tufts, e.g. outer tufts, tunnel tufts, filled tufts, nested tufts, corrugations may provide good reduction in the likelihood of rewet while also providing good liquid acquisition properties.

Figure 21:
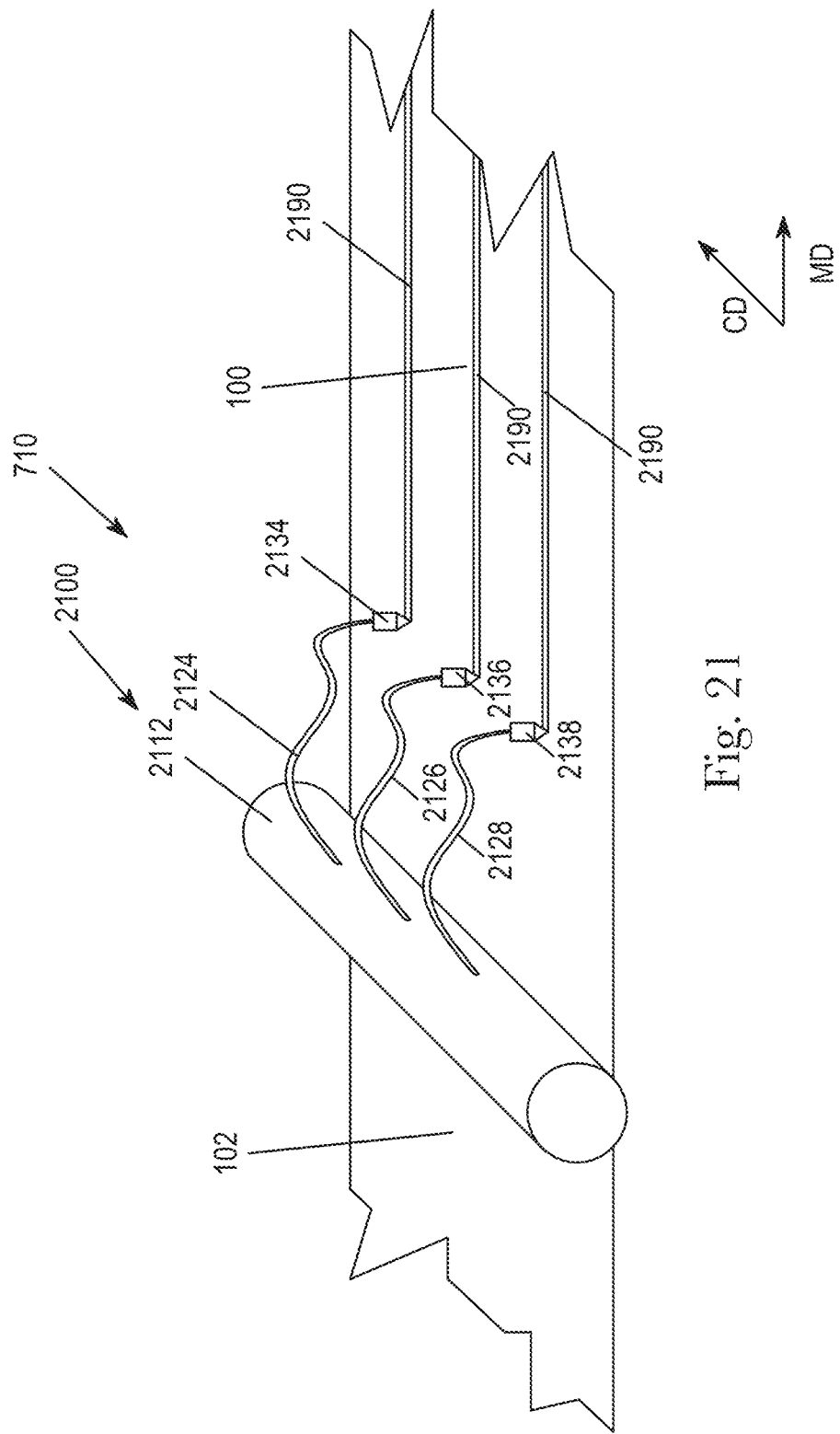
FIG. 21 is an isometric view of an exemplary process for manipulating the material web of the present disclosure.
Figure 22A:
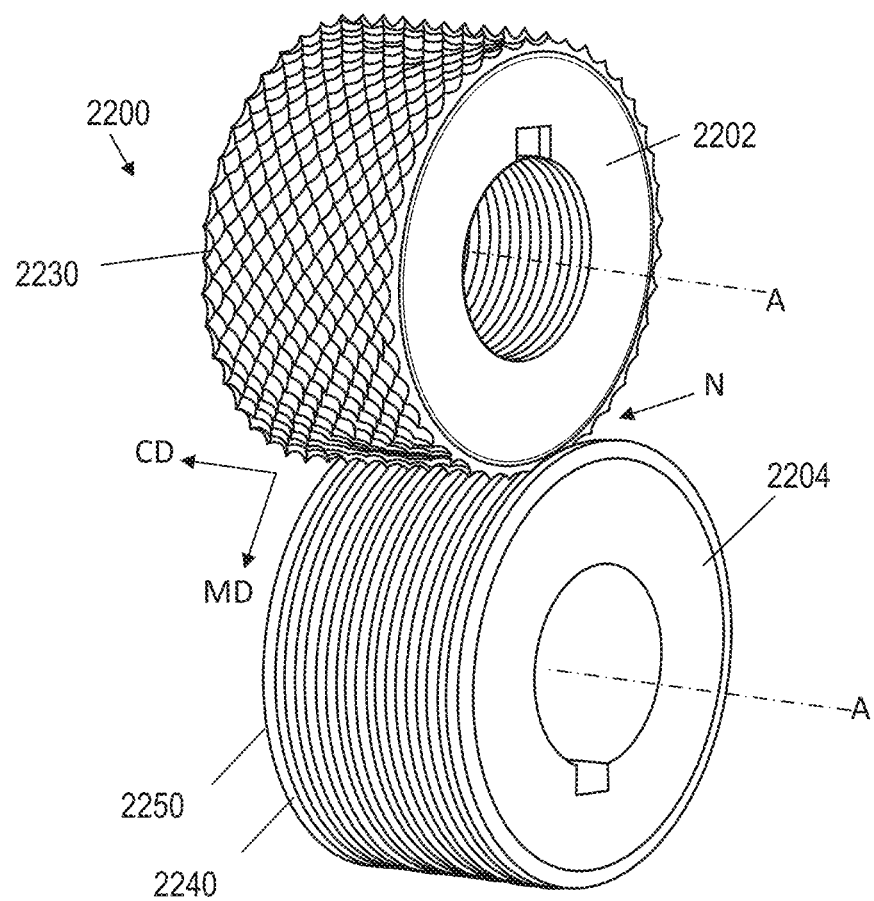
FIG. 22A is an isometric view of an exemplary process for manipulating the material web of the present disclosure.
Figure 22B:
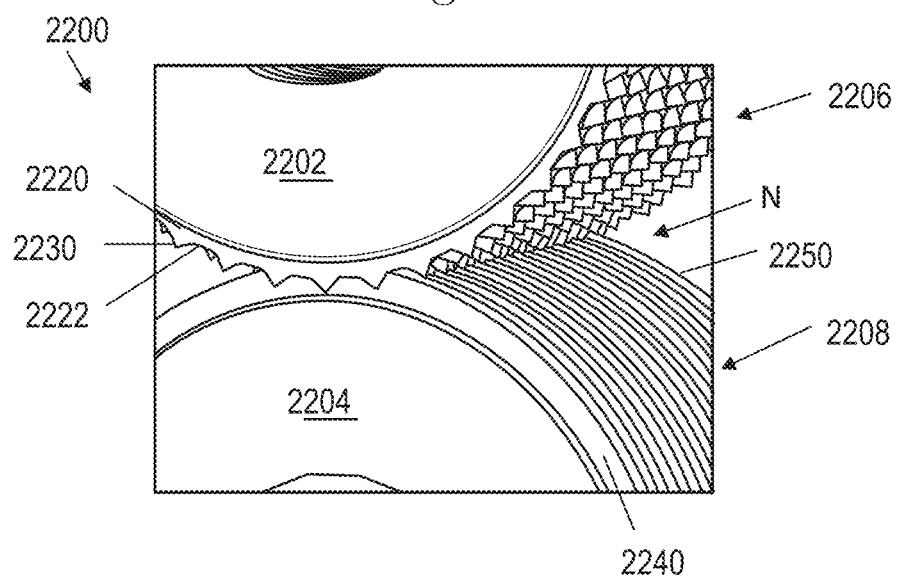
FIG. 22B is a close up view of a pair of rolls shown in FIG. 22A.
Figure 22C:
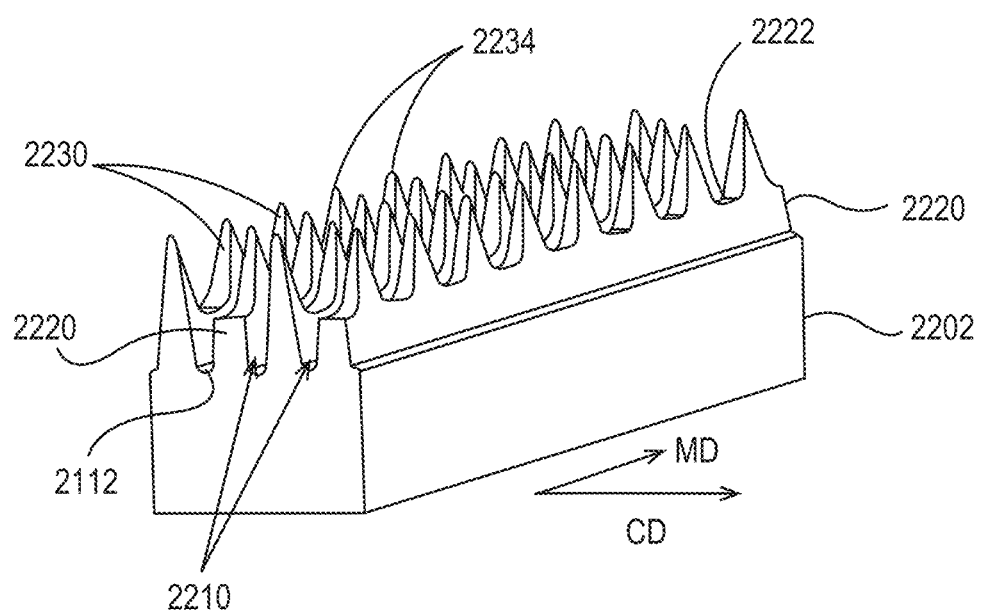
FIG. 22C is a close up view showing an exemplary configuration of one of the rolls shown in FIG. 22A.
Figure 22D:
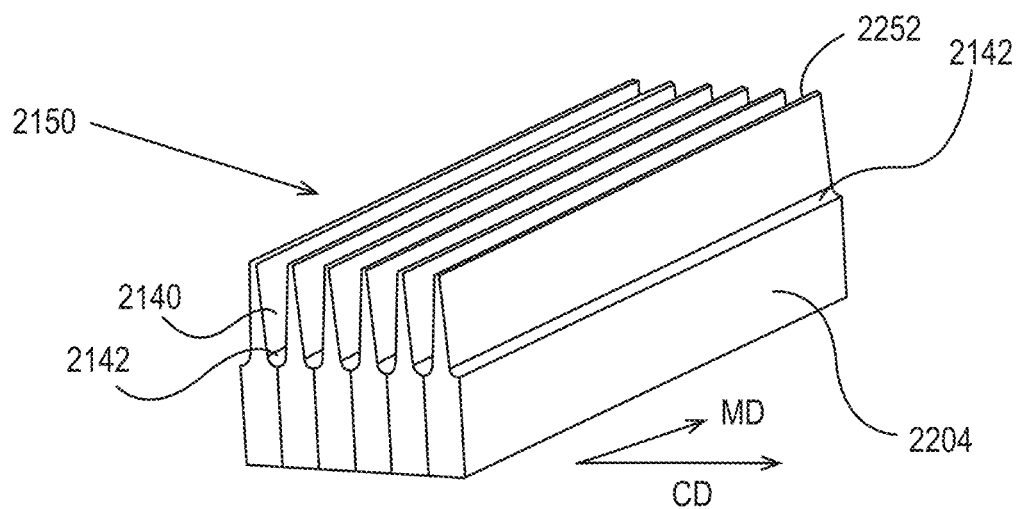
FIG. 22D is a close up view showing an exemplary configuration of the other of the rolls shown in FIG. 22A.

Another example of a process which can be utilized in the first unit operation 140 (shown in FIG. 2) is a hot air knife. Referring to FIG. 21, hot air knifes may be utilized to provide a plurality of melt additive bloom areas 2190 to the material web 100. As shown, an apparatus 2100 comprising a header 2112 which is supplied with hot air through an inlet. The hot air supplied to the header 2112 may have a temperature of about 200-550° F., more generally about 250-450° F., most commonly about 300-350° F. The optimum temperature will vary according to the polymer type, basis weight and line speed of the material web 100 traveling beneath the apparatus 2100. For a polypropylene spunbond web having a basis weight of about 0.5-1.5 osy, and traveling at a line speed of about 1000-1500 feet per minute, a hot air temperature of about 300-350° F. is desirable. Generally, the hot air temperature should be at or near (e.g., slightly above) the melting temperature of the material being bonded.

The air flow rate may be controlled by controlling the pressure inside the header 2112. The air pressure inside the header 12 is between about 1-12 inches of water (2-22 mm Hg) or between about 4-10 inches of water (8-18 mm Hg). The volume of hot air required to effect the desired level of inter-fiber bonding may be reduced by increasing the temperature of the hot air.

Extending from the header 2112 are three spaced apart hot air conduits 2124, 2126, and 2128. The conduits may be rigid or flexible, but are preferably made of a flexible material in order to permit adjustment and/or movement. The conduits are each connected at one end to the header 2112, and are connected at their other ends to a plenum/hot air knife slot 2134, 2136, and 2138. Hot air from the header 2112 is preferably supplied at roughly equal volume and velocity to each of the conduits 2124, 2126, and 2128. This equal division of flow can be accomplished in simple fashion, by ensuring that the conduits are of equal dimensions and size and that the air pressure is uniform at the entrances to the conduits. On the other hand, if a particular application warranted feeding more or less air into some of the conduits than the others, different flow rates can be accomplished by individually valving the conduits, by designing them with different sizes, or by valving the plenums.

As the precursor web 102 passes under the plenum/hot air knife slots 2134, 2136, and 2138, a stream of heated air at a very high flow rate, generally from about 1000 to about 10000 feet per minute (fpm) (305 to 3050 meters per minute), is directed at the precursor web 102. As noted above, the air is heated to a temperature insufficient to melt the polymer in the precursor web 102 but sufficient to soften it slightly. The focused stream of air is arranged and directed by at least one slot of about 3 to 25 mm in width, particularly about 9.4 mm, serving as the exit for the heated air towards the precursor web 102.

The application of heated air to the precursor web 102 as described above can increase bonding between constituent fibers of the precursor web 102—for those forms where the precursor web 102 is a nonwoven. Additionally, the application of heated air to the precursor web 102 can provide the material web 100 with a plurality of melt additive bloom sites 2190. The melt additive bloom sites 2190 may correspond to the width of the hot air knife slots which discharge the hot air that impacts the precursor web 102. As shown, the melt additive bloom areas 2190 may be provided to the material web 100 in a plurality of stripes. Forms of the present invention are contemplated where one or more hot air knife slots are provided which span the entire width of the precursor web 102 in the CD. In such forms, the melt additive bloom areas provided to the material web 100 may be across the width of the material web 100 in the CD.

Additional details regarding the use of hot air knifes is provided in U.S. Pat. Nos. 5,707,468 and 6,066,221.

Thermal Energy Application Across the Entire Web

In contrast to the aforementioned processes which can create discrete melt additive bloom areas, as noted previously, in some forms, it may be beneficial to provide melt additive bloom areas across the entirety the material web. In such forms, any suitable method of thermal energy application may be utilized.

Some examples include the use of microwave (radio frequency) radiation. This approach is particularly powerful if a salt solution (e.g. potassium acetate in poly ethylene glycol) has been sprayed onto the surface of the material web. The radiation will then let the ions of the salt vibrate, which causes friction, which causes heat. Ultrasonic may also be used alternatively. In one specific example, if hydrophobic melt additives are used to make carded nonwovens, the heat exposure of the carding process can be leveraged (hot air oven of 160° C. at a comparably long contact time of 1-2 s).

And, combining both on-line heating and tempering can synergistically increase the effect. An optimized heat activation step (highly effective in line heat insertion, e.g. via IR dryer) can be translated into further usage reduction and/or better performance.

The heat application of the aforementioned processes may be applied as part of the making process, directly after spinning of the fibers and laydown of the web—as part of the bonding process (via a heated calendar) or a subsequent step (e.g. drum dryer or, most effectively, infrared heater). In this case typically high temperatures can be applied. An exposure in the seconds or even mili seconds range may be sufficient depending on the composition of the material web. Additionally, the amount of thermal energy required to promote melt additive blooming depends on whether the application of thermal energy is performed within a short period of time after formation of the material web. For material webs which are subjected to thermal energy application immediately subsequent to production, a lower amount of thermal energy may be required to promote melt additive blooming as opposed to material webs which were not subjected to thermal energy application subsequent to formation.

Alternatively the heat activation can be done via tempering of the final material web over several days, e.g. 30 days. It has been found that for the Techmer glycerol tristearate Masterbatch that the temperature window for such tempering can be between about 30 to less than about 52° C. (as of 52° C. the glycerol tristearate fibrils will melt again) between about 32° C. to about 50° C., between about 35° C. to about 47° C., between about 37° C. to about 45° C., specifically including all values within these ranges and any ranges created thereby. In some forms, a temperature of 37° C. Tempering can be done with fresh samples (not more than a few hours after making). Older samples may require additional thermal energy input.

Melt Additive Bloom Areas

Referring to back FIG. 1, as stated previously, the precursor web 102 and therefore the material web 100 of the present invention comprise a melt additive. And as described herein, with the appropriate application of heat to the precursor web 102 and/or material web 100, one or more melt additive bloom areas may be provided to the material web 100. The melt additive bloom areas described herein may be in the form of a film, flakes, fibrils, or combinations thereof. For example, where the material web 100 comprises a nonwoven material, the melt additive bloom areas can bloom to the surface of the filaments of the nonwoven and create a film covering a portion of the external surface of the filament and/or can create fibrils, flakes, particles, and/or other surface features. Some examples of fibrils, flakes and films are provided with regard to FIGS. 28A-29B.

However, the inventors have also found that care must be taken when processing material webs particularly when discrete melt additive bloom areas are desired. Many nonwoven webs are calendar bonded to provide strength in the CD. The calendar bonding process is often a heated process which adds thermal energy to the web as it is bonded. Subsequently, the web is often rolled up for storage. But, such storage provides insulation for the thermal energy from the calendar bonding process. So, instead of melt additive bloom areas that are discrete, these webs often have melt additive boom areas well outside of the areas of applied localized thermal energy. Other processes which impart thermal energy to the material web may experience the same type of effect is rolled and stored. To counteract such heat diffusion in the material web, when not desired, chilled rolls may be utilized to cool the material web after the calendar bonding process or other thermal processes. Each of Examples 2-4 demonstrate this aspect of material webs which comprise melt additives and are subjected to calendar bonding.

The above phenomena can be even more prevalent in bi-component fibers/filaments. For example, where melt additive is provided in the sheath of sheath-core bi-component fibers/filaments, the diffusion length for the melt additive in the sheath will be shorter than the diffusion length for mono-component fibers. This phenomena is demonstrated with Examples 35 and 36 below. Each of these webs was subjected to calendar bonding and subsequently would up.

EXAMPLES

Exemplary material webs in accordance with the present disclosure were produced. The material webs were dual layer constructions. The upper layer was 25 gsm polypropylene 1/polypropylene 2 ("$PP_1/PP_2$") crimped fiber spun bond comprising a hydrophobic melt additive which was 16 percent by weight glycerol tristearate master batch (Techmer PPM15000) in both polypropylene components. The lower layer was 25 gsm $PP_1/PP_2$ crimped fiber spun bond comprising 0.4 percent by weight topical surfactant Silastol PHP26. The two layers were overbonded together (see FIGS. 3A and 3B) in a center zone and then stretched (see FIGS. 3A and 3C) to create apertures in the center and tufts on the sides. The upper and lower layers were then fusion bonded to secondary topsheet, thereby forming a laminate. The images shown in FIGS. 28A-29B are of the unmodified fibers in the upper layer (wrinkled surface), fusion bond sites (showing fibrils) and melt lips around the apertures (also showing fibrils). The presence of fibrils implies a higher concentration of the hydrophobic melt additive of the first layer at the surface.

Figure 28A:
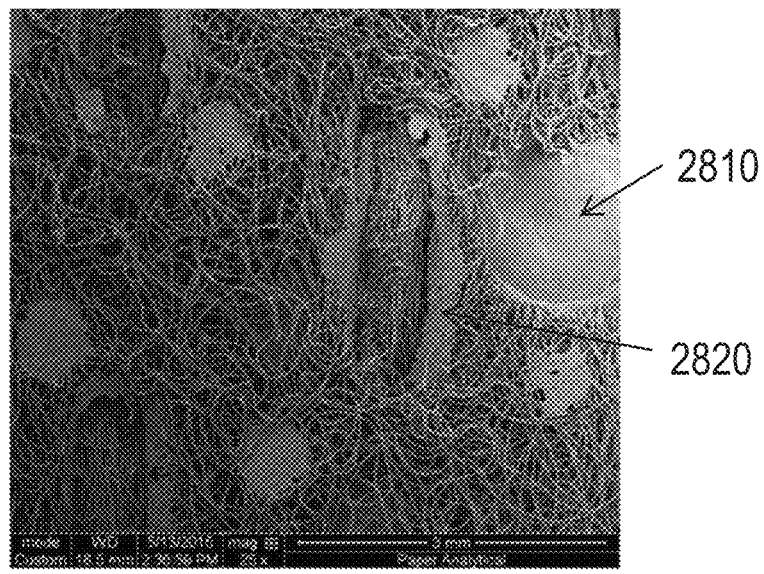
FIG. 28A is an SEM image showing apertures, calendar bond sites and fusion bond sites in a material web.
Figure 28B:
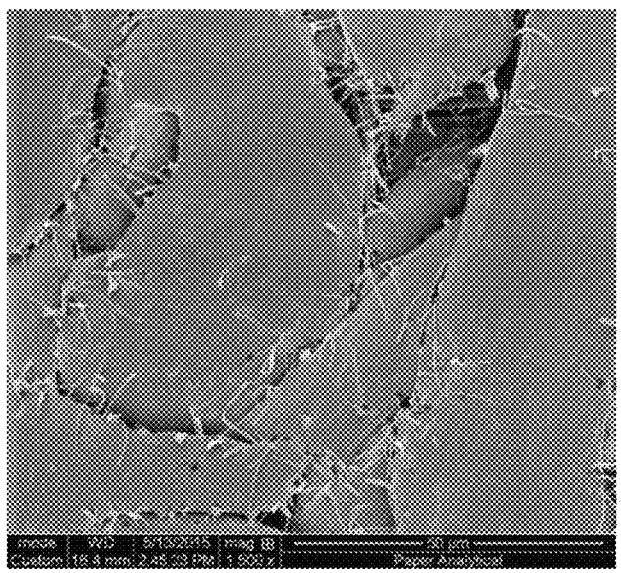
FIG. 28B is an SEM image of the fusion bond sites from FIG. 28A.
Figure 28C:
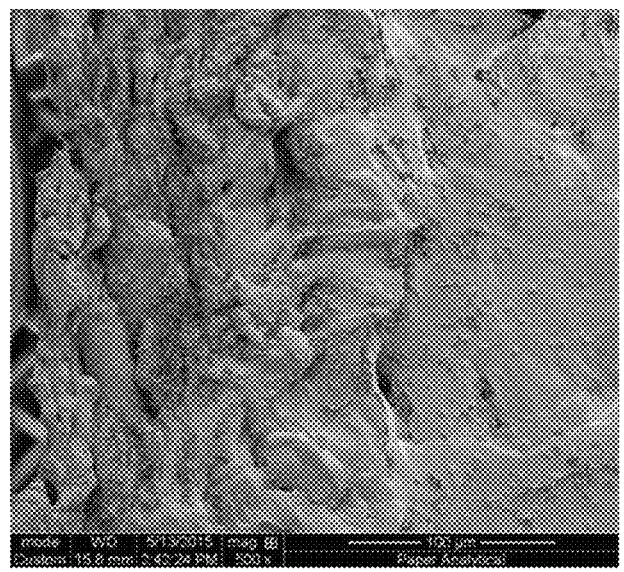
FIGS. 28C and 28D are SEM images of the apertures/melt lip of FIG. 28A, FIGS. 28C and 28D being at 500 times and 1500 times magnification, respectively.
Figure 28D:
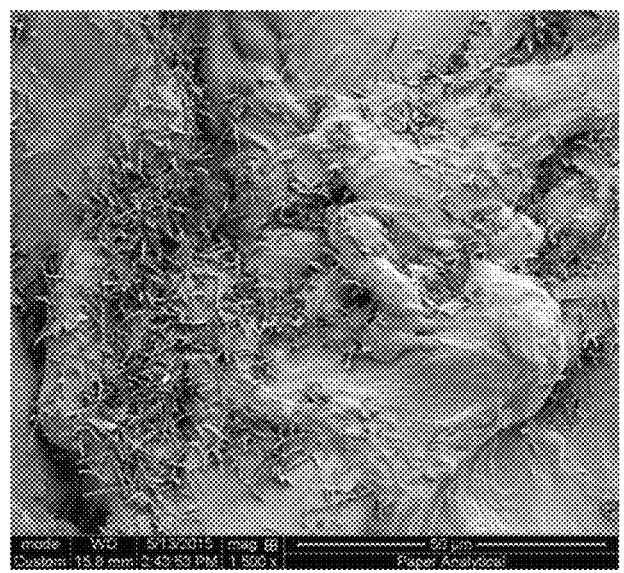
Figure 29A:
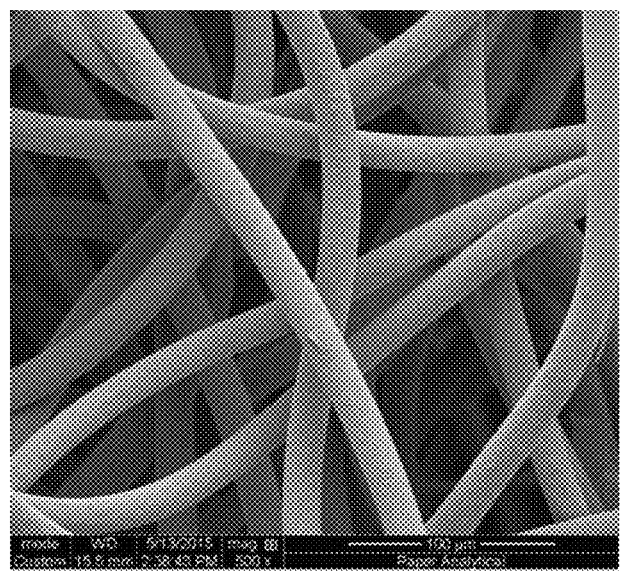
FIGS. 29A and 29B are SEM images of an exemplary material web which show melt additive bloom areas, FIGS. 29A and 29B being at 500 times and 1500 times magnification, respectively.
Figure 29B:
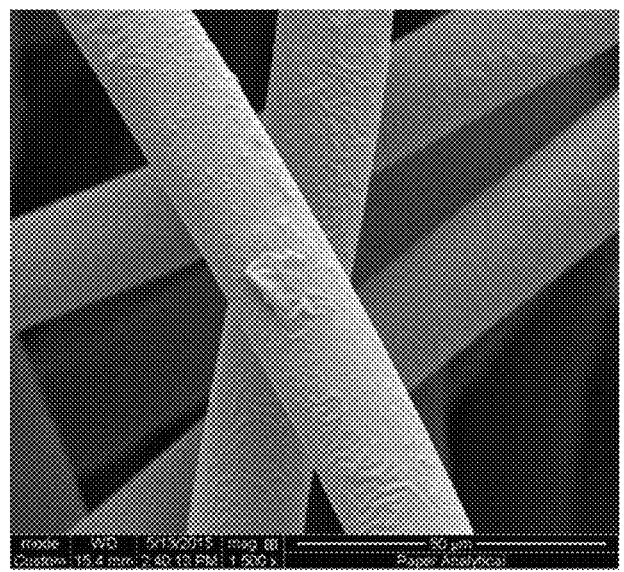

As shown in FIG. 28A, a low magnification plan view image of the above laminate. The image shows melt lips 2820 of the apertures, fusion bond sites 2810, and the upper and lower layer bond sites. FIG. 28B is a higher magnification of the same laminate. As shown in FIG. 28B, the fusion bond sites demonstrate fibrils (thread like elements shown in FIG. 28B) formed by the hydrophobic melt additive. FIG. 28C, shows that the melt lips of the apertures similarly comprise fibrils from the hydrophobic melt additive. FIG. 28D is a higher resolution image of the melt lips. Referring to FIGS. 29A and 29B, the fibers of the upper layer did not comprise fibrils outside of the melt lips and fusion bonds.

The melt additive may form between about 0.5 percent by weight to about 10 percent by weight of the material web 100. In some forms, the melt additives may be less than about 10 percent by weight, less, less than about 8 percent by weight, less than about 5 percent by weight, less than about 2.5 percent by weight, specifically including any values within these ranges or any ranges created thereby. In some forms, the melt additive may be about 6 percent by weight of a master batch containing 40 percent by weight of the melt additive. In some forms, the melt additive may form between about 0.5 percent by weight to about 6 percent by weight of the master batch or from about less than 4 percent by weight of the master batch or any value within these ranges and any ranges created thereby.

The inventors have found that if the concentration of melt additive by weight percent is too low, the melt additive bloom areas provided with localized heat application may not be sufficient to provide the desired functionality. In contrast, if the melt additive concentration is too high, melt additive bloom areas may occur without the localized heat application—auto blooming. Without wishing to be bound by theory, it is believed that the diffusion coefficient (explained in additional detail below) of the melt additive increases with the concentration of melt additive in the polymer matrix of the thermoplastic polymeric material of the material web.

Without wishing to be bound by theory, it is believed that the glass transition temperature of the polymer which makes up the material of the web, the molecular weight of the melt additive, as well as the chain length of the melt additive impacts the blooming capability of the melt additive. It is believed that where the polymer is in its glassy state, the glassy state of the polymer matrix can "lock away" the melt additive and discourage blooming.

For those polymers which comprise a high Tg, e.g. polystyrene—100 degrees C.; polycarbonate—145 degrees C.—the melt additives that can be utilized may be more extensive than for those polymers with lower glass transition temperatures. For those polymers with lower Tg's, e.g. polypropylene, polyethylene, the melt additives which can be utilized are limited to some extent. With lower Tg's of the thermoplastic polymeric material, some melt additives may auto bloom at room temperature.

For those polymers with a high Tg, any suitable melt additive may be utilized. Some examples of suitable hydrophobic melt additives include fatty acids and fatty acid derivatives. The fatty acids may originate from vegetable, animal, and/or synthetic sources. Some fatty acids may range from a C8 fatty acid to a C30 fatty acid, or from a C12 fatty acid to a C22 fatty acid. In other forms, a substantially saturated fatty acid may be used, particularly when saturation arises as a result of hydrogenation of fatty acid precursor. Examples of fatty acid derivatives include fatty alcohols, fatty acid esters, and fatty acid amides. Suitable fatty alcohols (R—OH) include those derived from C12-C30 fatty acids.

Suitable fatty acid esters include those fatty acid esters derived from a mixture of C12-C30 fatty acids and short chain (C1-C8, preferably C1-C3) monohydric alcohols preferably from a mixture of C12-C22 saturated fatty acids and short chain (C1-C8, preferably C1-C3) monohydric alcohols. The hydrophobic melt additive may comprise a mixture of mono, di, and/or tri-fatty acid esters. An example includes fatty acid ester with glycerol as the backbone as illustrated in [1].

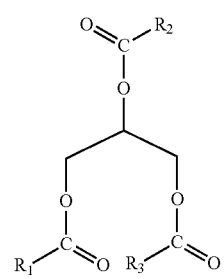

[1]

where R1, R2, and R3 each is an alkyl ester having carbon atoms ranging from 11 to 29. In some forms, the glycerol derived fatty acid ester has at least one alkyl chain, at least two, or three chains to a glycerol, to form a mono, di, or triglyceride. Suitable examples of triglycerides include glycerol thibehenate, glycerol tristearate, glycerol tripalmitate, and glycerol trimyristate, and mixtures thereof. In the case of triglycerides and diglycerides, the alkyl chains could be the same length, or different length. Example includes a triglyceride with one alkyl C18 chain and two C16 alkyl chain, or two C18 alkyl chains and one C16 chain. Preferred triglycerides include alkyl chains derived from C14-C22 fatty acids.

Suitable fatty acid amides include those derives from a mixture of C12-C28 fatty acids (saturated or unsaturated) and primary or secondary amines. A suitable example of a primary fatty acid amide includes those derived from a fatty acid and ammonia as illustrated in [2].

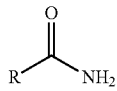

[2]

where R has a number of carbon atoms ranging from 11 to 27. In at least one other form, the fatty acids may range from a C16 fatty acid to a C22 fatty acid. Some suitable examples include erucamide, oleamide and behanamide. Other suitable hydrophobic melt additives include hydrophobic silicones, ethoxylated fatty alcohols. Additional suitable hydrophobic melt additives are disclosed in U.S. patent application Ser. No. 14/849,630 and U.S. patent application Ser. No. 14/933,028. Another suitable hydrophobic melt additive is available from Techmer PM in Clinton, Tenn. under the trade name PPM17000 High Load Hydrophobic. One specific example of a melt additive is glycerol tristearate.

Similarly, for those polymers with a high Tg, any suitable hydrophilic additive can be used. Some suitable examples include those available from Techmer PM, Clinton, Tenn. sold under the trade name of Techmer PPM15560; TPM12713, PPM19913, PPM 19441, PPM19914, (for polypropylene), and PM19668 (for polyethylene). Additional examples are available from Polyvel Inc. located in Hammonton, N.J., sold under the trade name of Polyvel VW351 PP Wetting Agent; from Goulston Technologies Inc. located in Monroe, N.C. sold under the trade name Hydrosorb 1001; as well as those hydrophilic additives disclosed in US Patent Application Publication No. 2012/0077886 and U.S. Pat. Nos. 5,969,026 and 4,578,414. Other suitable hydrophilic melt additives are Unithox 720 and Unithox 750 and Techsurf 15560 from Techmer in general.

For those polymers with a lower glass transition temperature, e.g. polypropylene, polyethylene, the list of available melt additives may be much more restrictive assuming that the desired outcome is to discourage auto blooming. Note, that the discouragement of auto blooming does not necessarily coincide with the preclusion of auto blooming. Without wishing to be bound by theory, it is believed that for those polymers with a lower Tg, the chain length and molecular weight of the melt additives become much more critical in whether auto blooming will occur. It is believed that for those melt additive compositions having a higher chain-length and a higher molecular weight, a lower diffusion coefficient in the polymer exists at room temperature. So, it is believed that for higher chain length melt additive compositions, auto blooming will be discouraged at room temperature, e.g. about 25 degrees C.

Some suitable examples of hydrophobic melt additives suitable for use in conjunction with polypropylene and/or polyethylene is glycerol tristearate. As used herein, glycerol tristearate is defined as a mixture of long-chained triglycerides containing predominately C18 and C16 saturated alkyl chain lengths. Additionally, there could be varying degrees of unsaturation and cis to trans unsaturated bond configurations. The alkyl chain lengths could range from about C10 to about C22. The degrees of unsaturation typically will range from 0 to about 3 double bonds per alkyl chain. The ratio of cis to trans unsaturated bond configurations can range from about 1:100 to about 100:1. Other suitable examples for use with polypropylene and/or polyethylene, a triglyceride which contains either stearic acid or palmic acid or both as the fatty acid components, or a mixture of such triglycerides.

In one specific example, polypropylene fibers which were spun from a mixture of the resin Polypropylene Moplen HP561R and 6 percent by weight glycerol tristearate Masterbatch (containing 40 percent by weight of the melt additive) from Techmer, processed at a temperature of 250° C. with a residence time of 9 minutes in the extruder showed no blooming at room temperature.

An exemplary hydrophilic melt additive which can be utilized in combination with polypropylene and/or polyethylene is Polyvel surfactant S-1416. It is believed that homologues with a higher molecular weight than Polyvel surfactant S-1416 in a polypropylene or polyethylene matrix may also be utilized.

The Polyvel S-1416 is a silicon surfactant with a (hydrophilic) poly ethylene oxide (PEO) chain and molecular weight above 700 g/mol. Polyvel S-1416 is available from Polyvel Inc. and is also known under the trade name "VW351." Without wishing to be bound by theory, it is believed that the "resistance to blooming" is controlled via the length of the PEO chain. Namely, it is believed that the longer the PEO chain, the larger the resistance to blooming. S-1416 has a chain of 10 or 11 ethylene oxide repeat units. Additionally, activation of S-1416 requires besides heating a humid environment (e.g. 80% relative humidity or in the presence of water sprayed onto the surface). It further believed that under these conditions the hydrophilic tail is flipped outward.

For those forms of the present invention where autoblooming is desired, then the melt additive list provided with regard to the higher Tg polymers may be utilized in conjunction with polymers having a lower Tg, e.g. polypropylene and/or polyethylene. And, in such instances, the application of heat to the material web as described herein can enhance the blooming of the melt additive, namely increasing the amount of melt additive which blooms to the surface. In contrast, for those forms of the present invention where the discouragement of auto blooming is desired, then the thermoplastic polymeric material and the melt additive may be matched as described herein such that auto blooming of the melt additive is discouraged.

For those forms where the material web 100 (shown in FIG. 1) comprises a hydrophobic melt additive, the material web 100 may be incorporated into a disposable absorbent article as a topsheet or overwrap in the case of a tampon. While conventional wisdom would typically advise against a hydrophobic topsheet, nonwoven webs of the present invention may comprise apertures which allow for rapid acquisition of liquid insults. In such forms, hydrophobic topsheets can provide a clean dry surface against a wearer's skin. Additionally, the hydrophobic treatment in the first plurality of filaments may reduce liquid rewet.

And, while conventional wisdom may promote post filament production enhancement of hydrophobicity/hydrophilicity, e.g. topical application, applications of such compositions may be cause additional strife. For example, many topically applied treatments can migrate to other structures within an absorbent article. However, the inventors have surprisingly discovered that where fibers being heat treated as described herein, the discrete melt additive bloom areas do not migrate or migrate to a much lesser extent than topically applied compositions. Migration of the melt bloom areas is discussed in additional detail hereafter.

In some forms of the present invention, additional melt additives are contemplated. For example, the melt additive may comprise a composition which improves tactile sensation, e.g. softness additive. A suitable example of an additive for softness includes Erucamide which may be provided in amounts ranging from about 0.1 to about 20 percent by weight. Additional suitable additive may be provided with regard to reduction of coefficient of friction, or the like. The melt additive which pertains to softness may be beneficial for those forms of the present invention where the material web 100 comprises a plurality of discontinuities selected from outer tufts, tunnel tufts, filled tufts, nested tufts, corrugations, and combinations thereof. While erucamide may auto bloom when used in conjunction with polypropylene and/or polyethylene, the erucamide which blooms to the surface can be enhanced, particularly in the tufts (described herein) and/or corrugations which in some forms may contact a user's skin. So for example, heat application as described herein may enhance the amount of erucamide that blooms in the distal ends of the tufts and/or corrugations. Additional melt additives for softness that are contemplated, include stereamide and oleamide or mixtures thereof. In some forms, mixtures of erucamid, stereamide and/or oleamide may be provided the melt additive.

In some forms, the melt additive bloom areas can be utilized to improve the adhesion of ink and/or of glues to the material web. For example melt additive bloom areas comprising hydrophilic compositions can increase the surface energy of the material web at the location of the melt additive bloom areas. The increased surface energy can increase the adhesion of inks and glues. In contrast, where the melt additive bloom areas comprise a hydrophobic composition, the melt additive bloom areas may be selected to occur where ink and/or glues will not be present. In general, inks and/or glues tend to wash off of hydrophobic compositions/substrates. In such forms, auto blooming may be desired.

In some forms, the melt additive bloom areas can be utilized to form anchoring points at which subsequent coupling of molecules can provide additional functionality of the melt additive bloom areas. For example the melt additive bloom areas may comprise a composition comprising a functional group which can be used for subsequent chemical reaction. The chemical reaction in the subsequent step should be carried out under mild enough conditions (e.g. low enough temperature, below the softening points of the polymer and the melt additive) so that the material web and the melt additive bloom areas are not damaged. The reaction can be any nucleophilic addition reaction or nucleophilic substitution reaction, e.g. with one reactant having hydroxyl groups and the chemical bond formed being an ester. In one specific form, the melt additive bloom may be utilized to improve the stability of other topical applications. For example, soil release polymers that wouldn't normally bind to polyolefins could bind to compositions in melt additive bloom areas.

In another example, the melt additive can comprise a carboxylic acid group (—COOH). This can be an anchoring point for a molecule comprising a hydroxyl group (—OH) as a second molecule which reacts with the carboxylic acid group to form an ester. Reversely, the melt additive can comprise a hydroxyl group and the second molecule can comprise a carboxylic acid group. The formation of an ester bridge is only one out of numerous examples for the formation of a chemical bond with one reactant being a carboxylic acid or a carboxylic acid derivative. The person skilled in the art will easily identify alternative routes. In the selection of the reactants it is important that the reaction can be carried out under mild enough conditions (e.g. low enough temperature, below the softening points of the polymer and the melt additive) so that the substrate and the patterned structure are not damaged. Also the reactant used as melt additive should not or only to a negligible degree decompose under the conditions of processing.

As discussed previously, the inventors have surprisingly found that the melt additive bloom areas do not migrate to the same extent as topically applied compositions. Without wishing to be bound by theory, it is believed that the glass transition temperature of the melt additive composition or the melt temperature of the melt additive (whichever is higher) needs to be above 40 degrees C. Additionally, it believed that the diffusion coefficient plays an important part of whether a melt additive blooms. The melt additive diffusion coefficient can be defined as:

$$D_{\mathit{eff}} = \frac{x^2}{2t}$$

where Deff is the diffusion coefficient, x=radius of the fiber or half caliper of the film, and t=storage time. In order for the melt additive to stay within the polymer matrix of the material web (no melt additive bloom areas sans the application of thermal energy), the diffusion coefficient needs to fulfill the condition:

$$D_{\mathit{eff}} < \frac{x^2}{6\ \text{years}}$$

at room temperature or $$D_{\mathit{eff}} < \frac{x^2}{1\ \text{year}}$$

at 40° C., assuming that 0.5 years accelerate aging at 40° C. is predictive of 3 years aging at room temperature (25° C.). With such low diffusion coefficients ($10^{-18}$ m$^2$/s at room temperature and $10^{-17}$ m$^2$/s at 40° C. for a fiber with 40 μm diameter) the melt additive is in practical terms immobile in the polymer matrix and does not diffuse to the surface. After 3 years at room temperature or 0.5 years at 40° C. the blooming to the surface outside the defined zones is so limited (if it happens at all) that the melt additive bloom areas provided by the application of thermal energy are maintained with little to no migration.

It is believed that these low effective diffusion coefficients ("locking the melt additive in the polymer matrix") can be achieved by using melt additives in a polymer matrix with (i) no non-glassy amorphous domains or (ii) large size melt additives in a polymer matrix with a very limited portion of non-glassy amorphous domains at temperatures up to 40° C. For case (i), the polymer matrix may for example, by a completely amorphous polymer which is in its glassy state at an environmental temperature of 40° C. (i.e. Tg>40° C.). For case (ii), the polymer matrix may for example, be a semi-crystalline polymer in which a large parts or all of the amorphous domains are in the glassy state at 40° C.

One example of a suitable polymer for use in the material webs of the present invention is polypropylene. Polypropylene (PP) can have two types of amorphous domains: type I and type II. Type I can be influenced by adjacent crystalline domains and has a Tg of ~75°. ("Influenced" means that one end of the chain is still tied to the crystal.) The diffusion coefficient for melt additives in these domains is close to zero below 75° C. Type II is uninfluenced by the crystalline domains and has a Tg of ~5° C. At room temperature the melt additive is only able to effectively migrate in these uninfluenced amorphous domains (Tg~5° C.). Dependent on the portion and size of the available Type II amorphous domains, the melt additive may not be able anymore to effectively migrate in the polymer matrix, particularly if the melt additive molecules are large and bulky. In undrawn fibers, the crystals are of the form of spherulites with sufficient uninfluenced amorphous domains around. In drawn fibers (rapid cooling with rate of 2000 K/s plus stretching), fibrillous crystals form with less and smaller amorphous domains around. Large melt additives, e.g. molecular weight of GTS=891.5 g/mol, entrapped in such structure are kinetically hindered from diffusion.

With the processes described herein, it is believed that the application of heat during processing can increase the diffusion coefficient into the range of:

$$D_{\mathit{eff}} > \frac{x^2}{48\,h}$$

Achieving the above diffusion coefficient, the melt additive is able to bloom to the surface of the material web in the areas of thermal energy application with an optional post-processing curing period of up to 24 hours. If the effective diffusion coefficient of the melt additive in the polymer matrix is, for example, changed to $10^{-13}$ m$^2$/s due to the application of thermal energy, the melt additive bloom areas may occur within 30 min for a fiber with 40 µm diameter. It is believed that the increase of the diffusion coefficient with the application of thermal energy is caused by a local change of the micro-structure of the host polymer upon application. For smaller diameter fibers, the melt additive bloom areas may occur even quicker than 30 minutes.

Some specific examples regarding thermal energy application across the entirety of a material web are provided below.

Examples 1-4

Spunbonded (S) single layer nonwoven fabrics were produced from 100-x wt % Ziegler-Natta polypropylene and X wt % of a hydrophobic melt additive (PPM17000 High Load Hydrophobic) and were thermally bonded. Each of the single S-layers had a weight of 20 g/m2. The contents of the hydrophobic additive in Examples 1-4 are summarized in Table 1.

TABLE 1

| Example | X [wt %] |
|---|---|
| 1 | 0 |
| 2 | 3 |
| 3 | 6 |
| 4 | 10 |

Examples 1-4 were tested for Low Surface Tension Strike Through (LST-ST)—measured in seconds. The results are summarized in Table 2. Each sample was tested 15 times, the average is provided below in Table 2.

TABLE 2

| | Example | | | |
|---|---|---|---|---|
| | 1 | 2 | 3 | 4 |
| Average | 4.86 | 8.15 | 11.20 | 13.59 |
| Std. Dev | 0.68 | 1.81 | 1.53 | 3.81 |
| Min | 3.80 | 6.97 | 8.25 | 8.80 |
| Max | 6.25 | 14.13 | 14.13 | 20.75 |

Example 5-7

Three S single layer nonwovens were produced from 100% Ziegler-Natta polypropylene and were thermally bonded. Each of the single S-layers had a weight of 20 g/m2. After the web making process of the nonwovens they were thermally treated with an in-line Omega Drying oven at 90° C., 120° C. and 135° C., for Example 5, 6 and 7, respectively.

Example 8

An S single layer nonwoven was produced from 100% Ziegler-Natta polypropylene and was thermally bonded. The single S-layer had a weight of 20 g/m2. After the web making process the nonwoven was thermally treated with an in-line IR-heater set to 65% power at the center and 60% at the edge of the nonwoven web.

Example 9

An S single layer nonwoven was produced from 100% Ziegler-Natta polypropylene and was thermally bonded. The single S-layer had a weight of 20 g/m2. After the web making process the nonwoven was thermally treated with an in-line Omega Drying oven at 120° C. Opposite Example 6, the through put had been decreased in the production of the material, resulting in a decreased line speed to increase the duration of the heat treatment. The resulting heat treatment of Example 9 was 15% longer than that of Example 6.

TABLE 3

| | Example | | | | |
|---|---|---|---|---|---|
| | 5 | 6 | 7 | 8 | 9 |
| Average | 6.27 | 7.14 | 7.03 | 6.89 | 7.81 |
| Std. Dev | 1.21 | 0.74 | 0.98 | 0.81 | 1.26 |
| Min | 3.27 | 5.95 | 6.01 | 5.73 | 5.97 |
| Max | 7.57 | 8.25 | 9.00 | 8.21 | 10.42 |

Examples 10-13

Four S single layer nonwovens were produced from 90 wt % Ziegler-Natta polypropylene and 10 wt % of a hydrophobic melt additive (PPM17000 High Load Hydrophobic) and were thermally bonded. Each of the single S-layers had a weight of 20 g/m2. After the web making process of the nonwovens they were thermally treated with an in-line Omega Drying oven set to 90° C., 105° C., 120° C. and 135° C. for Example 10, 11, 12 and 13, respectively.

Examples 14-17

Four S single layer nonwovens were produced from 90 wt % Ziegler-Natta polypropylene and 10 wt % hydrophobic melt additive (PPM17000 High Load Hydrophobic) and were thermally bonded. Each of the single S-layers had a weight of 20 g/m2. After the web making process of the nonwovens they were thermally treated with an in-line IR-heater set to 50% power at the center and 45% at the edge of the nonwoven web, 60% power at the center and 55% at the edge of the nonwoven web, 65% power at the center and 50% at the edge of the nonwoven web, and 70% power at the center and 65% at the edge of the nonwoven web for Example 14, 15, 16 and 17, respectively.

Example 18

An S single layer nonwoven was produced from 90 wt % Ziegler-Natta polypropylene and 10 wt % hydrophobic melt additive (PPM17000 High Load Hydrophobic) and was thermally bonded. The single S-layer had a weight of 20 g/m2. After the web making process of the nonwoven it was thermally treated with an in-line IR-heater set to 65% power at the center and 60% at the edge of the nonwoven web, followed by heating in an Omega Drying oven at 120° C.

The hydrophobic additive content and heat treatment for Examples 10-18 are summarized in Table 4 below.

TABLE 4

| | Configuration S 20 g/m2 | | |
| --- | --- | --- | --- |
| Example | PPM17000 in S [%] | IR heater, center/edge [%] | Omega Drying oven temperature [° C.] |
| 10 | 10 | N/A | 90 |
| 11 | 10 | N/A | 105 |
| 12 | 10 | N/A | 120 |
| 13 | 10 | N/A | 135 |
| 14 | 10 | 50/45 | N/A |
| 15 | 10 | 60/55 | N/A |
| 16 | 10 | 65/60 | N/A |
| 17 | 10 | 70/65 | N/A |
| 18 | 10 | 65/60 | 120 |

LST-ST was measured on Example 10-18. The results are shown in Table 5.

TABLE 5

| Example | 10 | 11 | 12 | 13 | 14 | 15 | 16 | 17 | 18 |
| --- | --- | --- | --- | --- | --- | --- | --- | --- | --- |
| Average | 58.87 | 98.99 | 186.30 | 461.72 | 19.25 | 19.90 | 221.99 | 84.40 | 230.33 |
| Std. Dev | 16.65 | 52.77 | 88.53 | 128.77 | 5.81 | 6.15 | 93.35 | 26.36 | 109.69 |
| Min | 35.59 | 37.91 | 51.80 | 198.51 | 11.38 | 12.71 | 95.32 | 33.97 | 110.34 |
| Max | 79.87 | 213.77 | 305.67 | 657.52 | 36.15 | 30.45 | 408.33 | 126.05 | 410.14 |

Example 19

An S single layer nonwoven was produced from 90 wt % Ziegler-Natta polypropylene and 10 wt % hydrophobic melt additive (PPM17000 High Load Hydrophobic) and was thermally bonded. The single S-layer had a weight of 20 g/m2. Compared to Example 4, the temperature of the calendar thermally bonding the nonwoven was increased with +10° C.

Table 6 below shows the LST-ST results from Example 19.

TABLE 6

| | Example 19 |
| --- | --- |
| Average | 27.25 |
| Std. dev. | 13.75 |
| Min | 14.50 |
| Max | 60.64 |

It can be see that when increasing the calendar temperature with 10° C., the LST ST increases from 13.59 seconds (4) to 27.25 seconds (19).

Example 20

An S single layer nonwoven was produced from 90% Ziegler-Natta polypropylene and 10 wt % of a hydrophobic melt additive (PPM17000 High Load Hydrophobic) and was thermally bonded. The single S-layer had a weight of 20 g/m2. After the web making process the nonwoven was thermally treated with an in-line Omega Drying oven at 120° C. As Example 13, the through put had been decreased in the production of the material, resulting in a decreased line speed to increase the duration of the in-line heat treatment. The resulting heat treatment of Example 20 was 15% longer than that of Example 12 and comparable to the heat treatment of Example 6.

Table 7 below shows the LST-ST results from Example 20.

TABLE 7

| | Example 20 |
| --- | --- |
| Average | 354.86 |
| Std. dev. | 194.08 |
| Min | 134.31 |
| Max | 656.06 |

It can be seen that when increasing the heat treatment time with 15%, it increases the performance in terms of LST ST from 186.30 seconds (Example 12) to 354.86 seconds (Example 20).

Example 21

A Spunbond single layer fabric was produced with bi-component core/sheath configuration, consisting of 70 wt % core and 30 wt % sheath. The core comprised 100% Ziegler-Natta polypropylene. The sheath comprised 67 wt % Ziegler-Natta polypropylene and 33 wt % hydrophobic melt additive (PPM17000 High Load Hydrophobic). The nonwoven was thermally bonded. The single S-layer had a weight of 20 g/m2.

Example 22-24

Spunbond single layer fabrics were produced with bi-component core/sheath configuration, consisting of 70 wt % core and 30 wt %. The core comprised 100 wt % Ziegler-Natta polypropylene. The sheath comprised 100-X wt % Ziegler-Natta polypropylene and X wt % hydrophobic melt additive (PPM17000 High Load Hydrophobic). The nonwoven was thermally bonded. Each of the single S-layer had a weight of 20 g/m2. After the web making process of the nonwovens they were thermally treated by an in-line IR-heater set to 65% power at the center and 50% at the edge of the nonwoven web.

The contents of the hydrophobic additive in the sheath of the fiber in Examples 22-24 are summarized in below Table 8.

TABLE 8

| Example | X [wt %] |
|---|---|
| 22 | 10 |
| 23 | 20 |
| 24 | 33 |

Table 9 below shows LST-ST results on Examples 21-24.

TABLE 9

|  | Example | | | |
|---|---|---|---|---|
|  | 21 | 22 | 23 | 24 |
| Average | 28.47 | 14.12 | 78.11 | 276.74 |
| Std. Dev | 11.73 | 2.50 | 21.32 | 112.54 |
| Min | 10.03 | 10.70 | 43.19 | 146.09 |
| Max | 50.50 | 20.02 | 117.86 | 502.41 |

Example 25

A spunbond single layer fabric was produced with bi-component core/sheath configuration, consisting of 70 wt % core and 30 wt %. The core comprised 100 wt % Ziegler-Natta polypropylene. The sheath comprised 67 wt % propylene-based elastomer (consisting of approx. 15 wt % ethylene) and 33 wt % of a hydrophobic melt additive (PPM17000 High Load Hydrophobic). The nonwoven was thermally bonded. The single S-layer had a weight of 20 g/m2.

Table 10 below shows the LST-ST results on Example 25:

TABLE 10

|  | Example 25 |
|---|---|
| Average | 100.34 |
| Std. Dev | 36.86 |
| Min | 38.32 |
| Max | 138.89 |

Example 21 to Example 25 reveals an increase in LST-ST from 28.47 seconds to 100.34 seconds when substituting Ziegler-Natta polypropylene in the sheath of the bi-component fiber with a propylene-based elastomer in the sheath of the bi-component fiber.

Example 26

A spunbond single layer fabric was produced was produced from 80 wt % Ziegler-Natta polypropylene, 10 wt % of a hydrophobic melt additive (PPM17000 High Load Hydrophobic), and 10 wt % of a Calcium Carbonate masterbatch (Fiberlink 201S). The fabric was thermally bonded. The single S-layer had a weight of 20 g/m2. After the web making process of the nonwoven it was thermally treated by an in-line IR-heater set to 65% power at the center and 60% at the edge of the nonwoven web followed by in-line heating in an Omega Drying oven at 120° C.

Example 27

A spunbond single layer fabric was produced was produced from 90 wt % Ziegler-Natta polypropylene, and 10 wt % of Calcium Carbonate masterbatch (Fiberlink 201S) and was thermally bonded. The single S-layer had a weight of 20 g/m2. After the web making process of the nonwoven it was thermally treated in an in-line Omega Drying oven at 120° C.

An overview of Example 26 and 27 is provided in Table 11 below.

TABLE 11

| Configuration S 20 g/m2 Example | PPM17000 in S [%] | Fiberlink 201S [%] | Omega Drying oven temperature [° C.] | IR heater, center/edge [%] |
|---|---|---|---|---|
| 26 | 10 | 10 | 120 | 65/60 |
| 27 | 0 | 10 | 120 | N/A |

LST-ST results on Examples 26 and 27 are illustrated in Table 12 below.

TABLE 12

|  | Example | |
|---|---|---|
|  | 26 | 27 |
| Average | 679.98 | 5.51 |
| Std. dev. | 158.50 | 0.61 |
| Min | 522.90 | 4.55 |
| Max | 898.10 | 6.84 |

The LST-ST results reveal a LST ST of 5.51 seconds for Example 27, which shows that the presence of CaCO3 alone does not increase the LST-ST performance. The LST-ST of Example 26 compared to Example 18, reveals that the presence of CaCO3 and the applied heat treatments of the IR-heater and Omega Drying oven increases the LST ST from 230.33 seconds to 679.98 seconds. When comparing the state of the art of Example 4 to Example 26, the performance increases from 13, 59 seconds to 679.98 seconds.

Examples 28-29

Two SMMS-multilayered nonwoven fabrics were produced from Ziegler-Natta polypropylene. A hydrophobic additive (PPM17000 High Load Hydrophobic) was added to the various layers as described in Table 13. After the web making process of Example 29 the fabric was heat treated with an in-line Omega Drying oven.

Table 13 gives an overview on material layup, additive content and heat treatment.

TABLE 13

| | Lay-up [g] | | | | Configuration SMMS 13 | |
|---|---|---|---|---|---|---|
| | S 5.5 | M 1 | M 1 | S 5.5 | Total | Omega Drying oven |
| Example | PPM 17000 per beam [%] | | | | PPM17000 [%] | temperature [° C.] |
| 28 | 0 | 6 | 6 | 6 | 3.5 | N/A |
| 29 | 0 | 6 | 6 | 6 | 3.5 | 120 |

Examples 28-29 were tested for Low Surface Tension Strike Through (LST-ST). The results are summarized in Table 14.

TABLE 14

| | Example | |
|---|---|---|
| | 28 | 29 |
| Average | 24.52 | 31.30 |
| Std. dev. | 5.03 | 4.70 |
| Min | 16.52 | 40.60 |
| Max | 36.19 | 59.50 |

Examples 30-32

Three SS materials were produced with the spunbond fibers in both layers being bi-component fibers of core/sheath configuration with a polyethylene sheath, accounting for 30 wt % of the total fiber, and polypropylene core, accounting for 70 wt % of the total fiber. A hydrophobic additive (PM16310) was added in 17% to the bi-component's PE sheath of both of S layers for Examples 30-32. After the web making process of Example 31-32, the nonwovens were heat treated with an in-line Omega Drying oven of 100° C. and 120° C. for Example 31 and Example 32, respectively.

Table 15 gives an overview on material layup, additive content and heat treatment.

TABLE 15

| Lay-up [g] | | | | | |
|---|---|---|---|---|---|
| | Sheath (PE) 3.75 | | | | Configuration SS 25 |
| S Core (PP) 8.75 | PPM17000 in sheath per beam [%] | S Core (PP) 8.75 | Sheath (PE) 3.75 Total PPM17000 [%] | | Omega Drying oven temperature |
| Example | | | | | [° C.] |
| 30 | 17 | 17 | 5.1 | | N/A |
| 31 | 17 | 17 | 5.1 | | 100 |
| 32 | 17 | 17 | 5.1 | | 120 |

Examples 30-32 were tested for Low Surface Tension Strike Through (LST-ST). The results are summarized in Table 16.

TABLE 16

| | Example | | |
|---|---|---|---|
| | 30 | 31 | 32 |
| Average | 25.52 | 22.49 | 31.64 |
| Min | 12.02 | 12.88 | 16.97 |
| Max | 47.98 | 44.03 | 54.21 |
| Std. dev. | 10.31 | 7.00 | 9.10 |

Some of the above samples were tested via FTIR along with some additional examples. The results are shown in Tables 17-19.

TABLE 17

| Example | Mono/bico | Heating information and misc. | ATR_Germanium_Measurement 1 (d_p = 0.41 µm) wt % Masterbatch | ATR_Germanium_Measurement 2 (d_p = 0.41 µm) wt % Masterbatch | ATR_Germanium_Mean wt % Masterbatch |
|---|---|---|---|---|---|
| 13 | Mono | 135° C. Oven | 69.6 | 70.6 | 70.1 |
| 12 | Mono | 120° C. Oven | 85.9 | 68.2 | 77.05 |
| 20 | Mono | 120° C. Oven | 71.5 | 74.5 | 73 |
| 11 | Mono | 105° C. Oven | 67.5 | 67.1 | 67.3 |
| 10 | Mono | 90° C. Oven | 68.5 | 70.2 | 69.35 |
| 18 | Mono | 120° C. Oven + IR | 75.8 | 72.3 | 74.05 |
| 14 | Mono | 50% IR | 71.4 | 72.9 | 72.15 |
| 16 | Mono | 70% IR (high strike through) | 91.5 | 90 | 90.75 |
| 2 | Mono | Reference 3 wt % GTS | 21.6 | 25.2 | 23.4 |
| 3 | Mono | Reference 6 wt % GTS | 42.1 | 42.8 | 42.45 |
| 4 | Mono | Reference 10 wt % GTS | 57.5 | 62.6 | 60.05 |
| 15 | Mono | 60% IR | 55.5 | 56.4 | 55.95 |
| 17 | Mono | 70% IR (low strike through) | 65.3 | 70.4 | 67.85 |
| 33 | Bico | Bico 3 wt % GTS + IR | 30.6 | 23.7 | 27.15 |
| 34 | Bico | Bico 6 wt % GTS + IR | 58.8 | 49.3 | 54.05 |
| 35 | Bico | Bico 10 wt % GTS + IR | 74.2 | 84.2 | 79.2 |
| 36 | Bico | Bico 10 wt % GTS no IR | 73.3 | 74.3 | 73.8 |

TABLE 18

| Example | Mono/bico | Heating information and misc. | ATR_Diamond_Measurement 1 (d_p = 1.51 μm) wt % Masterbatch | ATR_Diamond_Measurement2 (d_p = 1.51 μm) wt % Masterbatch | ATR_Diamond_Mean wt % Masterbatch |
|---|---|---|---|---|---|
| 13 | Mono | 135° C. Oven | 46.9 | 43.4 | 45.15 |
| 12 | Mono | 120° C. Oven | 44.9 | 39.3 | 42.1 |
| 20 | Mono | 120° C. Oven | 44.7 | 45.4 | 45.05 |
| 11 | Mono | 105° C. Oven | 39.3 | 38.9 | 39.1 |
| 10 | Mono | 90° C. Oven | 39.4 | 37.3 | 38.35 |
| 18 | Mono | 120° C. Oven + IR | 44.1 | 44.1 | 44.1 |
| 14 | Mono | 50% IR | 41 | 41.2 | 41.1 |
| 16 | Mono | 70% IR (high strike through) | 46.1 | 50.6 | 48.35 |
| 2 | Mono | Reference 3 wt % GTS | 12.2 | 10.6 | 11.4 |
| 3 | Mono | Reference 6 wt % GTS | 22.8 | 23.7 | 23.25 |
| 4 | Mono | Reference 10 wt % GTS | 33.2 | 32.9 | 33.05 |
| 15 | Mono | 60% IR | 34.1 | 35.7 | 34.9 |
| 17 | Mono | 70% IR (low strike through) | 41.6 | 39.5 | 40.55 |
| 33 | Bico | Bico 3 wt % GTS + IR | 14.8 | 13 | 13.9 |
| 34 | Bico | Bico 6 wt % GTS + IR | 29.8 | 27.1 | 28.45 |
| 35 | Bico | Bico 10 wt % GTS + IR | 43.2 | 48.2 | 45.7 |
| 36 | Bico | Bico 10 wt % GTS no IR | 39.8 | 45.4 | 42.6 |

FIG. 19

| Example | Mono/bico | Heating information and misc. | Transmission_Measurement 1 wt % Masterbatch | Transmission_Measurement 2 wt % Masterbatch | Transmission_Mean wt % Masterbatch |
|---|---|---|---|---|---|
| 13 | Mono | 135° C. Oven | 9.7 | 9.4 | 9.55 |
| 12 | Mono | 120° C. Oven | 8.7 | 8.7 | 8.7 |
| 20 | Mono | 120° C. Oven | 8.5 | 7.9 | 8.2 |
| 11 | Mono | 105° C. Oven | 9.4 | 9.9 | 9.65 |
| 10 | Mono | 90° C. Oven | 9.9 | 10.8 | 10.35 |
| 18 | Mono | 120° C. Oven + IR | 9.1 | 8.1 | 8.6 |
| 14 | Mono | 50% IR | 8.7 | 10 | 9.35 |
| 16 | Mono | 70% IR (high strike through) | 8.5 | 8.8 | 8.65 |
| 2 | Mono | Reference 3 wt % GTS | 3.6 | 3.7 | 3.65 |
| 3 | Mono | Reference 6 wt % GTS | 6.3 | 5.7 | 6 |
| 4 | Mono | Reference 10 wt % GTS | 9.1 | 8.5 | 8.8 |
| 15 | Mono | 60% IR | 10 | 8.9 | 9.45 |
| 17 | Mono | 70% IR (low strike through) | 8.6 | 8.6 | 8.6 |
| 33 | Bico | Bico 3 wt % GTS + IR | 3.3 | 3.2 | 3.25 |
| 34 | Bico | Bico 6 wt % GTS + IR | 5.3 | 5.9 | 5.6 |
| 35 | Bico | Bico 10 wt % GTS + IR | 8.5 | 9.2 | 8.85 |
| 36 | Bico | Bico 10 wt % GTS no IR | 8.3 | 8.3 | 8.3 |

For the bi-component nonwovens, no melt additive was provided in the core. The melt additive levels and fiber compositions are provided below with regard to Table 20.

TABLE 20

| Example | Mono/bico | Heating information and misc. | GTS addition in total fiber % | Addition, hydrophobic melt additive % |
|---|---|---|---|---|
| 13 | Mono | 135° C. Oven | 10 | 10 |
| 12 | Mono | 120° C. Oven | 10 | 10 |
| 20 | Mono | 120° C. Oven | 10 | 10 |
| 11 | Mono | 105° C. Oven | 10 | 10 |
| 10 | Mono | 90° C. Oven | 10 | 10 |
| 18 | Mono | 120° C. Oven + IR | 10 | 10 |
| 14 | Mono | 50% IR | 10 | 10 |
| 16 | Mono | 70% IR (high strike through) | 10 | 10 |
| 2 | Mono | Reference 3 wt % GTS | 3 | 3 |
| 3 | Mono | Reference 6 wt % GTS | 6 | 6 |
| 4 | Mono | Reference 10 wt % GTS | 10 | 10 |
| 15 | Mono | 60% IR | 10 | 10 |
| 17 | Mono | 70% IR (low strike through) | 10 | 10 |
| 33 | Bico | Bico 3 wt % GTS + IR | 3 | 10 |
| 34 | Bico | Bico 6 wt % GTS + IR | 6 | 20 |
| 35 | Bico | Bico 10 wt % GTS + IR | 10 | 33 |
| 36 | Bico | Bico 10 wt % GTS no IR | 10 | 33 |

Table 21 provides information regarding the style and temperature of the heating applied to the nonwoven examples.

TABLE 21

| Example | Mono/bico | Heating information and misc. | IR heater Y/N | IR heater power at center % | IR heater power at edge % | Drum dryer Y/N | Dryer temperature ° C. |
|---|---|---|---|---|---|---|---|
| 13 | Mono | 135° C. Oven | N | — | — | Y | 135 |
| 12 | Mono | 120° C. Oven | N | — | — | Y | 120 |
| 20 | Mono | 120° C. Oven | N | — | — | Y | 120 |
| 11 | Mono | 105° C. Oven | N | — | — | Y | 105 |
| 10 | Mono | 90° C. Oven | N | — | — | Y | 90 |
| 18 | Mono | 120° C. Oven + IR | Y | 65 | 60 | Y | 120 |
| 14 | Mono | 50% IR | Y | 50 | 45 | N | — |
| 16 | Mono | 70% IR (high strike through) | Y | 70 | 65 | N | — |
| 2 | Mono | Reference 3 wt % GTS | N | — | — | N | — |
| 3 | Mono | Reference 6 wt % GTS | N | — | — | N | — |
| 4 | Mono | Reference 10 wt % GTS | N | — | — | N | — |
| 15 | Mono | 60% IR | Y | 60 | 55 | N | — |
| 17 | Mono | 70% IR (low strike through) | Y | 70 | 65 | N | — |
| 33 | Bico | Bico 3 wt % GTS + IR | Y | 65 | 60 | N | — |
| 34 | Bico | Bico 6 wt % GTS + IR | Y | 65 | 60 | N | — |
| 35 | Bico | Bico 10 wt % GTS + IR | Y | 65 | 60 | N | — |
| 36 | Bico | Bico 10 wt % GTS no IR | N | — | — | N | — |

Table 22 provides information regarding permeability and basis weight and whether fibrillation was observed.

TABLE 22

| Example | Mono/bico | Information/what has changed to reference | LST ST s | Air permeability L/(m²*s) | Basis weight gsm |
|---|---|---|---|---|---|
| 13 | Mono | 135° C. Oven | 462 | | |
| 12 | Mono | 120° C. Oven | 186 | | |
| 20 | Mono | 120° C. Oven | 355 | | |
| 11 | Mono | 105° C. Oven | 99 | | |
| 10 | Mono | 90° C. Oven | 59 | | |
| 18 | Mono | 120° C. Oven + IR | 230 | | |
| 14 | Mono | 50% IR | 19 | 3083 | 19.8 |
| 16 | Mono | 70% IR (high strike through) | 222 | 2291 | 22.5 |
| 2 | Mono | Reference 3 wt % GTS | 8 | 4212 | 19.5 |
| 3 | Mono | Reference 6 wt % GTS | 11 | 4118 | 19.6 |
| 4 | Mono | Reference 10 wt % GTS | 14 | 3938 | 19.8 |
| 15 | Mono | 60% IR | 20 | 3604 | 21.5 |
| 17 | Mono | 70% IR (low strike through) | 84 | 2676 | 25.5 |
| 33 | Bico | Bico 3 wt % GTS + IR | 14 | 3486 | 21.9 |
| 34 | Bico | Bico 6 wt % GTS + IR | 78 | 2684 | 22.9 |
| 35 | Bico | Bico 10 wt % GTS + IR | 277 | 2408 | 24.9 |
| 36 | Bico | Bico 10 wt % GTS no IR | 28 | 3866 | 20.4 |

Examples 37-40 are polyethylene films comprising 0.6 percent by weight of melt additive. Sample 37 comprised 0 percent by weight of high density polyethylene and was exposed to a temperature of 25 degrees C. Sample 38 comprised 0 percent by weight of high density polyethylene and was exposed to a temperature of 35 degrees C. for 6 hours. Sample 39 comprised 40 percent by weight of high density polyethylene and was exposed to a temperature of 25 degrees C. Sample 40 comprised 40 percent by weight of high density polyethylene and was exposed to a temperature of 35 degrees C. for 6 hours.

TABLE 23

| Example | Total Melt additive Conc [wt %] | Temperature (° C.) | TD NMR surface surfactant [wt %] | STDEV |
|---|---|---|---|---|
| 37 | 0.6 | 25 | 0.15 | 0.02 |
| 38 | 0.6 | 35 | 0.22 | 0.02 |
| 39 | 0.6 | 25 | 0.06 | 0.00 |
| 40 | 0.6 | 35 | 0.08 | 0.00 |

Precursor Material

Similarly, the material webs of the present invention begin with the thermoplastic polymeric material. As noted previously, the material webs of the present invention may comprise any suitable material for example, nonwoven webs, film webs, or laminates created therefrom. Where the material webs of the present invention comprise laminates, the laminates may comprise a plurality of nonwoven layers, a plurality of film layers, or at least one nonwoven layer and at least one film layer. Additional forms are contemplated where the material webs of the present invention comprise a nonwoven web comprising multiple nonwoven strata. Regardless of the form of the material web, any suitable material may be utilized.

For those forms where the material webs comprise a nonwoven, any suitable thermoplastic polymer may be utilized. Some suitable thermoplastic polymers are polymers that melt and then, upon cooling, crystallize or harden, but can be re-melted upon further heating. Suitable thermoplastic polymers used herein have a melting temperature (also referred to as solidification temperature) from about 60° C. to about 300° C., from about 80° C. to about 250° C., or from 100° C. to 215° C. And, the molecular weight of the thermoplastic polymer should be sufficiently high to enable entanglement between polymer molecules and yet low enough to be melt spinnable.

The thermoplastic polymers can be derived any suitable material including renewable resources (including bio-based and recycled materials), fossil minerals and oils, and/or biodegradeable materials. Some suitable examples of thermoplastic polymers include polyolefins, polyesters, polyamides, copolymers thereof, and combinations thereof. Some exemplary polyolefins include polyethylene or copolymers thereof, including low density, high density, linear low density, or ultra low density polyethylenes such that the polyethylene density ranges between 0.90 grams per cubic centimeter to 0.97 grams per cubic centimeter, between 0.92 and 0.95 grams per cubic centimeter or any values within these ranges or any ranges within these values. The density of the polyethylene may be determined by the amount and type of branching and depends on the polymerization technology and co-monomer type.

Some suitable examples of polypropylene and/or polypropylene copolymers, include atactic polypropylene; isotactic polypropylene, syndiotactic polypropylene, and combination thereof, "hereafter propylene polymers" can also be used. Polypropylene copolymers, especially ethylene can be used to lower the melting temperature and improve properties. These polypropylene polymers can be produced using metallocene and Ziegler-Natta catalyst systems. These polypropylene and polyethylene compositions can be combined together to optimize end-use properties. Polybutylene is also a useful polyolefin and may be used in some embodiments. Other suitable polymers include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate; olefin carboxylic acid copolymers such as ethylene/acrylic acid copolymer, ethylene/maleic acid copolymer, ethylene/methacrylic acid copolymer, ethylene/vinyl acetate copolymers or combinations thereof; poly-lactic acid; polyacrylates, polymethacrylates, and their copolymers such as poly(methyl methacrylates).

Non-limiting examples of suitable commercially available polypropylene or polypropylene copolymers include Basell Profax PH-835 (a 35 melt flow rate Ziegler-Natta isotactic polypropylene from Lyondell-Basell), Basell Metocene MF-650W (a 500 melt flow rate metallocene isotactic polypropylene from Lyondell-Basell), Moplen, HP2833, HP462R and S, HP551R, HP552N, HP552R, HP553R, HP561R, HP563S, HP567P, HP568S, RP3231, Polybond 3200 (a 250 melt flow rate maleic anhydride polypropylene copolymer from Crompton), Exxon Achieve 3854 (a 25 melt flow rate metallocene isotactic polypropylene from ExxonMobil Chemical), Mosten NB425 (a 25 melt flow rate Ziegler-Natta isotactic polypropylene from Unipetrol), Danimer 27510 (a polyhydroxyalkanoate polypropylene from Danimer Scientific LLC) , , , Achieve 3155 (a 35 melt flow rate Ziegler-Natta isotactic polypropylene from Exxon Mobil), The thermoplastic polymer component can be a single polymer species as described above or a blend of two or more thermoplastic polymers as described above, e.g. two different polypropylene resins. As an example, the constituent fibers of the first nonwoven layer can be comprised of polymers such as polypropylene and blends of polypropylene and polyethylene. The second nonwoven layer may comprise fibers selected from polypropylene, polypropylene/polyethylene blends, and polyethylene/polyethylene teraphthalate blends. In some embodiments, the second nonwoven layer may comprise fibers selected from cellulose rayon, cotton, other hydrophilic fiber materials, or combinations thereof. The fibers can also comprise a super absorbent material such as polyacrylate or any combination of suitable materials.

The fibers of the first nonwoven layer and/or the second nonwoven layer can be monocomponent, bi-component, and/or bi-constituent, round or non-round (e.g., capillary channel fibers), and can have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >2 denier), shape (i.e. capillary and round) and the like. The constituent fibers can range from about 0.1 denier to about 100 denier.

As used herein, the term "monocomponent" fiber refers to a fiber formed from one extruder using one or more polymers. This is not meant to exclude fibers formed from one polymer to which small amounts of additives have been added for coloration, antistatic properties, lubrication, hydrophilicity, etc.

As used herein, the term "bi-component fibers" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement. Some specific examples of fibers which can be used in the first nonwoven layer include polyethylene/polypropylene side-by-side bi-component fibers. Another example, is a polypropylene/polyethylene bi-component fiber where the polyethylene is configured as a sheath and the polypropylene is configured as a core within the sheath. Still another example, is a polypropylene/polypropylene bi-component fiber where two different propylene polymers are configured in a side-by-side configuration.

Bi-component fibers may comprise two different resins, e.g. a first polypropylene resin and a second polypropylene resin. The resins may have different melt flow rates, molecular weights, or molecular weight distributions. Ratios of the 2 different polymers may be about 50/50, 60/40, 70/30 or any ratio within these ratios. The ratio may be selected to control the amount of crimp, strength of the nonwoven layer, softness, bonding or the like.

As used herein, the term "bi-constituent fibers" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise a multi-constituent components.

As used herein, the term "non-round fibers" describes fibers having a non-round cross-section, and includes "shaped fibers" and "capillary channel fibers." Such fibers can be solid or hollow, and they can be tri-lobal, delta-shaped, and can be fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

The fibers of the first nonwoven layer and/or the second nonwoven layer may comprise additives in addition to their constituent material. For example, suitable additives include additives for coloration, antistatic properties, lubrication, softness, hydrophilicity, hydrophobicity and the like and combinations thereof.

Further regarding coloration, the first layer and/or the second layer may comprise pigments, inks or dyes to achieve any color difference as provided herein. The fibers of the first layer and the fibers of the second layer may differ from each other in pigmentation. As used herein, to "differ in pigmentation" or "difference in pigmentation" means (a) the fibers of the first layer comprise a pigment which is different from the pigment of the second layer; or (b) the fibers of the first layer comprise a different combination of pigments; or (c) the fibers of the first layer comprise different amounts of the same pigment(s) versus the second layer; or (d) combinations of any of options a) to c). The pigment or colorant may be added uniformly throughout the fibers within each layer or may be added to one or both components in same or different type/amount within multicomponent fibers.

A pigment is a material, which can be organic or inorganic and may include activatable, structural and or special effects pigments. A pigment changes the color of reflected or transmitted light as the result of wavelength-selective absorption. This physical process differs from fluorescence, phosphorescence, and other forms of luminescence, in which a material emits light. A pigment is a generally insoluble powder, which differs from a dye, which either is itself a liquid or is soluble in a solvent (resulting in a solution). Dyes are often used to provide a print on the surface of a nonwoven web, such as graphics, pattern or images. Hence, these dyes do not form a part of the fibers of the nonwoven web but are rather applied on the web surface. In the present invention the pigments may be comprised within the fibers of the multilayered nonwoven web, which eliminates the risk of rub-off or wash-off of the color(s) imparted to the multilayered nonwoven web by the pigment.

For the present invention, the pigment will typically be mixed with the thermoplastic material, of which the fibers are made. Often, the pigment is added to the thermoplastic material in the form of a master batch or concentrate at the time of formation of the fibers. Colored master batches useful for the present invention include polypropylene based custom color master batches e.g. supplied by Ampacet; Lufilen and Luprofil supplied by BASF; Remafin for polyolefin fibers, Renol-AT for polyester fibers, Renol-AN for polyamide fibers and CESA for renewable polymers supplied by Clariant. Hence, the pigment will be suspended in the molten thermoplastic material prior to the thermoplastic material being forced through the spinnerets to form and lay down the fibers which form the nonwoven web.

To increase the whiteness and/or opacity of the fibers in either or both layers, titanium dioxide ($TiO_2$) may be used. Different crystal forms are available, however most preferred are rutile or anatase $TiO_2$. Other white pigments include zinc oxide, zinc sulfide, lead carbonate or calcium carbonate. To create a black color, carbon black or any other suitable colorant may be used. Various colored inorganic pigments may be used depending upon the desired color and may include metal oxides, hydroxides and sulfides or any other suitable material. Non-limiting examples of inorganic pigments include cadmium orange, iron oxide, ultramarine, chrome oxide green. One or more pigments may be combined to create the desired color. Non-limiting examples of organic colorants include anthraquinone pigments, azo pigments, benzimidazolone pigments, BONA Lakes, Dioxazine, Naphthol, Perylene, Perinone, Phthalocyanine, Pyranthrone, Quinacridones. Effects pigments including metal, pearlescent and fluorescent may also be used. Various colorants are described in *Plastics Additives Handbook,* 5th Edition.

The nonwoven materials suitable for use in the material webs of the present invention may be made from any suitable process. For example, as noted previously, the material web may comprise nonwoven layers or nonwoven strata produced via a spunbond process, or carded webs comprising staple fibers. Additional processes are contemplated, for example meltblown process. In some forms, the material web may comprise nonwovens which comprise spunbond filaments ("S"); meltblown fibers ("M"), finer fibers (fibers with average diameters less than one micron or 1000 nanometers (an "N-fiber")). In some forms, the material webs of the present invention may comprise a combination of fibers/filaments. For example, SMS, SM, SMMS, SMSS, SNS, SN, SNM, or SMN.

Forms are contemplated where melt additive is provided in one or more of the fiber/filament types. For example, an SMS may comprise melt additive in the M filaments and no melt additive in one or both S filaments. Additional examples are provided herein.

Other suitable processes for the material webs of the present invention comprise dry-laid and wet-laid. Dry-laid technologies include carding and air-laying. These technologies may be combined with each other, e.g., dry-laid with melt-spun, to form multi-layer, functional nonwoven substrates.

The air-laid process also uses fibers of discrete length, though these fibers are often shorter than the staple fibers used for carding. The length of fibers used in air-laying typically ranges from 2 mm to 20 mm, though lengths beyond this range may also be used. Particles may also be deposited into the fibrous structure during the air-laying process. Some fibers for air-laying may be prepared similarly as for carding, i.e., opening and blending as described above. Other fibers, such as pulp, may use mills, such as hammer mills or disc mills, to individualize the fibers. The various fibers may be blended to improve the uniformity of properties of the finished nonwoven substrate. The air-laying forming device combines external air and the fibers and/or particles so that the fibers and/or particles are entrained in the airsteam. After entrainment, the fibers and/or particles are collected as a loose web upon a moving foraminous surface, such as a wire mesh conveyor belt, for example. The air-laying process may contain a single air-laying forming device or multiple air-laying forming devices in line with one another, where the fibers and/or particles of the subsequent air-laying forming device are deposited on top of the fibers and/or particles from a preceding air-laying forming device, thereby allowing manufacture of a multi-layered nonwoven substrate.

Wet-laid nonwovens are made with a modified papermaking process and typically use fibers in the range of 2 mm to 20 mm, though lengths beyond this range have also been used. Some fibers for wet-laying may be prepared similarly as for carding, i.e., opening and blending as described above. Other fibers, such as pulp, may use mills, such as hammer mills or disc mills, to individualize the fibers. The fibers are suspended in water, possibly with other additives like bonding agents, and this slurry is typically added to a headbox from where it flows onto a wet-laid forming device to create a sheet of material. After initial water removal, the web is bonded and dried.

Spunlace nonwovens are typically carded and hydroentangled. The fibers of the spunlace nonwoven are first carded. In order to provide the carded fibers with integrity in the Z-direction and in CD, the carded fibers are then subjected to hydroentangling. Instead of carded nonwovens, spunlace nonwovens may be air-laid or wet-laid and subsequently hydroentangled.

The constituent layers/strata of the material web may be provided with structural integrity via a variety of different processes. Some examples include thermal point bonding, air through bonding, hydroentangling, and needlepunching each of which is well known in the art. Similarly, the attachment of the material web layers/strata may be achieved by a variety of different processes. Examples of such processes are discussed hereafter. The constituent materials of the material webs of the present invention can be joined together by any suitable process. An example of a suitable process include calendar bonding. It is worth noting that for those material webs of the present invention for which filled tufts are desired, the percentage of bond area between constituent filaments of the material web should be carefully considered. The inventors have found that with crimped filaments, too low of a calendar bond area does not allow for good formation of filled tufts. And too low of a calendar bond area yields a material web with low strength and poor abrasion resistance. However, too high of a calendar bond area reduces the length of filaments between adjacent bonds which inhibits the amount of uncoiling and/or displacement possible. Specifically, too high of a calendar bond area inhibits the movement of the filaments such that when subjected to the localized Z-direction urging, described herein for the formation of filled tufts and outer tufts, the crimped filaments have very limited ability to uncoil. In such configurations, the crimped filaments must undergo plastic deformation or break once the amount of uncoiling surpasses the amount of applied process strain. The inventors have found that calendar bond area above about 10 percent and less than about 18 percent allows for a good balance of filament mobility and free filament length available for uncoiling but still provides sufficient strength in the nonwoven web for manipulations of the crimped filaments as well as abrasion and tearing resistance in use.

In some forms of the present invention, the nonwoven webs comprising crimped filaments may comprise a calendar bond area of between about 10 percent to about 18 percent or between about 12 percent and 16 percent, specifically including all values within these ranges or any range created thereby. Nonwoven webs of the present invention which do not include crimped filaments may comprise a calendar bond area of between about 5 percent to about 30 percent, between about 10 percent to about 20 percent, specifically including all values within these ranges and any ranges created thereby. The bonds can be shaped like dots, diamonds, ovals or any other suitable shape and may be arranged in any suitable pattern to provide the desired mechanical properties.

The basis weight of nonwoven materials is usually expressed in grams per square meter (gsm). The basis weight of a single layer nonwoven material can range from about 8 gsm to about 100 gsm, depending on the ultimate use of the material. For example, each layer of a laminate may have a basis weight from about 8 to about 40 gsm or from about 8 to about 30 gsm. The basis weight of a multi-layer material is the combined basis weight of the constituent layers and any other added components. The basis weight of multi-layer materials of interest herein can range from about 20 gsm to about 150 gsm, depending on the ultimate use of the material.

Where material webs of the present invention comprise a film layer, any suitable film may be utilized. Exemplary films are discussed in U.S. Pat. Nos. 7,410,683; 8,440,286 and 8,697,218.

Forms of the present invention are contemplated where fillers—having a higher thermal conductivity than the polymer material—are included to the polymer material. Exemplary fillers include inorganic fillers such as calcium carbonate, which can have a higher thermal conductivity than the polymer matrix (e.g., than polypropylene), allowing faster and more homogeneous transfer of heat within the fiber matrix. This can allow for more benefit from the heat already applied in the processing of the material web and, if any, may increase the effect of heat treatment after the production of the material web. The particle size of the filler may be important for the observed effect. In one embodiment, the average particle size of the filler is hence 10 μm or smaller, preferably 1 μm or smaller (ISO 14688). The material may also be chosen to exhibit a thermal conductivity at room temperature of 1 W·m−1·K−1 or greater or more, 2.0 W·m−1·K−1 or more (DIN EN 12664). In some forms, the thermal conductivity could be 2.7 W·m−1·K−1, which approximately corresponds to that of CaCO3. Suitable CaCO3 can in one example be either ground CaCO3 (GCC) or precipitated CaCO3, or a combination thereof. For example, the CaCO3 can be micro-CaCO3 (GCC) having a Plus 325 Mesh of 0.002% and/or mean particle size of 1.6 microns and/or specific surface area of 4.5 m2/g. Such material is, for example, contained in a masterbatch under the trade name "Fiberlink 201S" from A. Schulman. In another example, the CaCO3 can be nano-CaCO3 (PCC) having a residue on sieve 45 micron<250 ppm and/or mean particle diameter of 0.07-0.13 microns and/or specific surface area 16 m2/g. Such material is, for example, found under the tradename SOCAL® U1S2 from Imerys Group. The use of $CaCO_3$ at around 10 percent by weight boosted blooming in materials tested. However, because of its size, $CaCO_3$ may not be appropriate for other types of material processing, e.g. meltblowing.

Forms of the present invention are contemplated where a nucleating agent(s) is (are) included in the polymer matrix. A nucleating agent can increase the number of sites where crystallites begin to form, thereby decreasing the area the crystallites have to grow before they will impinge on each other. Accordingly, the crystallites will be dimensionally smaller and the additive will have a shorter distance to travel before it reaches the fiber surface. In general melt additives may only be able to migrate through the amorphous domains of the polymeric matrix at room temperature, but dependent on the degree of crystallinity (or degree of amorphousness), the geometry and size of the amorphous regions, as well as the conformation and size of the migratory additive, the additive may not be able to migrate effectively at all, as it can be too constricted to move. So it is believed that the less constricted the path composed of the amorphous phase, the more additive will be able to reach the surface before the polymer has recrystallized. Nucleating agents can help to drive more or faster blooming of a melt-additive. In the specific case of hydrophobic or hydrophilic melt additives, the nucleating agent can create a more intensive hydrophobic or hydrophilic effect from the respective melt-additives than without the nucleating agent. Additionally, the provision of a nucleating agent can reduce the level of melt additive needed for effective blooming. This can be cost beneficial as less melt additive may be utilized to potentially achieve the same blooming effect to that achievable with higher levels of melt additive sans the nucleating agent.

Suitable nucleating agents can be both inorganic or organic, and insoluble and soluble in the polymer matrix. In some forms, the nucleating agent comprises a nonitol, trisamide and/or a sorbitol based nucleating agent. Specific but non-limiting examples are: organic nucleation agents such as Millad NX 8000 or (in its new trade name) NX UltraClear GP110B from the Milliken company. Trisamide can be obtained, for example, from Irgaclear XT 386 or any masterbatches containing that active component. An example of an effective inorganic nucleating agent is CaCO3, or other and especially nano-clay or nano-scale mineral molecules.

Where finer fibers than spunbond are being produced, a suitable nucleating agent is NX UltraClear GP110B. The NX UltraClear GP110B may be used from between 2 weight percent to 4 weight percent of NX UltraClear GP110B masterbatch (containing 10 percent of the active). The nucleating agent can boost blooming of the melt additive. Weight percentages of 0.5 weight percent to about 1.0 weight percent may be utilized; however, it is believed that such concentrations would be less effective than the former range based upon testing of an equivalent nucleating agent NX10 also from Milliken.

Including branched polymers and/or random co-polymers to the polymer material may result in a polymeric matrix that inherently allows the additive to move more freely and less constricted and therefore faster. Diffusivity may be promoted, e.g., by using/adding branched polymers or random-copolymers as/to the polymer material. As an example, bi-component technology may be utilized where the additive is added to only (or predominantly) the polymer feeds eventually forming at least the predominant part of the outermost area of the fibers e.g. sheath in a core-sheath configuration.

Disposable Absorbent Articles

The material webs of the present invention may comprise any suitable portion of a disposable absorbent article. Some suitable examples, include a topsheet, backsheet, barrier cuff, intermediate layers between the topsheet and an absorbent core and/or intermediate layers between the backsheet and the absorbent core.

Figure 17:
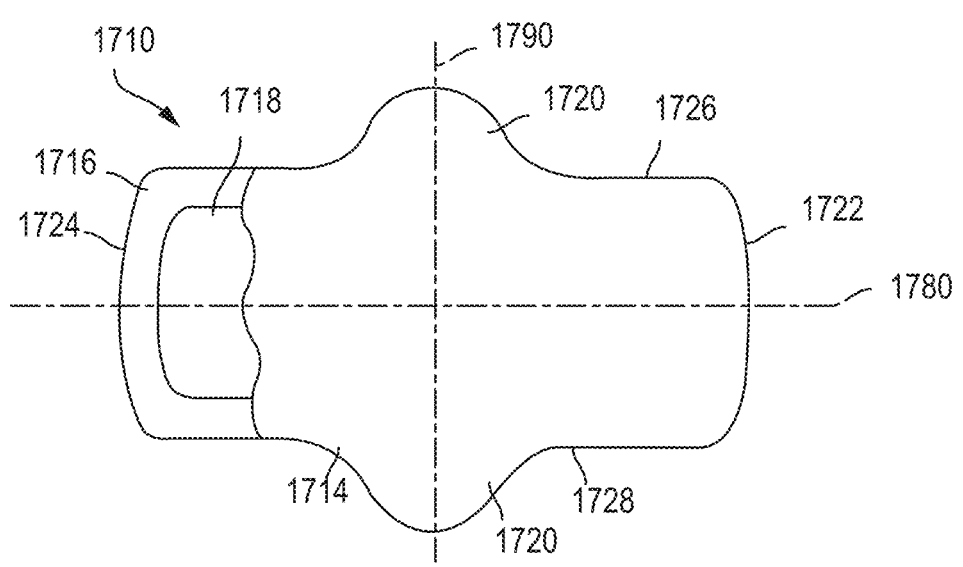
FIG. 17 is a top view of a feminine hygiene article, i.e. sanitary napkin, constructed in accordance with the present disclosure.

Referring to FIG. 17, an absorbent article 1710 which may utilize the material webs described herein may be a sanitary napkin/feminine hygiene pad. As shown, the sanitary napkin 1710 may comprise a liquid permeable topsheet 1714, a liquid impermeable, or substantially liquid impermeable, backsheet 1716, and an absorbent core 1718 positioned intermediate the topsheet 1714 and the backsheet 1716. The sanitary napkin 1710 may comprise wings 1720 extending outwardly with respect to a longitudinal axis 1780 of the sanitary napkin 1710. The sanitary napkin 1710 may also comprise a lateral axis 1790. The wings 1720 may be joined to the topsheet 1714, the backsheet 1716, and/or the absorbent core 1718. The sanitary napkin 1710 may also comprise a front edge 1722, a rear edge 1724 longitudinally opposing the front edge 1722, a first side edge 1726, and a second side edge 1728 laterally opposing the first side edge 1726. The longitudinal axis 1780 may extend from a midpoint of the front edge 1722 to a midpoint of the rear edge 1724. The lateral axis 1790 may extend from a midpoint of the first side edge 1726 to a midpoint of the second side edge 1728. The sanitary napkin 1710 may also be provided with additional features commonly found in sanitary napkins as is known in the art. In some forms of the present invention, the wings may be provided with zones of extensibility as described in U.S. Pat. No. 5,972,806.

Any suitable absorbent core known in the art may be utilized. The absorbent core 1718 may be any absorbent member which is generally compressible, conformable, non-irritating to the wearer's skin, and capable of absorbing and retaining liquids such as urine, menses, and/or other body exudates. The absorbent core 1718 may be manufactured from a wide variety of liquid-absorbent materials commonly used in disposable absorbent articles such as comminuted wood pulp which is generally referred to as airfelt. The absorbent core 1718 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 1718 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 1718 may comprise one or more channels, such as two, three, four, five, or six channels.

The absorbent core 1718 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The absorbent article 1710 may comprise additional layers between the top sheet 1714 and the absorbent core 1718. For example, the absorbent article 1710 may comprise a secondary topsheet and/or an acquisition layer positioned between the topsheet 1714 and the absorbent core 1718.

The backsheet can comprise a liquid impervious film. The backsheet can be impervious to liquids (e.g., body fluids) and can be typically manufactured from a thin plastic film. However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m$^2$ to about 35 g/m$^2$. However, it should be noted that other flexible liquid impervious materials may be used as the backsheet. Herein, "flexible" refers to materials which are compliant and which will readily conform to the general shape and contours of the wearer's body.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986 entitled "Disposable Waste-Containment Garment", which issued to Minetola et al. on Mar. 4, 1986. Another suitable attachment device including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

Still another example of a disposable absorbent article which may utilize the material webs of the present invention are diapers which include non-refastenable pants, re-fastenable pants and/or re-fastenable diapers. Diapers have can have a similar construction to that of sanitary napkins. An exemplary diaper is described below.

Figure 18:
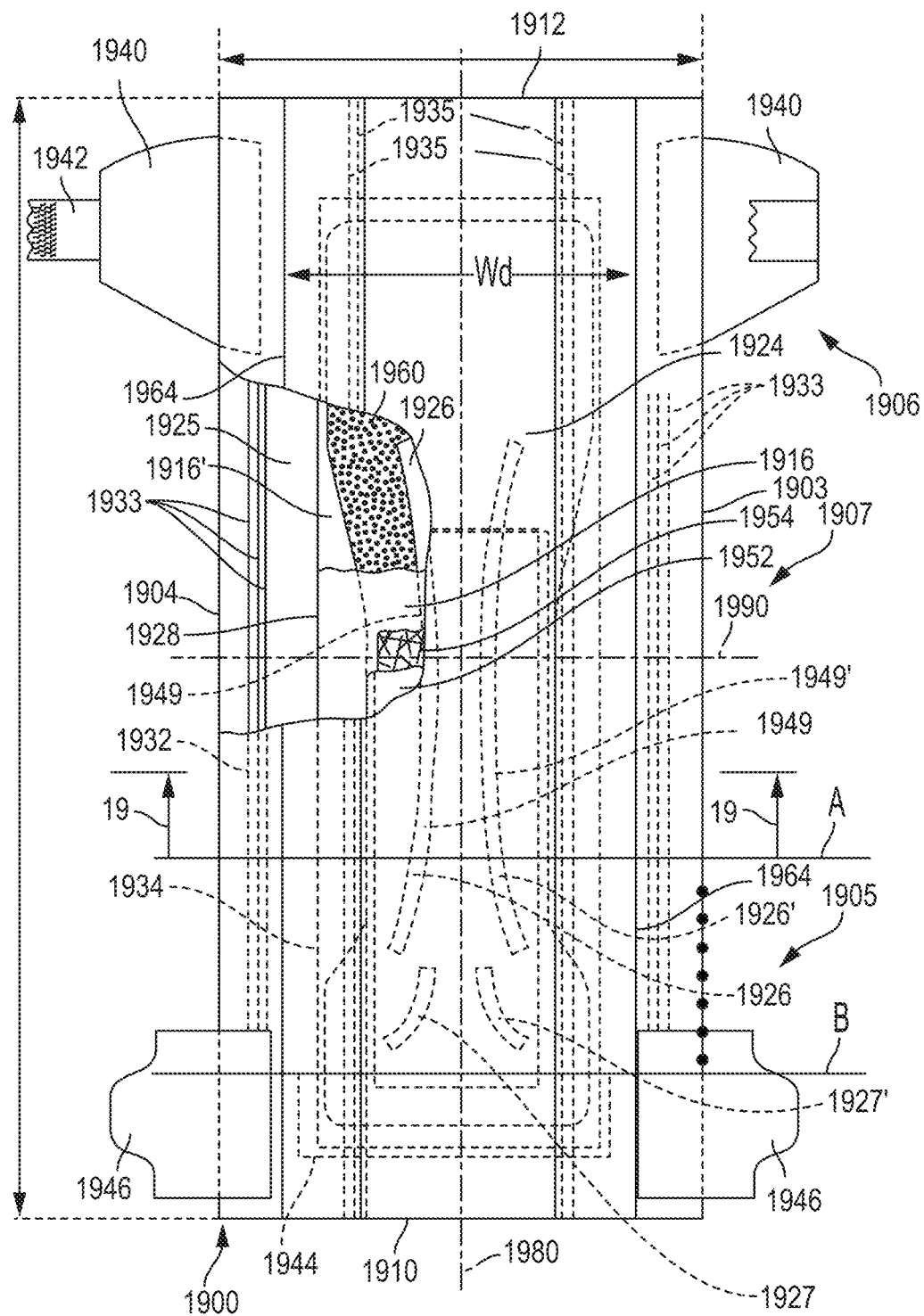
FIG. 18 is a top view of an absorbent article with some layers partially removed in accordance with the present disclosure.

Referring to FIG. 18, a plan view of an example absorbent article that is a diaper 1900 in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the present disclosure may be used for making a wide variety of diapers and other absorbent articles.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a liquid management system ("LMS") 1950 (shown in FIG. 19), which, in the example represented, comprises a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The LMS 1950 may also be provided as a single layer or two or more layers. The absorbent article may also comprise elasticized gasketing cuffs 1932 joined to the chassis of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1900 and cooperating with a landing zone on the front of the absorbent article 1900. The absorbent article may also comprise other typical elements, which are not represented, such as a rear elastic waist feature and a front elastic waist feature, for example.

The absorbent article 1900 may comprise a front waist edge 1910, a rear waist edge 1912 longitudinally opposing the front waist edge 1910, a first side edge 1903, and a second side edge 1904 laterally opposing the first side edge 1903. The front waist edge 1910 is the edge of the absorbent article 1900 which is intended to be placed towards the front of the user when worn, and the rear waist edge 1912 is the opposite edge. Together the front waist edge 1910 and the rear waist edge form waist opening when the absorbent article 1900 is donned on a wearer. The absorbent article 1900 may have a longitudinal axis 1980 extending from the lateral midpoint of the front waist edge 1910 to a lateral midpoint of the rear waist edge 1912 of the absorbent article 1900 and dividing the absorbent article 1900 in two substantially symmetrical halves relative to the longitudinal axis 1980, with article placed flat and viewed from the wearer-facing surface as illustrated FIG. 19. The absorbent article may also have a lateral axis 1990 extending from the longitudinal midpoint of the first side edge 1903 to the longitudinal midpoint of the second side edge 1904. The length L of the absorbent article 1900 may be measured along the longitudinal axis 1980 from the front waist edge 1910 to the rear waist edge 1912. The crotch width of the absorbent article 1900 may be measured along the lateral axis 1990 from the first side edge 1903 to the second side edge 1904. The absorbent article 1900 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The topsheet 1924, the backsheet 1925, the absorbent core 1928, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 1928 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core.

Figure 19:
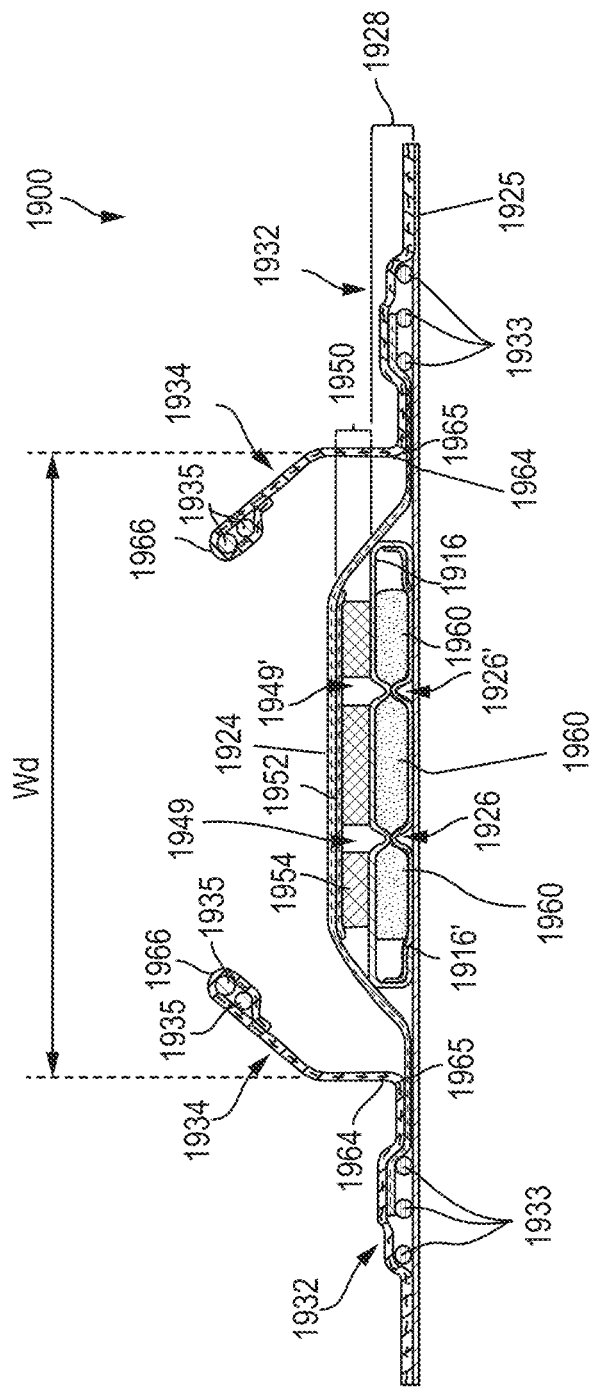
FIG. 19 is a cross-sectional view of the absorbent article taken about line 19-19 of FIG. 18 in accordance with the present disclosure.
Figure 20:
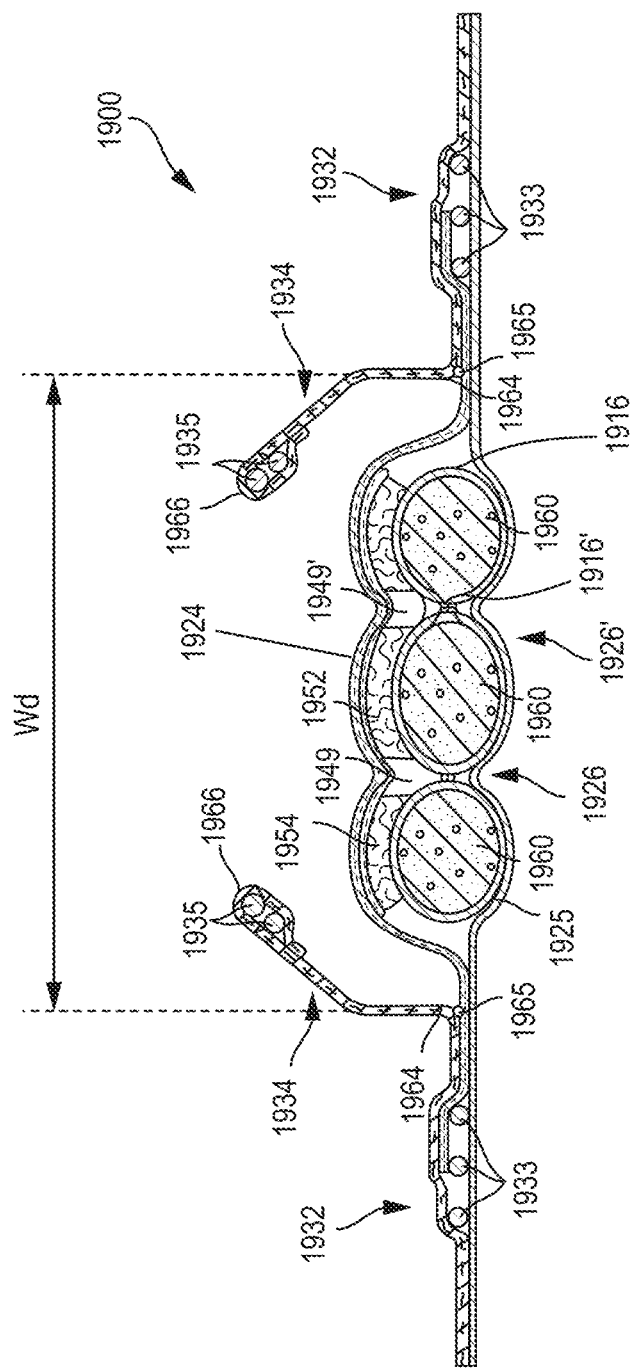
FIG. 20 is a view of the absorbent article of FIG. 19 where the absorbent article has been at least partially loaded with fluid in accordance with the present disclosure.

The absorbent core 1928 may comprises one or more channels, represented in FIG. 19 as the four channels 1926, 1926' and 1927, 1927'. Additionally or alternatively, the LMS 1950 may comprises one or more channels, represented in FIGS. 18-20 as channels 1949, 1949'. In some forms, the channels of the LMS 1950 may be positioned within the absorbent article 1900 such they aligned with, substantially aligned with, overlap, or at least partially overlap, the channels of the absorbent core 1928. These and other components of the absorbent articles will now be discussed in more details.

The topsheet 1924 is the part of the absorbent article that is directly in contact with the wearer's skin. The topsheet 1924 may be joined to the backsheet 1925, the core 1928 and/or any other layers as is known to those of skill in the art. Usually, the topsheet 1924 and the backsheet 1925 are joined directly to each other in some locations (e.g., on or close to the periphery of the article) and are indirectly joined together in other locations by directly joining them to one or more other elements of the absorbent article 1900.

The backsheet 1925 is generally that portion of the absorbent article 1900 positioned adjacent the garment-facing surface of the absorbent core 1928 and which prevents, or at least inhibits, the bodily exudates absorbed and contained therein from soiling articles such as bedsheets and undergarments. The backsheet 1925 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 1900 while still preventing, or at least inhibiting, bodily exudates from passing through the backsheet 1925. Example breathable materials may include materials such as woven webs, nonwoven webs, and composite materials such as film-coated nonwoven webs, microporous films, and monolithic films.

The backsheet 1925 may be joined to the topsheet 1924, the absorbent core 1928, and/or any other element of the absorbent article 1900 by any attachment methods known to those of skill in the art. Suitable attachment methods are described above with respect to methods for joining the topsheet 1924 to other elements of the absorbent article 1900.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 1928 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 1928 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

The absorbent core 1928 may also comprise a generally planar top side and a generally planar bottom side. The core 1928 may have a longitudinal axis 80' corresponding substantially to the longitudinal axis 80 of the absorbent article, as seen from the top in a planar view as in FIG. 19. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 1916, 1916' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 1916 may at least partially surround the second material, substrate, or nonwoven 1916' to form the core wrap. The first material 1916 may surround a portion of the second material 1916' proximate to the first and second side edges 1903 and 1904.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 1928 may comprise a first absorbent layer and a second absorbent layer. The first absorbent layer may comprise the first material 1916 and a first layer of absorbent material 1960, which may be 100% or less of SAP. The second absorbent layer may comprise the second material 1916' and a second layer of absorbent material 1960, which may also be 100% or less of SAP.

The fibrous thermoplastic adhesive material may be at least partially in contact with the absorbent material 1960 in the land areas and at least partially in contact with the materials 1916 and 1916' in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 1928 and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article 1900 may comprise a pair of barrier leg cuffs 1934. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 64 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings 1933 or elastic elements in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 1946 and rear ears 1940. The ears may be an integral part of the chassis, such as formed from the topsheet 1924 and/or backsheet 1925 as side panel. Alternatively, as represented on FIG. 19, the ears (1946, 1940) may be separate elements attached by gluing, heat embossing, and/or pressure bonding. The rear ears 1940 may be stretchable to facilitate the attachment of the tabs 1942 to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 1950 is to quickly acquire the fluid and distribute it to the absorbent core 1928 in an efficient manner. The LMS 1950 may comprise one or more layers, which may form a unitary layer or may remain as discrete layers which may be attached to each other. The LMS 1950 may comprise additional layers: a distribution layer 1954 and/or an acquisition layer 1952 disposed between the absorbent core and the topsheet, but the present disclosure is not limited to such a configuration.

The LMS 1950 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example.

The distribution layer 1954 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The acquisition layer 1952 may be disposed, for example, between the distribution layer 1954 and the topsheet 1924. The acquisition layer 1952 may be or may comprise a non-woven material, such as an SMS or SMMS material, comprising a spunbonded, a melt-blown and a further spunbonded layer or alternatively a carded chemical-bonded nonwoven. The acquisition layer 1952 may comprise air or wet-laid cellulosic, cross-linked cellulosic, or synthetic fibers, or blends thereof. The acquisition layer 1952 may comprise a roll-stock web of synthetic fibers (which may be processed to increase void space, such as by solid state formation), or a combination of synthetic and cellulosic fibers, bonded together to form a highloft material. Alternatively, the acquisition layer 1952 may comprise absorbent open cell foam. The nonwoven material may be latex bonded.

The LMS 1950 of the absorbent article 1900 may comprise channels that may generally enable better conformation of the absorbent article to the wearer's anatomy, leading to increased freedom-of-movement and reduced gapping. One or more of the channels of the LMS 1950 may be configured to work in concert with various channels in the absorbent core 1928, as discussed above. Furthermore, channels in the LMS 1950 may also provide increased void space to hold and distribute urine, BM or other bodily exudates within the absorbent article, leading to reduced leakage and skin contact. Channels in the LMS 1950 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

As stated previously, the material webs of the present invention may be utilized as a topsheet for a disposable absorbent article, examples of which include the sanitary napkin 1710 and diaper 1900 discussed heretofore.

The material webs of the present disclosure may be used as components of absorbent articles. More than one material web may be used in a single absorbent article. In such a context, the material webs may form at least a portion of: a topsheet; a topsheet and an acquisition layer; a topsheet and a distribution layer; an acquisition layer and a distribution layer; a topsheet, an acquisition layer, and a distribution layer; an outer cover; a backsheet; an outer cover and a backsheet, wherein a film (nonapertured layer) forms the backsheet and a nonwoven web forms the outer cover; a leg cuff; an ear or side panel; a fastener; a waist band; belt or any other suitable portion of an absorbent article. The number of strata in a nonwoven web may also be determined by the nonwoven laminates' particular use.

In some forms, additional layers may be positioned between the topsheet and the absorbent core. For example, a secondary topsheet, acquisition layer, and/or distribution layer, each of which are known in the art, may be positioned between the topsheet and the absorbent core of the absorbent article.

Arrays of Absorbent Articles

As mentioned heretofore, material webs of the present invention may be utilized in a plurality of absorbent articles. Forms of the present invention are contemplated where an array of absorbent articles, each comprising a topsheet, backsheet, and an absorbent core disposed therebetween comprise material webs of the present invention. The array comprises a first plurality of absorbent articles comprising a first material web. The first material web comprises a first plurality of melt additive bloom areas. The first material web may form at least a portion of each of the first plurality of absorbent articles, e.g. topsheet, backsheet, absorbent core.

The array further comprises a second plurality of absorbent articles. Each of the second plurality of absorbent articles comprises a second material web which forms a portion of at least one of the topsheet, backsheet and/or absorbent core. The second material web may comprise a second plurality of melt additive bloom areas. The first plurality of melt additive bloom areas and the second plurality of bloom areas may be different. For example, the first plurality of melt additive areas may comprise a hydrophobic composition while the second plurality of melt additive areas comprise a hydrophilic composition. In such forms, the first material web may form a portion of the topsheet of the first plurality of absorbent articles, and the second material web may form a portion of the topsheet of the second plurality of absorbent articles. In some forms, the first plurality of absorbent articles may be the same type of article as the second plurality of absorbent articles, e.g. sanitary pads. In other forms, the first plurality of absorbent articles may be different than the second plurality of absorbent articles, e.g. diapers versus sanitary pads. Still in other forms, the first material web may form a portion of the first plurality of absorbent articles which is different than what the second material web forms for the second plurality of absorbent articles, e.g. backsheet versus topsheet.

In some forms of the present invention, the first material web may comprise a different combination of discontinuities than the second material web. For example, the first material may comprise a combination of apertures and tunnel tufts while the second material web comprises a nested tufts and apertures. In some forms, the first plurality of absorbent articles may comprise a different discontinuity or combination thereof than the second plurality of absorbent articles. In such forms, the melt additive bloom areas for the first plurality of absorbent articles may comprise a different composition than the melt additive bloom areas for the second plurality of absorbent articles. Additionally, in such forms, the first plurality of absorbent articles may be different than the second plurality of absorbent articles, e.g. diaper versus sanitary pad.

Forms of the present invention are contemplated where the array comprises additional pluralities of absorbent articles. Such additional pluralities may comprise material webs of the present invention. These material webs may be different than the first material web and/or second material web.

As another example, forms of the present invention are contemplated where a nonwoven comprises a hydrophobic melt additive. The nonwoven comprises a hydrophilic fiber composition or a fiber composition which is more hydrophilic than the melt additive. In such forms, the nonwoven may be processed such that a plurality of discrete melt additive bloom areas are provided on the nonwoven. The melt additive bloom areas may correspond to the distal ends of at least one of tufts or corrugations. The nonwoven, in some forms, may further comprise apertures, embossments, and/or fusion bonds. In some forms, the apertures may be provided in an intermediate zone, while the tufts are provided in laterally outboard zones from the intermediate zone. The fusion bonds and/or embossments may be in the intermediate zone and/or in the laterally outboard zones. In some forms, the embossments may be limited to the intermediate zone while the fusion bonds are in the intermediate zone and in the lateral zones.

As yet another example, forms of the present invention are contemplated where a nonwoven comprises a hydrophilic melt additive. The nonwoven comprises a hydrophobic fiber composition or a fiber composition which is more hydrophobic than the melt additive. In such forms, the nonwoven may be processed such that a plurality of discrete melt additive bloom areas are provided on the nonwoven. The melt additive bloom areas may correspond to the undeformed regions of the material web. The nonwoven web may further comprise a plurality of tufts and/or corrugations. The nonwoven web may further comprise at least one of fusion bonds, embossments, and/or apertures.

As yet another example, forms of the present invention are contemplated where a film comprises a melt additive. The film may be subjected to processing which applies thermal energy across the film thereby creating promoting the creation of melt additive bloom areas. The melt additive bloom area may comprise a hydrophobic composition. Forms of this invention are contemplated where the film further comprises at least one of apertures, embossments, tufts, corrugations, fusion bonds, and/or distal end/land area bonds. Additionally, such films may be utilized in the context of a portion of a backsheet which is air permeable but impervious to liquid.

As yet another example, forms of the present invention are contemplated where a material web comprising a melt additive is subjected to thermal energy application across the entirety of the web. The material web may be a nonwoven and the melt additive may comprise a hydrophobic composition. The nonwoven web may further comprise apertures. Additionally, the nonwoven web may further comprise at least one of embossments, tufts, corrugations, or fusion bonds. The apertures, embossments, tufts, corrugations and/or fusion bonds may be arranged in zones as described herein.

Packaging

In some forms of the present invention, the material webs of the present invention may be utilized as packaging. For example, as packaging of disposable absorbent articles. In such forms, the material web may be provided with discrete melt additive bloom areas as described herein. The melt additive bloom areas may alter the coefficient of friction in a plurality of localized areas. In some forms, the melt additive bloom areas may increase the coefficient of friction to provide for better grip of the packaging. In some forms, the melt additive bloom areas may form anti-stick regions to control fluid dispensing. In such forms, hydrophobic compositions may be leveraged due to its liquid repelling effect that gives a cleanliness benefit in "critical areas", e.g. close to an opening for fluid dispensing aperture.

In some forms, the melt additive bloom areas may alter the coefficient of friction of discrete portions of packaging, e.g. by providing softness, to reinforce the haptic perception of a 3D structure on the package. In some forms the haptic perception on the package may correspond to a haptic perception of the product within the package. In such forms, a consumer may more easily recognize the package and may associate the "special feel" with the product.

In some forms, the melt additive bloom areas can be utilized to improve the adhesion of ink and/or of glues to the material web, which as noted above can be packaging for articles. For example melt additive bloom areas comprising hydrophilic compositions can increase the surface energy of the material web at the location of the melt additive bloom areas. The increased surface energy can increase the adhesion of inks and glues. In contrast, where the melt additive bloom areas comprise a hydrophobic composition, the melt additive bloom areas may be selected to occur where ink and/or glues will not be present. In general, inks and/or glues tend to wash off of hydrophobic compositions/substrates.

Forms of the present invention are contemplated where the packaging comprises a composition having a higher Tg, e.g. polystyrene—100 degrees C., polycarbonate—145 degrees C. In such forms, as noted previously, it is believed that suitable melt additives are much easier to find given the high Tg.

Tests

Glass Transition Temperature and Melting Temperature

Tg and melting point are determined in accordance with ASTM D3418-15 for both the base matrix polymer and the neat melt-additive. When melt additive is not directly available, it can be collected from heat treated substrate using the extraction described in "Solvent Wash Procedure".

Surface Tension of a Liquid

The surface tension of a liquid is determined by measuring the force exerted on a platinum Wilhelmy plate at the air-liquid interface. A Krüss tensiometer K11 or equivalent is used. (Available by Krüss USA (www.kruss.de)). The test is operated in a laboratory environment at 23±2° C. and 50±5% relative humidity. The test liquid is placed into the container given by the manufacturer and the surface tension is recorded by the instrument and its software.

Surface Tension of a Fiber

Basis Weight Test

A 9.00 cm2 large piece of web, i.e. 1.0 cm wide by 9.0 cm long, is cut out of the product, and it needs to be dry and free from other materials like glue or dust. Samples are conditioned at 23° Celsius (±2° C.) and at a relative humidity of about 50% (±5%) for 2 hours to reach equilibrium. The weight of the cut web pieces is measured on a scale with accuracy to 0.0001 g. The resulting mass is divided by the specimen area to give a result in g/m2 (gsm). Repeat for at least 20 specimens for a particular sample from 20 identical products, if the product and component is large enough, more than one specimen can be obtained from each product. An example of a sample is the left diaper cuff in a bag of diapers, and 10 identical diapers are used to cut out two 9.00 cm2 large specimens of cuff web from the left side of each diaper for a total of 20 specimens of "left-side cuff nonwoven." If the local basis weight variation test is done, those same samples and data are used for calculating and reporting the average basis weight.

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad. As a default, this is also called the 32 mN/m Low Surface Tension Fluid Strikethrough Test because of the surface tension of the test fluid and each test is done on two layers of the nonwoven sample simply laid on top of each other.

For this test, the reference absorbent pad is 5 plies of Ahlstrom grade 989 filter paper (10 cm×10 cm) and the test fluid is a 32 mN/m low surface tension fluid.

Scope

This test is designed to characterize the low surface tension fluid strikethrough performance (in seconds) of webs intended to provide a barrier to low surface tension fluids, such as runny BM, for example.

Equipment

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strike-through time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Cut the required number of nonwoven web specimens. For web sampled off a roll, cut the samples into 10 cm by 10 cm sized square specimens. For web sampled off of a product, cut the samples into 15 by 15 mm square specimens. The fluid flows onto the nonwoven web specimen from the strike through plate. Touch the nonwoven web specimen only at the edge.

Neatly stack 5 plies of the Reference Absorbent Pad onto the base plate of the strikethrough tester.

Place the nonwoven web specimen on top of the 5 plies of filter paper. Two plies of the nonwoven web specimen are used in this test method. If the nonwoven web sample is sided (i.e., has a different layer configuration based on which side is facing in a particular direction), the side facing the wearer (for an absorbent product) faces upwards in the test.

Place the strikethrough plate over the nonwoven web specimen and ensure that the center of the strikethrough plate is over the center of the nonwoven web specimen. Center this assembly under the dispensing funnel.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for the required number of nonwoven web specimens. A minimum of 5 specimens of each different nonwoven web sample is required. The average value is the 32 mN/m low surface tension strikethrough time in seconds.

Filament Diameter and Denier Test

The diameter of filaments in a sample of a nonwoven substrate is determined by using a Scanning Electron Microscope (SEM) and image analysis software. A magnification of 500 to 10,000 times is chosen such that the filaments are suitably enlarged for measurement. The samples are sputtered with gold or a palladium compound to avoid electric charging and vibrations of the filaments in the electron beam. A manual procedure for determining the filament diameters is used. Using a mouse and a cursor tool, the edge of a randomly selected filament is sought and then measured across its width (i.e., perpendicular to filament direction at that point) to the other edge of the filament. For non-circular filaments, the area of the cross-section is measured using the image analysis software. The effective diameter is then calculated by calculating the diameter as if the found area was that of a circle. A scaled and calibrated image analysis tool provides the scaling to get actual reading in micrometers ($\mu$m). Several filaments are thus randomly selected across the sample of the nonwoven substrate using the SEM. At least two specimens from the nonwoven substrate are cut and tested in this manner. Altogether, at least 100 such measurements are made and then all data is recorded for statistical analysis. The recorded data is used to calculate average (mean) of the filament diameters, standard deviation of the filament diameters, and median of the filament diameters. Another useful statistic is the calculation of the amount of the population of filaments that is below a certain upper limit. To determine this statistic, the software is programmed to count how many results of the filament diameters are below an upper limit and that count (divided by total number of data and multiplied by 100%) is reported in percent as percent below the upper limit, such as percent below 1 micrometer diameter or %-submicron, for example.

If the results are to be reported in denier, then the following calculations are made.

$$\text{Filament Diameter in denier} = \text{Cross-sectional area (in m2)} \times \text{density (in kg/m3)} \times 9000 \text{ m} \times 1000 \text{ g/kg}.$$

For round filaments, the cross-sectional area is defined by the equation:

$$A = \pi*(D/2)^2.$$

The density for polypropylene, for example, may be taken as 910 kg/m3.

Given the filament diameter in denier, the physical circular filament diameter in meters (or micrometers) is calculated from these relationships and vice versa. We denote the measured diameter (in microns) of an individual circular filament as D.

In case the filaments have non-circular cross-sections, the measurement of the filament diameter is determined as and set equal to the hydraulic diameter, as discussed above.

Mass-Average Diameter

The mass-average diameter of filaments is calculated as follows:

mass average diameter, $$d_{mass} = \frac{\sum_{i=1}^{n}(m_i \cdot d_i)}{\sum_{i=1}^{n} m_i} = \frac{\sum_{i=1}^{n}(\rho \cdot V_i \cdot d_i)}{\sum_{i=1}^{n}(\rho \cdot V_i)} = \frac{\sum_{i=1}^{n}\left(\rho \cdot \frac{\pi d_i^2 \cdot \partial x}{4} \cdot d_i\right)}{\sum_{i=1}^{n}\left(\rho \cdot \frac{\pi d_i^2 \cdot \partial x}{4}\right)} = \frac{\sum_{i=1}^{n} d_i^3}{\sum_{i=1}^{n} d_i^2}$$

where
filaments in the sample are assumed to be circular/cylindrical,
$d_i$=measured diameter of the $i^{th}$ filament in the sample,
$\partial x$=infinitesimal longitudinal section of filament where its diameter is measured, same for all the filaments in the sample,
$m_i$=mass of the $i^{th}$ filament in the sample,
n=number of filaments whose diameter is measured in the sample
$\rho$=density of filaments in the sample, same for all the filaments in the sample
$V_i$=volume of the $i^{th}$ filament in the sample.

The mass-average filament diameter should be reported in μm.

Gravimetric Weight Loss Test

The Gravimetric Weight Loss Test can be used to determine the amount of lipid ester (e.g., GTS) in a nonwoven substrate of the present disclosure. One or more samples of the nonwoven substrate are placed, with the narrowest sample dimension no greater than 1 mm, into acetone at a ratio of 1 g nonwoven substrate sample per 100 g of acetone using a refluxing flask system. First, the sample is weighed before being placed into the reflux flask, and then the mixture of the sample and the acetone is heated to 60° C. for 20 hours. The sample is then removed and air dried for 60 minutes and a final weight of the sample is determined. The equation for calculating the weight percent lipid ester in the sample is:

weight % lipid ester=([initial mass of the sample−final mass of the sample]/[initial mass of the sample])×100%.

Presence of a Melt Additive

Presence of a melt additive (as opposed to a surface coating) is determined by comparison of non-heat activated substrate with and without solvent wash. Non activated regions can be identified using the "Determination of Activated Zones by FTIR/ATR" method as described previously and excised from the substrate for analysis. Approximately 2.0 grams needs to be collected.

An appropriate solvent is identified which is effective to dissolve the additive but will not swell the matrix or dissolve any further additive from the matrix. For GTS in PP, acetone is an appropriate solvent.

1.00 g±0.01 g of the non-heat activated substrate is weighed into a 500 mL flask and 100 mL of a solvent is added. The substrate with solvent is then stirred for 30 minutes at 900 rpm at 20° C. The solvent is decanted and the flask is refilled with a second 100 mL of solvent. The mixture is stirred again for 30 minutes at 900 rpm at 20° C. The solvent is decanted and the nonwoven is dried overnight at 40° C.

Two melt films are prepared, the first of the non-activated area unwashed, and a second of the non-activated substrate after solvent wash, for analysis. Melt film were prepare and analyzed as described in "Quantification of Total Melt-Additive Concentration by FTIR". FTIR transmission measurements are made on three (3) randomly selected sites from each of the washed and non-washed films to calculate the total concentration. Calculate and record the arithmetic mean of the triplicates separately, and record as Concentration Washed and Concentration Unwashed to the nearest 0.1%. Report the ratio of the Unwashed Concentration divided by the Washed Concentration. A ratio greater than indicates a surface coating instead of a melt additive was used.

The FTIR (reflectance and ATR) measurements of melt additives in a polymer matrix are quantified by peak normalization. One absorption band is selected which is attributed exclusively to the melt additive and must be free of interference from other components or impurities in the sample mixture. This signal is denoted as $E_1$. An example is the peak between 1806 cm$^{-1}$ and 1660 cm$^{-1}$ for the GTS. A second band is selected that which is attributed exclusively to the polymer matrix and must be free of interferences from the sample matrix or other impurities in the sample mixture. The signal is used to normalize for path length of the specific specimen. This signal is denoted as $E_2$. An example is the peak between 985 cm$^{-1}$ and 950 cm$^{-1}$ for polypropylene (PP). The FTIR methods described herein are written directed specifically toward these examples, GTS in PP, but one skilled in the art, can select analogous peaks to facilitate analysis of other melt additives and matrixes.

Quantification of Total Melt-Additive Concentration by FTIR

Total GTS in fibers, is measured using transmission FTIR (a suitable instrument is the Nicolet 6700, Thermo Scientific, or equivalent). Calibration was performed using standard films prepared from known mixtures of GTS in PP and can be used to quantify the total concentration of GTS on and within a fiber. All testing is performed in a conditioned room maintained at 23° C.±2° C. and 50%±2% relative humidity. Samples are conditioned under the same conditions for 2 hours prior to testing.

Calibration Standards are prepared by mixing the base polymer (e.g. polypropylene) with the active GTS. A volume of 55 cm$^3$ of each standard was prepared at a concentration of 0.0%, 0.4%, 1.2%, 2.0%, 4.0%, 12.0% and 20.0% wt/wt of GTS in PP. First the components were accurately weighed and then placed into a laboratory tumble mixer (a suitable mixer is the Turbula T2C available from Willy A. Bachofen AG Maschinenfabrik, or equivalent) and mixed for 10 min. Next the mixture was added to a laboratory kneader (a suitable instrument is a Haake Polydrive Mixer, Thermo Electron GmbH, or equivalent) and kneaded at 180° C. at 10 rpm for 2 min and then again at 60 rpm for an additional 8 min. After kneading, each mixture is ground (a suitable grinder is the Wanner C13.20sv or equivalent) before being pressed into a film.

One melt film was prepared for each concentration using a hot press (a suitable press is the Graseby Specac Hot Press, or equivalent). A standard mixture of 25 mg was placed between two aluminum foils and melted until the pressing form reached 175° C., pressed for 2.0 min with a 5000 kg weight and then cooled for 20 min in a water cooled form under no pressure. The resulting film should have a uniform thickness from 59 μm to 62 μm.

Transmission FTIR is performed on three different locations on each calibration film under the following conditions: 64 scans at a resolution of 1.0 and amplification of 1.0 from 550 to 4000 cm$^{-1}$. Background scans are performed before every new specimen. Two peaks were measured for quantification, one associated with the PP and the second associated with the GTS. Using an appropriate software, draw a baseline between 1025 cm$^{-1}$ and 950 cm$^{-1}$ and measure the vertical drop from highest peak between 985 cm$^{-1}$ and 950 cm$^{-1}$ wavenumbers. Secondly, draw a baseline between 1806 cm$^{-1}$ and 1660 cm$^{-1}$ and measure the vertical drop from highest peak between those two wavenumbers.

Calibration is performed using peak ratio normalization. Extinction E at a specific wave length λ is defined as:

$$E(\lambda) = \epsilon \cdot c \cdot d$$

with c=weight fraction of the absorbing substance; d=thickness of the radiated sample path length and ϵ=coefficient of absorption. For a two-component-system from substance A and substance B, the equation would be expressed as:

$$E(\lambda) = \epsilon_A(\lambda) \cdot c_A \cdot d + \epsilon_B(\lambda) \cdot c_B \cdot d$$

To eliminate contribution from the path length, a ratio of the area of two peaks can be used:

$$\frac{E_1(\lambda)}{E_2(\lambda)} = \frac{\epsilon_{A,1}(\lambda) \cdot c_A \cdot d_p + \epsilon_{B,1}(\lambda) \cdot c_B \cdot d_p}{\epsilon_{A,2}(\lambda) \cdot c_A \cdot d_p + \epsilon_{B,2}(\lambda) \cdot c_B \cdot d_p}$$

Here $E_1$ refers to the peak between 1660 and 1806 cm$^{-1}$ and $E_2$ refers to the peak between 950 and 985 cm$^{-1}$. Taking into account that in a two component system, the single weight fractions χ add up to 1, this gives:

$$\frac{E_1(\lambda)}{E_2(\lambda)} = \frac{\epsilon_{A,1}(\lambda) \cdot c_A + \epsilon_{B,1}(\lambda) \cdot (1 - c_A)}{\epsilon_{A,2}(\lambda) \cdot c_A + \epsilon_{B,2}(\lambda) \cdot (1 - c_A)}$$

Here the weight fraction of the component is independent of the path length. Plot the ratio of $E_1/E_2$ versus the concentration of the calibration sample and perform a least square linear fit.

The calibration is defined as:

$$\frac{E_1}{E_2} = x \cdot c_{initial}$$

with x corresponding to a calibration coefficient used to relate the peak ratio to concentration as % GTS.

Analysis of a sample nonwoven is performed on 25 mg of nonwoven excised from the site of interest. Once again a film is prepared using a hot press with the specimen placed between two aluminum foils and melted until the pressing form reached 175° C., pressed for 2.0 min with a 5000 kg weight and then cooled for 20 min in a water cooled form under no pressure. The resulting film should have a uniform thickness from 59 μm to 62 μm.

Transmission FTIR is performed on three different locations on each specimen film using the identical conditions as the standards. Peak heights in the 1025 cm$^{-1}$ and 950 cm$^{-1}$ region and 1806 cm$^{-1}$ and 1660 cm$^{-1}$ region are collected in like fashion as the standards. The % GTS is calculated using the calibration coefficient derived above for the three replicates and reported as the arithmetic average to the nearest 0.1%.

Quantification of Heat Activated Zones via FTIR/ATR

GTS surface enrichment on fibers, is measured using Attenuated Total Reflection (ATR) FTIR (a suitable instrument is the Nicholet 6700, Thermo Scientific, or equivalent) utilizing both a Germanium and Diamond crystal. The instrument should be capable of correcting the ATR signal to match transmission FTIR signal in accordance with the Advanced ATR Correction Algorithm as described in Thermo Scientific Application Note 50581. The correction is applied as specified by the manufactures operating procedures. All testing is performed in a conditioned room maintained at 23° C.±2° C. and 50%±2% relative humidity. Samples are conditioned under the same conditions for 2 hours prior to testing.

Surface enrichment of GTS is measured using FTIR ATR with both a germanium crystal and diamond crystal. Selecting the germanium crystal, the specimen is placed on the ATR stage with the site of interest centered beneath the crystal. The crystal is pressed against the specimen using the probe to a pressure of 68.9 N/mm$^2$. 64 scans are collected at a resolution of one data point per every 0.482 cm$^{-1}$, amplification of 1.0, 64 scans are collected at a resolution of one data point per every 0.482 cm$^{-1}$, amplification of 1.0, and 1 bounce measurement type, between a wave number of 550 cm$^{-1}$ to 4000 cm$^{-1}$. Between each measurement the crystal and plunger must be cleaned thoroughly with isopropanol to prevent carry-over from the previous analyses. After cleaning wait at least 10 min before starting a new measurement to ensure no residual isopropanol is present on the stage and crystal. Background spectra, using the parameters specified above, were collected every 15 minutes. This background spectrum is subtracted from each measured sample spectra. A spectrum is collected on three different but equivalent sites for a total of 3 spectra. Spectra were repeated using this protocol for both the germanium and diamond crystals. Two peaks were measured for quantification, one associated with the PP and the second associated with the GTS.

The ATR signal can be corrected to match transmission FTIR signal by application of the following equation (equation was derived from Thermo Scientific Application note 50581):

$$A = -\log_{10(ART)} = (\log_{10} e) \frac{n_2}{n_1} \frac{E_0^2}{\cos \varnothing} \frac{d_p}{2} \alpha$$

where:
A=ATR intensity
$E_0$=electric fields of the evanescent wave at the boundary
α=absorption coefficient per unit thickness of sample
$d_p$=penetration depth
$n_1$=refractive index of the crystal
$n_2$=refractive index of the sample
Ø=incident angle The penetration depth ($d_p$) for each crystal is calculated using the following equation:

$$d_p = \frac{\lambda}{2\pi n_{Crystal} \sqrt{\sin^2(\theta) - \left(\frac{n_{Sample}}{n_{Crystal}}\right)^2}}$$

with n is the refractive index, Θ is the incident angle, and λ is the incident wave length. The refractive index of the sample is taken as 1.49 for PP and PE. For example, a germanium crystal (refractive index=4.0 and incident angle=42°) would give 0.41 µm penetration and a diamond crystal (refractive index=2.4 and incident angle=42°) would give 1.51 µm penetration. Values must be calculated based on the specific configuration of the instrument used.

Using an appropriate software draw a baseline between 1806 cm$^{-1}$ and 1660 cm$^{-1}$ and measure the vertical drop from highest peak between those two wave numbers. This is $E_1$. Secondly, draw a baseline between 1025 cm$^{-1}$ and 950 cm$^{-1}$ and measure the vertical drop from highest peak between 985 cm$^{-1}$ and 950 cm$^{-1}$ wave numbers. This is $E_2$. Quantification is performed with the calibration coefficient x as determined herein from the "Quantification of Total Melt-Additive Concentration by FTIR" method using the equation:

$$c = \left(\frac{E_1}{E_2}\right) / x$$

The % GTS is calculated for the three replicates and reported as the arithmetic average to the nearest 0.1%.

Determination of Activated Zones by FTIR/ATR

Heat activation zones are determined using FTIR with Attenuated Total Reflection (ATR) (a suitable instrument is the Nicholet 6700, Thermo Scientific, or equivalent) utilizing both a Germanium and Diamond crystal. Peak ratios internal to the same spectrum are proportional to the additive concentration and therefore can be utilized as a measure to describe the additive concentration without any further calibration. All testing is performed in a conditioned room maintained at 23° C.±2° C. and 50%±2% relative humidity. Samples are conditioned under the same conditions for 2 hours prior to testing.

Measurements are made by placing the specimen on the ATR stage with the site of interest centered beneath the crystal. The crystal is pressed against the specimen using the probe to a pressure of 68.9 N/mm$^2$. 64 scans are collected at a resolution of one data point per every 0.482 cm$^{-1}$, amplification of 1.0, and 1 bounce measurement type, between a wave number of 550 cm$^{-1}$ to 4000 cm$^{-1}$. Between each measurement the crystal and plunger must be cleaned thoroughly with isopropanol to prevent carry-over from the previous analyses. After cleaning wait at least 10 min before starting a new measurement to ensure no residual isopropanol is present on the stage and crystal. Background spectra, using the parameters specified above, were collected every 15 minutes. This background spectrum is subtracted from each measured sample spectra. Using an appropriate software draw a baseline between 1806 cm$^{-1}$ and 1660 cm$^{-1}$ and measure the vertical drop from highest peak between those two wave numbers. This is $E_1$. Secondly, draw a baseline between 1025 cm$^{-1}$ and 950 cm$^{-1}$ and measure the vertical drop from highest peak between 985 cm$^{-1}$ and 950 cm$^{-1}$ wave numbers. Measurements are made at the same site using both the Germanium and Diamond crystals.

When the location of heat treated regions and non-heat treated regions are known a Migration Coefficient (MC) can be calculated for activated and non-activated areas as follows:

$$MC_{non\text{-}activated} = \left(\frac{\left(\frac{E_1}{E_2}\right)_{Ge, not\, activated\, area}}{\left(\frac{E_1}{E_2}\right)_{Dia, not\, activated\, area}} - 1\right) \times 100\%$$

and $$MC_{activated} = \left(\frac{\left(\frac{E_1}{E_2}\right)_{Ge, activated\, area}}{\left(\frac{E_1}{E_2}\right)_{Dia, not\, activated\, area}} - 1\right) \times 100\%$$

With an activated area having an MC equal to or greater than twice the MC of a non-activated area. But in most cases with respect to a product heat activated and non-activated areas are not known, so they need to be determined empirically.

Select a region of the sample substrate to analyze for heat activated zones. An x-y test grid 50.0 mm in the machine direction and 50.0 mm in the cross direction is constructed. Using the Germanium crystal, an FTIR/ATR spectrum is measured every 5.0 mm within the test grid from x,y coordinates 1,1 (upper left position) to coordinate 50,50 (lower right position) for a total of 250 spectra indexed by coordinate. Measure the peak signal for $E_1$ and $E_2$ for each spectrum and calculate the ratio of $E_1/E_2$ and tabulate into a 50×50 Geranium Peak Ratio (PR) Grid. A 3×3 mean filter is applied to the Geranium PR Grid using the following equation:

$$PR_{x,y} = \frac{PR_{x+1,y} + PR_{x-1,y} + PR_{x,y} + PR_{x,y+1} + PR_{x,y-1}}{5}$$

A Germanium Results Grid is tabulated, starting at x,y coordinate 2,2 calculate $PR_{2,2}$ then increment x by 1 and calculate $PR_{3,2}$ and so forth until coordinate 49,2. Next increment y by 1 and calculate $PR_{2,3}$ through $PR_{49,3}$ and so forth until all coordinates between 2,2 and 49,49 have been calculated and recorded.

These measurements and calculations are repeated in like fashion at the same physical test sites using the diamond crystal to tabulate a Diamond Results Grid.

Survey the Diamond Results Grid and identify the lowest value for $PR_{x,y}$. This value is $PR_{Dia,min}$. Survey the Germanium Results Grid and identify the lowest value for $PR_{x,y}$. This value is $PR_{Ger,min}$. From these values, calculate a Migration Coefficient (MC) for a non-activated region as:

$$MC_{non\text{-}activated} = \left(\frac{PR_{Ge,min}}{PR_{Dia,min}} - 1\right) \cdot 100\%$$

Using $PR_{Dia,min}$, calculate a MC for each value in the Germanium Results Grid as:

$$MC_{x,y} = \left(\frac{PR_{Ge,x,y}}{PR_{Dia,min}} - 1\right) \cdot 100\%$$

to tabulate a MC Results Grid. To be identified as a heat activated zone $MC_{activated}$, a $MC_{x,y}$ must be at least 2× the $MC_{non\text{-}activated}$:

$$2 \cdot MC_{non\text{-}activated} \leq MC_{activated}$$

Using this criteria, assign all coordinate sites in the physical test grid as either Activated or Non-activated.

SEM Method for Determining Contact Angle on Fibers

A rectangular specimen measuring 1 cm×2 cm is cut from the topsheet of a disposable absorbent product taking care not to touch the surface of the specimen or to disturb the structure of the material. The specimen shall be inclusive of any heat activated zones identified via the Determination of Activated Zones by FTIR/ATR test method described heretofore. To the extent that additional heat activated zones lie outside of the specimen, additional specimens shall be obtained to accommodate all of the identified heat activated zones. The length of the specimen (2 cm) is aligned with a longitudinal centerline of the article. The specimen is handled gently by the edges using forceps and is mounted flat with the skin-facing side up on an SEM specimen holder using double-sided tape. The specimen is sprayed with a fine mist of water droplets generated using a small hobby airbrush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a Cryo-SEM prep chamber at −150° C., coated with Au/Pd, and transferred into Cryo-SEM chamber at −150° C. A Hitachi S-4700 Cry-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. This is further discussed with regard to FIGS. 31-34. The contact angle between the droplet and the fiber is determined directly from the images taken as is shown via lines 3700A, 3700B, 3800A, 3800B, 3900A, 3900B, 4000A, and 4000B. Twenty separate droplets are imaged from which forty contact angle measurements are performed (one on each side of each imaged droplet), and the arithmetic average of these forty contact angle measurements is calculated and reported as the contact angle for that specimen.

Figure 31A:
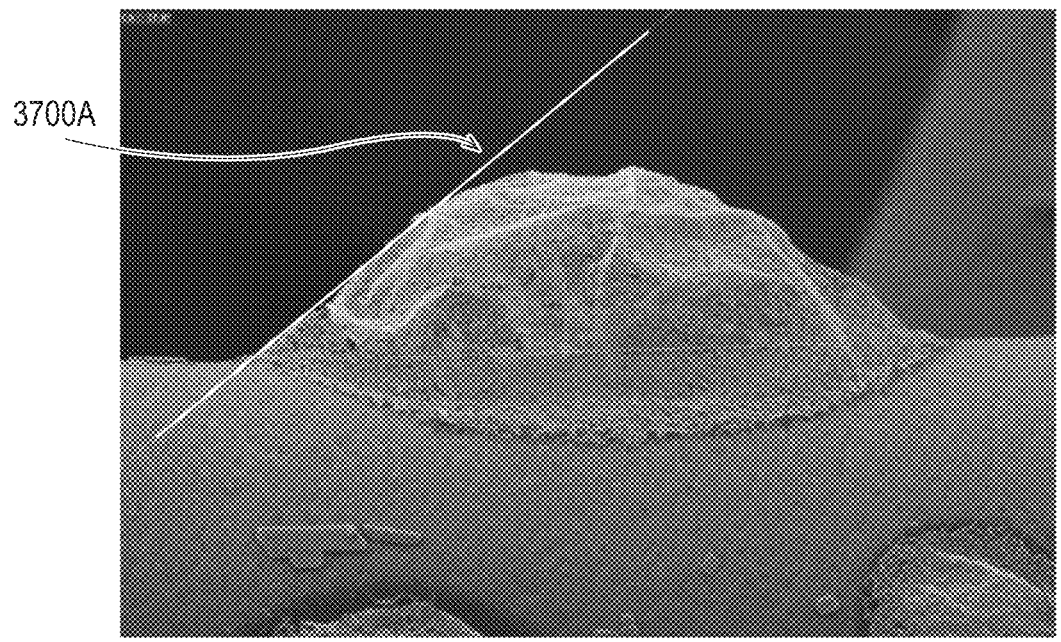
FIGS. 31A-34B are photomicrographs depicting exemplary water droplets on fibers for the SEM contact angle measurement method disclosed herein.
Figure 31B:
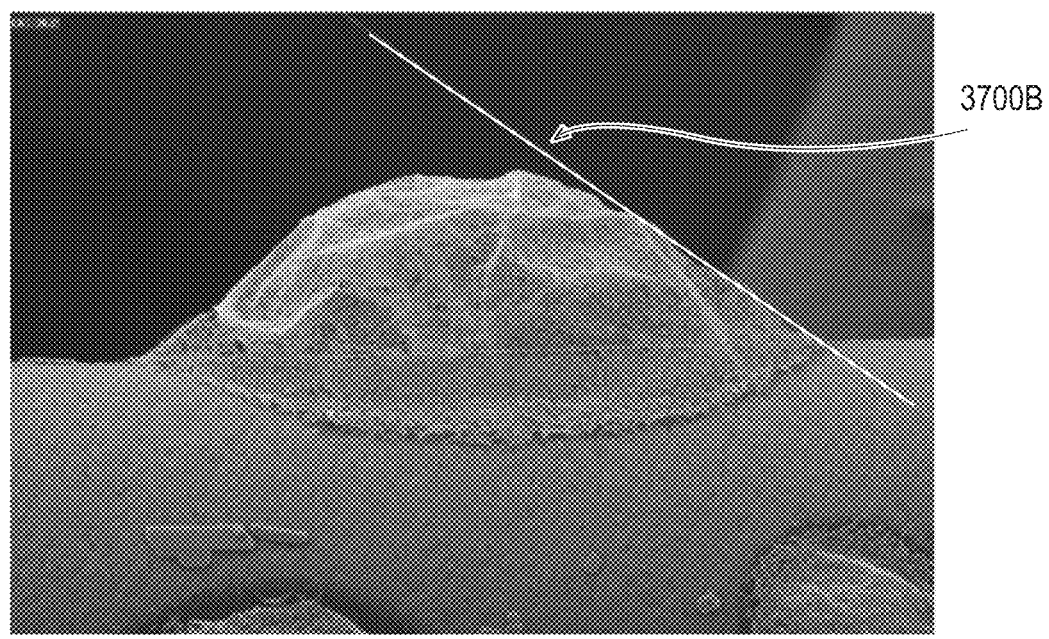
Figure 32A:
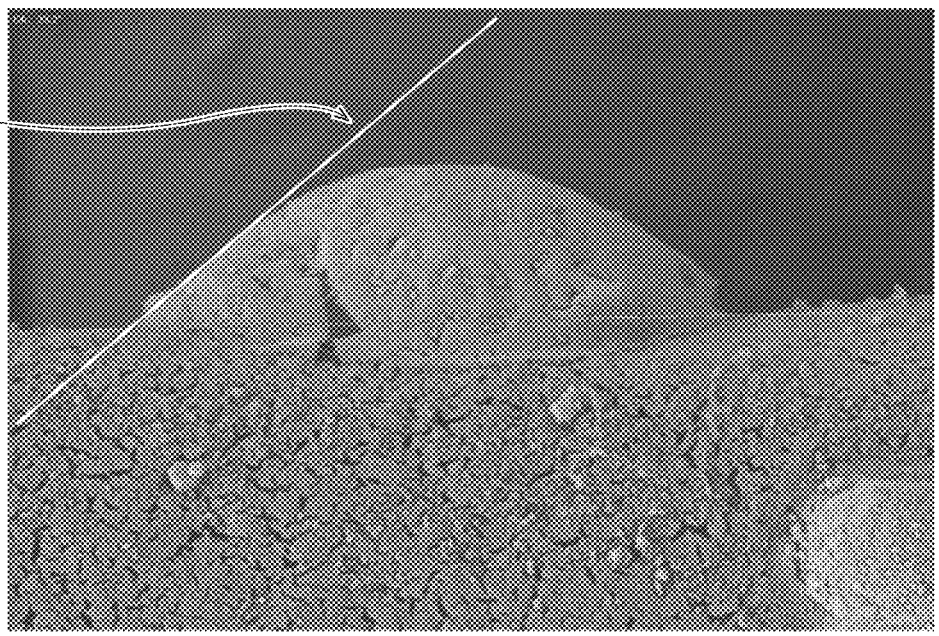
Figure 32B:
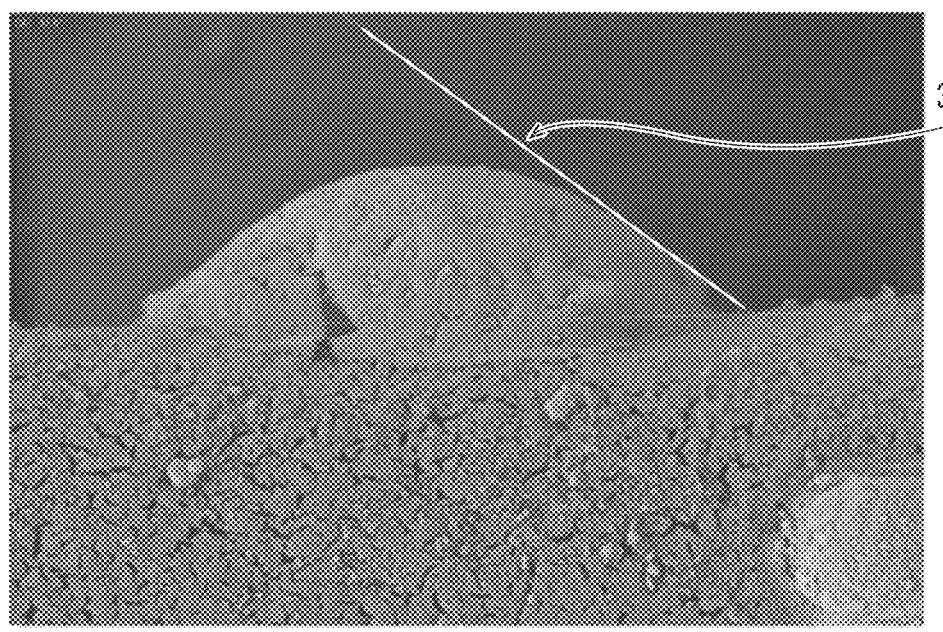
Figure 33A:
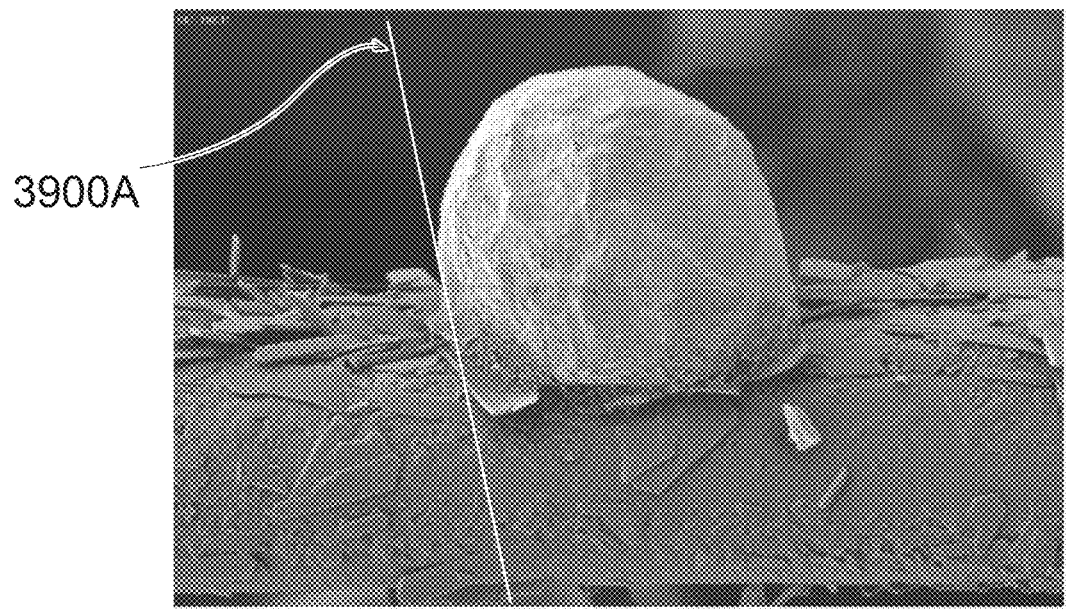
Figure 33B:
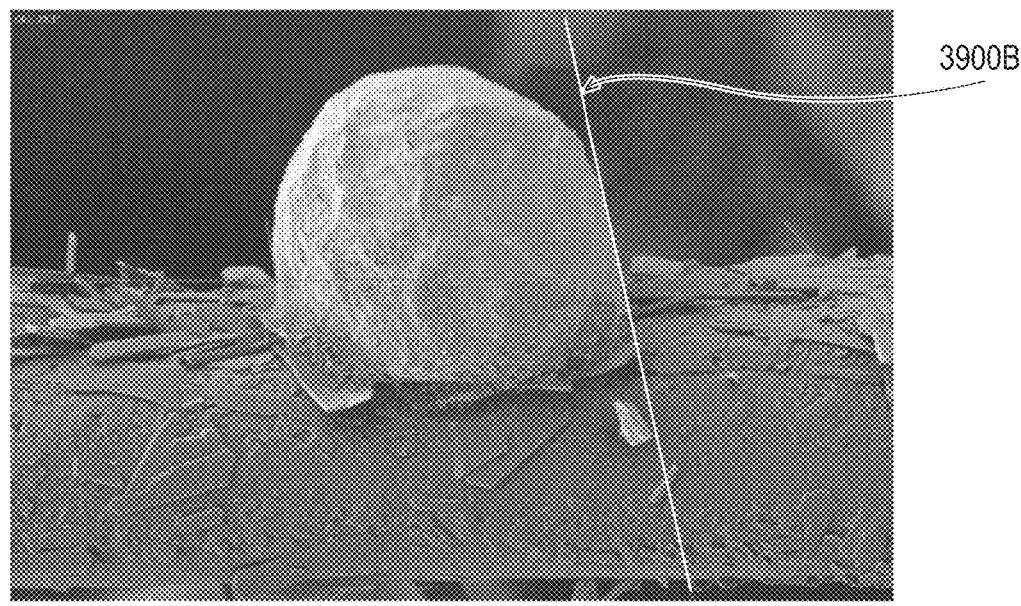
Figure 34A:
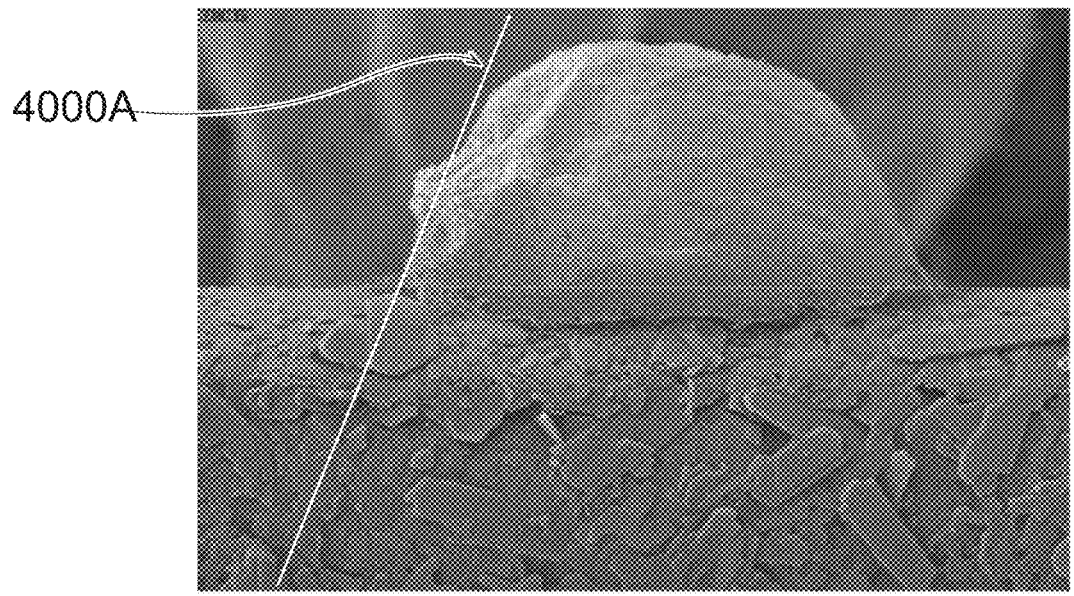
Figure 34B:
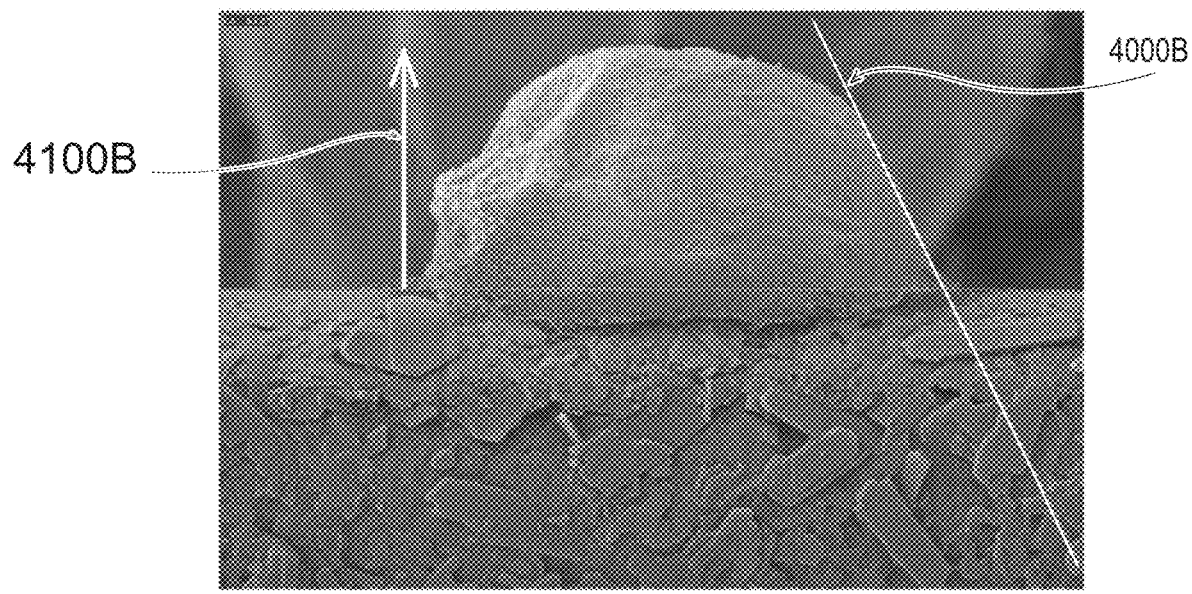

Examples of images are provided with regard to FIGS. 31-34. FIGS. 31 and 32 are exemplary images depicting water droplets cryogenically frozen on fibers upon which no composition has been applied. FIGS. 33 and 34 are exemplary images depicting water droplets cryogenically frozen on fibers upon which composition has been applied. As noted previously, the projection of the droplet should be maximized to ensure that the appropriate contact angle is measured. An exemplary droplet projection 4100B is shown in FIG. 34B.

Method for Measuring the Pattern of the Zoned Activation

X-Ray Photoelectron Spectroscopy (XPS) and Time-of-Flight Secondary Ion Mass Spectroscopy (TOF-SIMS) Imaging techniques are very surface sensitive (penetration depth below 0.5 µm) with a lateral resolution of <10 µm which can be used to visualize the distribution of the melt additive on the surface of the polymer after the activation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a topsheet;
   a backsheet;
   an absorbent core disposed between the topsheet and the backsheet; and
   a material web forming a portion of the absorbent article, the material web having a first surface and an opposing second surface, and wherein the material web comprises a thermoplastic polymeric material, a melt additive homogeneously mixed with the thermoplastic polymeric material, and melt additive bloom areas disposed on the first surface, the second surface, or both the first and the second surface of the material web, and wherein the thermoplastic polymeric material and the melt additive are matched to discourage auto blooming of the melt additive at room temperature;
   wherein the thermoplastic polymeric material comprises a plurality of filaments or fibers, at least a portion of the plurality of filaments or fibers being bi-component filaments or fibers comprising a core and a sheath, wherein the sheath comprises the melt additive homogeneously mixed therewith, and wherein the core comprises: (i) no melt additive, (ii) a different melt additive, or (iii) a different amount of the melt additive;
   wherein the material web forms a portion of the topsheet;
   wherein the material web further comprises a plurality of discontinuities; and
   wherein at least a portion of the plurality of discontinuities comprise a base, a distal end, and sidewalls extending between the base and the distal ends, wherein the melt additive bloom areas are discrete and are disposed on either the distal ends, the sidewalls, or both the distal ends and the sidewalls of the discontinuities, wherein the distal ends are disposed superjacent to the first surface of the material web.

2. The absorbent article of claim 1, wherein the melt additive bloom areas are more hydrophobic than the thermoplastic polymeric material, as determined by a Scanning Electron Microscope (SEM) Method for determining contact angle on fibers.

3. The absorbent article of claim 1, wherein at least a portion of the plurality of discontinuities comprise apertures.

4. The absorbent article of claim 3, wherein some of the melt additive bloom areas are disposed about a portion of the apertures.

5. The absorbent article of claim 1, wherein at least a portion of the plurality of discontinuities comprise a base, a distal end, and sidewalls extending between the base and the distal ends, wherein the melt additive bloom areas are discrete and are disposed on the distal ends, the sidewalls, or both the distal ends and the sidewalls of the discontinuities, wherein the distal ends are disposed subjacent to the first surface of the material web.

6. The absorbent article of claim 5, wherein each of the melt additive bloom areas are more hydrophilic than the thermoplastic polymeric material, as determined by an SEM Method for determining contact angle on fibers.

7. The absorbent article of claim 1, wherein the material web is a nonwoven material comprising a plurality of staple length fibers.

8. The absorbent article of claim 7, wherein a first plurality of staple length fibers comprise the melt additive and a second plurality of staple length fibers do not comprise the melt additive of the first plurality of staple length fibers.

9. The absorbent article of any of claim 1, wherein the material web is a nonwoven material comprising continuous filaments.

10. The absorbent article of claim 1, wherein the melt additive bloom areas are discrete and wherein a first migration coefficient of the melt additive bloom areas is at least two times a second migration coefficient of a non-activated area of the thermoplastic polymeric material.

11. The absorbent article of claim 1, wherein the melt additive bloom areas are homogeneous on the first surface, the second surface, or both the first and the second surface of the material web, and wherein the material web forms a portion of the backsheet or a portion of the leg cuffs and has a low surface tension liquid strike-through time of greater than 20 seconds.

12. The absorbent article of claim 11, wherein the material web has a basis weight of 5 gsm to 35 gsm.

13. The absorbent article of claim 1, wherein the melt additive bloom areas are homogeneous on the first surface, the second surface, or both the first and the second surface of the material web, and wherein the material web forms a portion of the topsheet or a portion of an intermediate layer between the topsheet and the backsheet, wherein the melt additive bloom areas are more hydrophilic than the thermoplastic polymeric material.

14. The absorbent article of claim 1, wherein the material web comprises the thermoplastic polymeric material, the melt additive, and an additive which influences crystallinity of the thermoplastic polymeric material, the additive being selected from at least one of a nucleating agent, branched polymers, or random co-polymers.

15. The absorbent article of claim 1, wherein the core comprises the different melt additive or the different amount of the melt additive homogeneously mixed therewith.

16. The absorbent article of claim 1, wherein said melt additive bloom areas are in the form of a film, flakes, fibrils, or combinations thereof.

* * * * *